United States Patent
Mahan et al.

(10) Patent No.: US 6,548,246 B1
(45) Date of Patent: Apr. 15, 2003

(54) METHOD AND PROBES FOR THE IDENTIFICATION OF MICROBIAL GENES SPECIFICALLY INDUCED DURING HOST INFECTION

(75) Inventors: Michael J. Mahan, Santa Barbara, CA (US); Christopher P. Conner, Santa Barbara, CA (US); Douglas M. Heithoff, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/194,036

(22) PCT Filed: May 16, 1997

(86) PCT No.: PCT/US97/08208

§ 371 (c)(1),
(2), (4) Date: Nov. 17, 1998

(87) PCT Pub. No.: WO97/44487

PCT Pub. Date: Nov. 27, 1997

(51) Int. Cl.⁷ ................................................. C12Q 1/68
(52) U.S. Cl. ........................... 435/6; 435/471; 435/477; 435/479; 435/480
(58) Field of Search ............................. 435/6, 471, 477, 435/479, 480

(56) References Cited

U.S. PATENT DOCUMENTS

| 4,358,535 A | 11/1982 | Falkow et al. .................. 435/5 |
| 5,434,065 A | 7/1995 | Mahan et al. ............. 435/172.3 |

OTHER PUBLICATIONS

"PhoE Porin of *Escherichia coli* and Phosphate Reversal of Acid Damage and Killing and of Acid Induction of the CadA Gene Product," Rowbury, et al., *Journal of Applied Bacteriology*, Jun. 1993, 74(6):652–61.
"Studies on Phospholipids of Different Mutants of *Salmonella minnesota*," Saha, et al., *Indian Journal of Biochemistry and Biophysics*, Aug. 1992, 29(4):355–9.
"Transport of Iron Across the Outer Membrane," Braun, et al., *Biology of Metals*, 1991, 4(1):14–22.
"Methylchloroisothiazolone–induced Growth Inhibition and Lethality in *Escherichia coli*," Chapman, et al., *Journal of Applied Bacteriology*, Feb. 1995, 78(2):134–41.
"Interaction of Lead Nitrate and Cadmium Chloride with *Escherichia coli* K–12 and *Salmonella typhimurium* Global Regulatory Mutants," LaRossa, et al., *J Ind Microbiol*, Mar.–Apr. 1995, 14(3–4):252–8.
"Construction of a Family of Biphenyl Combinatorial Libraries: Structure—Activity Studies Utilizing Libraries of Mixtures," Neustadt, et al., *Bioorganic & Medicinal Chemistry Letters*, 8 (1998) 2395–2398.
"Application of Combinatorial Library Methods in Cancer Research and Drug Discovery," Lam, Kit S., *Anti–Cancer Drug Design*, V. 12, 145–167 (1997).

"Relative Expression of the Products of Glyoxylate Bypass Operon: Contributions of Transcription and Translation," Chung, et al., *Journal of Bacteriology*, Jul. 1993, 175(14):4572–5.
"Isocitrate Dehydrogenase Kinase/Phosphatase: Identification of Mutations Which Selectively Inhibit Phosphatase Activity," Ikeda, et al., *Journal of Bacteriology*, Feb. 1992, 174(4):1414–6.
"Regulation of the Acetate Operon in *Escherichia coli*: Purification and Functional Characterization of the Ic1R Repressor," Cortay, et al., *Embo Journal*, Mar. 1991,10(3):675–9.
"The Absense of Glyoxylate Cycle Enzymes in Rodent and Embryonic Chick Liver," Holmes, *Biochimica et Biophysica Acta*, Aug. 20, 1993, 1158(1):47–51.
"The Isocitrate Dehydrogenase Phosphorylation Cycle: Regulation and Enzymology," LaPorte, *Journal of Cellular Biochemistry*, Jan. 1993, 51(1):14–8.
"Isolation and Properties of a Mutant of *Escherichia coli* with an Insertional Inactivation of the uspA Gene, Which Encodes a Universal Stress Protein," Nystrom, et al., *Journal of Bacteriology*, Jul. 1993, 175(13):3949–56.
"Regulatory Circuits Involved with pH–Regulated Gene Expression in *Salmonella typhimurium*," Foster, et al., *Microbiology*, Feb. 1994, 140(Pt. 2):341–52.
"Characterization of the Micro–Environment of *Salmonella typhimurium*–Containing Vacuoles Within MDCK Epithelial Cells," Garcia–del, et al., *Molecular Microbiology*, Nov. 1992, 6(22):3289–97.
"Altered pHand Lysine Signalling Mutants of cadC, a Gene Encoding a Membrane–bound Transcriptional Activator of the *Escherichia coli* cadBA Operon," Dell, et al., *Molecular Microbiology*, Oct. 1994, 14(1):7–16.
"Roles of LysP and CadC in Medrating the Lysine Requirement for Acid Induction of the *Escherichia coli* cad Operon," Neely, et al, *Journal of Bacteriology*, Jun. 1994, 176(11):3278–85.
"Identification of Elements Involved in Transcriptional Regulation of the *Escherichia coli* Cad Operon by External pH," Watson, et al., *Journal of Bacteriology*, Jan. 1992, 174(2):530–40.
"*Escherichia coli* Cad Operon Functions as a Supplier of Carbon Dioxide," Takayama, et al., *Molecular Microbiology*, Mar. 1994, 11(5):913–8.

(List continued on next page.)

*Primary Examiner*—James Martinell
(74) *Attorney, Agent, or Firm*—Morrison & Foerster LLP

(57) ABSTRACT

The present invention relates to a class of microbial coding sequences the transcription or cotranscription of which is specifically induced during microbial infection of a host. These particular coding sequences or defined regions thereof may be used as probes to identify and isolate microbial virulence genes. The products of these virulence genes will provide potential targets for the development of vaccines or antimicrobial agents.

13 Claims, 1 Drawing Sheet

OTHER PUBLICATIONS

"Cyclopropane Fatty Acid Synthase of *Escherichia coli*: Deduced Amino Acid Sequence, Purification, and Studies of the Enzyme Active Site," Wang, et al., *Biochemistry*, Nov. 17, 1992, 31(45):11020–8.

"Synthesis of Methyl 3–(2–Octadecylcyclopropen–1–yl) Proponoate and Methyl 3–(2–Octadecylcyclopropen–1–yl) Pentanoate and Cyclopropane Fatty Acids as Possible Inhibitors of Mycolic Acid Biosynthesis," Hartmann, et al., *Chemistry and Physics of Lipids*, May 6, 71(1):99–108.

"Fatty Acid Profile and Acid Phosphatase Activity of Fresh Isolates of *Pseudomonas pseudomallei*," Kondo, et al., *Japanese Journal of Medical Science and Biology*, Oct.–Dec. 1991, 44(5–6):195–211.

"Adaptational Changes of Fatty Acid Composition and the Physical State of Membrane Lipids Following the Change of Growth Temperature in *Yersinia enterocolitica*," Nagamachi, et al., *Microbiology and Immunology*, 1991, 35(12):1085–93.

"A Novel Antifungal Antibiotic, FR–9008848. I. Production, Isolation, Physico–Chemical and Biological Properties," Yoshida, et al., *Journal of Antibiotics*, Jul. 1990, 43(7):748–54.

"Unusual Fatty Acid Substitution in Lipids and Lipopolysaccharides of *Helicobacter pylori*," Geis, et al., *Journal of Clinical Microbiology*, May 1990, 28(5):930–2.

"Roles of Different Coli Surface Antigens of Colonization Factor Antigen II in Colonization by and Protective Immunogenicity of Enterotoxigenic *Escherichia coli* in Rabbits," Svennerholm, et al., *Infection and Immunology*, Feb. 1990, 58(2):341–6.

"The Binding of Colonization Factor Antigens of Enterotoxigenic *Escherichia coli* to Intestinal Cell Membrane Protein," Wenneras, et al., *Fems Microbiology Letters*, Jan. 1, 1990, 54(1–3):107–12.

"In Vivo Requirement of Integration Host Factor for nar (Nitrate Reductase) Operon–Expression in *Escherichia coli* K–12," Rabin, et al., *Proceedings of the National Academy of Sciences of the United States of America*, Sep. 15, 1992, 89(18):8701–5.

"Localization of Upstream Sequence Elements Required for Nitrate and Anaerobic Induction of FDN (Formate Dehydrogenase–N) Operon Expression in *Escherichia coli* K–12," Li, et al., *Journal of Bacteriology*, Aug. 1992, 174(15):4935–42.

"Structural Genes for Nitrate–Inducible Formate Dehydrogenase in *Escherichai coli* K–12," Berg, et al., *Genetics*, Aug. 1990, 125(4):691–702.

"Fur Regulon of *Salmonella typhimurium*,: Identification of New Iron–Regulated Genes," Tsolis, et al, *Journal of Bacteriology*, Aug. 1995, 177(16):4628–37.

"The TonB–Dependent Ferrichrome Receptor FcuA of *Yersinia enterocolitica*: Evidence Against a Strict Co–Evolution of Receptor Structure and Substrate Specificity," Koebnik, et al., *Molecular Microbiology*, Feb. 1993, 7(3):383–93.

"Structure and Function of X–Pro Dipeptide Repeats in the TonB Proteins of *Salmonella typhimurium* and *Escherichia coli*," Brewer, et al., *Journal of Molecular Biology*, Dec. 20, 1990, 216(4):883–95.

"TonB Protein of *Salmonella typhimurium*. A Model for Signal Transduction Between Membranes," Hannavy, et al., *Journal of Molecular Biology*, Dec. 20, 1990, 216(4):897–910.

"Energy–Coupled Transport Through the Outer Membrane of *Escherichia coli* Small Deletions in the Gating Loop Convert the FhuA Transport Protein into a Diffusion Channel," Braun, et al., *Febs Letters*, Jun. 6, 1994, 346(1):59–64.

"Energy–Dependent Receptor Activities of *Escherichia coli* K–12: Mutated TonB Proteins Alter FhuA Receptor Activities to Phages T5, T1, phi 80 and to Colicin M," Killmann, et al., *Fems Microbiology Letters*, Jun. 1, 1994, 119(1–2):71–6.

"Lytic Conversion of *Escherichia coli* by Bacteriophage T5: Blocking of the FhuA Receptor Protein by a Lipoprotein Expressed Early During Infection," Decker, et al., *Molecular Microbiology*, Apr. 1994, 12(2):321–32.

"The FhuA Protein is Involved in Microcin 25 Uptake," Salomon, et al., *Journal of Bacteriology*, Dec. 1993, 175(23):7741–2.

"The Conserved Proline–Rich Motif is Not Essential for Energy Transduction by *Escherichia coli* TonB Protein," Larsen, et al., *Molecular Microbiology*, Dec. 1993, 10(5):943–53.

"Conversion of the FhuA Transport Protein into a Diffusion Channel Through the Outer Membrane of *Escherichia coli*," Killmann, et al., *Embo Journal*, Aug. 1993, 12(8):3007–16.

"Domains of Colicin M Involved in Uptake and Activity," Pilsl, et al., *Molecular and General Genetics*, Jul. 1993, 240(1):103–12.

"The Wild–Type Allele of TonB in *Escherichia coli* is Dominant Over the TonB1 Allele, Encoding TonBQ160K, Which Suppresses the btuB451 Mutation," Anton, et al., *Molecular and General Genetics*, Jun. 1993, 239(3):371–7.

"Insertion Derivatives Containing Segments of Up to 16 Amino Acids Identify Surface–and Periplasm–Exposed Regions of the FhuA Outer Membrane Receptor of *Escherichia coli* K–12," Koebnik, et al., *Journal of Bacteriology*, Feb. 1993, 175(3):826–39.

"Cloning, Sequencing, and Recombinational Analysis with Bacteriophage BF23 of the Bacteriophage T5 OAD Gene Encoding and Receptor–Binding Protein," Krauel, et al., *Journal of Bacteriology*, Feb. 1991, 173(3):1287–97.

"Mutual Inhibition of Cobalamin and Siderophore Uptaka Systems Suggests Their Competition for TonB Function," Kadner, et al., *Journal of Bacteriology*, Sep. 1995, 177(17):4829–35.

"The Peptide Antibiotic Microcin 25 is Imported Through the TonB Pathway and the SbmA Protein," Salomon, et al., *Journal of Bacteriology*, Jun. 1995, 177(11):3323–5.

"Ferrioxamine Uptake in *Yersinia enterocolitica*: Characterization of the Receptor Protein FoxA," Baumler, et al., *Molecular Microbiology*, May 1992, 6(10):1309–21.

"Iron (III) Hydroxamate Transport Into *Escherichia coli*. Substrate Binding to the Periplasmic FhuD Protein," *Journal of Biological Chemistry*, Dec. 15, 1990, 265(35):21407–10.

"In Vivo Evidence for FhuA Other Membrane Receptor Interaction With the TonB Inner Membrane Protein of *Escherichia coli*," Gunter, Braun, *Febs Letters*, Nov. 12, 1990, 274(1–2):85–8.

"Colicin M is Only Bactericidal When Provided from Outside the Cell," Harkness, et al., *Molecular and General Genetics*, Jun. 1990, 222(1):37–40.

"Insertion Mutagenesis of the Gene Encoding the Ferrichrome–Iron Receptor of *Escherichia coli* K–12," Carmel, et al., *Journal of Bacteriology*, Apr. 1990, 172(4):1861–9.

"Sequence and Characterization of the *Escherichia coli* Genome Between the ndk and gcpE Genes," Baker, et al., *Fems Microbiology Letters*, Sep. 1, 1994, 121(3):293–6.

"Sequence and Characterization of the gcpE Gene of *Escherichia coli*," Baker, et al., *Fems Microbiology Letters*, Jul. 1, 1992, 73(1–2):175–80.

"Cloning and Nucleotide Sequence of the gcv Operon Encoding the *Escherichia coli* Glycine–Cleavage System," Okamura–Ikeda, et al., *European Journal of Biochemistry*, Sep. 1, 1993, 216(2):539–48.

"Roles of the GcvA and PurR Proteins in Negative Regulation of the *Escherichia coli* Glycine Cleavage Enzyme System," Wilson, et al., *Journal of Bacteriology*, Aug. 1993, 175(16):5129–34.

"Positive Regulation of the *Escherichia coli* Glycine Cleavage Enzyme System," Wilson, et al., *Journal of Bacteriology*, Feb. 1993, 175(3):902–4.

"The lpd Gene Product Functions as the L Protein in the *Escherichia coli* Glycine Cleavage Enzyme System," Steiert, et al., *Journal of Bacteriology*, Oct. 1990, 172(10):6142–4.

"gltF, a Member of the gltBDF Operon of *Escherichia coli*, is Involved in Nitrogen–Regulated Gene Expression," Castano, et al., *Molecular Microbiology*, Sep. 1992, 6(18):2733–41.

"Identification of Phosphate Starvation–Inducible Genes in *Escherichia coli* K–12 by DNA Sequence Analysis of psi::lacZ(Mu d1) Transcriptional Fusions," Metcalf, et al., *Journal of Bacteriology*, Jun. 1990, 172(6):3191–200.

"Mutants Defective in the Energy–Conserving NADH Dehydrogenase of *Salmonella typhimurium* Identified by a Decrease in Energy–Dependent Proteolysis After Carbon Starvation," Archer, et al., *Proceedings of the National Academy of Sciences of the United States of America*, Nov. 1, 1993, 90(21):9877–81.

"Characterization of the hemA–prs Region of the *Escherichia coli* and *Salmonella typhimurium* Chromosomes: Identification of Two Open Reading Frames and Implications for PRS Expression," Post, et al., *Journal of General Microbiology*, Feb. 1993, 139 (Pt 2):259–66.

"A hemA Mutation Renders *Salmonella typhimurium* Avirulent in Mice, Yet Capable of Eliciting Protection Against Intravenous Infection with *S. typhimurium*," Benjamin, et al., *Microbiol Pathogenesis*, Oct. 1991, 11(4):289–95.

"*Salmonella typhimurium* prfA Mutants Defective in Release Factor 1," Elliott, et al., *Journal of Bacteriology*, Jul. 1991, 173(13):4144–54.

"Cloning and Sequence of the *Salmonella typhimurium* hemL Gene and Identification of the Missing Enzyme in hemL Mutants as Glutamate–1–semialdehyde Aminotransferase," Elliott, et al., *Journal of Bacteriology*, Dec. 1990, 172(12):7071–84.

"Phenotypic Suppression of DNA Gyrase Deficiencies by a Deletion Lowering the Gene Dosage of a Major tRNA in *Salmonella typhimurium*," Blanc–Potard, et al., *Journal of Bacteriology*, Apr. 1994, 176(8):2216–26.

"Role of tRNA Modification in Translational Fidelity," Hagervall, et al., *Biochimica et Biophysica Acta*, Aug. 27, 1990, 1050(1–3):263–6.

"Altered Growth–Rate–Dependent Regulation of 6–Phosphogluconate Dehydrogenase Level in hisT Mutants of *Salmonella typhimurium* and *Escherichia coli*," Jones, et al., Journal of Bacteriology, Mar. 1990, 172(3):1197–205.

"Sequence Analysis of Four New Heat–Shock Genes Constituting the hslTS/ibpAB and hslVU Operons in *Escherichia coli*," Chuang, et al., Gene, Nov. 30, 1993, 134(1):1–6.

"Threonine Formation Via the Coupled Activity of 2–Amino–3–Ketobutyrate Coenzyme A Lyase and Threonine Dehydrogenase," Marcus, et al., *Journal of Bacteriology*, Oct. 1993, 175(20):6505–11.

"Regulation of kdp Operon Expression in *Escherichia coli*: Evidence Against Turgor as Signal for Transcriptional Control," Asha, et al., Journal of Bacteriology, Jul. 1993, 175(14):4528–37.

"The Products of the kdpDE Operon are Required for Expression of the Kdp ATPase of *Escherichia coli*," Polarek, et al., *Journal of Bacteriology*, Apr. 1992, 174(7):2145–51.

"Thiogalactoside Transacetylase of the Lactose Operon as an Enzyme for Detoxification," Andrews, et al., *Journal of Bacteriology*, Oct. 1976, 128(1):510–3.

"The nodL Gene from *Rhizobium leguminosarum* is Homologous to the Acetyl Transferases Encoded by lacA and cysE," *Molecular Microbiology*, Nov. 1989, 3(11):1649–51.

"Genetic Rearrangements and Gene Amplification in *Escherichia coli*: DNA Sequences at the Junctures of Amplified Gene Fusions," Whoriskey, et al., *Genes and Development*, May 1987, 1(3):227–37.

"Specific Endonucleolytic Cleavage Sites for Decay of *Escherichia coli* mRNA," Cannistraro, et al., *Journal of Molecular Biology*, Nov. 20, 1986, 192(2):257–74.

"Coordinate Expression of a Small Polypeptide with the Lactose Carrier of *Escherichia coli*," Lagarias, et al., *Journal of Biological Chemistry*, Nov. 15, 1985, 260(26):14235–41.

"DNA Sequence of the Lactose Operon: The lacA Gene and the Transcriptional Termination Region," Hediger, et al., *Proceedings of the National Academy of Sciences of the United States of America*, Oct. 1985, 82(19):6414–8.

"An Extraintestinal, Pathogenic Isolate of *Escherichia coli* (04/K54/H5) Can Produce a Group I Capsule Which is Divergently Regulated from its Constitutively Produced Group 2, K54 Capsular Polysaccharide," Russo, et al., *Journal of Bacteriology*, Dec. 1993, 175(23):7617–23.

"Nucleotide Sequence of rmpB, a *Klebsiella pneumoniae* Gene that Positively Controls, Colanic Biosynthesis in *Escherichia coli*," Vasselon, et al., *Research in Microbiology*, Jan. 1991, 142(1):47–54.

"The Occurrence of Duplicate lysyl–tRNA Synthetase Gene Homologs in *Escherichia coli* and Other Procaryotes," Saluta, et al., *Journal of Bacteriology*, Apr. 1995, 177(7):1872–8.

"Control and Function oflysyl–tRNA Synthetases: Diversity and Co–Ordination," Nakamura, et al., *Molecular Microbiology*, Oct. 1993, 10(2):225–31.

"Multiple Control of *Escherichia coli* lysyl–tRNA Synthetase Expression Involves a Transcriptional Repressor and a Translational Enhancer Element," Ito, et al., *Proceedings of the National Adacemy of Sciences of the United States of America*, Jan. 1, 1993, 90(1):302–6.

"Differential Regulation of Two Genes Encoding lysyltRNA Synthetases in *Escherichia coli*: lysU–Constitutive Mutations Compensate for a lysS Null Mutation," Kawakami, et al, *Molecular Microbiology*, Jul. 1992, 6(13):1739–45.

"Overproduction and Purification of lysyl–tRNA Synthetase Encoded by the herC Gene of *E coli*," Nakamura, et al., *Biochimie*, Jun. 1992, 74(6):581–4.

"Control of *Escherichia coli* lysyl–tRNA Synthetase Expression by Anaerobiosis," Leveque, et al., *Journal of Bacteriology*, Dec. 1991, 173(24):7903–10.

"Roles of the Two lysyl–tRNA Synthetases of *Escherichia coli*: Analysis of Nucleotide Sequence and Mutant Behavior," *Journal of Bacteriology*, Jun. 1990, 172(6):3237–43., Clark et al.

"Homology of lysS and lysU, the Two *Escherichia coli* Genes Encoding Distinct lysyl–tRNA Synthetase Species," Leveque, et al., *Nucleic Acids Research*, Jan. 25, 1990, 18(2):305–12.

"Magnesium Transport in *Salmonella typhimurium*: mgtA Encodes a P–type ATPase and is Regulated by Mg2+ in a Manner Similar to That of the mgtB P–type ATPase," Tao, et al., Journal of Bacteriology, May 1995, 177(10):2654–62.

"Magnesium Transport Systems: Genetics and Protein Structure (a review)," Roof, et al., *Journal of the Americal College of Nutrition*, Oct. 1994, 13(5):424–8.

"Molecular Aspects of Mg2+ Transport Systems," Smith, et al., *Mineral and Electrolyte Metabolism*, 1993, 19(4–5):266–76.

"MgtA and MgtB: Prokaryotic P–type ATPase that Mediate Mg2+ Influx," Maguire, *Journal of Bioenergetics and Biomembranes*, Jun. 1992, 24(3):319–28.

"Magnesium Transport in *Salmonella typhimurium*. Regulation of mgtA and mgtB Expression," Snavely, et al., Journal of Biological Chemistry, Jan. 15, 1991, 266(2):824–9.

"Membrane Topology of a P–type ATPase. The MgtB Magnesium Transport Protein of *Salmonella typhimurium*," Smith, et al., Journal of Biological Chemistry, Oct. 25, 1993, 268(30):22469–79.

The mgtB Mg2+ Transport Locus of *Salmonella typhimurium* Encodes a P–type ATPase, Snavely, et al., Journal of Biological Chemistry, Jan. 15, 1991, 266(2):815–23.

"Nucleoside Diphosphate Kinase from *Escherichia coli*; Its Overproduction and Sequence Comparison with Eukaryotic Enzymes," Hama, et al., *Gene*, Aug. 30, 1991, 105(1):31–6.

"Location of the Gene (ndk) for Nucleoside Diphosphate Kinase on the Physical Map of the *Escherichia coli* Chromosome," Hama, et al., *Journal of Bacteriology*, Jun. 1991, 173(11):3276.

"Cotranscription of the Electron Transport Protein Genes nifJ and nifF in *Enterobacter aglomerans* 333," Kreutzer, et al., *Journal of Bacteriology*, May 1991, 173(10):3252–6.

"Identification of a Promoter Dependent on NifA and Sigma 54 Upstream of nifH in *Azospirillum lipoferum*," Tripathi, et al., *Molecular and General Genetics*, May 1991, 227(1):86–90.

"Growth of the *Cyanobacterium anabaena* on Molecular Nitrogen: nifJ is Required When Iron is Limited," Bauer, et al., *Proceedings of the National Academy of Sciences of the United States of America*, Oct. 1, 1993, 90(19):8812–6.

"Oxygen Inhibition of Nitrogenase Activity in *Klebsiella pneumoniae*," Kavanagh, et al., *Journal of General Microbiology*, Jun. 1993, 139 (Pt 6):1307–14.

"Two Divergent MET10 Genes, One from *Saccharomyces cerevisiae* and One From *Saccharomyces carlsbergensis*, Encode the Alpha Subunit of Sulfite Reductase and Specify Potential Binding Sites for FAD and NADPH," Hansen, et al., *Journal of Bacteriology*, Oct. 1994, 176(19):6050–8.

"The *Klebsiella pneumoniae* nifJ Promoter: Analysis of Promoter Elements Regulating Activation by the NifA Promoter," Charlton, et al., *Molecular Microbiology*, Mar. 1993, 7(6):1007–21.

"Identification of the nifJ Gene Coding for Pyruvate: Ferredoxin Oxidoreductase in Dinitrogen–fixing Cyanobacteria," Schmitz, et al., *Archives of Microbiology*, 1993, 160(1):62–7.

"Isolation and Characterization of the Proton–translocating NADH: Ubiquinone Oxidoreductase From *Escherichia coli*," Leif, et al., *European Journal of Biochemistry*, Jun. 1, 1995, 230(2):538–48.

"Transcriptional Control of the Nuo Operon Which Encodes the Energy–Conserving NADH Dehydrogenase of *Salmonella typhimurium*," Archer, et al., Journal of Bacteriology, May 1995, 177(9):2335–42.

"Mutations in NADH: Ubiquinone Oxidoreductase of *Escherichia coli* Affect Growth on Mixed Amino Acids," Pruss, et al., *Journal of Bacteriology*, Apr. 1994, 176(8):2143–50.

"The Gene Locus of the Proton–translocating NADH: Ubiquinone Oxidoreductase in *Escherichia coli*. Organization of the 14 Genes and Relationship Between the Derived Proteins and Subunits of Mitochondrial Complex 1," Weidner, et al., *Journal of Molecular Biology*, Sep. 5, 1993, 233(1):109–22.

"Demostration of Separate Genetic Loci Encoding Distinct Membrane–bound Respiratory NADH Dehydrogenases in *Escherichia coli*," Calhoun, et al., *Journal of Bacteriology*, May 1993, 175(10):3013–9.

"Molecular Genetic Analysis of a Locus Required for Resistance to Antimicrobial Peptides in *Salmonella typhimurium*," Parra–Lopez, et al., Embo Journal, Nov. 1993, 12(11):4053–62.

"Membrane Topology of the Integral Membrane Components, OppB and OppC, of the Oligopeptide Permease of *Salmonella typhimurium*," Pearce, et al., Molecular Microbiology, Jan. 1992, 6(1):47–57.

"The Leucine–responsive Regulatory Protein, a Global Regulator of Metabolism in *Escherichia coli*," Calvo, et al., *Microbiological Reviews*, Sep. 1994, 58(3):466–90.

"Turnover and Recycling of the Murein Sacculus in Oligopeptide Permease–negative Strains of *Escherichia coli*: Indirect Evidence for an Alternative Permease System and for a Monolayered Sacculus," Park, *Journal of Bacteriology*, Jan. 1993, 175(1):7–11.

"Expression of Periplastic Binding Proteins for Peptide Transport in Subject to Negative Regulation by Phosphate Limitation in *Escherichia coli*," Smith, et al., *Fems Micriobology Letters*, Dec. 15, 1992, 79(1–3):183–90.

"UDP–Glucose is a Potential Intracellular Signal Molecule in the Control of Expression of Sigma S and Sigma S–dependent Genes in *Escherichia coli*," Bohringer, et al., *Journal of Bacteriology*, Jan. 1995, 177(2):413–22.

"Analysis of the otsBA Operon for Osmoregulatory Trehalose Systhesis in *Escherichia coli* and Homology of th OtsA and OtsB Proteins to the Yeast Trehalose–6–phosphate Synthase/Phosphatase Complex," Kaasen, et al., *Gene*, Jul. 22, 1994, 145(1):9–15.

"Molecular Cloning and Physical mapping of the otsBA Genes, Which Encode the Osmoregulatory Trehalose Pathway of *Escherichia coli*: Evidence that Transcirption is Activated by katF" (AppR) [published erratum appears in J Bacteriol May 1992:174(10):34422], Kaasen, et al., *Journal of Bacteriology*, Feb. 1992, 174(3):889–98.

"The Bcl–2 Oncoprotein Functions as a Pro–Oxidant," Steinman, *Journal of Biological Chemistry*, Feb. 24, 1995, 270(8):3487–90.

"Mutational Analysis of the Redox–Sensitive Transcriptional Regulator OxyR: Regions Important for DNA Binding and Multimerization," Kullik, et al., *Journal of Bacteriology*, Mar. 1995, 177(5):1285–91.

"Mutational Analysis of the Redox–sensitive Transcriptional Regulator OxyR: Regions Important for Oxidation and Transcriptional Activation," Kullik, et al., *Journal of Bacteriology*, Mar. 1995, 177(5):1275–84.

"OxyR Regulon," Storz, et al., *Methods in Enzymology*, 1994, 234:217–23.

"Effects of Peroxides on Susceptibilities of *Escherichia coli* and *Mycobacterium smegmatis* to Isoniazid," Rosner, et al., *Antimicrobial Agents and Chemotherapy*, Aug. 1994, 38(8):1829–33.

"The dps Promoter is Activated by OxyR During Growth an by IHF and Sigma S in Stationary Phase," Altuvia, et al., *Molecular Microbiology*, Jul. 1994, 13(2):265–72.

"Redox–dependent Shift of OxyR–DNA Contacts Along an Extended DNA–binding Site: A Mechanism for Differential Promoter Selection," Toledano, et al., *Cell*, Sep. 9, 1994, 78(5):897–909.

"Comparison of the Sensitivities of *Salmonella typhimurium* oxyR and kat G Mutants to Killing by Human Neutrophils," Papp–Szabo, et al., Infection and Immunity, Jul. 1994, 62(7):2662–8.

"Role of rpoS (katF) in oxyR–independent Regulation of Hydroperoxidase I in *Escherichia coli*," Ivanova, et al., *Molecular Microbiology*, May 1994, 12(4):571–8.

"Induction of *Escherichia coli* Hydroperoxidase I by Acetate and Other Weak Acids," Mukhopadhyay, et al., *Journal of Bacteriology*, Apr. 1994, 176(8):2300–7.

"Protein–sulfenic Acid Stabilization and Function in Enzyme Catalysis and Gene Regulation," Claiborne, et al., *Faseb Journal*, Dec. 1993, 7(15):1483–90.

"Susceptibilities of oxyR Regulon Mutants of *Escherichia coli* and *Salmonella typhimurium* to Isoniazid," Rosner, Antimicrobial Agents and Chemotheraphy, Oct. 1993, 37(10):2251–3.

"Isolation and Characterization of *Escherichia coli* Strains Containing New Gene Fusions (soi::lacZ) Inducible by Superoxide Radicals," Mito, et al., *Journal of Bacteriology*, May 1993, 175(9):2645–51.

"Involvement of the RNA Polymerase Alpha Subunit C–terminal Region in Co–operative Interaction and Transcriptional Activation with OxyR Protein," Tao, et al., *Molecular Microbiology*, Mar. 1993, 7(6):859–64.

"Modulation of the $H_2O_2$–induced SOS Response in *Escherichia coli* PQ300 by Amino Acids, Metal Chelators, Antioxidants, and Scavengers of Reactive Oxygen Species," Muller, et al., *Environmental and Molecular Mutagenesis*, 1993, 22(3):157–63.

"Physical Map of the OxyR–trmA Region (minute 89.3) of the *Escherichia coli* Chromosome," Gustafsson, et al., *Journal of Bacteriology*, Dec. 1992, 174(23):7878–9.

"Structural and Biochemical Characterization of the *Escherichia coli* argE Gene Product," Meinnel, et al., *Journal of Bacteriology*, Apr. 1992, 174(7):2323–31.

"OxyR: a Regulator of Antioxidant Genes," Storz, et al., *Journal of Nutrition*, Mar. 1992, 122(3 Suppl):627–30.

"Multidegenerate DNA Recognition by the OxyR Transcriptional Regulator," Tartaglia, et al., *Journal of Biological Chemistry*, Jan. 25, 1992, 267(3):2038–45.

"Assessment of Oxidative DNA Damage in the OxyR–deficient SOS Chromotest Strain *Escherichia coli* PQ300," Muller, Janz, *Environmental and Molecular Mutagenesis*, 1992, 20(4):297–306.

"Oxidative Stress Responses in *Escherichia coli* and *Salmonella typhimurium*," Farr, et al., Microbiological Reviews, Dec. 1991, 55(4):561–85.

"Purification and Characterization of the *Escherichia coli* OxyR Protein, the Positive Regulator for a Hydrogen Peroxide–Inducible Regulon," Tao, et al., *Journal of Biochemistry*, Feb. 1991, 109(2):262–6.

"The OxyR Regulon," Storz, et al., *Antonie Van Leeuwenhoek*, Oct. 1990, 58(3):157–61.

"Transcriptional Regulator of Oxidative Stress–Inducible Genes: Direct Activation by Oxidation," Storz, et al., *Science*, Apr. 13, 1990, 248(4952):189–94.

"Identification and Characterization of a Gene that Controls Colony Morphology and Auto–Aggregation in *Escherichia coli* K12," Warne, et al., *Journal of General Microbiology*, Mar. 1990, 136(Pt 3):455–62.

"Increased Mutability by Oxidative Stress in OxyR–deficient *Escherichia coli* and *Salmonella typhimurium* Cells: Clonal Occurrence of the Mutants During Growth on Nonselective Media," Blanco, et al., Mutation Research, Apr. 1995, 346(4):215–20.

"Transcriptional Autoregulation of the *Salmonella typhimurium* phoPQ Operon," Soncini, et al., Journal of Bacteriology, Aug. 1995, 177(15):4364–71.

"The Role of the PhoP/PhoQ Regulon in Salmonella Virulence," Vescori, et al., *Research in Microbiology*, Jun.–Aug. 1994, 145(5–6):473–80.

"Spontaneous pmrA Mutants of *Salmonella typhimurium* LT2 Define a New Two–Component Regulatory System with a Possible Role in Virulence," Roland, et al., Journal of Bacteriology, Jul. 1993, 175(13):4154–64.

"The Outer Membranes of Brucella Spp. are Resistant to Bactericidal Cationic Peptides," Marinez de Tejada, et al., *Infection and Immunity*, Aug. 1995, 63(8):3054–61.

"Role of an *Escherichia coli* Stress–Response Operon in Stationary–phase Survival," Weiner, et al., *Proceedings of the National Academy of Sciences of the United States of America*, Mar. 15, 1994, 91(6):2191–5.

"Expression of the pspA Gene Stimulates Efficient Protein Export in *Escherichia coli*," Kleerebezem, et al., *Molecular Microbiology*, Mar. 1993, 7(6):947–56.

"Stress–induced Expression of the *Escherichia coli* Phage Shock Protein Operon is Dependent on Sigma 54 and Modulated by Positiveand Negative Feedback Mechanisms," Weiner, et al., *Genes and Development*, Oct. 1991, 5(10):1912–23.

"The *Salmonella typhimurium* Virulence Plasmid Encodes a Positive Regulator of a Plasmid–encoded Virulence Gene," Caldwell, et al., Journal of Bacteriology, Nov. 1991, 173(22):7176–85.

"Molecular Analysis of spv Virulence Genes of the Salmonella Virulence Plasmids," Gulig, et al., *Molecular Microbiology*, Mar. 1993, 7(6):825–30.

"Stress Induction of the Virulence Proteins (SpvA, –B, and –C) from Native Plasmid pSDL2 of *Salmonella dublin*," Valone, et al., *Infection and Immunity*, Feb. 1993, 61(2):705–13.

"A New Gene Involved in Stationary–phase Survival Located at 59 Minutes on the *Escherichia coli* Chromosome," Li, et al., *Journal of Bacteriology*, Oct. 1994, 176(19):6015–22.

"Purification, Gene Cloning, and Sequence Analysis of an L–Isoaspartyl Protein Carboxyl Methyltransferase from *Escherichia coli* [Published Erratum Appears in J Biol Chem Jun. 5, 1992;267(16):11660]," Fu, et al., *Journal of Biological Chemistry*, Aug. 5, 1991, 266(22):14562–72.

"Isolation and Characterization of a Tn–5 Induced tolQ Mutant of *Escherichia coli*," Madrid, et al., *Canadian Journal of Microbiology*, Jun. 1994, 40(6);503–7.

"Colicin A and the Tol Proteins Involved in its Translocation are Preferentially Located in the Contact Sites Between the Inner and Outer Membranes of *Escherichia coli* Cells," Guihard, et al., *Journal of Biological Chemistry*, Feb. 24, 1994, 269(8):5874–80.

"Membrane Topology and Mutational Analysis of the TolQ Protein of *Escherichia coli* Required for the Uptake of Macromolecules and Cell Envelope Integrity," Vianney, et al., *Journal of Bacteriology*, Feb. 1994, 176(3):822–9.

"Energy Transduction Between Membranes. TonB, a Cytoplasmic Membrane Protein, Can be Chemically Cross–Linked in vivo to the Outer Membrane Receptor FepA," Skare, et al., *Journal of Biological Chemistry*, Aug. 5, 1993, 268(22):16302–8.

"Membrane Topologies of the TolQ and TolR Proteins of *Escherichia coli*: Inactivation of TolQ by a Missense Mutation in the Proposed First Transmembrane Segment," Kampfenkel, et al., *Journal of Bacteriology*, Jul. 1993, 175(14):4485–91.

"The Proton Motive Force Drives the Outer Membrane Transport of Cobalamin in *Escherichia coli*," Bradbeer, *Journal of Bacteriology*, May 1993, 175(10):3146–50.

"Evolutionary Relationship of Uptake Systems for Biopolymers in *Escherichia coli*: Cross–complementation Between the TonB–ExbB–ExbD and the TolA–TolQ–TolR Proteins," Braun, et al., *Molecular Microbiology*, Apr. 1993, 8(2):261–8.

"Role of tol Genes in Cloacin DF13 Susceptibility of *Escherichia coli* K–12 Strains Expressing the Cloacin DF13–Aerobactin Receptor IutA," Thomas, et al., *Journal of Bacteriology*, Jan. 1993, 175(2):548–52.

"A New colicin that Absorbs to Outer–membrane Protein Tsx But is Dependent on the TonB Instead of the TolQ Membrane Transport System," Bradley, et al., *Journal of General Microbiology*, Dec. 1992, 138 (Pt 12):2721–4.

"TolQ is Required for Cloacin DF13 Susceptibility is *Escherichia coli* Expressing the Aerobactin/Cloacin DF13 Receptor IutA," Thomas, et al., *Fems Microbiology Letters*, Mar. 1, 1992, 70(2):107–11.

"The TonB Gene of *Serratia marcescens*: Sequence, Activity and Partial Complementation of *Escherichia coli* TonB Mutants," Gaisser, et al., *Molecular Microbiology*, Nov. 1991, 5(11):2777–87.

"Phospholipase–A–Independent Damage Caused by the Colicin A Lysis Protein During Its Assembly Into the Inner and Outer Membranes of *Escherichia coli*," Howard, et al., *Journal of General Microbiology*, Jan. 1991, 137 (Pt 1):81–9.

"vacB, a Novel Chromosomal Gene Required for Expression of Virulence Genes on the Large Plasmid of *Shigella flexneri*," Tobe, et al., *Journal of Bacteriology*, Oct. 1992, 174(20):6359–67.

"vacC, a Virulence–associated Chromosomal Locus on *Shigella flexneri*, is Homologous to tgt, a Gene Encoding tRNA–Guanin Transglycosylase (Tgt) of *Escherichia coli* K–12," Durand, et al., *Journal of Bacteriology*, Aug. 1994, 176(15):4627–34.

"The Promoter of the tgt/sec Operon in *Escherichia coli* is Preceded by an Upstream Activation Sequence that Contains a High Affinity FIS Binding Site," Slany, et al., *Nucleic Acids Research*, Aug. 25, 1992, 20(16):4193–8.

"Exploring New Strategies to Fight Drug–Resistant Microbes," Gibbons, *Science*, Aug. 1992, 257:1036–38.

"The Crisis in Antibiotic Resistance," Neu, *Science*, Aug. 1992, 257:1064–72.

"Vancomycin Resistance: Decoding the Molecular Logic," Walsh, *Science*, Jul. 1993, 261:308–9.

"The Origin of Plagues: Old and Nwe," Krause, *Science*, Aug. 1992, 257:1073–77.

"Structure–Based Strategies for Drug Design and Discovery," Kuntz, *Science*, Aug. 1992, 257:1078–82.

SEQUENCE LISTING (1) GENERAL INFORMATION:

(iii) NUMBER OF SEQUENCES: 255

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (iii) HYPOTHETICAL: NO (iv) ANTI-SENSE: NO (vi) ORIGINAL SOURCE:
      (A) ORGANISM: DNA (other)

(xi) SEQUENCE DESCRIPTION: SEQ ID NO: 1:

CATTGGGTGC CCAGTACG                                                18

(2) INFORMATION FOR SEQ ID NO: 2:

(i) SEQUENCE CHARACTERISTICS:
      (A) LENGTH: 18 base pairs
      (B) TYPE: nucleic acid
      (C) STRANDEDNESS: single (D) TOPOLOGY: linear (iii) HYPOTHETICAL: NO (iv) ANTI-SENSE: NO (vi) ORIGINAL SOURCE:
            (A) ORGANISM: DNA (other)

(xi) SEQUENCE DESCRIPTION: SEQ ID NO: 2:

TGTGCCTTCG TCGAGCAC                                                   18

(2) INFORMATION FOR SEQ ID NO: 3:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (iii) HYPOTHETICAL: NO (iv) ANTI-SENSE: NO (vi) ORIGINAL SOURCE:
            (A) ORGANISM: DNA (other)

(xi) SEQUENCE DESCRIPTION: SEQ ID NO: 3:

CAACGGTGGT ATATCCAG                                                   18

(2) INFORMATION FOR SEQ ID NO: 4:

(i) SEQUENCE CHARACTERISTICS:
            (A) LENGTH: 390 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 4:

GATCCGGATG GAATGGCTCC AGCGCGTCGG TTTTCTCGCC GACACCGAGG                 50

AATTTAATCG GCTTGCCGGT GATATGACGA ATAGAGAGCG CCGCACCGCC                100

ACGCGCATCA CCATCAACTT TGGTCAGCAC CACGCCGGTT AACGGCAGCG                150

CTTCGTTAAA GGCTTTTGCG GTATTCGCCG CATCCTGACC GGTCATCGCA                200

TCGACGACAA ACAGCGTTTC TACTGGCTTG ATAGAAGCGT GGACCTGTTT                250

GATTTCGTCC ATCATCGCTT CGTCAACATG CAGACGACCG GCGGTATCCA                300

CCAGCAGCAC GTCGTAGAAT TTGAGCTGCT TCTTGGCGGT TGACAGTATC                350

ACGTTCTGCG AAATCAGACG GAGAATCACG CAATTGTACA                           390

(2) INFORMATION FOR SEQ ID NO: 5:

(i) SEQUENCE CHARACTERISTICS:
            (A) LENGTH: 238 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 5:

```
GATCATAGAG GTGGATACGG CTTTTCAACG CCTGTTGGAC GGCGTGCCAG        50

TCGGCCTGTT CAAAACGCTG CTGCGCGCCG GAAGTCACTT CCAGAAATCG       100

ACCATACTGC GCGTCAAAGC CTTGCAGGAT GGTTTGAGCA ATCAGTAATT       150

CCAGGCCACG CGGCATTTTT TTACCTCATC CGGCACCACG TCATGCCGGA       200

TGCGCGTTCG CTTATCCGGC CTACGCTATC TGTAGGCC                   238
```

(2) INFORMATION FOR SEQ ID NO: 6:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 6:

```
GATCGAGAGG ATGCGGTGGT GGATGCGCAT ATTACCGGAT GACGGCGTGA        50

ACGTGTTATG CGGCCTACCA GCCCAATGCG CGATACCAAG CCGGATAAGC       100

CGCCAACGCC CACCCCGGCC CCGCCGCGTA TTTAATCAAG TTATTACCTT       150

TGATCGCACC CTTGAGGTCA GGCGCGTGAT AAGTTCGTAA GCACTTACTT       200

TTGTCATTTC AGCGATACGT TCAACCGGCA GACTTACCCA TAGACACGAT       250

CGCGGTATCT CGGTTGCCAA TTCGAATCTA TCCATGGACG CGACATCGAC       300

TACGACATT                                                    309
```

(2) INFORMATION FOR SEQ ID NO: 7:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 7:

```
GATCCGTTTT GACCATCCCG TGTTTGGTCG AAACCGTGCA GCCTTCTACC        50

AGCGGCAGTA AGTCGGGCTG TACGCCTTCG CGTGAAACAT CCGGGCCGGA       100

GGTTTCGGCA CGCTTACAAA TTTTGTCAAT TTCATCGATA AACACGATGC       150

CGTGCTGTTC AACGCGTCG ATAGGTCCTG TTTCAGCTCT TCCGGGTTGA        200

CCAGTTTAGC AGCCTCTTCT TCAACCAACA GTTTCATCGC GTCTTTAATT       250

TTCAGCTTAC GGGTTTCTGT TTCTGACCGC CCAGGTTCTG GAACATAGAC       300

TGCACTGCTG TCATCTCTCA TGCCGAGCCA TATCTCTAGC CATCGGCGCA       350
```

GTATTGACTT TA                                                   362

(2) INFORMATION FOR SEQ ID NO: 8:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 8:

GATCAAGAAT GTGTTCTCCC AGCGCATCCT TGATGGTTTC TCCCAGCACC           50

TTGCCGAGCA TACTGACATT ACTAGCAACG CGGAATATTG TTCGTTCATA          100

TGCCCCCAGA CGCCCCATCT TTAATGTAAT TGCCCTGTCT CTTTCATGCC          150

ACAGCGCAGT GGCTGCGTGC GTATGCAGTT ATGCGAATGC TCGTGCTGCG          200

ACTAAT                                                          206

(2) INFORMATION FOR SEQ ID NO: 9:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 9:

GATCGTCGGT GCGAATGGTG ACGTCGGCAA TCTCTTCGTA CAGCGGATTG           50

CGTTCGTTAG CCAGCGCTTC CAGAACTTCG CGAGGCGGTG CTTCAACCTG          100

CAACAGCGGG CGTTTTTTAT CACGCTGCGT GCGGCAGTTG TTTTTCGATC          150

GGTCGTTTCA AGGTAGACCA CGACGCACGG CGAGAGACGG TTACGGTTTC          200

ACAATTTTAC AGAGCCACAT CGGAACACAC ATACCTTTAT ATCTATACTT          250

(2) INFORMATION FOR SEQ ID NO: 10:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 10:

GATCCAGGCT TCGCGTTCTG ATAGCTGTCA TACGGTACGG TGGTGATTTC           50

```
CGGATGCTTA TCCATGATGA ATTTCTGGTG TCGTCGTACC GTTCTGTACG            100

CCGACTTTCT TGCCTTTCAG TTGATCAACG CTGGTGTATT GCCTGCTGAC            150

CACGAACAGC GTGAGTAGGG TATATG                                     176
```

(2) INFORMATION FOR SEQ ID NO: 11:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 11:

```
GATCTTCCGC CCAGCCTGCG ACTTCTACTT TCGAGGCCTG GATTTCGAAA             50

CTTTGCCCCT GTGCCGGCGA CGCGACAACC TTACCTGTTA CTACCACGGA            100

GCAGCCTGTC GACAGGTGTA ATACTTCTTC ATTATAATTG GGCAGAGAAT            150

TATTAATGAC AGCCTGTACA GGATCAAAGC AGGAGCCGTC ATAAACGGCG            200

AGGAAGGAGA TGTCCAGCTT TTGAATCTCG GTCGGGTACG ACCCATCCCG            250

CGCAGTGACT TCTTGGTCAA CGGCTACTGG CCTGGAGTAC TGCGGCTACG            300

GCACACGTCA TA                                                    312
```

(2) INFORMATION FOR SEQ ID NO: 12:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 12:

```
GATCCCAGAT AATCGCCAGG ATCACCATCA CCACCGTTGG CATCAACCAA             50

GCCAGTCCCT GTTCCGCCAG CGCAAACGCT GACTCCAGGC TGGCAGCATA            100

TCGCCGAAGG ATGCTTTGAT GCCGTCAAGG ATACCAAAAA GCAGACTGAT            150

AAACATGGCC GGCGCCGATG ATACGGGTGG AATTATGCCA CCATGAGCGG            200

GTAAAACTTA ATACAACCAG TGCGATACAC GGCGGATAGA TAGCGTCATG            250

ACGGAATTGG AGATTATCAG ATCGCTCAGT CGAGGTTGA                        289
```

(2) INFORMATION FOR SEQ ID NO: 13:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 13:

GATCAATAAT GTTATCCCGG CTTAACACTT CATCCGGGTG ATGCGCAAAA            50

TACATCAGAA GATCGATCAG CCGTGGTTCA AGAGTAATCT GGCGTCCCTG           100

ACGACTGATC TGACCAACAG AAGGTATAAC CAGCCACTCT CCAATGCGTA           150

CAACAGGTTG CTGCATAAAA AGATGCCTAA CGAGCTAAGT CATACGTATA           200

TACACGATTG CACAGACTTT TATCCTTTGT AAGAAGCTAA                      240

(2) INFORMATION FOR SEQ ID NO: 14:

(i) SEQUENCE CHARACTERISTICS:
            (A) LENGTH: 260 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 14:

GATCAGAACC TTAAAACAGC GTAGACACTT TTTTGGCTTT GTGAGAAATC            50

CACGGACAAT TCCGCGAGCC AGTTATCGAC GTAGAACAGA GGAAGGGAGG           100

AGCCCTTGCC GAAAAGGCCA TCCCATGGTG AATCGGAAC GCTCCGGTTC            150

CCGTTAATGC CTAATAATTA TCGTAATATA AACAACCGGA AATCAGTATA           200

GGCCGCAATT TTGACGATTC ACCGAAATTG TTAGCGTGCT AATTACAGAG           250

TACAGTTAGT                                                       260

(2) INFORMATION FOR SEQ ID NO: 15:

(i) SEQUENCE CHARACTERISTICS:
            (A) LENGTH: 314 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 15:

GATCGGCATA CAGCGCGTAC ACTTCATCCA GACGTTTGAG GGCGTTAACC            50

ACTTCCGAAA CGGCCTCTTC AATCGACTCG CGTACCGTGT GTTCCGGGTT          100

TAGCTGAGGT TCCTGCGGCA GGTAGCCAAT CTTAATGCCG GGCTGCGGGC           150

GCGCTTCGCC CTCGATATCT TTATCGAGCC CCGCCATGAT GCGCAGCAGG           200

GTAGACTTAC CGGCGCCGTT AAGGCCCAGC ACATCCGATT TGGGCCCAGG           250

AGAGCTCAGG CAGATGTTTC AGATATGACG TTCAGACACT GCGAACCGAT           300

GCTGATAGAT GAGC                                                  314

(2) INFORMATION FOR SEQ ID NO: 16:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 16:

```
GATCGCCATT CTGCTAACGA CTCTGACGCT GGCGCTGCTC TCCAGGCTGC          50

ATCGGTTATA ACATTCTGGC GACACGGGCA AAACGCGGCT GTCGCCAGTC         100

TCTGTCAGAA ACGGTAATCC ACCGCCATAA AGTAACGACG TCCGTCTTCG         150

GTATAACCGT AGTCGTCGCG TTTGAGATCT TTATCGCCCA CGTTCAGAAC         200

GCCCGCACGC AGTTTAACGT TTTTCGTCGC CTGCCATGCC GCGCCGGTAT         250

CCCAGACCAC GTACCCGCCC GGCGTTTTTC GCTGTTTGCC TCTGTCGGCC         300

CGCTTACGCC GGTATAATTC CTGATACGTA GATGACAGTT GAGCTGACCG         350
```

(2) INFORMATION FOR SEQ ID NO: 17:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 17:

```
GATCGTGCAA ATGCGCGCTA AAGGTGGCGG CGTCCATAAA GCCGGTGACT          50

CGCGATTGCG GCTGTTCCTG GCCTTGGGTA TTAAAGAACA GAATGGTGGG         100

CAGCCCGAGG ACTTGCAGAT GCTTTAACAG CGCGACATCC TGCGCATTGT         150

TAGCGGTGAC GTTAGCCTGC AAGAGCACCG TGTCGCCGAG CGCCTGCTGG         200

ACCCGCGGAT CGCTGAAGGT ATACTTTTCA AACTCTTTTA CAGGCCACGC         250

ACCAGTCGGC GTAGAAATCA GCATAACGGT TTGCCTTTGG CCTGCGCCTG         300

ATTGAGTTCA TCCACGTAGA ATAGCCGTGA ATTGAG                        336
```

(2) INFORMATION FOR SEQ ID NO: 18:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 18:

| | |
|---|---|
| GATCCGCGAG GTGCGCCAGT TGCACCATCT CCAGCAATTG CGTCACTTTG | 50 |
| TTTTAATCGC CGCCGCCGCA GTTGGGCGTC GCTCGCGCAG ACCGTAGCCA | 100 |
| AAAGCGATGT TGTCAAACAC CGTCATATGG CGAAACAGCG CATAGTGCTG | 150 |
| AAAACACAAA ACCGACTTTA CCTACTGGTG AGGCGCTAAC GTCGTACGTG | 200 |
| GAAACGATAT ACCGTGGACT GTGTCAGCCC GGCAATAATC CCGGCTGTTT | 250 |
| GCGGAACTAC GCACAGGACA TTGCGAGATA TTACGG | 286 |

(2) INFORMATION FOR SEQ ID NO: 19:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 19:

| | |
|---|---|
| GATCGCGAAA GGCGTACATC TCACGGAATT TCCAACCGGT ATCAACGTGC | 50 |
| AATAGCGGGA ACGGCAACGT ACCCGGATAA AACGCCTTAC GCGCCAGATG | 100 |
| CAGCATGACG CTGGAGTCTT TACCAATGGA GTACAGCATG ACCGGATTAG | 150 |
| CGAATTCCGC TGCCACTTCA CGATAATGTG ATACTTCGCA CAGTTGCGCA | 200 |
| GTGGTGAGTC GTTTTGATCA TACGTCTTTG CATCGTTTTG CTAACTGATA | 250 |
| CGACTAGGCG GTATATCGAT GATGTGTCTA GATACGCACA TCACACCGAT | 300 |
| CCTGCAATTC ACGTACACGA TCTGC | 325 |

(2) INFORMATION FOR SEQ ID NO: 20:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 20:

| | |
|---|---|
| GATCAGGTGC GGTCGGTAAT TGACAAAATA TGGGCAAATG GCCACGACAT | 50 |
| TACCCCTTAA TTGATTGGCA GCAGCTCGTG GCTGATTGAT TTTAGCCGGA | 100 |
| GCCGGACGCT CCGATTTTGG CGTCAGATAC CAATAACCCA ATCCATGAAT | 150 |
| ACACACGACA AGTATACGGG TTACACACAG TATACATCGC AGATCGCTGT | 200 |

(2) INFORMATION FOR SEQ ID NO: 21:

(i) SEQUENCE CHARACTERISTICS:
        (A) LENGTH: 264 base pairs
        (B) TYPE: nucleic acid

```
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 21:

GATCGGTTTT ACCCTTCGTC CCTTTGATAT AACGCGTGAC GCCGTTAACG          50

TACCGCCAGT GCCGACGCCG AGATAAACAC ATCCACCTGA CCATCGGTCT         100

CCAGAGTTTC CGGGCCGGTG GTTTTTCATG GATTCTCGGG TTGGCAGGGT         150

TGCTGAACTG CTGGAGCAGG AGATATTTTT GCGGATCCGT GGCGACAATT         200

TCTTCGGCTT TCTTGAATAG CGCCTTCATC CTGGCCTTGT CAGCACCAGA         250

TTGGCTATGC TTAG                                                264

(2) INFORMATION FOR SEQ ID NO: 22:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 22:

GATCAGAATC TATGTTGTCA CAGATTAATA GTTTATTATA TATTTCATCA          50

AAATAATCGA CGTCAAGTTC TTTGTTTTTA TTTAGAGTGA ATACTTCCTG         100

TCGTTTTTTA TCGTTTACAT AATCGACTAC CGTAACTGCA ACATTCTTAT         150

TTTTTTGTTT CTCTATACAT AGTAATATGG TGTCAAGTTC AAATTTTATT         200

TCTTCAAATC GCAAATCAAA GAAAAAATCT ATATTTTTAT TTAAAATCGT         250

TGTCAATTAT CTTTAAAACG ATGTTTTACG TAACATTGTC GTATATATCG         300

TCTGAGTCTA ATCAATATCA TAGT                                     324

(2) INFORMATION FOR SEQ ID NO: 23:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 23:

GATCTTCGCC TACCGGCACC AGATTGGTTT GGTACAACAG AATGTCTGCC          50

GCCATCAGCA CCGGGTAATC AAACAGGCCG GCGTTAATGT TTTCCGCATA         100

GNNNCAGATT TATCTTTAAA CTGCGTCATA CGGCTCAGCT CGCCGAAATA         150
```

| | |
|---|---|
| GGTATAGCAG TTCAGCGCCC AGCCAAGCTG CGCATGTTCC GGCACATGGG | 200 |
| ACTGAACGAA AATAGTGCTC TTTTAGGATC ATACCACATG CCAGGTACAG | 250 |
| NNAGATTCCA GGCGTTTACG TAGTGT | 276 |

(2) INFORMATION FOR SEQ ID NO: 24:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 24:

| | |
|---|---|
| GATCCGGCGC CGGAGCCACC ACGCCTTCAC GCGGGGCTCC GGGTTCGGCG | 50 |
| CGGGCAGATT CATCAGCTTC GCCAGAATGC TCGCCAGCTT CAGGCGCATT | 100 |
| TCCGGGCGGC GGACTATCAT ATCAATAGCG CCTTTTTCGA TCAGGAACTC | 150 |
| ACTGCGCTGG AATCCTGGCG GCAGTTTTTC GCGAACGGTC TGTTCGATAA | 200 |
| CGCGCGGGCC GGCGAAGAAT CGAGACTTTT GGCTCGGCGA TGTTGAGATC | 250 |
| GCCAGCATCG CAAAACTGGC GGAAAAGGCC CATTGTCGAT CGTACTACGA | 300 |
| AATGTAGGGC AGACGCTCTG CATTTAGAC | 329 |

(2) INFORMATION FOR SEQ ID NO: 25:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 25:

| | |
|---|---|
| GATCCCTAAC ACCCGGTCAG TTCCCGACAG GCCGGTCTTT TCTACTAGCT | 50 |
| GACCTATCAC AAAATTCACG ACAGCGCCGA TCGATAAGCG TCGCGATAAA | 100 |
| CAGTACCGCG ATACGAATTC CCATTACGAA CCAGTTCGTC TTCAAAGCCC | 150 |
| GTAAACCAGA CAGACAGGTA AGTGTAGTAG TGACTGGCGA CAAAGAAGCA | 200 |
| CACCCACGTA CCAGCATACG TC | 222 |

(2) INFORMATION FOR SEQ ID NO: 26:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 26:

GATCAGTATA CAACTATCAG TAATTCGACG ATAGACCGAA GTGTGCTTGC     50

TGGCGCTTTA TCGTCAAGGA TAATTGCCGC TTTGACGGCC TTCGCGCTTC    100

CTGCCAACTG GCTTCGTCTT TGTGCATGAA TCACCGCCAG CGGCTCTGCC    150

GCTCGATNTG TCGATC                                         166

(2) INFORMATION FOR SEQ ID NO: 27:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 27:

GATCGCTTAA CAGATAATGA CTGGCGCTGC GGGGCTCCAG TACGATATAG     50

CCGCCTAGCA ACACGACAGG CGCGCTTTTA TGGTTCAGGT CGCGACGAAT    100

GGTCATTTCA GAGACGCCCA ACAGGGTCGC GGCTTCTTTA AGATGAAGTT    150

TATCGCTGCG TTTTAAGGCC TGCAGCAATT GACCAATAGC GTCGTCGCTC    200

GGCTTTCCAT AGTTCCCCTG GAGAGTTAAA TAAGCGCTCC GCACCATACA    250

GAGCGCTTAA TATTACTCTT TTTTGCGCTA TTTAGTCACG TACCCAGCCT    300

TTTCGAATGG GCAATGCAAC AGAACGTACA CGT                      333

(2) INFORMATION FOR SEQ ID NO: 28:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 28:

GATCGCGCTC AATCGCTTCC GCCGCCAGTT TAGCCGCCAG CTCCGGCGTT     50

TTTTCATGCA CCAGAGCTTT CTTAAGCGCT TTTGGCGTAG CACCACTTCT    100

TTGGTTTGTA CTACCGGCGT GGTGGCCTTC CAGCGATAAG CCTCTTTCTT    150

TACTGGCGGT TTCCAGCGGG ACGGNGGGNT GTACNNTCCG AAACCGAGGA    200

GCGTCAGNAG AGTTATTACG G                                   221

(2) INFORMATION FOR SEQ ID NO: 29:

(i) SEQUENCE CHARACTERISTICS:
        (A) LENGTH: 368 base pairs (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 29:

| | |
|---|---:|
| GATCGTCGTA CCGCCAACCG AGCCGCCGGG TATGTGTCGT TAAACTCTGT | 50 |
| CGCCAGACCA TAGTTAGAGG TAATAGAAGC CCCCCAGCCA AACTGGTCGT | 100 |
| TAATCGGGGC GACAAAATGG ACGTTCGGCA CCCAGGCCGT CAGCGCGATG | 150 |
| TTATCCGCAT CTAACGTCCG ACGAGATGGC GATGTCCCGC TAATATTAAC | 200 |
| ATCAGGATCA ATATAAACGC GCCCGCTGAA AACGTCGGGC GGTCAAACAT | 250 |
| GTATTACGCG GGTGCGCTAC GTACGCATCA TCTGCGATGC GCTCACGATA | 300 |
| GCGCAGCAGA GAGAATCGTA CTGAGCTCGC GACAGTGTGA TGTCGATCGG | 350 |
| ATCGCGCTTT GCAGTTTG | 368 |

(2) INFORMATION FOR SEQ ID NO: 30:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 30:

| | |
|---|---:|
| GATCTCCACA AACTGTTCCG GCTGAGCGAT AGCTTAAGTA GCGCATGTTT | 50 |
| CCTCCAGGTA TGGAAATGCT CTGTGAGGCG GTAAGTCGAG CCCACGTACG | 100 |
| GCCCCTGCTC CTTCTTACCC ATGCGCAGCA TCTTCTTCAT ACAGACGCGC | 150 |
| CGCCGGGTTC GAGACCACAT TCGGGTGCAG CGGGTTAGTG CCCAGCGGCG | 200 |
| TTTCATCGCT CGTAGTGTCA GGAACGCCTT CGCATTATCA TAGCAAACGA | 250 |
| ACGTTCCAGC CCTTTCGCGT CATGAAAGAT GCGTCCGG | 288 |

(2) INFORMATION FOR SEQ ID NO: 31:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 31:

| | |
|---|---:|
| GATCAATAAC CGCATCGTTG TAGAAGTTCC CCTGCAATTT CANNNNATCC | 50 |

| | |
|---|---|
| AGATAGTTGT TCTGGCTCAG GCCGACGGAA GAGAAGCCAC GGATAATCAC | 100 |
| GAAGTCATAG GTATTGGAAG CGCCGCGCTG CTTACCGTTA CACCCGCGTG | 150 |
| TAACCCAACG CTTCTTTACT GACTGGAATT GATGCATCTG CATCTCTTCG | 200 |
| TTAGTGACCA CCGAAACCGA CTGTGCGTTT TTCGATAGTA TCAGTTTGTG | 250 |
| TGCG | 254 |

(2) INFORMATION FOR SEQ ID NO: 32:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 32:

| | |
|---|---|
| GATCTTGTTG GCTCGCCTCT CCCCTCGGAC AACACGGTAT AAAACGCGGT | 50 |
| GATAGAGCCA CCGCCGTGGA TGCCATTACC GGCACGCTCG ACCAGCGCCG | 100 |
| GCAGCTTTGC GAACACCGAG GGCGGATAAC CTTTGGTGGC TGGCGGTCGC | 150 |
| GATTGCCAGC GCATTAGTGC ATTGAT | 176 |

(2) INFORMATION FOR SEQ ID NO: 33:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 33:

| | |
|---|---|
| GATCGTGATA TTCAATGCAC GCCTGCAGCG TGTTTTCGAT AAGCGTGGCG | 50 |
| ACCGTCATCG GGCCGACGCC GCCCGGTACT GGCGTGATGT ATGACGCGCG | 100 |
| CGCCCGGGCT TCGTCAAACA CGACGACGCC AACGACCTTG CCATTTTCCA | 150 |
| GACGGTTAAT ACCGACATCA ATCACAATTG CGCCTTCTTT AATCCATTCG | 200 |
| CCGGGAATAA AGCCCGGTTT ACCTACGGCG ACAATGAGCA AATCAGCATG | 250 |
| CTCGACATGG TGACGCAGAT CTTTGGTAAA GCGTGCGTAA CGGTAGTCGT | 300 |
| ACAGCCAGCC AGCAACAGTC ATGCTCATTG GGCTCAAC | 338 |

(2) INFORMATION FOR SEQ ID NO: 34:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
              (A) ORGANISM: DNA (other)

(xi) SEQUENCE DESCRIPTION: SEQ ID NO: 34:

GATCTTGCAG CGCGCCGTGC CAGGCATAGC GCACCTGCTC ATTAAAGACG            50

TTCGTTTTAC GTGAGTTCGG TTTCGGCGTC GGCTTCTGGC GTGCTGGCGC           100

GTTGCCGCCG CCTGTTCCGC GCGAGACTTA CGCAGTCGAT CCAGCCGTGC           150

GCGAACTGCC TGATTTGGTT AATCGCGTGG GCCTATTCAT TGGCCAGGCC           200

ACCATGCAGA TGTCCATCGT CAGGACGAGC TGCCTATAGG AACGACGGGA           250

CATAAGTCCA ATATGTGCGA GCGTCAGTAC CGTACCCTAA GTAAACTCTT           300

CAACAGAAGT AAATGCCTT                                             319

(2) INFORMATION FOR SEQ ID NO: 35:

(i) SEQUENCE CHARACTERISTICS:
              (A) LENGTH: 418 base pairs
              (B) TYPE: nucleic acid
              (C) STRANDEDNESS: single
              (D) TOPOLOGY: linear (iii) HYPOTHETICAL: NO (iv) ANTI-SENSE: YES (vi) ORIGINAL SOURCE:
              (A) ORGANISM: DNA (other)

(xi) SEQUENCE DESCRIPTION: SEQ ID NO: 35:

GATCGATTTG CGCTGGCAGG TTGCTGCCGG TATTGACCTC TTTGTACATA            50

TTCAGCGGCG CGTTCTGCGA GTAGCGCAGG TTATCTTCGA TATAGGTATT           100

AAACACGCCT TTGGAGAGCG CGGCTTCATC ACCGCCGCCC GTCCAGACGC           150

GTTGGCCTTT TTTACCCATG ATAATCGCCG TGCCGGTATC CTGGCAGGTC           200

GGCAGAATGC TTTGGGCGAT CTGCAGGTGG CACTTTTCGG GGAAATGTGC           250

GCGGAACCCC TATTTGTTTA TTTTTCTAAA TACATTCAAA TATGTATACG           300

CTCATGAGAC AATAACCCTG ATAAATGCTT CAATAATATT GAAAAGGAAG           350

AGTATGAGTA TCACATTCGG GCTATCTTTG GATTCTCGTT GACACAGAAC           400

GAGGAAGAAG CGAGACAT                                              418

(2) INFORMATION FOR SEQ ID NO: 36:

(i) SEQUENCE CHARACTERISTICS:
              (A) LENGTH: 350 base pairs
              (B) TYPE: nucleic acid
              (C) STRANDEDNESS: single
              (D) TOPOLOGY: linear (iii) HYPOTHETICAL: NO (iv) ANTI-SENSE: YES (vi) ORIGINAL SOURCE:
              (A) ORGANISM: DNA (other)

(xi) SEQUENCE DESCRIPTION: SEQ ID NO: 36:

GATCAAGAGT CAGGGGTAAT TTTACCTTTT GCATAGGGCG CGCATATTAA            50

CTTCGTAACG TCATATAGTC AAAGAAAAAG GCAGCCTGCG GTTGCCTTTT           100

```
GCCAATAATT CGCACACATT GCGGGTTACA GACTTATTTT CGCTCAAGAC          150

GAGTCAGTAT GACAGGCTTG AAGACCGAAG AGCTATGTTT AAGATGGCTC          200

TCATCATTAC GCTATATCTG AGGGAAAAAA TATGCCCCGT CTCATCCTTG          250

CGTCTACCTC TCCCTGGGCG TCGCGCGCTG CTGGAAAAGC TGACGATGCC          300

TTCCGATGCG CGCGCGATGT GATGAACCCA TGCCGGGCAC GCGCTCAGTG          350

(2) INFORMATION FOR SEQ ID NO: 37:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 37:

TGCGACAACA CACCCGCCAA AGCCGCCGCC GGTCATGCGC ACGGCGCCTC          50

GATCGCCGAT GGTCGCTTTG ACGATGTCTA CCAGCGTGTC TATCTGCGGG          100

ACGGTAATTT CGAAATCATC GCGCATTGAG GCATGGGACT CCGCCATCAG          150

TTGGCCCATA CTTCGAAATC ACCTTTCTCC AGCAGGCTTG CCGCTTCAAC          200

GGCGGGCATT TTCGGTCAAT ACATGGCGAA CCGTTTTCGG ATACCGGGAC          250

AGTTCCGTGG CAACGGCATT                                          270

(2) INFORMATION FOR SEQ ID NO: 38:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 38:

GATCCAGTGC TTTCGCCGCG TCATCCACAA TGACGTCAAA GCCAAAGGTT          50

TCGGCGCGAG TACGCACGAC GTCCAGAGTT TGCGGATGGA CATCAGAGGC          100

GACAAAGAAC CGGTTGGCAT TTTTCAGTTT GCTGACGGCT TTGCCATCGC          150

CATCGCTTCA GCGGCGGCGT CGCTTCATCC AGCAGCGAGG CGAACGATGT          200

CCAGCCCTGT AGTACAGCGT ACTGTTGAGT TACAGACTCA AACTAAATCG          250

TATAGATTTA GCCTACACTG ATTTACATTA                               280

(2) INFORMATION FOR SEQ ID NO: 39:

(i) SEQUENCE CHARACTERISTICS:
        (A) LENGTH: 275 base pairs
        (B) TYPE: nucleic acid
        (C) STRANDEDNESS: single
        (D) TOPOLOGY: linear
```

(iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 39:

| | |
|---|---|
| GATCATCGCC TTCAAATTGA CCTGCTTGAG ATCGAAAATG AGCTGCGCTA | 50 |
| AGTCCTCGAT AGAGTAGATA GCGTGGTGCG GTGGCGGGGA GATCAGCGTC | 100 |
| ACGCCCGGCA CTGAATACGC GAGTTTAGCG ATATACGGAG TGACTTTATC | 150 |
| CCCCGGCAAC TGACCGCCTT CGCCGTTCGC CTCACTTTAA TCTGAATCAC | 200 |
| ATCGGCATGA CAGTAGGTCG GTCACAAGCG CGACGACTCT ATCGCAATAT | 250 |
| GTCAATCCGG TCCTACATAT CATTT | 275 |

(2) INFORMATION FOR SEQ ID NO: 40:

(i) SEQUENCE CHARACTERISTICS:
      (A) LENGTH: 333 base pairs
      (B) TYPE: nucleic acid
      (C) STRANDEDNESS: single
      (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 40:

| | |
|---|---|
| GATCTTTCGA CTCGATGTTG GCGACGAAGA TAAAGTTCGG CAGCAGCTTG | 50 |
| CCCGCGTTGT CATAAACCGG GAAATACTTC TGGTCGCCCT TCATGGTGTA | 100 |
| CACCAGCGCT TCGGCAGGCA CGGCGAGGAA TTTCTCTTCG AATTTCGCCG | 150 |
| TCAATACCAC CGGCCATTCC ACCAGCGAAG CTACTTCTTC CAGCAGGCTT | 200 |
| TCGCTCAGGT CGGCATTACC GCCAATATTA CGTGCTGCTC TCAGCGTCCG | 250 |
| TTTGATTTGG CTTAGGCTCG TAGTCGCATG ACTTACGGAC TCAGAGAATT | 300 |
| GCGGTACTGT CAGATGTGAG GACCGTACAT AAG | 333 |

(2) INFORMATION FOR SEQ ID NO: 41:

(i) SEQUENCE CHARACTERISTICS:
      (A) LENGTH: 233 base pairs
      (B) TYPE: nucleic acid
      (C) STRANDEDNESS: single
      (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 41:

| | |
|---|---|
| GATCGGGCAT CGGCACGACA CCGGTATTCG GTTCGATAGT GCAGAACGGA | 50 |
| AAGTTTGCCG CTTCAATACC GGCTTTTGTC AGCGCGTTGA ACAGGGTGGA | 100 |
| TTTCCCGACG TTGGGCAGAC CGACGATACC GCATTTGAAT CCCATGATTT | 150 |
| AACTCACCTT AATATCTTAA TAATCAACCT GTTATAGAAA ACAGATTGCA | 200 |

GAATGGAATA CTCGCTATTA TCACGCGCGC AAA                                        233

(2) INFORMATION FOR SEQ ID NO: 42:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 42:

GATCAAGCGT GTCCGGCGAA AACGTTACGC GTTCTCGCAG CGATACAGGT                       50

GCCGTTTTAT GGTTAATACC GAGCGCTAAA AGGGTCATGT CTGCGGGAGT                      100

AGTACCAGCG TTGATATGGT TAGTCTGCTT GCATCATACA GGATGCGCGT                      150

GGTCAATAAA AGAGAGAGCC CCCTTTTGGA GTAATTGGCA GCGCTCGCTA                      200

ATTTGATGAT TTAAGACACT TGAAAGTAGA CGATGTCACC AGGCGCCTAC                      250

ATTAAAGGCT ATACTGTACG ATAGCAAAAT TTCCGATCCG CCACTTTCAC                      300

TC                                                                         302

(2) INFORMATION FOR SEQ ID NO: 43:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 43:

GATCTACTTT CGGGATGGCA GCGTATCTGC CGCAATACAC CCTGATGGAT                       50

GTTATGCCTG GATCTGATTA CTCTTCTTTG GGCGAAGTTT TCGACCCGGC                      100

TCTTTAACTT CTGCCCGGGT CTGAAGGTCA CCACGCGCCG TGCTGTAATA                      150

GGAATATCTT CACCCGTTTT CGGTTACGCC CCGGACGTTG ATTTTTATCA                      200

CGCAGATCGA AGTTACCAAA ACCAGAGAGT TCACCTGCTC ACGTTTCAGA                      250

GCACGACGAT CT                                                              262

(2) INFORMATION FOR SEQ ID NO: 44:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 44:

| | |
|---|---|
| GATCAGGTCC ATATTTGTCT TTGCCTTTCT ACCCGACACG TTTCGGGTGT | 50 |
| GCGATTCGGA TTAGTCCGCC AGAAATAGCG GGCCCATTGG CGGTTTTGGA | 100 |
| AGGTCAAAAA GGTCAGGGTA ATCCACCGCA ACCAAATATA GCCCTTCCGC | 150 |
| CTT | 153 |

(2) INFORMATION FOR SEQ ID NO: 45:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 45:

| | |
|---|---|
| GGCGCGTTGG CAGATTTTGC CAGACGACGG GCGATTTCGG TTTTACCGAC | 50 |
| GCCGGTCGGC CAATCATCAG AATATTTTTC GGCGTTACTT CGTGGCGCNN | 100 |
| CTTCATCAAG CTGCATACAC GCACGTTACN ATCNNGACGG AACCTTTGTA | 150 |
| TCTGCGATAA TNNTTGTAG | 169 |

(2) INFORMATION FOR SEQ ID NO: 46:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 46:

| | |
|---|---|
| GATCGCTGTA GATTTTACAA GTCTTCTTCA GCGATACACG TCTGCACAGC | 50 |
| AGGCCGAAAC CGGTGTTGAT GCCGTAGGAG TACGCCTTCA GGCAACGATA | 100 |
| TCATTGACAA CGCGACGTGG CGTTAATACG TCAATGGCAT GGCCTTCCAG | 150 |
| CGAAAGCTGT ACGATGAGAT ATGACATGAG AGAGACTTAA CTGCCCCAGA | 200 |
| GTATATATTG TGTTCATATC AGCCTTTCCT CAACAACCAT CGTAAATTCA | 250 |
| GACTTACTCA CACACATTCA CGTAGATCAT TC | 282 |

(2) INFORMATION FOR SEQ ID NO: 47:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 47:

```
GATCGCGGGT CAGTGTACGC ACCGCTTCCG GCGTATTTTT CCCGCTATTA          50
AAATAGAGCT TGTCGCCAAC AATCAGGTTA TCGAGATTAA TGACCAGCAG         100
CGTATTTTTC TTCTCAGCGT CACTCATCGT TTGAGTAAAT TTGGGGGCCT         150
AGCTTTCCCT CTTCTTCCCC GCTGGTGGCG ATAAAACGAA TCCCGTAATG         200
GGTCGGTATA TCTTTCAGAC GGCGCAGTTC CAGCATAAGC CCTAATCCCG         250
CGGCATTA                                                       258
```

(2) INFORMATION FOR SEQ ID NO: 48:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 48:

```
GATCGCGACA TGCGCAACAT CTACCAGTTT ACTTAACTGA CTAAACAGTA          50
AGTCGACCGA CCGGGGACTG GCAACGGTCA ATTCAATATT TATATTCTGC         100
GCATCGGTCG CGGCTTCCAT ATTCAATGGA GCACACCTGA AAACCACGAT         150
GGCGCACCAC GCGTAAAACA CGTTCTAAGG TTTCTGGATT ATAGCGTGCC         200
GATACATTGA CCTGATGTTG CATCATGATA TTTCACGATT TCAGAGTCAT         250
GGCGCAGGCG CACACGCAGA CATTTGAAGT CTCGATGAGA CGAGAGACGC         300
CTCAGTCACT GTCGA                                               315
```

(2) INFORMATION FOR SEQ ID NO: 49:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 49:

```
GATCCAACGT CTGGCGTAAT GCCAGCATGT CGTACTGGGT GTTGTTGCCC          50
AGCTCCGCAC GTGGGTCGCC TTTCGCCACC ACGTTGAACG CCAGACCATC         100
TTTAATTTGC GGCGTCGGCC AGCATGGTAA AGCGGTTGCT GAGTACACGC         150
GCTTCACGGA ATACCGTGGT GGCTTGAGCA CCGCTCACCT GCTTGAGTCG         200
GCTGTTCAAC TCGGCGTAGT CCCCACATTA AGGCTGGTTG TACACGTCGT         250
TGTTGGTGTA ACCGCGGT                                            268
```

(2) INFORMATION FOR SEQ ID NO: 50:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 50:

```
GATCTAAAAT TCAAATACAG GAACAGGGAG TTCTGGTGCA GAGGGTACTA            50

TGTCGATACG GTGGGTAAGA ACACGGCGAA GATGCAGGAC TACATAAAGC           100

ACCAGCTTGA AGAGGATAAA ATGGGTGAGC AATTATCGAT CCCGTATCCG           150

GGCAGCCCGT TTACGGCGTA AGTAACGAAG TTTGATCGAA ATGTCAGATC           200

GTATGCGCTG TTAGGCGGCT GGTAGAGAGC CTTATACCAT CTGAAAACTC           250

CGTATCCGAG ATATTATAGA CTATTGGCAA CCTGAATCTC TCGATT               296
```

(2) INFORMATION FOR SEQ ID NO: 51:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 51:

```
GTACACAGAC GCCTTTCAGA TTGGCGATGA CGCATCCATT GAGAACACCC            50

CATCGGTGGC GATCAGGACA TGACGCGCGC CGGCCTCACG CGCCTCTTTC           100

AGCCGCGCTT CCAGCTCTGC CATATCGTTG TTGGCATACG CTTCGCTTTA           150

CACAAACGCA CGCGTCAATG ATAGACTGGT TCAGCGCGTC GGAATATAGC           200

GTTCGCGCAG CAA                                                   213
```

(2) INFORMATION FOR SEQ ID NO: 52:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 52:

```
GATCGAAACT CGCCACGTTA ATCACCGTCG CCACCACCGG CGGCCAGCGT            50
```

| | |
|---|---|
| CCGTAAAGCA GCGCAATCAC CACTACGGCC CAGGCAAATC GATGCATTAC | 100 |
| CAGATTGGCG GCG | 113 |

(2) INFORMATION FOR SEQ ID NO: 53:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 53:

| | |
|---|---|
| GATCTTCCGG GTTAAATTGC AACAATGCTT CGCTAACGCG CAGCCAGCTC | 50 |
| CATTTGCGGT TCCTCCATCA GCGAGGATTT CAGCGTATCC AGTAGCTTAC | 100 |
| GAATCACTTC GGCGTTATCC GCTTCGTCCA AATCTTCATT AAACAACTCG | 150 |
| GCGACCGGAC TAATATTGCC TTTTAACCAG ACTTCCAGAG TATGTTCATC | 200 |
| AAGCGTTTTC ACCGTTCGAA CGGTTAATCA GCCACATTTC CCCTTTCCAG | 250 |
| CGATTCAATA CGCAAATCAA CTGCGTTGGG AAGATAACCT AGGCACAACG | 300 |
| GCAAATCAAG ACGTTGCATA CATATAAATA GCGCCAC | 337 |

(2) INFORMATION FOR SEQ ID NO: 54:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 54:

| | |
|---|---|
| GATCATAAAA CTTCCGCGTG TATATGTTGG TTGGAACCGT AGAGATATAG | 50 |
| ACAGGTGGTT CTACACAGGC GTTTACCCCT ACCGTCGCAA ACATTTCTTT | 100 |
| AATCAGGCTT TCTCTTTTTT CTTCTGATGG ATGCGAGTGA TTAAACTCAT | 150 |
| ACATTAACGT TTTCCCACGA AGTCTTTTTT CCGGTAAGCC TTCGCATATA | 200 |
| TCGGTAAATA GCTTGCCTGC TCTTATCTTT CGGTCATGGC ATGTTCATCG | 250 |
| CGATCACTCC GTTATGATAT GTCTCGATAG CCTCGATCCA ATGATGCTAC | 300 |
| GCATCATCAC TCA | 313 |

(2) INFORMATION FOR SEQ ID NO: 55:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 55:

GATCGAATTC AGATTCCATT ATCGCCATCA GATATTCCAG ACGTTCAGAT         50

TAACGTCGGA CATCTCCAGT ACGGACTGTT TATCCGCCAG TTTCAGCGGC        100

ATATGCGCGG CGATGGTGTC AGCCAGACGT GCAGGGTCGT CAATGCTATT        150

GAGTGACGTC AGCACTTCCG GCGGAATTTT TTTGTTCAGC TTGATGTAGC        200

CTTCGAACTG GCTGATAGCG GTACGACCAG CACTTCTTGT TCACGCTCAT        250

CAATGGCTGG CGAATAAGGT ACTCGCTTCG CGAGAAATGT CGCGTGCAGA        300

(2) INFORMATION FOR SEQ ID NO: 56:

(i) SEQUENCE CHARACTERISTICS:
            (A) LENGTH: 423 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 56:

GATCCCACTT CTTGAACTGC TCGAAGCAAA CGCCTTCCGG CAGATCATCG         50

CGCGCCACAT ACAGCTGAAT GCGGCCGCCT ACGTCTTGCA GGGTAACAAA        100

AGAGGCTTTA CCCATAATAC GGCGCGTCAT CATACGGCCC GCGACGGACA        150

CTTCAATATT CAGCGCTTCC AGTTCTTCAG CTTCTTTCGC GTCAAACTCT        200

GCGTGCAGTT GGTCTGAGGT ACGGTCAGAC GGAAATCGTT GGAACGGATA        250

CCTGCTCACG CAGTCAGCCA GCTTTGCACG TGCCTTATTT ATTGTTAAGA        300

TCGACTACTG TACGCCTGTC TTTGTCAGAC ATGTGATCTC ATAGCCTGGC        350

TTTCAAACTT GCTCGATATG ATCAGACTAC GTCAGTACGC TGGATGCGTC        400

ACAGTACAGC TTAATCGATC AGA                                    423

(2) INFORMATION FOR SEQ ID NO: 57:

(i) SEQUENCE CHARACTERISTICS:
            (A) LENGTH: 173 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 57:

ACAGAATCTT TTTCACGACG TTCTCGTTAA TAACCGATAA GACGTGAGGA         50

GTTTAGCAGA TTTAGTGCTT GATTTCGTGG CTTGTTTACA GTCAAAGAAG        100

CCGGAGCAAA AGCCCCGGCA TCGGCAGGAA CNCTTATTTA TTAATAAAAT        150

CTTCCCCAAC TAATATCTTT TTT                                           173

(2) INFORMATION FOR SEQ ID NO: 58:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 58:

GATCCTCCGT GGCATAAGAA ATGCCGCCAA GAATCGTGAG TAAGATGTTG               50

AAAGGATTGC GATAACATAC CCACAGATGC ACCCACCACG GCGAGGGTTT              100

CTGTGCCGGA ACGGTTTTCG CCATGCTTTT CACGCGCNNT CACCTCGGCA              150

GCGTTTAATC CTCGGTGCGT ATCAAAACCT GCAGAGAGTC TCTGCTCATG              200

CGCGACTTCA GACAGTAG                                                 218

(2) INFORMATION FOR SEQ ID NO: 59:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 59:

GATCGAGAAA AGTGAGCATC CCTTCGATGG TAAGTTCGGT CTCATCCTCC               50

ACACTTAATG TCGGATTGTT CCCGGAACCA TCCAGCTTAC GTGTCGCTAT              100

CAGCAATACT CGGAATCCCT GCGCATTGTA ATCTTCGGTT TTCGCCAGCA              150

GTAGCTCGCG GCGTGTTTCC GTCAAGCGCC ACCACACGAT CGCCTTCGCG              200

AAGATGGGTG GCTACCATCA TCATCTCTTC AACGGCGCTT TGCAGATCAG              250

GCATCTGTCT CATGCTGCGC ATCTCACAGA CGATACCGCG ACGTACAAGT              300

CGATGCAGTC ATCGTTATGA GCCCTTGCGA TGTGCATGAC TGCAAC                  346

(2) INFORMATION FOR SEQ ID NO: 60:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 60:

```
GATCCTGACG AATGGCCACA ACGGAAGGCT CATTCAATAC GATGCCTTGT         50

CCTTTTACAT AAATGAGGGT ATTCGCGGTA CCCAGGTCAA TGGACAGGTC        100

ATTGGAAAAC ATGCCACGAA ATTTTTTCGA ACATACTAAG GGATTAATTC        150

CTTGAAAGCT GGGGCGAAAA CAAAATGCGT TTACTTTACC AACCACACGC        200

AGCAGCGACA AGCGCGAAAA TCATCTGCTA CGTGAATTAG TGCGTCGTTC        250

TTTGTACAAT CTCGCTGAGT CAGCTGAAAA TCACGCGATC TGCTCGTGAC        300

TTGAAGATCT CGATTCTCGA CAT                                    323

(2) INFORMATION FOR SEQ ID NO: 61:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 61:

GATCGCGCGT GGTTTGCAGC GTCGGTTCCA CCACCAGTTG GTTAATGCGG         50

TTCGTTTCCA GACCACCAAT CTCTTTCATA AAATCTGGCG CTTTGATACC       100

CGCCGCCCAC ACCATCCAGA TCGGCCTGAA TATATTCACC TTCTTTCGTA       150

TGCAGACCGC CTTCGGCGGC GCTGGTGACC ATAGTTTGCG TCAGCGCGAA       200

CGCCAGTTTG GTCAGTTCAT TATGCGCGGC GTGGAGATAC GCGCGCACGA       250

GGCAGATACG CGCAGTCACA CGAGTC                                 276

(2) INFORMATION FOR SEQ ID NO: 62:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 62:

GGGCCAGAGG TATGACTCCA CCAGACCGTC AAAGACGGCG TTGCGTCGTG         50

CTCAGCATAG AAGCCGCGCG CCTGCTCAAC GGTCAGGTGC AGCATTATTA       100

GTGCCCAACA ATTTTGAACC CTGCAGCTTC AAACGCGCGA AAGATCGTCC       150

AATACGTTCT CCGACC                                            166

(2) INFORMATION FOR SEQ ID NO: 63:

(i) SEQUENCE CHARACTERISTICS:
        (A) LENGTH: 425 base pairs
        (B) TYPE: nucleic acid
        (C) STRANDEDNESS: single
        (D) TOPOLOGY: linear
```

(iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 63:

| | |
|---|---|
| GATCTTTAGC CGGGCAGACC TCTACGCATA AATTACAGCC AGTACAGTCT | 50 |
| TCCGGCGCGA CCTGCAGCAC ATATTTCTGG CCGCGCATAT CGCGGACTTC | 100 |
| ACGTCCAGCG AATGCAGACT GGCTGGCGCG TTCTCCATCG CCTGCGGGA | 150 |
| AACGACTTTC GCACGAATTG CCGAGTGAGG GCAGGCAGCG ACGCAGTGAT | 200 |
| TACATTGTGT ACACAGTTCC TCTTTCCAGA CAGGAATCTC TTCGGCGATA | 250 |
| TTGCGTTTTT CCCAGCGGTG GTGCCCATTG GCCATGTTCC GTCGGCGGCA | 300 |
| GGGCGGAAAC AGGCAGTGCG TGCCGAGGCC CGCCAACATG GGCCGTAACG | 350 |
| TTTCAGAAAT CGCAGTGAGA CGGCGGCATC CCATAGGATT ACGCTGAGAT | 400 |
| CCAGATCTCC AACATCTCAT CTAAA | 425 |

(2) INFORMATION FOR SEQ ID NO: 64:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 64:

| | |
|---|---|
| GATCTACCGG GTGAGCGTAT AACCNATCTT AATCCCTCCC GGTTAGGTTG | 50 |
| ACATTAGGAT CCTGTTCCTT TCGGGTTATA CTGCGCTGAA CGCGGGTCCA | 100 |
| GTCCAACGTG AATACGGCAG ATAAACCAGA CCAGCCAGTA ACACAAAAAT | 150 |
| AAAAATTCGC AGCTTCCACA AAGCCAACCC AGCCGCTTTC GCGATAGAAG | 200 |
| TCGACCATGC GAACAGATAC AGCGCTTCAA CGTCGAAGAT AACGAAGAAC | 250 |
| ATGGCTACCA GGTAAAATTC GGAGACAGGC GTAAGGCGCG CCGGTGCGAC | 300 |
| CATTCATCTC CATCCTTTGA ATTACGGACA GCA | 333 |

(2) INFORMATION FOR SEQ ID NO: 65:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 65:

| | |
|---|---|
| TTATCAATAC CCGCATTTTT ACTGAAACCG GGCGTGATGT TTTTGGCTTT | 50 |

```
GACATTGCGA ATGACGAAAT GTTTGCCATT TTCTACGTGC ACAAGCTGTC         100

GGCAATCAGA TCCGGTAATA TTGGCCACCA CAAAGTTTTT TACTGCCTGG         150

TCTTCAGGAT AACTGTTGTC ATAGGTGCTA CCCGCCAGCC CGATCCCCCA         200

GTTGATTTTG CCATTGGTAC AATTAATGCG TTCGATGACA TGATCGGAAA         250

TCAGGATGTC GCGGTCGTGA TCGCGACATT CCACTCATGG CGTCCCCTGT         300

AATCGCTAAG CGCTATCGTA ATCGCGCGCA TCCATTGTTA TGAATCCTGC         350

GAGATGGCGA GTGCGTGGTA CGGA                                    374
```

(2) INFORMATION FOR SEQ ID NO: 66:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 66:

```
GATCCTGAAA TGCCCATCCA CGCCAGCTTG GGTATAGAGC AATCTGGCAG          50

TATAAGATTT GGGATGTATT TTGGCCGCAG CCGCAAAAAA CGCGTCTGGG         100

CGATTCGGAC AACCAGAAAG AGGCGCTCTG TAATGCGGTC TGGGCTATGG         150

GACGAATTTC CAGATAATAG TAAACGATTA ACCCTACACG AAAGCGTAAC         200

AGAAGCGCAT AACGCCTTTA AAAACCACAG TAACACGCCT GCATTATAGT         250

TTTTCTTACT CAACATCTAT CGTTCGCATA CCGGATGTAA TAGGCT             296
```

(2) INFORMATION FOR SEQ ID NO: 67:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 67:

```
GATCGGCAAA GGTACCGGTG GTGCCGTCGT AGTTTTCTCC GCGCCGGGCG          50

TTAACGTTCT GGCCCAGCAG GTTGACCTCA CGCGCGCCCT GGCCGCTAAC         100

TGGGCGATTT CGAACCGGAT CATCGTCTCA GGGCCGGCTG ACTTCTTCGC         150

CGCGGGTATA CGGCGCACAC GTAAGTAC                                 178
```

(2) INFORMATION FOR SEQ ID NO: 68:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 68:

| | |
|---|---|
| GATCAAAAGT TTTCTGCGCC GCCTCGTTCA TCAGTTTATA AGGATTGCTC | 50 |
| TGATCCGCTG CCGTTGCTGC GCTTAATGGC GCAATGACCA GCAGGGCCAC | 100 |
| CATCATCAGT CGTTTAAACA TGCCTCAATT CTCCTGAGAT TATTTCGTTT | 150 |
| CGCCCGCGGG CTTGTGGCTT CAGTATGACC TTCCGTTGCG GGCTGGCGCA | 200 |
| TCGCAGAATT CTTATTGTCG TCGCCTTCGT GTTATAAGGA ACTGCCAATC | 250 |
| ATATCTCCAG CACATGCAGA CGGTCTGATC GTACTGCACG CTAGATAGAC | 300 |
| GTCAGACTCA ACACAACGAG CTAGCGA | 327 |

(2) INFORMATION FOR SEQ ID NO: 69:

(i) SEQUENCE CHARACTERISTICS:
            (A) LENGTH: 375 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 69:

| | |
|---|---|
| GATCCAGCAG GTTGATTTTT GTTTCTTTGT TAGGAACTAC CGGGGTACTG | 50 |
| CTTTCAGGTG TGACAATTTG TTCAGACATA TGCTATTCCG GCCACGTTAT | 100 |
| TACACGTTAT GGCCCCTGGA GGTTGAAAAA AGAAACGCCC CGGTAAGCTT | 150 |
| ACTGCTCGTC CGGGGGCGCT GCATTGTACA AATTCTGGCG TAAGGAGTCC | 200 |
| ACGTCTGCAC GCGCATTAGC AAAAATAATA TTTGAACCGA TAATTTATCG | 250 |
| CCAACGCATT TACAGCGTGA AGACGAAGG AGATTAACGG GTGGGGCCA | 300 |
| CTCGCTTCAC GAGAAAAGCG ATTCGGCTGG CGATTCAGCG AATCGACGTG | 350 |
| TGCGTTCAGT ACTATCACGT AGTCG | 375 |

(2) INFORMATION FOR SEQ ID NO: 70:

(i) SEQUENCE CHARACTERISTICS:
            (A) LENGTH: 298 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 70:

| | |
|---|---|
| GATCGGACGG CGCCTTATCT TCTTCAATAT CGCGCGTACC GTAGAAACCT | 50 |
| TCAGGCAAGG TCGCTCAGCG ACAGCCTGCT GGCTGAGTCC GAGTTGTTCA | 100 |

CGGGCATTGC GCAGACGAAC GCCGGTGGTT TGTGCTTCAT TTTGGTCGTG     150

CGTTGCTTCA GTATTCATTC GCTACAGCTA ACGGTACGTG TAAATTAGGA     200

TTCAGGCGCC GACGAGCGTA ATGCCGCCAC GCGCAAACAT CGTAGTACTT     250

AGTCAGACAG TATACGTTAG CGCGCGATAC AGCTAGAACG CTAACTGT      298

(2) INFORMATION FOR SEQ ID NO: 71:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 71:

GATCTCACCT TTTTTTAGCT GCGGCATCGC TTCCAGAGTG GCGACCGCCG      50

GGTACGGGCA AGGTTCGCCA ACCATATCCA GACGGTAATC AGGGACGATA     100

TTTTTCATAC AGATTCCTTA GCAGGCGTCA GCCCGCACGG CGAAAAAACG     150

TTTTTTTCCC AGCCGATGAT TAACATTCAG TGGTAAATAA CAACAAAGTA     200

GGTGACACGC AGACCGTAGG ACCAAGTATT CAGC                     234

(2) INFORMATION FOR SEQ ID NO: 72:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 72:

AGCTCTGATT TCGGTAGCGA TACGTCATCC ATCAGATTCG CCAGCGGATG      50

GACAAACGGC AGGATGACCA GGCTGCCGAT CAATTTGAAC AATAGGCTGC     100

CGAGCGCTAC CGGACGCGCG GCAGCATTGG CGGCGCTGTT ATTGAGCATC     150

GCCAGCAGCC CCGATCCCCA GATTGGCGCC GATGACCAGG CACAACGCCA     200

CCGGGAACGA TATAATCCCG CCGCCGTCAG GTCGCCGTCA GCAACACCGC     250

CGCCACTGGG AATAACTGAT AATAGCGAAC ATCCGGCCAA TAGCGCATCA     300

GCATATGTGC CTGAGAG                                        317

(2) INFORMATION FOR SEQ ID NO: 73:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 73:

| | |
|---|---|
| GATCGAGGGC ACAGGAGAAA CGGGCATTTT CGCCGCAATT AGTTGACCTG | 50 |
| ATCTCCCAAG ACCAAATTTT CCTCAGCCGG AATATACCAG AACTGGTCGC | 100 |
| GATATCCGCA AGATCGCGCT TCACGGCGTC GCTT | 134 |

(2) INFORMATION FOR SEQ ID NO: 74:

(i) SEQUENCE CHARACTERISTICS:
       (A) LENGTH: 387 base pairs
       (B) TYPE: nucleic acid
       (C) STRANDEDNESS: single
       (D) TOPOLOGY: linear (iii) HYPOTHETICAL: NO (iv) ANTI-SENSE: YES (vi) ORIGINAL SOURCE:
       (A) ORGANISM: DNA (other)

(xi) SEQUENCE DESCRIPTION: SEQ ID NO: 74:

| | |
|---|---|
| GATCGTAATG TGCGGCCAGT TCAAAACCGA AGCGGCTATA TAACGCCGGA | 50 |
| TCGCCCAGCG TCACGACCGC CGCGTAGCGA ACTCGTTGAG CGAATCCAGC | 100 |
| CCTTCATACA CTAACTGGCG CGCCAGCCCT TGCCCGCGAT ACTTTTCATC | 150 |
| GACCGCCAGC GCCATGCCGA CCCACTGTAA ATCTTCGCCT GCACATCAAC | 200 |
| CGGGCTAAAG GCGACATAGC CACACTGACC TTCATCATCG TGCACAGTCG | 250 |
| AGGTAGAAAA CATCTCACGA AATCGTGAAC AGCTTGCTTC GCATGTTTCG | 300 |
| ATGACGGCGT ACACGCGATC AATACAGCGC ATCATAGATT TATGATAGAT | 350 |
| GTATAGAGTG TGTCTAGAGT TTATCGCTAC ATCGAGT | 387 |

(2) INFORMATION FOR SEQ ID NO: 75:

(i) SEQUENCE CHARACTERISTICS:
       (A) LENGTH: 189 base pairs
       (B) TYPE: nucleic acid
       (C) STRANDEDNESS: single
       (D) TOPOLOGY: linear (iii) HYPOTHETICAL: NO (iv) ANTI-SENSE: YES (vi) ORIGINAL SOURCE:
       (A) ORGANISM: DNA (other)

(xi) SEQUENCE DESCRIPTION: SEQ ID NO: 75:

| | |
|---|---|
| GATCGTAAGG ATTGACGATT AACGCCGACG TCAGTTCATT CGCCGCTCCG | 50 |
| CAAACTGTGA CAGTACCAGT ACTCCAGGGT TAGCGGGGTC CTGCGCGGCG | 100 |
| ACAAACTGTT TGTGGACCAG GTTCATCCCG TCACTCAACG GGTTACTAGC | 150 |
| CCGACGTCTG AATAACGGAA TATACTTCAT TAACAGTTT | 189 |

(2) INFORMATION FOR SEQ ID NO: 76:

(i) SEQUENCE CHARACTERISTICS:
       (A) LENGTH: 217 base pairs (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 76:

```
GATCACGAAT ATTCATTATT CATCCTCCGT CGCCACGATA GTTCATGGCG          50

ATAGGTAGCA TAGCAATGAA CTGATTATCC CTATCAACCT TTCTGATTAA         100

TAATACATCA CAGAAGCGGA GCGGTTTCTC GTTTAACCCT TGAAGACACC         150

GCCCGTTCAG AGGGTATCTC TCGAACCCGA AATACTAAGC CAACCGTGAC         200

TTTGCGACTT GGTTTTT                                              217
```

(2) INFORMATION FOR SEQ ID NO: 77:

(i) SEQUENCE CHARACTERISTICS:
            (A) LENGTH: 275 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 77:

```
GATCCCTTCT TTTGCTGATG CAGTAGCGGA CCAGGCTACC ACAAGGGGAA          50

TGATGCAGAC TGCGAAAAAG TTTTTCATTT CAGAACCTGC CTTAATATTG         100

GGCTAAAAGA CAAGTTTCAC GGTATAGGGT ATGATATAAC GATTCAATAA         150

ACGAAGCCCA AAAACGGTC TATTGTAACG CTGGGTTTCT GTAAGCGGGT          200

AAAATGAGAT GAGATTTAAT AACATCAGAT ATCTCGGATG AATCACTCTC         250

GAATCCGCAG CGTCCATCTA CGTAT                                    275
```

(2) INFORMATION FOR SEQ ID NO: 78:

(i) SEQUENCE CHARACTERISTICS:
            (A) LENGTH: 101 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 78:

```
GATCTTCATA CAGGCCCAGA TAGCCGTCAT AAATGCCCAT GACTTCCAGC          50

CCTTACGTCA ACGCTGCAAC ACAACACCGC GGATTTTTGA TTCATTCTCT         100

T                                                               101
```

(2) INFORMATION FOR SEQ ID NO: 79:

(i) SEQUENCE CHARACTERISTICS:
    (A) LENGTH: 303 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 79:

| | |
|---|---|
| GATCCGCACG GATAAAAACT CGTTTCCCGG CCAGATCCAG ATCGGTCATC | 50 |
| TTAATTACAG ACATGGTGAA TCCTCTCAAT GATGCTTAAA GTTTTGTCGA | 100 |
| CGCTGACGCG TGAGCCTGAA ACCAACTGCG GCCATCGCTA ACGTGGTGTC | 150 |
| GAGCATCCTG TTAGCAAAGC CCCATTCATT ATCGCACCAG ACCTAGCGTC | 200 |
| TTGATCAGTG GGCGCACTGA CCGGGTTGGG CATCACATGG CGTGGCTGGT | 250 |
| AATTTGGACG GTGCATGTAC TCATGATGGC TTGGTTGGCC GGATTGCTTG | 300 |
| CTT | 303 |

(2) INFORMATION FOR SEQ ID NO: 80:

(i) SEQUENCE CHARACTERISTICS:
    (A) LENGTH: 257 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 80:

| | |
|---|---|
| GATCGTGACC CGGATAACGC TCATCATCTT TGGTCAGTTC CGGCGGCGTC | 50 |
| ACGGCAAAAC CGCGGCGCCA CTGTTTAACC TGCTCGTCAC CATATTTTTC | 100 |
| TGCCGTTTGC GCTTTATTCA GCCCCTGCAA CGGCCATAGT GACGTTCATT | 150 |
| GAGTTTCCAG GATTTTTTCA CCGGCAGCCA CGCTGATCCA GTTCATCCAG | 200 |
| TACGTTCACA GGCTATGGAT AGCGCGTTTC AAGTACGGAA GGTAGGCAAA | 250 |
| TCAAGCG | 257 |

(2) INFORMATION FOR SEQ ID NO: 81:

(i) SEQUENCE CHARACTERISTICS:
    (A) LENGTH: 290 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 81:

| | |
|---|---|
| GATCGAGCAG GCATTGCAGC AGCAGACTTT TGCCCTCCCC GCTGCCGCCA | 50 |

```
ACCAATGCCA CCATTTCGCC GGGCGCGATA TCAAAAGAGA CATTCTGTAA              100

TAACGGCGAC CAGCGTCTCG CGCCATACCA GCGATAACGG CGCTTTCCAG              150

CGTAACCTGT TGTAAACTCA GATACGTCAC TCCTTAGCAC AGCCGCTGAA              200

TGGCGGAAAC TGTCGAAGAG CATCACAGCG TGAATAACAT TAGGCCGGGA              250

ATAGACAGCA CAGTTCATGG CTAATAACGT ACCGTCGAGA                         290
```

(2) INFORMATION FOR SEQ ID NO: 82:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 82:

```
TGCAGATCCA CCTGGAACGG CGGGATGTTG ATCACCTGGG AGGCCAGACC               50

GCTATTACGG CGCATTAACG CGCCATTACC TCTTCGATGT GGAATGGCTT              100

CGTCACGTAG TCATCGGCCC GGAGCTGAGA ACCTCGACTT TATCCTGCCA              150

GCCTTCGCGC GCGTTAACAC CAGAACCGGC AGTGAAACAT CACTCGTGCG              200

CCCACGGGTA TTAAGGAAAG GCCGTCTTCA TCC                                233
```

(2) INFORMATION FOR SEQ ID NO: 83:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 83:

```
GATCTCATCA AAACGGTTGA GTACCAGCGC CAGGGTCATA CCCGCCTGGT               50

TCAACGCCGT CAGGTGCGCC AGTTGTTGAC GGGCGGTCAC GTCAAGCCCG              100

TCGAACGGTT CATCAAGGAT CAATAACTCT GGCTCAGACA TCAGCACCTG              150

ACACAGCAGC GCTTTTCGCG TCTCGCCGGT AGAAAGGTAT TTAAAACGCC              200

TGTCGAGTAA AGCGGAAATC CGCGAACTGC TGCGCCAGTA TCGCACAGCG              250

CAGGATGGTG ACATATCCTG AATATTCGCG TAGT                               284
```

(2) INFORMATION FOR SEQ ID NO: 84:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 84:

| | |
|---|---|
| GTTGCGATTA TCCCGCAGCG CCTGCTCGAA CAATTGGATT TGCTCAGTGC | 50 |
| TTTCATGCCA TAACCAGAAG GTACTGATTA ACTGGAACAC CAGCAGAATA | 100 |
| AGACCAATTG TCAGCATTAA ACGCTGGCGA AGGGTCACTG CTCTTCGCTG | 150 |
| AAAACGCATC AGGCTCACTT AGCTTTCCTC AGTGGCAACC AGCATGTAGC | 200 |
| CAAACCCGCG AACCGTGCGA ATGCGACTTG CCGACTTTGT CGCGCAAATT | 250 |
| ATGTATAGCA CTTCCAGAGT GTTGGTCGAG GGTTCGTTAT CCCAGTTGTG | 300 |
| ATATCGTTAT AAAGAATTTC CGGTGCACGA CTGCCTGAGA CTAACCGTGA | 350 |
| GAGCACGTAT CTAGCTC | 367 |

(2) INFORMATION FOR SEQ ID NO: 85:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 85:

| | |
|---|---|
| GATCGTTGAT CGCCTGGATA ACAACCTGCT GCTGCTCGTG ACCGAATACC | 50 |
| ACCGCGCCCA GCATAGTGTC TTCGCTCAGC AGTTCAGCTT CGGATTCCAC | 100 |
| CATCAGCACA GCCGCTTCGG TACCGGCAAC CACCAGGGTC CAGCTTGCTT | 150 |
| CTTTCAGCTC GTCTGGGTCG GGTTCAGCAC GTACTGGTCA TTGATGTAAC | 200 |
| CTACGGCGCG CGATTGGGCC GTTGAACGGA ATGCGGACAG CGACAGCACG | 250 |
| ATGCGATCAT CGCACGATGA TCAGGTACTG CGTACGAACG ACGTCCGATA | 300 |
| ACTCGATGTA CAGCTCGGAA | 320 |

(2) INFORMATION FOR SEQ ID NO: 86:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 86:

| | |
|---|---|
| GATCAATAAA TACTTTACGA ACTTCACTGG AGATTTCCCA TTTAGTGTCA | 50 |
| TTTGGGCAGT TTATAAACAA ACGCGCGGTA GTATAAAGGC AAGCCAGACG | 100 |
| CATTGATATA CCCGTTAACG CCGACGGGTG ATAAGGAGAT CGACCGTTAT | 150 |

```
GGCTTTTAAA CCTGGCAAAT AGGATTGCAT TATTCCAGCC ATGAAGCGCT         200

GGCCATCGCG TTATTCACGC GCATCGGCTG ACACGCACTG TGCACTGCG          249
```

(2) INFORMATION FOR SEQ ID NO: 87:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 87:

```
GATCGCCTTT TGCTGCCAAC GCTGCGGGAG AAAGAGCAGA AAGAGCGAAA         50

ACAGCTGCGA CAGCCGCCAG AGTCGATTTG AGCATGAGAT TTCCTTAAAG         100

AGAGCAGAAA TAAAGCAAGT GGAATGATTT TAAAGAGCCT TCTGGGCCAG         150

GCAGCCTTTA CTATTTACGT ATATGAACAA TGTACGTTAC GACGACGCGT         200

ATCTGCATAT GATGTGACAA CATAATAATA AATGCATGAC ATACTATACT         250

ATATATTAGC TACAAGCTAT GCTCA                                    275
```

(2) INFORMATION FOR SEQ ID NO: 88:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 88:

```
GATCGCCGCG AACCAGCAGA GCCACCAGCG GAGACTTGCT GTCTTTCACC         50

GCTTTCACCA GCAGCGTTTT TACCGTTTTT TCAATTGGCA GGTTGAATTG         100

TTCCACCAGC TCCGCGATGG TTTTGGCATT TGGCGTATCG ACCAGAGTCA         150

TTTCCTGCGT CGCGCTGCGC GGCTTTGCGG GATAGCTTCT GCAGTTCAAT         200

GTTAGCCGCG TAATCAGAAA CATCAGAGAA AACGATATCG TCTTGCGCTT         250

TGGCAGCCTG GAATTCATGC TGGTTGGCGA TAGACGTATG CTGTACGGGA         300

ATCAGCCATA GTGAGATACG CTATA                                    325
```

(2) INFORMATION FOR SEQ ID NO: 89:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 89:

GATCGATACG ACGTTCAAAG GATTCAAACC GCGCCATGGC TTCATCCAGT        50

TTGCCGCTGT CAAGCTGACG ACGGACATCG CGGGAAGAAC TCGCCGCCTG       100

ATGACGCAGC ATCAGCGCCT GCGGGCGAGC GCGCGTGTTT CGCTGAGTTT       150

GTTTTCCAGC GTCGCCAATC TCTTTCTTCA TGCGCGCAGT GTCATCACAG       200

CGTGACTTCT GTTCAGCTAG CATAATCGTC                             230

(2) INFORMATION FOR SEQ ID NO: 90:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 90:

GATCCCATCG CTTTTTCAGA TATCATGCAC TTTTTGCACT CAATCTGCGG        50

CAAATCCGAC CACTTTTTGC TCAGCCAGAA TGCAGTATTT CCGTCATACA       100

TCGATTAGCT ACGACTCTAC GAACTACCTC GACCACAAGA TCACCG           146

(2) INFORMATION FOR SEQ ID NO: 91:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 91:

GATCTTTGTT AATAACAGTG AGAGAACCGT ACGAATGTAG AAGAACTCCC        50

GCCAGGCGGC AACATCTTTC ATAGTAGACC AAGCGTTAAC CCCTGCTGAT       100

GTAAAAACGC TTCTATCTCT TGCGCACCAC GGAACGGAAG GTTGCGCGCC       150

TTTAGCGCTT ACGGCAATAG CCGCGGCGGA TGGG                        184

(2) INFORMATION FOR SEQ ID NO: 92:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 92:

```
GATCAAACAC ATGAATACCG AGGCCTTTGA GTTTTTCAGT CGAGGCGTCC         50

GAGCTGGAGA CCGCGCCTTC AATCTGGCCT TTCATTGTGC CCAGCGCATC        100

AATAAAGTCT GCGGCCGTTG AGCCTGTACC AACGCCCACA ATGGTGCCGG        150

GCTGTACTAT CTGAAGTGCC GCCCATCCTA CCGCTTTTTT CAGTTCATCT        200

GCGTCATAGA TCGTTAGAAT GTGTGTGAAA TACGCCGCAT TATAGAACAT        250

GTCCGGGAAA ATCTCGGTCG TACACAGCTA CGATTCGATT GCGCGCAATT        300

TTGAGGGAAA A                                                  311
```

(2) INFORMATION FOR SEQ ID NO: 93:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 93:

```
GATCCTCGAT TAGGGAGGC GCTAATTGAA TGTGGCGAGG TGTAAGAAAG          50

CAGAAAAGCA AAGTGGGTTC TCGTTGCTCT GCATGTCGTC AAATTCAATT        100

AAACGCATAA AAAAACCCCG CCGGGCGTTT TTCTTCAACT TCCAGGCGAT        150

TACGGCGAAC GAAGTCGATG TGAGTCAGCT TCGGTTTGTA AGCGTGACCG        200

TGTACAGCCT GAGCTTTAAC TTTTACTTCT TTACCGTCAA CAACGAGGGT        250

CAGAACTTCG TGTAGAATTC AGCTTTAGCT TGCATGTTCA TCACCTGGTC        300

GTGGTCAGTT CGATAGCAAT CGGGCTTCAG AACCGCGTAG ATGATTGCCG        350

GACTGTAGCG CGCAGGCGGC AGCTCCTACA TGCTCTTACG TACTCTGCGT        400

GATAGTAACA TTAATCTCTT ATATCTGCAG ACTGCACGAG ACTCGTCG          448
```

(2) INFORMATION FOR SEQ ID NO: 94:

(i) SEQUENCE CHARACTERISTICS:
        (A) LENGTH: 359 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 94:

```
GATCATATCG ACGGTATCGG CGTAATTATT TTGCAGATGG CGTAACACAT         50

CCAGATTATC TCCGGTCAGA AAAGATTAT GGCTGTTTTT ATTTTCTGCC         100

AGAGTATTGT GTTCCACGTC AGGAACGATA ACGGTAACGG ATTTTTCACC        150
```

CGCCTGTTTT TTTGCCGTAA TCTTTGCCAA TAAAATCAAT CTGATAACCG         200

CTAGTCAGCT CAATATTACG CGCTTTCAGG CGCTCAAATC TGGCGAGATC         250

AATCCGCCTT TCGCGATCAG TTCGCCCTCT CGTTATAGCG GATCGCGGTA         300

AAAATTCCGC GGTAATCGCA GTTGTAACTC AGACAGAAGC GCGTATTCGG         350

CGCAGACGC                                                     359

(2) INFORMATION FOR SEQ ID NO: 95:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 95:

GATCCAGTTT AACCTCTGGC TGCCAAATCT TTCTGGAAAA CATGCGGTGC          50

GTTTGGCGCT TCGAAAGAAA CATCCTGGTA TAGATACGTT GGATCTGGAA         100

AGCCATTTCA GTGTTATTTT TGTTCTGACA TGTGTAAAAC CCTTTAGTGT         150

TGTTCCTTAA ATACTTGAGT AACGCCTTAA CGCAACAGCG GATCCAGTCC         200

ACCACGCGCA TCCAGCGATA CAAGTCGTCA CAAGCGCAAT GTGCTGTGCC         250

TCAATCAAAT TTGCGACGTC GTCGCACTAC GTTGATATCT TTACGTCA           298

(2) INFORMATION FOR SEQ ID NO: 96:

(i) SEQUENCE CHARACTERISTICS:
        (A) LENGTH: 217 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 96:

GATCGTAAGA GTCAGAAATA AGCAGGCGTA ATGTTGTCAT AGTGGTTTTC          50

CTTACCTTTA TTAAGCCGTC ATTTTACTCT TTTTCCTCAC GCTCTTCCTC         100

TTCCGGAACA GGCTTGCTGG CCGTTAGCAG GAAGGGCGAC TGCTGCCAGC         150

GGGTGCGTTT ACCTTGTAGC AAGGTGNNNC AGACACCACG CCTATCGCAG         200

CGAGAGTAGC AGCATCA                                            217

(2) INFORMATION FOR SEQ ID NO: 97:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
         (A) ORGANISM: DNA (other)

(xi) SEQUENCE DESCRIPTION: SEQ ID NO: 97:

GATCGAACTC TTTAAGCAGC ATCTTGGTAT GGAAAATATT TTCCTGATAC          50

ACGTTTACAT CCACCATGTC ATACAGCGAC TTCATATCTT CCGACATAAA         100

ATTCTGAATA GAATTAATCT CATGATCGAT AAAGTGCTTC ATACCGTTGA         150

CGTCGCGTGT AAAGCCGCGC ACGCGTAATC GATGGTGACG ATATCGGACT         200

CTAGCTGGTG GATCAGGTAA TTGAGCGCTT TTAGCGTGAA ATCACCCCGC         250

AGGTTGACAC TTCGATCGTC GGCGGAAAGG TGCATAGCCC GCCTTCCGAT         300

CGCTTCGATA GGTATCGACG CAGATATGCT CTATG                         335

(2) INFORMATION FOR SEQ ID NO: 98:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
         (A) ORGANISM: DNA (other)

(xi) SEQUENCE DESCRIPTION: SEQ ID NO: 98:

GATCGTCGTA GCTGCCGGCA TTGTGGTTGG GTAAATACTG GCGGCAAAAC          50

GAGACTACGC CAGCGTCTAT CTCTACCATG GTGATGGTTT CGACGTTTTT         100

ATGCCGGGTA ACTTCACGTA GCATTGCGCC GTCGCGCCGC CGATAATCAG         150

AACGCTGTTT CGCATGACCG TCCGCCACAG CGGGGACATG GGTCATCATT         200

TCATGATAAA TAAACTCGAC GCGTTCGGTC GGTCTGTACC AGCCGTCCAG         250

CGCCATCACG CGGCCAAAAG CGGCTTTTCA AAGATGATTA AATCCTGGTG         300

ATCGTTTTCA TGATACAGAA CTTGTCTACG GCAAGTCATG ACCAAACTGG         350

TC                                                             352

(2) INFORMATION FOR SEQ ID NO: 99:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
         (A) ORGANISM: DNA (other)

(xi) SEQUENCE DESCRIPTION: SEQ ID NO: 99:

GATCTGTTTC GGGAAGTGAA CTTAAGGCCT CCGCAATATC ATTTATATAA          50

ACTGACATGG CATTTTTAAA CTGCTCAGTA CTGCGTTTAC ATTTGTGGAA         100

GATAGTCTCT GAGAGCAGAG TTTCTTT                                  127

(2) INFORMATION FOR SEQ ID NO: 100:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 100:

```
GATCGGCAAC CTGCATTGCC AGTTCGCGGG TTGGCGTCAG GATCAGAATG         50

CGCGGCGGCC CCGATTTTTT ACGCGGAAAG TCGAGCAGGT GCTGCAACGC        100

CGGCAGCAGA TATGCCGCCG TTTTACCGGT GCCTGTCGGC GCAGAACCGA        150

GTACATCACG GCCATCGAGC GCAGGCGTAA TGGCGGCGCT GAATGGCGTC        200

GGGCGAGTGA AACCTTTATC CTGGAGGGCA TCCAGACAGG CTTTCGTCAG        250

ATTCAAGTTC GGAAAAAGTG TTACAGTCAT GTCTACCTCT GTGTGGGCGC        300

TGATTATAGA CTTACGCGCA TCTCATCTGT GATGATATCT CTCAG             345
```

(2) INFORMATION FOR SEQ ID NO: 101:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 101:

```
GATCCGGGAC ATTCACGTTG AGAATACGCC CGGTACGCAA CGGCTCCCGG         50

CTTAACCCTC GCAAAAGCGC ACAAGTCACG GCCGCAGCGA TACATAATGC        100

TGATAGCCGT TAAGGGAGAC CGCTAATGCC GGAAAGCCGA GATGACGACC        150

TTCATCGCGC GCACAGTACC GGAATAGATC AACATCATCG CCAGATTCGG        200

ACCGCGTTAT ACCGGAAACG ACATATCGGT GACGATTAGC TTACGCAGAT        250
```

(2) INFORMATION FOR SEQ ID NO: 102:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 102:

```
GATCCCGGCT TACGACGGTT GGCTGGATGA CGGTAAATAC TCATGGACTA         50
```

```
AGCTGCCGAC ATTCTACGGC AAAACCGTCG AAGTCGGGCC GCTGGCGAAC           100

ATGCTGTGTA AACTGGCTGC AGGTCGTGAA TCCACGCAGA CCAAGCTCAA           150

TGAAATCATT GCGCTTTATC AGAAGCTGAC CGGCAAAACG TCTTGGAAAT           200

TGGCGCAACT TCACTCTACG TGGGTCGATA CATCGGGCGT ACCGTTCACT           250

GTTGTGAACT GCAAAACATA TTGCAGGATC ATACAGCTGA TTGTAATATC           300

GGCAAGGATT ACACCAGTTT GAGACGGCAA TCG                             333
```

(2) INFORMATION FOR SEQ ID NO: 103:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 103:

```
GATCCAGCCA GACGGAACCC CACGGCGGCG GAGACGGCAG AGCGTAAGGG            50

CCGATAAACA GACGCTGCCA GGCCTGTGCA ACGACTCTTC GCTGTGGGTC           100

TTAAACATAG CCGCCACAGG GCAAGGCTCG GCATCAAGCG GCCACTGCGC           150

CTGCAGTCGT CGTTTAATAG TCGTCCTGGA CCAGAGGAGC GGTTTCGTGG           200

CTTTCCGCGA ATAATAAAAC AAGTGCCAAG AACAGTGTTA CTGCAAATCA           250

TCTCGTTGTA AAAGTGTAT TAAACATCCG TAAA                             284
```

(2) INFORMATION FOR SEQ ID NO: 104:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 104:

```
GATCAACGCA AACAATCAGA ACCTCTGCTT CATTTAGCAG CGTGTTCTCT            50

GCGTTGACAA TGCGTTGCGT GAAAACCAAA GCGGTGCCAC GCATTGACGT           100

AATTTCTGTT TGAGCTTCAA GCATATCGTC GAGCCGCGCA GGCCATAGTA           150

TTCCAGCTTC ATCTTGCGCA CCACAAAGGC TACCCGCTCC GCAGCAGCAC           200

CTGTTGCTGA AGTGATGGTG GACGTCAGCA TCTCGNNNTC TTCATAAAA            249
```

(2) INFORMATION FOR SEQ ID NO: 105:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 105:

```
GATCCCTTTA CGACCAGGCG TCCCGGCGCC GTTATAGTGC CAGCCAAAAC          50
CAAAGCCGCC GCCCGGTAAA CCAATCTGTT CCAGCATTGC GGCCAGCACG         100
ACGACCATCC ATGACCACTG TTCGCATGCT GCATACGTTG TACGACCAGC         150
CAGCGATGAT TTCGGTTCTG TCGTCGCATC TGTGGCAACG CGACTGGGTG         200
GTGTAATCAA GATCATTTCG CAGGACTTGG TGCATTGTAG AATCGAGA           248
```

(2) INFORMATION FOR SEQ ID NO: 106:

(i) SEQUENCE CHARACTERISTICS:
    (A) LENGTH: 175 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 106:

```
GGCGGAGGAT TGCCACGTNG CAGCCTGCTA CGCCCGTCAG TTCTTTACGC          50
AGGTTAGCCA CCAGTTCGTT TACCATGTGG CGGCTCCNTG TCAGTTTCCA         100
GTTACCCATC ACTAAAGGAT GTGATTTATT TNTCCACGTT AGTAGCGAAT         150
TAAGGAAGAT GGCCGCTCGT AGAGA                                    175
```

(2) INFORMATION FOR SEQ ID NO: 107:

(i) SEQUENCE CHARACTERISTICS:
    (A) LENGTH: 307 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 107:

```
GATCATTATC TTAACCTAAA ACCGCTATAT TTATAAGTAT TATTACGAAT          50
AATCTTAACC TGGGATATGT TATACTAATC GGACCAGAAA GATATTATTA         100
CGACTTTAGT AAATGCTTTT TAAATATTAA ATAATAATTA ATTAAGATTT         150
CTACCATTCA TTAATTATAC TTAACAATAG TTTCACACCC CGCGCCGGAA         200
AGGTCTAACC TTCTCATTTA CCTTTAATAC TCAGTATTCC CGAATAGCCG         250
ACCGACACTA ATGATGAATG CTTATCTCTC ATAAACCAGA TATTATGACA         300
CATAACC                                                        307
```

(2) INFORMATION FOR SEQ ID NO: 108:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 108:

```
GATCAGGATA TGCCGCCGCC AGTAGCGATA GGGCGTCAAC CTCGTGCTTA          50

TCGGTGATGA GCGGCGCGTT GGCCGGGGCT TTTAAAAACG AAAGCATTAT         100

CCTTCCTTAA ACGTAACGCT GGGGCAACGA GACGCTCACC CGCGTACCGT         150

GGGTACAAGA GATGGTTAGC GTCCGCCGAG CGACGACACG CGCTTCGCAT         200

TCGGTCAGGC CGAAGCCTCT TGGTGAGACC GCCG                         234
```

(2) INFORMATION FOR SEQ ID NO: 109:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 109:

```
GATCGAGCGC GGAGAACGGT TCATCCAGCA GCAGTACCGG CTGTTCGCGT          50

ACCAGGCAGC GCGCCAGCTA CCCGCTGACG CTGGCCGCCG GACAGTTCGC         100

CCGGTAAACG CGTCATCAGA CTCTCAATGC CCATCTGATG TGCGATAGCT         150

CCCGTTTTTC CCGCTGGCTG GCGTTGAGCG TTAACCCAGG GTTTAGCCCC         200

AGACCGATAT TTTGCCTGCA CATTCAGGTG GCTGAATAAA TTATTCTCCT         250

GAAACAGCAT TGAGACCGGA CGGCGTGAGG GCGGCGTAAG CTATGATCGT         300

CGGCAATAGT AGCGTACGCT GGCCAGGCGC AAGAAACCGC ATAATCTCTC         350

TT                                                            352
```

(2) INFORMATION FOR SEQ ID NO: 110:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 110:

```
GATCAGGGTC AGACGCTTGT GCGCCCATAC AACGTTTTGT TCCAGTTGGC            50

CTTTCTCGTT AACGTTTTGG GAGCGCCAGA GCTGTTTAAC GCTCATGGGG           100

CATTCCAGAA CGGGCAGTAT CTCTTCAAAG GACGTTATCG TTTGTCAACG           150

GCGGACAGCA TTTTCAAA                                              168
```

(2) INFORMATION FOR SEQ ID NO: 111:

(i) SEQUENCE CHARACTERISTICS:
        (A) LENGTH: 211 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 111:

```
GATCTTCGGG GCGCACCCAC GGGGTTTTTG CGCGGGGGAC GCCTGTGTTA            50

TCAGCATTGT AGAAACTGCG ATAGATATTT CCGGTGAGGC AATTTTCGCT           100

CGGCACGATG TGTCGCTTAT CCGGTATGTG GTGAGCAGTG TGCGCCGGGG           150

CGTGTGATAG AGCCATTGCG CGATGGATCG TCTAGTGAGT TTCTCAGATA           200

GGGGGTGACG A                                                     211
```

(2) INFORMATION FOR SEQ ID NO: 112:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 112:

```
GATCCGCAGA TCCATCTAAT CGGATTAGGC GCATACTGGT AAAGATTCAG            50

CCCCCCCGCC AGCCCAATCG GATCCTGACT GACGAACCGT CCACACTCCG           100

GTGCATAATA TCTGAACAGA TTGTAATGCA GCCTGTCTCG TCGTCAAAAT           150

ACTGCCCCGG CAGCCGCAGA CCGGCTGGTG AAGTACGCCC GCTGTTGCTG           200

ATGTCCGCCG CATTTCTCCA ACCCTGATAT ACCGCCACAC AGCGTCGTCG           250

CGCGTAC                                                          257
```

(2) INFORMATION FOR SEQ ID NO: 113:

(i) SEQUENCE CHARACTERISTICS:
        (A) LENGTH: 359 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 113:

| | | |
|---|---|---|
| GATCCTGACT GGTACGACTT AACGTTTTAG GCTCGCCAAA ACTCAGCCCC | | 50 |
| GCCGCTTTCA TCGCTTCCGC GCCTTTGCCC GCTTTCAGCT CGACCAGCAG | | 100 |
| TTTTTCCGCA TCCAGCTTCG CCTGTTGTTC CGCTTTATTA TGCTTCACCA | | 150 |
| GGGCAGTGAC CTGTTCTTTC ACTTCTGCCA ACGGCTTCAC GGCTTCAGGT | | 200 |
| TTATGTTCGC TCACGCGTAC GACAAAAGCC CGGTCAACCA TCCACGGTGA | | 250 |
| TAATGTCTGA ATTCGGCCCG GCGTACCGTT TGCACAGACG CATAAGATAG | | 300 |
| CATCGGCTAA CGTTGAAGTC AGCCTTCGGT AAGGTGTACG GCTAACAGCG | | 350 |
| GTTACGCTT | | 359 |

(2) INFORMATION FOR SEQ ID NO: 114:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 114:

| | | |
|---|---|---|
| GATCGCGTAC CGCCAGTAAC GCCGCCGCTT TACCGTCAAT CGCCAGCAGG | | 50 |
| ACCGGAGTCG AGCCTTGCGA GGCCTGCGCG GTGATTTCCG CCGTCATGTC | | 100 |
| ATCCGTGGCG ACGTGCTGTT CGTTCAGCAA CGCCTGGTTC CCCAGAAGCA | | 150 |
| GTTGATGACC TTCCGCTTCA CCGCTGACGC CCAGTCCGCG CAGCTTCTGA | | 200 |
| AACCGTTCAC CTGCGGCAGT TTATCATCGC CGGCTTTTTC CAGAGAATCG | | 250 |
| CATGGGCCAG CGGGTGGCTG GAGCTTGTTC GAGCGCGGCA GCCAGACGTA | | 300 |
| ATGCCTGAGC TTCTCAACGC GTTAAAGGTT TTATCGCACA CTTGCGGCTT | | 350 |
| GCTCGTCAGC GTCCGGTTTA TCAAACTGAG GTATCAACGT ACTGGCGCGT | | 400 |
| GCAGGATGGC ATGTACAGAG CGATGAG | | 427 |

(2) INFORMATION FOR SEQ ID NO: 115:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 115:

| | | |
|---|---|---|
| GATCTGGAGG TAGAGGTTAT CGAGGCCAGC GGTAAAACCT CACGTTTCAC | | 50 |
| CGTGCCTTAT TCTTCCGAGC CGGATTCGGT TCGCCCCGGT AACTGGCACT | | 100 |

```
ATTCGCTGGC CTTCGGCAGG GTTCGTCAGT ACTACGATAT TGAAAATCGT        150

TTCTTTGAGG GAACGTTCCA GCACGGCGTT AATAACACCA TTACCCTCAA        200

CCTCGGTTCA CGAATTGCGC ACGGTTACCA GGCATGGCTG GCGGGCGGCG        250

TCTGGGCCAC CGGTATGGGC GCGTTCGGCC TTAACGTCAC CTGGTCGAA         299
```

(2) INFORMATION FOR SEQ ID NO: 116:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 116:

```
GATCAGAGTA AAACCTGGCT GCTATGGTGC GAACGTGGCG TAATGAGTCG         50

CCTGCAGGCC TCTATCTGCG CGACGAGGGG TTTGCCAATG TGAAGGTGTA        100

TCGTCCGTAA TTCCTTTGCC GGGTGGCGGC TATGTCCTAC CCGGCCTATC        150

GTTTTATTTC TGCCCCAACC GTTTTGCAAT GCGCTCCAGC TTCATCATCA        200

GCAGCAGCGT AATGGCCACC AGCACAATGG TCAGCGCGGC GTCAGCATAT        250

TTCACGTCGG TCAAGCTAAA GATAGCCACC GGCAGCGTCG TCAGCCGGCG        300

ATAATCATCA TCGTGGCCAA CTCCCATGAG AGCATAACT                    339
```

(2) INFORMATION FOR SEQ ID NO: 117:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 117:

```
GATCGATATC AGGGAGGAAG TGGTTGCCCG CCACCAGCGT ATCGGTACTG         50

ATCGCCAGGG TCTGCTTTTC AGGAATATCA GGAGCGCGCA ATCGTCGCCA        100

ATACCGGTTT CAACATCAAG ACGAGAGCTT CTTACACGGT CAAAATAACG        150

GGCAATCAGG GAAAACTCGC CACATGCCAT ACGTTATGCC TCAGCAGAAA        200

AAAGAAAAG GCCGGAGACG CGGGTATCGA GCGCCCGCTA TCTTTCCGGC         250

CTGTGAATCA CTTTTTGTTG GGACGAATCA CCGGAGCTGC TTTATCAGTA        300

CGCGTTGACG ATTTGTGGCT GTCTTCACGC GCCAAAGTTT GAGTTCATCG        350

CTTCGTTGAT GGCCATTATA AGCCAATC                                378
```

(2) INFORMATION FOR SEQ ID NO: 118:

(i) SEQUENCE CHARACTERISTICS:
        (A) LENGTH: 266 base pairs

```
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 118:

GATCTCTTAC GATAAAGAGC ACATTATCAA CCTTGGCGCG CCAGATTGGT       50

ACGGAAGATT TTGCCCGTGC GATGCCTGAA TACTGTGGCG TGATTTCAAA      100

AAGTCCGACG GTGAAAGCCA TTAAAGCGAA AATTGAAGCC GAAGAAGAAA      150

ACTTCGACTT CAGTATTCTC GATAAGGTGG TAGAAGAGGC GAACAACGTC      200

GATATTCGTG AAATCGCCAG CAGACCCAGC AGGAGGTGGT GGAGTAGAAC      250

GTGATGATCG GTTTCT                                           266

(2) INFORMATION FOR SEQ ID NO: 119:

(i) SEQUENCE CHARACTERISTICS:
            (A) LENGTH: 345 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 119:

GATCATCTTC CACTTCCAGA TGCACCGTCA CATCCGGGTT AGTGAGCTTC       50

ACGCGCGCCG ATTCAATATG CTGATTTAAT CCGCCGCCAA CATAGCGCTC      100

CACTTCAATG GAGCTAAACT CATGCTTACC GCGACGTTTT ACCCGCACGC      150

AGAAGGTTTT GCCTTCAAGC TGTTCGCGAT ACTGCGCCAA ACGCTTTCTC      200

GAAAATGTCG TGCATATCGG TGAACGGCAC ATCTCGACTT CAAGAATATG      250

TGAATCCCGG GATCGTGGTC AGCGCTCGGA ATCACAGACG CTGGTTTCAC      300

TTGCGCGACT CATTTACAGT CAGACACGTG TAGTGCTTAA CTCAG           345

(2) INFORMATION FOR SEQ ID NO: 120:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 120:

GATCATCCTG GAGGTCTTTA TGGCTGATTT CACTCTCTCA AAATCGCTGT       50

TCAGCGGGAA GCATCGAGAA ACCTCCTCTA CGCCCGGAAA TATTGCTTAC      100
```

```
GCCATATTTG TACTGTTTTG CTTCTGGGCC GGAGCGCAAC TCTTAAACCT              150

GCTGGTTCAT GCGCCGGGCA TCTATGAGCA TCTGATGCAG GTACAGGATA              200

CAGGTCGACC GCGGGTAGAG ATTGGGCTGG GCGACGGACG ATTTTGGCTG              250

GTCCTTCTCA GGCGCTATTA GTACGCGGTT CATGCAGTAC ATACTACCTG              300

AAGTCACGAT GCACCGAATA G                                             321
```

(2) INFORMATION FOR SEQ ID NO: 121:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 121:

```
GATCGGCGCG CGTATCTCAG GCATGTGCGC CGCCAGTTGG GAAACGCGCC              50

CGCCGGGGCC CTCAATTTCA TACGCAGAAT ATCCGCGCGC GCCGACCGCG              100

CCGGCAACGG CGCGGCAGAC ATTGACGCCG GCGGGCAGCT CGCGGGCTGT              150

GGCAGAAGGG CGTCACGCTG CCAGGCCTCG TCTGGATAGA TTGATATTCT              200

CGACCACATC CCGAAA                                                   216
```

(2) INFORMATION FOR SEQ ID NO: 122:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 122:

```
GATCGGCAAA CAGATAGTCC TGCGACGCAT TAAATCCAGG CATTGCCGAG              50

GAGCACGCCG AAGCGGATAC GCCAGGCGGG CAGGCCATAC CTACGGTATT              100

TGTCAGACCA AACGCCTGCG GGTTGGCAAG AATTTCCTTA AAGAGGCCGT              150

TGATATCGGC ACGGGCTATA TTGCCGCCGT GTTGCTCCAG CCCCTTCTCT              200

TCCATCTGAT TATAATAATC GGTCAGAGCT GACGCTGCCC TGCCGCCGTT              250

CATAGTTGCA GAGTGTCACG AGCAGTGTGA TAATGATGGG TT                      292
```

(2) INFORMATION FOR SEQ ID NO: 123:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 123:

GATCAGCGCC GCGCTACGTT AATAGCCGGT TGCGACGACC GTGGACGCTA           50

GCAGAGTCGC GGATGACTTC CGTATCGGTT GGTCCACGCG TGAAATTAGT          100

TGCGCGACA                                                      109

(2) INFORMATION FOR SEQ ID NO: 124:

(i) SEQUENCE CHARACTERISTICS:
            (A) LENGTH: 258 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 124:

GATCGGTCGC ACGCCGGAAT ATCTGGGAA AAAAATCGGC GTGCGTGAAA            50

TGAAAATGAC CGCGCTGGCG ATTCTGGTCA CGCCGATGCT GGTCTTGTTG          100

GGTTCGGCCT GGCGATGATG AACGGATGCC GGACGCAGCG CAATGCTGAA          150

CCCTGGCCGC ACGGTTTTAG CGAAGTGCTA TATGCCGTCT TCCTCTGCCG          200

CCAACAACAA CGTAGATTTT TAGTCTACCT AACTACTTCT GAACTACGGC          250

ATCTCGAC                                                       258

(2) INFORMATION FOR SEQ ID NO: 125:

(i) SEQUENCE CHARACTERISTICS:
            (A) LENGTH: 384 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 125:

GATCGTTGGT CTTTAAGGCC GCCGCCAAAT CGCTGTCGAC CTGCTTGTTG           50

CTGTAAAAAG CGGTATTAAA CTGCGTCGGC GGCCAGTTTT GTGATGCGAA          100

GAGCGGCGAT AACGCCCAGT CAGCTTCGCC CGTCAGACGC CGACCAGCCT          150

GTATAGAACA TTCGCACGCG CTCTCTTTTT GCCCTTTGCC CTCGACTTCC          200

GCGGCGGCTG GCCGGCGTAC ATCGCGGTTA TCCGGGCTTT AACGACCAAT          250

CTGCGCCAGT TGCTGTTGGG TAAACTGCAA GAGTTTTTGG GTGCTATGGT          300

TGTGCATGAC ACAGCGTGTA CTGAACGTCT GATACCGCTT TCACGTCCCC          350

TAGCGATCAT GGCCAGTGAA GTTGCATAGC TAGA                           384

(2) INFORMATION FOR SEQ ID NO: 126:

(i) SEQUENCE CHARACTERISTICS:
    (A) LENGTH: 448 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 126:

| | | |
|---|---|---|
| GATCATACCT TGCTTGATGA CTGCGCCACT AAAAACCTGA CGCCGGCGAA | 50 | |
| AACCCACTGG GCGCGCCCGC TTGATGCGCC GCCCTACTAC GGTTATGCGC | 100 | |
| TGCGACCCGG CATCACGTTT ACCTACCTGG GTCTGAAAGT CAATGAACGT | 150 | |
| GCCGCGGTGC ATTTGCCGGT CATCAAGCCG CAACCTGTTT GTTGCCGGCG | 200 | |
| AGATGATGGC AGGAAATGTT CTGGGCAAGG GGTATACCGC AGCGTAGGCA | 250 | |
| TGTCTATCGG CACAACCTTT GGCCGCATTG CAATAGAAGC CGCCCGCGCA | 300 | |
| CAAGGAGGCG CACGATGAAA CAGCTTGAAA ATTATCATTG AGGCACGTGC | 350 | |
| TTACGAACGA AGCGAGGTGA ACTGTCATGC AGTGTGTACG TGTGTGCTAC | 400 | |
| TCGAAGGTTT GCGGATTCGC ATGACAGGTG ATGTAGCGAT ATATCGAT | 448 | 448 |

(2) INFORMATION FOR SEQ ID NO: 127:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 127:

| | |
|---|---|
| GATCCCCAGG AGGTCTGGTT TGTCAAATCG CCGAAATCCT TTTTAGGCGC | 50 |
| CACGGGCCTG AAACCGCAGC AGGTCGCGCT GTTTGAAGAT TTAGTCTGCG | 100 |
| CCATGATGGT ACATATTCGT CATACGGCGC ACAGCCAATT GCCGGACCGA | 150 |
| TTACCCAGGC AGTGATCTGC AGGTGGCACT TTTCGGGGAA ATGTGCGCGA | 200 |
| ACCCTATTTG TTTATTTTTC TAAATACATT CAAATATGTA TCGCTCATGA | 250 |
| GACAATAACC TGACAAATGC TTCAATAATA TTGAAAAGGA AGAGTATGAG | 300 |
| TATTCAACAT TTCGTGTCGC TTATCCTTTT TCGCATTTGC TTCCTGTTTG | 350 |
| CTCACCAGAA CGCTGGTGAA GTAAAGATGC CTGAAGATCA GT | 392 |

(2) INFORMATION FOR SEQ ID NO: 128:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 128:

GATCTTGTCA AGCTGGTCAG CATATCCCGG ATATCCTCCG CCTCCCCCCC         50

CGCCACTCCG CGCGGCTTAT GAATCATCAT CATGGCGTTT TCCGGCATAA        100

TGACGGGATT ACCTACCATC GCAATAGCGG ATGCCATTGA GCAGGCCATT        150

CCATCGATAT ACACCGTTTT TTTCGCCGGA TGATTTTTCA GGAGGTTATA        200

AATGGCTATT CCGTCCAGTA CTGCTCCGCC AGTGAATGAA TATGCAGATT        250

TATACGGTTA ATCTGTCCAG TGCAGCCAGT TCTCTGCAAA CCAGCGAGCC        300

GAAATTCCCA TCTCAATCTG TCATAAT                                 327

(2) INFORMATION FOR SEQ ID NO: 129:

(i) SEQUENCE CHARACTERISTICS:
            (A) LENGTH: 306 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 129:

GATCCGCAGG AGAAAACACG ATTGTACAAA GAGGCGCAGG ATATTATCTG         50

GAAAGAGTCG CCCTGGATAC CGTTGGTGGT GGAGAAATTG GTTTCTGCTC        100

ACAGTAAAAA TTTGACCGGT TTCTGGATTA TGCCGGATAC CGGTTTCAGC        150

TTTGACGATG CGGATTTAAG TAAGTAATGC GATGGGCTG GATGGCGCGC        200

GGTTGTCGCC ATCCGTAAAA GGTTCGTGTA TGCTAACTAT GTTCTCAGCG        250

CTGCTGGATT ATTCTACGTG TTGATTGTGC AGTGCTGGTG TTTATTGTCA        300

TTGTCC                                                        306

(2) INFORMATION FOR SEQ ID NO: 130:

(i) SEQUENCE CHARACTERISTICS:
            (A) LENGTH: 301 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 130:

GATCTCAGCG ATGTTCAGTT AAACGCTGTG CCGGATGCGG CGTAAACGTC         50

TTACCCTGCC AACGGGTTGG GTAAGCCGAA TAAGCGCCGC TCCATCCGGC        100

AGCATTCACA TAAAGTCCGG CACCAGACGC TGTAACGCGC CTTGCGCAGC        150

AGCGCCGTCG CACACTCAAT ATCGGGCGCG AAAAAACGAT CCTGCGTATA        200

| | |
|---|---|
| GTGCGCCTCC TGCTCGCGCA GTGTCTGCCG CGCCTGTTCC AGTAACGGGC | 250 |
| TGGAGGTTAA CCTTCCGTAA TTATCCTGAC AGCAGCAGCA TCACGCATAT | 300 |
| G | 301 |

(2) INFORMATION FOR SEQ ID NO: 131:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 131:

| | |
|---|---|
| GATCGCCGGT CAGTTCCTCC ATTAAGAGCG GCGCGCGCGC CAGCATCTCC | 50 |
| ATGCAGAAGA GCCGCGACGC CTGCGGATAA TCACGCGAAA CTTCCAGCTT | 100 |
| GAGACGGATA TACTCTTTGA TGGCCTCCAT AGGGGAAAAT TCTGCGCGAA | 150 |
| ACGCTTGAGC GGCGCACGAG ACATCCAGAA TCTCGTCGCA TTACCGCGAC | 200 |
| ATACAGCGCC TCTTTCGAGG GATAATAATA AAGCAGATTG GTTTGGAGAC | 250 |
| GCTGCCGTAG CGGCGACTGC TCAAGACGCG CGATGATGCA TACTGGAAAC | 300 |
| ACGAGCGCGT AGATAGCTGC GTTGCACGG | 329 |

(2) INFORMATION FOR SEQ ID NO: 132:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 132:

| | |
|---|---|
| GATCCGCCCA CGCGTTAAGG GCCGTAAACA GAGCGTCATT CATCATTACC | 50 |
| GCTGGATTCA CCGCCCTTCG TTCTTCTTCT GTTAACACCA CGCGTAATCG | 100 |
| CAGACAGGCC GGGCCGCCGC CGTTGGCCAT ACTTTCTCGC AAATCAAACA | 150 |
| CCTGCATCGC GCTGATGGGG TTATCCTCCG CCACCAGCTT ATTCAGATAG | 200 |
| CGTCCAGACG CGACATGGTC TGACTTCCGC GCACCTACGC TTGAGCCGTG | 250 |
| TTCGCTTGCA CTGCTT | 266 |

(2) INFORMATION FOR SEQ ID NO: 133:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 133:

| | | |
|---|---|---|
| GATCAAATGC AGGCAGTAAA AGGGCGTCAT CAAGATTATC GGTACACTGT | 50 |
| GTAGCGGCGG TTTGCAGAGT ACCATGTAGC GCCGGATAAT TATGCCGGGT | 100 |
| CAGGTTGACA CCGTGCGTAC CGTTAATAGC TTCAAAGGCG TCGCAAAACG | 150 |
| CGCGGTGTTT TTCTGCGGTG ACGGGGTCTC CCGGCGCTTC AAAAGTTCGC | 200 |
| ATCAAATGCG GGCGATGCTC TGATTCTGGT ACTTATCGTA CAAAACGACG | 250 |
| ATCGCTCTCT CATGATATAC GCATATAGCA TCATGCCTGT CCGTGCATAG | 300 |
| TCGTAACTAG AGACATCAC | 319 |

(2) INFORMATION FOR SEQ ID NO: 134:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 134:

| | | |
|---|---|---|
| GATCAACCTG AACTCAACGG ACCCTGTACC GTCTAAAACG CCCTTAGCGT | 50 |
| GAGTGATGCG GATTCGTATA ACAAAAAAGG CACCGTCACC GTTTATGACA | 100 |
| GCCAGGGTAA TGCCCATGAC ATGAACGTCT ATTTTGTGAA AACCAAAGAT | 150 |
| AATGAATGGG CCGTGTACAC CCATGACAGC AGCGATCCTG CAGCCACTGC | 200 |
| GCCAACAACG GCGTCCACTA CGCTGAAATT CAATGAAAAC GGGATTCTGG | 250 |
| AGTCTGGCGG TACGGTGAAC ATCACCACCG GTACGATTAA TGGCGGAGCC | 300 |
| ACCTTCTCCT CAGCTTCTTA CTCATGCAGC AGACACGGGC TATACATGGA | 350 |
| CATCAAACGG CTATAGGGGA CTGTGAGCTA CAGATTACAC TGATGGCACG | 400 |
| TGTTGGCACT ACACGCGCGT TCGGCGATGT GTATGAAC | 438 |

(2) INFORMATION FOR SEQ ID NO: 135:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 135:

| | | |
|---|---|---|
| GATCTTATCC TTCCGCTACA AAATCAACTG CGCCATCTGA CGCATATTGT | 50 |
| CGGCGTGGAT AAACTGGCGG CTGCCACCAC AGCGCTTGCG TTAGTCAAAT | 100 |

-continued

```
CATCGACCGC AGCGAACCGT TGCAGTCAGA CATTAACATT CACGGTGATG        150

AACTGGCGGC AGTGCTGTTT ACCTCCGGCA CAGAAGGAAT GCCGAAAGGG        200

TGATGTTGAC CCACAATAAT ATTCTTGCCA GCGAACGGGC GTATTGGGGG        250

TTGAATTTAA CCTGGCAAGA TGTGTTCCTG ATGCTGGCGC ACTGGGAGAC        300

CGGATTTTAA GGAGGCTTTT ATGGGGTAGT ATTGCTGGAC ATCTTACCAG        350

AGCTCTACTA TAG                                                 363
```

(2) INFORMATION FOR SEQ ID NO: 136:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 136:

```
GATCGATTTT CCCCTCCATG TTTTCATAGG GGAACAGGTT CGGGTTAAAA         50

ACCACCTGAC GGATATCGCA CAAAAAGCCA ATCCGCTCCG CCCAGTAACC        100

GCCCAGCCCC ACGCCACAGA TTAAAGGGCG CTCGTCCACA TTCAACTGCA        150

ACATTTGTC CACTTCTTTC AGCAGATGCT GCATATCGTG CTTAGGATGC         200

CGCGTACTGT AGCTTACCAG CCGAACATCG GGTCGATAAA CTGGTAATTG        250

CGAACACTTT TTCATGGTGC GCGGACTATA TGAGTCAAAA CGTGTGATAT        300

ATATCATCTG GCACCTCACG AGACTGAGTG ATGCGTGCGT TTCTGCA           347
```

(2) INFORMATION FOR SEQ ID NO: 137:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 137:

```
GATCCCAGAC AATACCGTTA CTGTTATCCA ACGATACCCC TGCCAGTGAG         50

GTACGCAGGA ATCCATATTG GGTGTGATGC GCGTAAGAAA CGCCCGCCAT        100

CATAGTACTT TTACGCCTGT CCAGACGACG CAACTGATGG TCATCGCTGT        150

CGCCCGGTTT GAAGTACATC GGGGACCAGT ATGCCATGAT TGACAACTTA        200

TCGGCATTGT CATTCACAAG TAGTACCGCG CCAGACACGA CAGAGTTNTT        250

CATAGGCATG ACGATCGATA ACAGCTAT                                 278
```

(2) INFORMATION FOR SEQ ID NO: 138:

(i) SEQUENCE CHARACTERISTICS:
        (A) LENGTH: 385 base pairs

```
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 138:

GATCGTTATG AATCGCTTGC GTGATTTCCA GCGTCACCGG GTCGAGACGA          50

TAAACTACGC CGCCTTTATC CAGTTTACGG CTTTGCGATG TAGCCAGCCA         100

GAGCGCGTTT TCTTGCTGAC TCCAGGCCAT CTCATAACGC CTTTGCCTAC         150

CGCTTTACGC AGCATGTCTT CCGCGCCAGC GTGCTAAATG AGGATGCGAC         200

GAGGAGCGAA CCTAACAATA AAGAACCACG CAGGCTGGCG AAAAAAGATG         250

ACGTAAGTGC ATGACGACTC CTTTGATAAA ACGTGTATAG CTGCTTCACA         300

CTACTTCGCT GCGTGGATCT GCAGGTGGCA CTTTTCGGGA AGTGCGCGAC         350

CCTATTGTAT TTCTAATACT CAATATGATC GTTAT                         385

(2) INFORMATION FOR SEQ ID NO: 139:

(i) SEQUENCE CHARACTERISTICS:
            (A) LENGTH: 282 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 139:

GATCAGCGGC TATGGCGGTC CGGAAGGCGC GAAGATGGCA CGCCGGCGGG          50

CACAGTTTGG TTTGCCTGGA ATATTAACAA TACAACTTTT ACAAGCCGAC         100

AACATTTCAA CGGAGATTGT CAGGAAGTAT TGGAAAAATG CGTACGCTTC         150

GCCCTCGCTG AATTGCTTTT CTGTTAACGA AGAAAGCATA ACATAATTTC         200

ACTGACGTCA GATACTCCGG CTAGATAAAT CGAGCTTACC GCGTGTTCGG         250

AATTCGATGA TTCGGATATC GGTCGCCATC GT                            282

(2) INFORMATION FOR SEQ ID NO: 140:

(i) SEQUENCE CHARACTERISTICS:
            (A) LENGTH: 179 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 140:

GATCGGCGAC TACAAAACCA ATCACCGCGG CTTTACCATC GAGTTCCATA          50
```

```
TGCGTACGTT TTATCGCTGG GAGTATGGCG AGAATATGTC CCCGGCCGGA            100

TAGAACCGGT TAAAGAGACC ATGCGTTACT TTTTCATGGC GGTATACATG            150

CACAGTTGCT TGGTGGCATG ACATTGGAA                                  179
```

(2) INFORMATION FOR SEQ ID NO: 141:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 141:

```
GATCAGTAAC AGGACGGTAG CAAAATTCGC ACTGAGCCCG GCGACATTCT             50

GAACGAACGG TTCAATATAG CTATAACTGT GTAATGCGCA GTCACCACAA            100

CGACGGTCAG TACATAGAGG CTCATCAGCG CCGGGCGTCT GAATAGCAAA            150

AGGTAAACTT TTTAGTGAGC CGGAATGCTC GTCTGGCAAT TTCGGTAGAG            200

CTTATCAGAA TAGCAGCGTA TATCTCCATG CGATGCAAAG TGGCCCAGCA            250

AATCTGACAC T                                                     261
```

(2) INFORMATION FOR SEQ ID NO: 142:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 142:

```
GATCATTTTG GTGCCGGTGT CAGCCTGCTG ATGTCCACTG GTCAGCGCAA             50

CGGAATAGAA CTCGCCGATA TAATTATCAC CGCGCAGAAT GCAGCTCGGG            100

TATTTCCAGG TAATCGCCGA ACCGGTTTCC GACTGGGTCA ACGACATCTT            150

GCTGTTTTCC CTTCGCACAA GCCCGCTTGG TCACAAAGTT CAGATCGCCG            200

TGTGTGTGCC GGACAGTTGA CGTGA                                      225
```

(2) INFORMATION FOR SEQ ID NO: 143:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 143:

| | |
|---|---|
| GATCATCCTC GGCGCGGGAG TGAATCACTG GTATCACATG GATATGAATT | 50 |
| ACCGTGGGAT GATTAACATG CTGGTGTTCT GCGGCTGTGT TGGACAAACC | 100 |
| GGCGGCGGCT GGCCGCACTA TGTCGGCCAG GAGAAGCTGC GGCCGCAAAC | 150 |
| CGGCTGGCTG CCGCTGGCTT CGCGCTGGAC TGGAATCGCC GCCGCTCAGA | 200 |
| TGAACAGTAC TCGTTTTCTA CACCATGCCA GCCAGTGGCC TATGAAACTG | 250 |
| ACTGCGCAAG AGTTGCTGTG CGCTGCGATC GCTAATTCGA CTATCGATTA | 300 |
| C | 301 |

(2) INFORMATION FOR SEQ ID NO: 144:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 144:

| | |
|---|---|
| GATCATGTGG GTTTAACCCG TTGATTAAAC ATTGGATTAC GGAATAGCAA | 50 |
| TTGCTTATTT TATTTGTCAT ACAAATAAGT ATAATACCCG CTTCCGATGT | 100 |
| AGACCCGTCC TCCTTCGCCT GCGTCACGGG TCCTGGTTAT ACGCAGGCGT | 150 |
| TTCTGTATGG AATACGCCAT CCCCTCTGAT AGATGCCTTG TTGCCTTAAG | 200 |
| CAGTTAACCC GCCTGAAGCA AACGACAAGA CGGCAGACGC TTACCGGCAT | 250 |
| ACGACACGGA TGCTTCAGAA GA | 272 |

(2) INFORMATION FOR SEQ ID NO: 145:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 145:

| | |
|---|---|
| GATCTGCGCA CATCATTCGG GTCATCGCTA AATTTTTCAC TTTTAATTCG | 50 |
| CCGTCCGACA GTTTTCCTTC GCCGGTGAAT TGATTGCACA TTTTGCCGGA | 100 |
| TACCGTCATG TCCTCGCCAA GGCTAGAGCT CCGGGCCGGT GACCGTTTTA | 150 |
| CCGTTTACGC TTTCCAGAAC AAAGCGGTGG TGCTCCAGTT CGTCGCGTTT | 200 |
| GACGGACACT TTTCACTGCT CACACACCTG TCATTATGAT GCTCAGGGCG | 250 |
| ACCAGCGTGA TTTCTTCATT GATATTCTCT GTAATCTGAT AGGTTAACAC | 300 |
| TGACTATAGT AATGATATGA CCGGATAGAT CTTCAGGGTA TCCGAAAATC | 350 |

| GTCCCTGA | 358 |

(2) INFORMATION FOR SEQ ID NO: 146:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 146:

| GATCTGTTGT TACAGCATGG AATGCGCCGT CCTCCTCACC GGCCAGGCAA | 50 |
| ACGGCGCGAT CGTATCGAAC TGTGCGCCGC GCCGAAAGAA GGGGGGCTTA | 100 |
| GCCCTTCTTT CGGCGTCTTA CGCAGCGTAG CCAGCATATT AGCATTGCCT | 150 |
| AACTGCATTA TTGTCTGCGG CGGGGATTTT ACTACGTAGC GCAATTTGGC | 200 |
| ACGTCTAGAA ATTCGTAAAG GTTC | 224 |

(2) INFORMATION FOR SEQ ID NO: 147:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 147:

| GATCCTGAAT CGCCACGACA CGGGCGCCAG GCCTGCAAAC AGACGCGCGG | 50 |
| CTTCGCTGCC GACGTTACCA AACCCTGAA CCGCAACGCG AGCGCCTTCA | 100 |
| ACAGCAATAT TCGCCCGACG TGCGGCTTCC AGCCCGCTGA CGAAAACGCC | 150 |
| GCGCCCCGTC GCTTTTTCAC GGCCCAGCGA ACCGCCAAGA TGGATAGGCT | 200 |
| TACCGGTGAC GTAAGATAGT GACCGTGTGC ATGATTCATG GAATACGTAT | 250 |
| CATATCATCA ATATTACT | 268 |

(2) INFORMATION FOR SEQ ID NO: 148:

(i) SEQUENCE CHARACTERISTICS:
        (A) LENGTH: 314 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 148:

| GATCCTGAAA AATACCAATT TTCAGCGGGC GAGCTTCGCC TTCCGCACTA | 50 |

```
AAACAGTGAG GAAAACGCTC GGCCAGAAAC GCGATAACTT CTTTACTGCT           100

ATTCAACTTA GGTTGATTTT CCATGAAATT TCCTGATTAC AACGGACGTA           150

GCCAACAAGC AGCAGGCATG AACAGGCGTC ATTATAATGA CGCCATCAGT           200

AATTGCTACG TTATCCGTTG ATTATCCTGC GACGTCGCAA AGATTTTTTG           250

TATCCGTCGT GCAGCACGTT CAGCTGTCAC CAGCGTACCA GGCGTGTCAT           300

CTCTCGTAAC GCAA                                                  314
```

(2) INFORMATION FOR SEQ ID NO: 149:

(i) SEQUENCE CHARACTERISTICS:
        (A) LENGTH: 379 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 149:

```
GATCCAGAAT ATATAAAACC CCATTAACNC CAGCGCGCTT AATAACCATG            50

TGGTCATCTG CGCTCCGTGG CTGGTTACGT TGTTATAAAT AAGGATGGCG           100

ACCAGCCCAA CGAAGATAAC GCTGTCTACG CGACCGCGGC GGAGAGGGCT           150

ATAGAAAGCA GAGTGGGGCC ATTGCGACGG GGCATGATGA ACTGATCGTA           200

GAGAGCGTAA GCCAATAATT CGGCAATAAA GAGAATCAGC ACCAGGTCCG           250

TGATAGTCAT TTATCTCAGA GAAATAAAAA ACGGGCGTTT GCGTAGTGTA           300

CAACAGCCTT ACTGGCCAGC AGTCTACGAG TAGCCGGCGA TACCAATGAC           350

GAGAGCCACG ATATCACAGC GTACTTCTA                                  379
```

(2) INFORMATION FOR SEQ ID NO: 150:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 150:

```
GATCCAACAA GCGGCTGGCG CCATAGCCGC CGCGAACCGG CATGACGATT            50

GTATCCGGCG ACGTTAGCGA GGCCAGCGAA TTAACATCGG CCAGCCGTTC           100

CGCGTCCGTA CCGGCAAAAC GCTGAAAGGG CGACGAATCA CCTCGTCATT           150

CTCCACCTGA TGACCCGCGT CAGTCAGGCG CTGAACGCCG CGTAACGGCT           200

GTTGGTTAAT ACAGTAGCCC GACTGGGCGA TTAATGAAAC AGAGACATGG           250

TAATTCCTTG CTGACAATAG AATCGAATGT ATATCATGCG CATATATAGG           300

CGATGTCTCG TGTCGCAGTT CTGATCGGAC AGGAGGCACT AGCTCGGGGT           350
```

ACTTT                                                                   355

(2) INFORMATION FOR SEQ ID NO: 151:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 151:

GATCCTTATT CCCGATGTGT TCACCTTTAA TATTCTCCAC TCGCGCGTGG                    50

AGGAGATGAG CGGCGTTCCG GTCGTTCCGC TATATGACAC GCCGCTATCA                   100

GGGATTAACC GTCTGCTTAA ACGGGCAGAA GATATCGTGC TGGCGTCGCT                   150

GATTCTGCTG CTCATCTCAC CGGTACTGTG CTGCATTGCG CTGGCGGTCA                   200

ATTGAGCTCG CCGGGCCGTG ATTTGCCGCA GACGCTACGG ATGGCAGGCA                   250

AGCGATCAAG CTGAAGTCGT CATAGGAG                                           278

(2) INFORMATION FOR SEQ ID NO: 152:

(i) SEQUENCE CHARACTERISTICS:
        (A) LENGTH: 394 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 152:

GATCAAAATA AAACTTTAAT CCCACTGGGG CAAGAGAGTG ATGTGGTGAC                    50

GCTCAGTCCG GGTCAGGCGT CGGCGCATCT GCAATTTTAC GCGCGTTATC                   100

TTGCCGATGG CGGCGCGGTA ACGCCGGGGA CGCCAATGCC TCCGCAACCT                   150

TCATTCTTGC CTATGAATAA GTTCTTTTTA CGCTGCGCGC ATATATTGGT                   200

GCTTGCTTCC CATATCATGG GCGCAGGCTG GCGTGGTAAT TGGCGGTACT                   250

CGCTTTATCT ATCATGCGGG CGCCCGGCAT TAAGCGTACC GGTAAGTAAC                   300

CGTTCAGAAG TCGTTCTGTT AATTGATACG CATATTTACT GGTGGGTCGG                   350

TTACGGAACA AAACGATGGA TATAGTCCTG TGTAGTGATA TGCT                         394

(2) INFORMATION FOR SEQ ID NO: 153:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 153:

GATCGTTAGC AAGGTTTGCT GCGTCATCTG CTGGGTTTCA CGCAATGTGT           50

GCGCGTTAAG CATCACAAAA TGGCTGGCGC GCGTCGCCCA GTGGGCATTG          100

ATTTGTAATT CAAGCATACA AACCAGGTTG CGGTTGATGG TCTGAATGGC          150

CTCGAAAATA GATTTTTGTA TCCGGGTTTC TTTACTGGCA GGCGTTATCA          200

GCCCGCGCAT TTTGACGACA TCGTTCAGCA ACCGTTGCAA ATGTTATCCA          250

ACCGGGGAGT CAGCAATCGC GACAGCTGCC TTGATACCCA GTTACCTGAC          300

CGATCCGGAT GATCCGATCG GAAA                                     324

(2) INFORMATION FOR SEQ ID NO: 154:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 154:

GATGGCTGGG AAGACGGGTG CCGTTCTGGT TAAGCGTATT CAGCTCTTCG           50

CGCGGGAAAT AGCCTTTAAT CGCCAGGGTA CTGTACAACG CGGGGCCCGC          100

ATGGCCTTTC GACAGTACGA AGTAATCGCG TTCCGGCCAG TCCGGGTCGG          150

AGGGTCGATT TTCATCACCG CGCCGTACAG AACCGCCAGA GTCTCCACTA          200

CCGACATGCT GCCGCCATAG TGACCAAAAG CCAAAGATGG TTTAAGGATT          250

TGACGGTGGA CCGAATATCG ACAGTTGGGT GATTTCGGTT ACGTTCATTC          300

TTCCTGAA                                                       308

(2) INFORMATION FOR SEQ ID NO: 155:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 155:

GATCGTGGTC CAGCTTATGA ACGGTATAAC TGAGGGCGGA CGGCGTTTTA           50

AATAATTTTG CCGACGCCGC CGCGAACGTG CCTTCTTTTT CTAACGCATC          100

AAGAATAATC AGAACGTCCA GCAGTGGTTT CATACTCGTC CCCTTGCCGC          150

TATATGGCGA CCACCTGCTG GACAGCGACT CACTCCATCG GCATCACCAA          200

CGGATCGGGA TATTGATATT CAAATCCCAG CTCATTACAA ATCGGCTACC          250

| | |
|---|---|
| GTCGATAATC TTCCCTTTTG CCGTTGTCGG TGGTACGAAA ATCGCGGCGG | 300 |
| CGATTCCCAG CAAGCGTATT GCGATAAACA CTG | 333 |

(2) INFORMATION FOR SEQ ID NO: 156:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 156:

| | |
|---|---|
| GATCCACCCA CGTCATCAGT TGTTCAAAAC CCTGCTTCAC GGTGTGTTCC | 50 |
| CATGGACCGA CCATGTGGAA AGCGGCTATC TTGCGTTTTT GTGGCTGCCT | 100 |
| GATTTCGTAA TCCATGCTGC CTCCGTCACT TCACAATGCT GTATGAATGT | 150 |
| ACAGTATAAT TACAGCCTTT TACGGTCACA AGGACAGCGT GATCATTTTG | 200 |
| TGAGCAACCT CGCAATCCCG CCCTTTTGAC ACCTCAGATG ACGGTGAACG | 250 |
| GTGTGTGTGA CAACGGCTTA CGCTTTATGT GAAAATAGTC GTCAGACGAG | 300 |
| AGAACATACC GCCTTTACCA CGATTCAGAG TGAC | 334 |

(2) INFORMATION FOR SEQ ID NO: 157:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 157:

| | |
|---|---|
| CGTTTGCTAT CGACCTGCAG ATCGGAACGG ATTGGCGTCA CGTGATGGAT | 50 |
| AAGACCGTGT TCTTCAATGT TATCTCGGCG ACACGAGCGC ATCCGGCGAA | 100 |
| ATATCGACCG CATCAACCTC TGCGTCGGGA AGCATAACA CAGGCATGGC | 150 |
| AT | 152 |

(2) INFORMATION FOR SEQ ID NO: 158:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 158:

```
GATCGAACGC GCGTTGCAGC AGCGCCCGGC TATTTTCTAC CCGTGTCGTA         50

TCGCCGAAGT TGTGCCATAA CCCCAGCGAA ATAGCGGGAA GTTTGACGCC        100

GCTGCGTCCG CAGCACGATA CTCCATTGTG TGATAACGAT TCTCATCGGG        150

CTGATAAATC ATGACCTTTC CCCTGTGGCG AGAATAATAT GTGTACGGTT        200

ACTC                                                          204
```

(2) INFORMATION FOR SEQ ID NO: 159:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 159:

```
GATCTTACCG AGTGGGAAAC TAATCCGCAA TCGACCCGCT ATCTGACGTT         50

TCTCAAAGGT CGGGTAGGGC GCAAGGTCCG CTGACTTCTT TATGGATTTC        100

CTCGGCGCCA CGGAAGGGTT GAACGCCAAA GCGCAGAATC GCGGCCTGTT        150

GCAGGCAGTG GATGATTTCA CCGCAGAAGC GCAGTTGGAT AAAGCGGAAC        200

GTCAGAACGT GCGCCACGAG GTGTACAGCT ACTGCAATGA GCAATTACAG        250

AGGGAGAATG AGCTGGATCG CTGTCTAAGA GCT                          283
```

(2) INFORMATION FOR SEQ ID NO: 160:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 160:

```
GATCGCGTTC GCCAGGCAAA ATATTACCGT GCTCAAGAAT ACCGCTGCGC         50

ACGGCATCCT TTACCGTCTG GGCGAATTTC ATGTATAGCG GCGTATTATC        100

CGCCGCTGAA ATTCGTTCAT TCAGTTGCGC GATGAGCCGG GTATGCGCTT        150

GTTCCATTTA TCTTTCCTGA CGACGGGTCT GTAGGCAGTA TACTACCACC        200

ACGCGTGGAA ATGATGTACC GGACCAATGC CCTTCCCCAC TTCCAGCCGT        250

GTACGCTGGC AGCGCCGAAG CATGCCTTGC TCGTTTACCG TCTCTCCCAA        300

CT                                                            302
```

(2) INFORMATION FOR SEQ ID NO: 161:

(i) SEQUENCE CHARACTERISTICS:
        (A) LENGTH: 233 base pairs
        (B) TYPE: nucleic acid (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 161:

| | |
|---|---|
| GATCCTGAAT GAAAATCTCA CTGCTCGGCT TGTTGGTCAG TTCGGCCATG | 50 |
| GTCTGGCGCA CGTGCTCCAG CATGCCGCCG ATATTGGTCC CGGCCTCGCC | 100 |
| GTGACGTTGT CGAGCTTGCC GCAACCGTCC ACCGCTTTGC TGATGGCTTC | 150 |
| GGACGCCGGC GGCAACATCC ACACAGCGCA CCGAGACCCT GAGCCTGACG | 200 |
| CTACCGGATC CGGCGGTATG AGCGGTTAGC GAG | 233 |

(2) INFORMATION FOR SEQ ID NO: 162:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 162:

| | |
|---|---|
| GATCTGTTCC GTCTGACGGC GGGTAAACTG ACCGGCCTGG ACCGAATGGG | 50 |
| GCCAAAGTCC GCGCAAAATG TTGTTAACGC GCTGGAAAAA TCCAAAACGA | 100 |
| CGACCTTTGC GCGTTTTCTC TATGCGCTGG GCATCCGTGA AGTGGGTGAA | 150 |
| GTGACGGCGG CGGGGCTGGC GGCTTATTTC GGTACGCTGG AGGCGCTGCA | 200 |
| GGCCTCCGAC CATTGACGAG TTCGAGAAGT ACTACT | 236 |

(2) INFORMATION FOR SEQ ID NO: 163:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 163:

| | |
|---|---|
| GATCGCGTGT CGGTGCGTGA TTTAAGCCGT GGCTTAATCG TGGATTCCGG | 50 |
| TAACGATGCC TGTGTGGCGC TGGCGGATTA TATCGCGGGC GGGCAGCCGC | 100 |
| AGTTTGTGGC GATGATGAAC AGCTATGTGA AAAAACTCAA TTTACAGGAT | 150 |
| ACCCATTTTG AAACCGTCCA CGGTCTTGGA TGCGCCGGGA CAACATAGCT | 200 |
| CCGCGTATGA CCTGGCGTAC TCTACGGCGA TTATTCACCG GCCGAAGCCT | 250 |
| TGAATTTATC ACATGTACAC GAGAAAAGCC TTGACCTTGA ACCGATTAGA | 300 |

GCAGAACCGA ACGCTTGATG GATAGACACG AATG    334

(2) INFORMATION FOR SEQ ID NO: 164:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 164:

GATCGTAGTG GAGAGTGTCG CCGAACGTCT GGTGCAGCAA ATGCAAACCT    50

TCGGCGCGCT GCTGTTAAGC CCTGCCGATA CCGACAAACT CCGCGCCGTC    100

TGCCTGCCTG AAGGCCAGGC GAATAAAAAA CTGGTCGGCA AGAGCCCATC    150

GGCCATGCTG GAAGCCGCCG GGATCGTCTG TCCCTGCAAA AGCGCCGCGT    200

CTGCTGATTG CGCTGGTTAA CGTCTGACGA TCCGTGGGTA CCAGCGAACA    250

GTTGATTGCC GATGCTGCCA GTGTAAAGTC AGCGATTCGA TAGTGTGTGG    300

CGCCTGAG    308

(2) INFORMATION FOR SEQ ID NO: 165:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 165:

GATCCCATCG CGAATATCGG TAAAACAGCG CTTCTGCTGA CCGCCGTCGA    50

TAAGCTTGAT CGGCGTTCCT TCTACCAGGT TCAGAATCAA CTGCGTTATC    100

GCGCGTGAAC TGCCGATACG CGCCGCGTTC AGGCTATCCA GCCGCGGCCC    150

CATCCAGTTA AAGGGACGGA AAAGCGTGAA GCCAATCCCT CTTTTTGCCA    200

TAAGCCCAAA TCACCCGTCG AGAAGCTGTT TGGAAACGGA GTAAATCAGG    250

GCTTATTCAC CGGCCCGACG ATCAGATTGA TTGTGTTGTA AAGAGGCTCT    300

AATCGGTCAC ATTAGAGAGA GGAAACATTT AGTATTAGAT AAGATACCGA    350

GTTTAATAGT AA    362

(2) INFORMATION FOR SEQ ID NO: 166:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 166:

ATCGCGTTGT GTTGCCGAGC ATTTATTACA AGGCGCTTCT GTGTGNCNCT        50

CGAATGGTGC NGCAAGACTG C                                      71

(2) INFORMATION FOR SEQ ID NO: 167:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 167:

GATCGTGTCG CAATTCTTAA TGCCATAGAG GGTAATCATA TTGAATCCTT        50

TAACGCGAAA TTCGAATAAA TAATCAATAG TATCGTCTGC GGGATAATAA       100

GTGTGGCCGT TTATGGTTAT TTATCCAGCG CTGATCGGCA ATCAATATAA       150

CATTGTTGAG TGAATGTGAA TAATGATTCC TTTTCGTTCC AGATGTGGCT       200

TGTTTATACT TCGCCGGTAT AATCCTATTT GGGCAAATGC AATTGTGTTT       250

ACCATTGATA AGGTAGGTAG GAAAGGTATA TGTGCTAATA TGGCGTAGTC       300

ACATAATTAG TCTACGGCCA TGATCAGACG CAACAGGATC GACTCGTATG       350

ACTTTACGAC CGC                                              363

(2) INFORMATION FOR SEQ ID NO: 168:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 168:

GATCCGGCGC TGATTTTCAC CATCACGTTT TTCATCGGCT GACCTGCGGC        50

GTCTTTCACG TCGATGGTGG CGGCCATCTG CTCGCCCTTC TTCGCCTTTG       100

CGCTTCCGGT GGTTTCATCC TGGCCTGCCA GCGTCAGCTC AGGCTGGCGG       150

CGGCGCTGCG GGCGAGGCAA GACAGGTCTG CATGTAGTAC ATCGAGGTGC       200

TGGTCGTCGT TTGACATCAT TGCCGTCGTT AAACAGGTTG ACCGCCGCAT       250

AGAGCGACTT GTGCCGTCTG ACGATATCAC GTAATCCCGC CACAGTAGCG       300

CTGAGCTGTG TGCTGACTGT ATGCACTAG                             329

(2) INFORMATION FOR SEQ ID NO: 169:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 169:

```
GATCTGGCGG GCGCGTGAAA ATATGTTGCT GGCCTCCTGT ATGGCGGGAA        50

TGGCCTTTTC CAGCGCCGGT CTGGGGCTGT GTCATGCGAT GGCACACCAG       100

CCTGGGGGGC GCTGCATATT CCGACGGCCA GGCCAACCGA TCGTCGTCGC       150

AACAGTCATG GGCTTTAACG GATCAGTTTA CGGAAAGTTC AGTAATAT         198
```

(2) INFORMATION FOR SEQ ID NO: 170:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 170:

```
GATCAACATC AATAACTAAA ACTCTTTTAC CAAGATAGTT AGCCATGAAC        50

TCAGCAATGC CAACACATAG AGTTGTTTTT CCTACCCCGC CTTTCATATT      100

AATAAAGCTA ATTACCGATG CTGGCATAAT TATTCCTTGC TATGTTGAGA      150

ATGAGTCATT TTGATAATTA CTCGAGCTTT TATCTTAATC TTCGCGCGTT      200

CGAATCCTTC CCTTCATGTA CTTCTCGTAC ATGGCATCCA GTTCCTTGAG      250

ACGAGATAAT ACCCGAAGAA AAT                                   273
```

(2) INFORMATION FOR SEQ ID NO: 171:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 171:

```
GATCGCTGGT TCTGGCGGCA CCCTGGCGCC AACCCAAGCA ACGTCGCGCG        50

CGCGGCATGG CAGGATCTTA CCGCCGGGCG CGTTATTATT TCCGGCGGCA      100

GTACGCTGAC TATGCAGGTG GCGAGACTGC TGGACCCCGC ATTCGCGCAC      150

GTTCGGCGGT AAAATCCGCC AGCTTTGGAG CCCTCCAGCT TGAATGGCAT      200
```

TTGTCCAAGC GCGATATCCT GACGCGTGTA CTGAACCGAG AGTG                              244

(2) INFORMATION FOR SEQ ID NO: 172:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 172:

GATCGCGCAG CGCTCTCATA GCACAAAACG AGGTTTTCCA TTCTGTTATG                        50

TTCCCTGGCG ACGATAAACG TTCGATTGTC TCATGGCGCT GGTGAACCTT                        100

ATTTTTTAAC GGAGATGTTG AATGGCGGTA GAGGTTGTAC GTAATGGCCA                        150

AACCCGGCGG CGGATCTCGA ATATTGATTC GGCAATATTC GTTCTATCTT                        200

GGAAAAGGAG CGCTGTACCG GAACGGAATA AAACTGCGAT GTGCAGA                           247

(2) INFORMATION FOR SEQ ID NO: 173:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 173:

GATCAGCTTG CCGCACTGTA TGCCTCCAGC GACGGCAATA AAATCCACAC                        50

CGTATCCGGC TGGCCGACTG AGTATGACTA CTGGTCATCC ACCTTCGCCA                        100

GCGCCGCTAC ATGGCAGGCG GTATCACTGG CTGCGGGCGG CTATACCGCT                        150

TCCGGCGATG CGGTCGGACT ACGTGAGCTG TCTGGTCAGC AAAAATCGAC                        200

GCGCGTCTAT CACCATTGAG CCGGTGGATG CGCATTGTGT ATACGCAACA                        250

GCGAACACGC GTGAAGGTGA AAGGCATACG TCAGCTTAAG TGACGTAAGA                        300

(2) INFORMATION FOR SEQ ID NO: 174:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 174:

-continued

| | |
|---|---|
| GATCCGGACC GTGCCTTATA CCCTGAAAAA GGGGGAGACG GTGGCGCAGG | 50 |
| CGCACGGCCT GACCGTCCCA CAGCTGAAAA AACTGAACGG GCTCCGCACT | 100 |
| TTCGCCCGCG GCTTTGACCA CCTGCAGGCC GGCGACGAGC TTGACGTTGC | 150 |
| CGGCGGTCCC GCTGACCGGC GGGAAAGGTG ACAATAACCG CCATGACGTC | 200 |
| CGCGGTCCGT TTGCTGCTGA CCGGGAAAAT GAGGACGATC GCAGGCAGCA | 250 |
| GATGGCCGGC ATGGCTCACA GGCGGCAGCT TCTGCCAGCC ATCGGACGTT | 300 |
| AGGCCGCCGC GGATGGTTCG TATTCGCGTT GACATGT | 337 |

(2) INFORMATION FOR SEQ ID NO: 175:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 175:

| | |
|---|---|
| GATCAATGAA GCTTTGTGGG AAGTCTTGAC TTTCGTCGAT AAATACGTAA | 50 |
| TCAAGTGCCT TTTTATCAGC TCTCCCACTA TTATTTATAT CTGCAATGGC | 100 |
| TTTCTTACAT AGGGCATCAA AATCGCCATT ACCAAATCCC CCAAATGGAA | 150 |
| TTTCGCTAAT AATGGCATAT ATATCTGGTA CATTCCAGAA AAAGGTTCTT | 200 |
| TACGTCAAAC CCCAAGAGTT GAAGCAAAAA AGTTTTTGTA CCCCATTCTA | 250 |
| TCTGTTTTTC GACTCGCATA AATCGAAAAA CTCAGGGATT CTGGTTCTCA | 300 |
| TTGTGGAGCA GATTATAAGC AGTAATGCAT CTAGATACGG TTTGATACTC | 350 |
| TCTAGTGTAG TATCAGTTAC TGACAGCTAC TGCATAACCC TTTCAGCACT | 400 |
| GAGACACGTG CGCAAATGTG TAAA | 424 |

(2) INFORMATION FOR SEQ ID NO: 176:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 176:

| | |
|---|---|
| GATCATTTGA TTAAAACCTC ACACCGCAAG ATGCGACTTT TTGTAAACCT | 50 |
| GCTTTACCGC TGACACATTT CTCCGCATTA CTGCGGAACA AGGCTTAAAA | 100 |
| AGCGTATCCG AACGTATAAC CCTCCAACGT TCGCTACGGG AAAAATGGGG | 150 |
| ATGAGTACTG GAAGGTCGCA TATATGACCA AGCCAGACAT | 190 |

(2) INFORMATION FOR SEQ ID NO: 177:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 177:

| | |
|---|---|
| GATCCATGCC TGTGATGCCT GGATGTCCCG AATACTTGAA GGTTTGATCG | 50 |
| AACGGCAGGC CAGTAATGGC AACGCCACTA TTCTGTTATC TGCGACGCTA | 100 |
| TCGCAGCAGC AGCGAGATAA GCTGGTGGCG GCATTTTCCC GTGGGGTGAG | 150 |
| GCGTAGTGTG CAGGCGCGTT GCTAGGCATG ACGATTATCC CTGGCTGACT | 200 |
| CAGGTCACAC AAACAGAGCT GATTTCTCAG CGGGTTGATA CACGCAAAGA | 250 |
| GGTTGAGCGT TCGGTAGATA TTGGCTGGCT ACATAGTGAA GAGGCGTGTC | 300 |
| TGAACGTATA GTGAGCAGTG AAAGAACTGT ATCGCTGATA CGTACTCGTG | 350 |
| ATGATCGATC GATCTACCGA GCTACTCACT GGTAGGGCAG AACTTACTCA | 400 |
| AGGCTCTCAG GCGTCTAACA GGCGTCTAAC ACGTGGAAGT T | 441 |

(2) INFORMATION FOR SEQ ID NO: 178:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 178:

| | |
|---|---|
| GATCGTCGTT ACCGGCGACG GTTAAAGCAA ACTGGGCATC AATGGGCCGT | 50 |
| AAGAGTTTTT GTTCAACGGC CTCCAGCAAC CGCTCCTGGA TTGTCATTGC | 100 |
| GCCTCCTCAC TCATTTCACC TGCAAACATA TCATCCAGTT GGTTAATTAA | 150 |
| CGCCGCCGCA GGACGAGTGG TAAAAATACC CTGCTGCGGA CTGTCGCCAT | 200 |
| CCACCCCGCG TAAAAAGAGA TAGATGACTG CCGCCGAAAT GGCGTTCATA | 250 |
| GTCGTAATTC GTCATTCGAT GACGAAGGTA ACGGTGCAAT GCCAGCGTAT | 300 |
| AAAGCTGGTA CTGCAAATAT AGCGATCGCG TGCTCCGCGC AGCCATGCGT | 350 |
| CTGGATAGCG CTATCTGCCG | 370 |

(2) INFORMATION FOR SEQ ID NO: 179:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 179:

```
GATCCGGGTA CTATGAGCCC AATCCAACAC GGGGAAGTGT TCGTTACTGA          50

AGACGGCGCT GAAACCGACC TGGACCTGGG GCACTACGAG CGTTTCATCC         100

GACCAAGATG TCTCGCCGCA ACAACTTCAC GACTGGCCGC ATCTACTCGA         150

CGTTTCTGCG TAAAGAACGG TGACTATCTG GACGACAGT ATCTAATATA          200

CGGATTAAGA GG                                                  212
```

(2) INFORMATION FOR SEQ ID NO: 180:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 180:

```
GATCTTCTTC ACGTCTGGCT TCATCACTCT GATGAACGAT ATGCTCGGTC          50

AGATGACCTT TAATCACCTC GCGCATTAAG CCATTTACCG CGCCGCGAAT         100

CGCCGCGATC TGTTGTAACA CGGCCGCGCA TTCATGCGGT TCATCCAGCA         150

TTTTTTTTAG CCGCTATCAC CTGTCCCTGA ATCTTGCTGG TTCTGGCTTT         200

AAGCTTTTGT TTGTCCCGGA TGGTATGTGA CATTACAACA CCTCACTAAA         250

CATTAACGAA TACAAATTAT AGCATTACCA GATGCTACTG GGGGGTAGTA         300

TCTATACTGG GGGAGTAGA ATCGACGCCC ACATAAAACA ACTAAGAATC          350

ACTCATGGGT GAATTTC                                             367
```

(2) INFORMATION FOR SEQ ID NO: 181:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 181:

```
GTATCACGTT TGATGCGGCT GTTATCGTCC AGATAGCCGG TGCGATAGGC          50

AAAATAATGC GGCAATGAAA GCGCCAATCG CCAGGGGGA TCCCCACAAT          100

ATATGCCAGC ACGACCCCGG GGAATACCGC ATGACTCATT GCATCGCATT         150

CGCGCTTTTA CACTAAAACC CGCGTAGGAG ATCGCAATCG GACTAG             196
```

(2) INFORMATION FOR SEQ ID NO: 182:

(i) SEQUENCE CHARACTERISTICS:
    (A) LENGTH: 266 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 182:

| | |
|---|---|
| GATCTGTCGC GTTTTCGCCA GAATAGCGCG CGGAATAGAT ACCCGGCGCG | 50 |
| CCGCCTAAAA CGTCAACGGC CAGACCGGAG TCATCGGCAA TGGCGGGCAG | 100 |
| GCCGGTCATT TTGGCGGCAT GGCGCGCTTT GAGAATCGCG TTTTCAATAA | 150 |
| ACGTCAGGCC GGTTTCTTCC GCGGAATCGA CGCCCAGTTC CGTTTGCGCT | 200 |
| ACCACATCAA GCCAAAATCG CTTAACAGCG AGCNNCACTT ACGCGTNTGC | 250 |
| GAGACACTTT NCTGAG | 266 |

(2) INFORMATION FOR SEQ ID NO: 183:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 183:

| | |
|---|---|
| GATCATCATC ATTCCGCAGC CAAACGCGCG GCTTTTACCG AACCCCTGCG | 50 |
| CCAGACGTTG CAGGAAAAGC GCGGGTTCGT TAATCACCAG CACGCCGGTA | 100 |
| TAGTCCACGC TGCTAAACTG AATCATCTGG CCGATCTTTT CCCGCGACGT | 150 |
| ATCTGCCTGC CTGCCGATAA GCATCAACGC TCGGCTCGGC AGAGTAAAGC | 200 |
| CATTTTGCCT CCCCCTGCGC GCCAACCACG CAGGCGCTGC TGCTGATAAG | 250 |
| ACCAAATATG CTGGCTATCA CCTGCGTTTA GTGGCGATTT AGACTCATCA | 300 |
| GCAAATCGTG AGTTGCGTTT TGCAACGAGA TTGGGAGGTT AACGAGATGA | 350 |
| A | 351 |

(2) INFORMATION FOR SEQ ID NO: 184:

(i) SEQUENCE CHARACTERISTICS:
        (A) LENGTH: 398 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 184:

```
GATCATGTGG TGATCTGCGC CGGACAGGAA CCTCGCCGCG AGCTGGCGGA            50

CCCGTTACGC GCCGCAGGTA AAACGGTACA TCTTATCGGC GGATGCGATG           100

TCGCGATGGA GCTGGATGCC CGACGGCGAT TGCCAGGGCA CCCGACTGGC           150

ACTGGAGATT TAACGACTTT GCCTGATGGC GCTACGCTTA TCGGGCTTAC           200

GCCGTCATAC CGGTTTTATA GGCCGGTATG ACGCTTGAGC GCTTATCGAC           250

GGCGTCCTGC TTCACCGCTT TCAAAATGAC AAATTTATTG TTGGTGCTAT           300

CGTCGCGCAA TTACCGAAAT CTTCTTCAGC TGTGGAAATA GTCAGATGGC           350

GTTCGCACAT ATACAGTTGC CGTGATTAGC ACACGCTATG CAATTCAG             398
```

(2) INFORMATION FOR SEQ ID NO: 185:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 185:

```
GATCGCTATT GGTATGGCCC CACTTGCCGT ATTTCACCGG AAGCGCCGGT            50

GCCCGTGGTT AAGGTAAATA CCGTTGAGGA ACGCCCGGGC GGCGCGGCGA           100

ACGTGGCGAT GAACATTGCG TGCTCTGGGA GCGAACGCCG TCTGGTCGGC           150

CTGACGGGTT ATTGATGACG CCGCGGCGCC TGAGCAAAAC GCTGGCGGAG           200

GTCAATGTGA AGTGCCGACT TCGTTTCTGT GCCGACGCAT CCGACGATTA           250

CCAAACTGCG AGTACTATCT ACGTAATCAG CAGCTCATTC GTTTGATTTG           300

AAGAAGGCTT TGAGGATGAC CGCAAGCCGT TGCATGAGCT ATAACCA              347
```

(2) INFORMATION FOR SEQ ID NO: 186:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 186:

```
GATCGGCGTG CTGGCGGCGA CCTGGCCGCG GGAAATACCC TGGAAGAGGC            50

GTGTTATTTC GCCAATGCGG CGGCGGGCGT AGTGGTAGGT AAACTCGGGA           100

CGTCAACGGT TTCCCCTATT GAGCTGGAAA ACGCAGTGCG CGGACGGATA           150

CCGGCTTCGG CGTTATGACC GAAGAGGAGT TGAGACAGGC CGTCGCCAGC           200

GCGTAAGTCG CGAGAAGTGT CATGACCAAC GCGTTCGATA TCTGACGGCA           250

TTATGACGCA ACTGGACCTA TCGGATACTT ACTAGACTAC ATAC                 294
```

(2) INFORMATION FOR SEQ ID NO: 187:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 187:

```
GATCCGCATT GTCAGGGATA TCGCCCTGAA CGCGAGCTAC GCCGGCATCT        50

GCTGCTGATT ATTGCCATTG ATCACCGCCA GCTTAACGGC CCGTCGCCCT       100

GGAGCTGTAC CGTAATGTCA CCAGCAAACT TCAGCGTCGC GTCAGTAGGC       150

TAGTGGCGAC CAGCAGTTCG GCAGTACGTT TTCACCGGCT GCGGATAGTT       200

ATGATTGTCG AGGATCTGTT GCAAGGTTTC CGAAACAGTT ACCAGCTCGC       250

CGCGAACACA AAGTTTTCAA ACAGATAACG ATGTAATTGG TCATGTTGCG       300

CATAATCATC TCTCTTCAGT ACATTATTCA CTATACGTGT TTAAATCGTA       350

CA                                                          352
```

(2) INFORMATION FOR SEQ ID NO: 188:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 188:

```
GATCCTTACC GTTTTGGTCC ATTAATACAG GAAATGGATG CCTGGCTATT        50

GACGGAAGGC ACCCACCTGC GTCCTTATGA AACGCTGGGC GCGCACGCCG       100

ATACGATGGA TGGCGTCACC GGCACCCGTT TCTCCGTCTG GGCGCCTAAT       150

GCTCGTCGCG TTTCGGTTGT CGGGCAATTC AACTATTGGG ATGCGCCGTC       200

GCACCCGTAT GCGTCTGCGC AAAGAGAGCG TATTTGGGAG CTGTTATCCC       250

GGCATAATGG ACACTGATAA TCGAGCTCGT ATCGCAAGAA                  290
```

(2) INFORMATION FOR SEQ ID NO: 189:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 189:

| | |
|---|---|
| GATCTTCAGC AACCACGACA GGAATGCCCG TCTCTTCCAT TAACAGACGG | 50 |
| TCAAGGTTAC GCAGCAGGCG CCGCCCCGGT GAGCACCATA CCGCGCTCGG | 100 |
| AGATGTCTGA CGCAGCTCCG GCGGACACTG TTCCGGCGCA CCATTACCGC | 150 |
| GCTGACGATA CCGGTCAACG GTTCCTTGCA ACGTTCCAGA ATCTCGTTTG | 200 |
| CGTTCAGGGT AAA | 213 |

(2) INFORMATION FOR SEQ ID NO: 190

(i) SEQUENCE CHARACTERISTICS:
        (A) LENGTH: 256 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 190:

| | |
|---|---|
| GATCGCTTTG GTTAAATCCC CGCCGCCAGT GTCGGCGCGA CCAGAGCGGA | 50 |
| ACGTGACGAT TCTGTCGGGA AGCTGCAAGC CAGTGCTGCG GCGGCCATGA | 100 |
| GGACTTCCTG CAACAGTAGA CGCGCCAGTG CGGCGGCAAT TTCGCTGCGG | 150 |
| CGGGTAAATT TAAGCTGATG CACCAGTAAA CTCAAGGCGG TGTATAGTCA | 200 |
| CTGACGCTCA CCAGACTTGC AGGGTGGCGG TTTTTTCAGG CAGCGACCGC | 250 |
| ATGGGG | 256 |

(2) INFORMATION FOR SEQ ID NO: 191:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 191:

| | |
|---|---|
| GATCGTGGCT GCCGGTGCTG TCGGTGTAGC CACCACATTG ACGGCGGTCT | 50 |
| TGGGATACTC TTTCAGCACC ATCGCCACGG CGGTCAGCGT CTTAGCGCCT | 100 |
| GCCGGCTTTC AGCGTCGGCT GCTGCTGTCG AAGGTGACAT TATTCGGCAT | 150 |
| ATTAGAATGA CTACTTACTC GCCCGCCTTC GGCTCACGCT AACGCCTGTG | 200 |
| CCCCGATTTG TAGAGTTTGC TTCTGTACGT AGAGTAACCA GCGCGCA | 247 |

(2) INFORMATION FOR SEQ ID NO: 192:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 192:

| | |
|---|---|
| GATCCATTTT AACTTTAGCG GCCCTTTTGG CGAGGAGATG ACTCAGCAAC | 50 |
| TGGTCGGGCT GGCGGAGTCT ATCAATGAGG AGCCGGGCTT CATCTGGAAA | 100 |
| ATCTGGACAG AAAGCGAGAA AAACCAGCAA GCTGGCGGTA TTTACTTGTT | 150 |
| TGAATCCGAA GAAACGGCGC AGGCTTATAT TAAAAAACAC ACTGCGCGTC | 200 |
| TTCGAAAAAT CTTGGCGTTG ATGAGGTGAC GTTTACATTA TTTGGCGTGA | 250 |
| ACGACGCGCT GACGAAAATA AATCACGGCA ACCTTTGCCG CTAAATCACA | 300 |
| TAACGCAGGT TCTGTTCCGG TGCTGCTGAC CGCAACGGTA ATCTTTATAC | 350 |
| CGGGCGAGTA CCTAAGAGGC TTTATGGACG ACAGCGACAC GACGTTTCAG | 400 |
| CG | 402 |

(2) INFORMATION FOR SEQ ID NO: 193:

(i) SEQUENCE CHARACTERISTICS:
            (A) LENGTH: 240 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 193:

| | |
|---|---|
| GATCGCGAAG CCGCACAACG TAAGCAGGGG TTATGTAGTG TGTTCTTCAA | 50 |
| CACCACGCTA TTCATGCCGT ACCGCAGGTA GATGTCCCCC TTAGGAGCAT | 100 |
| CGCTTACGCT GGGAACAGCG TTTAAGCAGC TTTTTGACAA GGGAGCTTTG | 150 |
| ATGTATTGTT TGCAGTTCTA GACCTGACAC GGGCGATGAA TAGGAGCAAA | 200 |
| GCGTGGTTTA CACATCCATA TTGCTATGTT ACACTATTAC | 240 |

(2) INFORMATION FOR SEQ ID NO: 194:

(i) SEQUENCE CHARACTERISTICS:
            (A) LENGTH: 248 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 194:

| | |
|---|---|
| GATCCCCTCT ATACCGCAGA CAACACAAGG CGCGCTTGCT AACGCGGTGT | 50 |
| TACAGGGCGA AATCTTTCTA CAGCGCGAGG GACATATCCA GCAACGGATG | 100 |
| GGCGGGATGA ATGCGCGCTC GAAAGTCGCA GGAATGTTAA TGCGCCAGGA | 150 |

```
TAACGCCCTC CGCTAAATTC TTGGTATTTT ATTTGGCTGG CCGACGTCGC          200

AAATTAGCCA AAGTTAGCCA ACTTCTAGCT GATTCATCTA CGATAATT           248
```

(2) INFORMATION FOR SEQ ID NO: 195:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 195:

```
GATCGGGGTT CAGCTCAAAT TTTTCAATCG CCCAGGCAAC ACCATCTTCA          50

AGGTTCGATT TAGTCACAAA GTTAGCCACC TCTTTGACCG ACGGAATGGC         100

GTTGTCCATT GCCACGCCCA TACCGGCGTA TTCGATCATC GCAATGTCGT         150

TTTCCTTGAT CGCCATCACC TCCTCTGCTT AATACCCAGC GCCTCGACCA         200

GTGATTTACG CCAGTGCCTT TATTAACCGT TATCGAGGAT TCAAGGAAAT         250

ACGACACTTA CGCACGGTAC TTCTCATTGC GAACGCATGC GCGAACGCAG         300

TCAT                                                           304
```

(2) INFORMATION FOR SEQ ID NO: 196:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 196:

```
GATCTGCGCC CCAGCGTTTG CAGCAGAAAA TAAAAGCCGA AAATCACCAC          50

TAAACAGGCG ATCAACACGT AGAGAAGCAA CCTCCCAATC AATTTCATGG         100

TCTTCCATCC CGTGAAATGC ACATAGGGGA TTTATGCACG ATTTGCGTGC         150

AATCCTCAAG ACAGGAATGG TGAAAGAGCG TTACAGCAGC GGCGAATCGT         200

GTCGCGCGCA GGGTTTTTAC GGTTTTTCGG CGGAGAATCA GTCAGCACGA         250

TAGCGTGATG CGCAGCGATC GATGAGAGCG ATTTACCATC GGACTGAGAT         300

T                                                              301
```

(2) INFORMATION FOR SEQ ID NO: 197:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 197:

| | |
|---|---|
| GATCCAATCC TGAACGCCGA ATTTTCACCA CAGGGCGTTG CGCTACGCCA | 50 |
| GTTCACTACC CGCTGGGAAG GCGGTATGGT CAGAACTTCC GGCGCCTGGT | 100 |
| TACGCGAAGG CAAAGCGCTT ATTCTGGACG ATACCGCTAT CGCCGGGCTG | 150 |
| GAGTATACGC TGCCGGAAAA CTGGAAGCAG TTATGGATGA AGCCGCTGCC | 200 |
| CGACTGGTTG AACAGCTGAC GCTGAAAAAT TCAGGCAGCG CAATCTGGTG | 250 |
| ATTGATATCG ACCCGGCCTT CCGTGCAAAT CACCGCTCTG ACGCTACGCG | 300 |
| CAAACTGAGC TGTACAACCA TCATCAATGG GCTCTGAGCG CATCGACTAC | 350 |
| GGCAGCGGAA CTTTAC | 366 |

(2) INFORMATION FOR SEQ ID NO: 198:

(i) SEQUENCE CHARACTERISTICS:
        (A) LENGTH: 310 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 198:

| | |
|---|---|
| GATCGCTACC CAATTCCGCG CCCACACAGC CTGCTTTAAT CCATTGCGCT | 50 |
| AGGTTTTCCG GCGTCACGCG CCGACGCAAA TAGCGGAACA TCCGGCGGAA | 100 |
| GTACCGCTTT CAGCGCGCTG ATGTAGCCCG GACCAAACGC CGACGACGGG | 150 |
| AAAATTTTTA ACTTCTGTGC TCTCTGCATC CAGCGCAGAA AAGGCTTCCG | 200 |
| TTGCCGTCGC GCAGCCGACA CACGTCATGC CATAGCTCAC CGCCGCGAAT | 250 |
| CACTCGGTTG ATATCGCGTA CATCACTTCG CCATCGCACG TGTTCTTCGT | 300 |
| TAGCTGTACA | 310 |

(2) INFORMATION FOR SEQ ID NO: 199:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 199:

| | |
|---|---|
| TCGAAAATAC GTATACCCTG ACAGTGAAAG CAACCGATGT TGCAGGCAAC | 50 |
| ACGGCGACGG AAACGCTCAA TTTTATCATT GATACCACAT TGTGGACACC | 100 |
| GACCATCACG CTGGATAGCG CAGATGATAG CGGCACCGCC AACGATAATA | 150 |

```
AGACTAACGT TAAAACGCCC GGGTTTTATT ATCGGCGGTA TTGATTGATT              200

CTGACGTGAC TCAGGTCGTC GTGCAGGTGA TGCGCGATGG TCACAGCGAG              250

GAGGTGGAGC TGACCGAGAC TAACGGGCAG TGGCGTTTGT ACCGGCACGC              300

GTGGACTGAT AGGCGACTAT CGCGTACGTA GTGAAGATAG CGTATATA                348

(2) INFORMATION FOR SEQ ID NO: 200:

(i) SEQUENCE CHARACTERISTICS:
          (A) LENGTH: 279 base pairs
          (B) TYPE: nucleic acid
          (C) STRANDEDNESS: single
          (D) TOPOLOGY: linear (iii) HYPOTHETICAL: NO (iv) ANTI-SENSE: YES (vi) ORIGINAL SOURCE:
          (A) ORGANISM: DNA (other)

(xi) SEQUENCE DESCRIPTION: SEQ ID NO: 200:

GATCGGATAA CGACTCCGCG GTGGATGCGC AAATGTTGCT TGGCCTGATT               50

TACGCCAACG GTGGGCATTG CCGCCGATGA TGAAAAAGCC GCCTGGTATT              100

TCAAACGCAG TTCCGCCATT TCCGTACCGG CTATCAGAAT ACTGCGGGAA              150

TGATGTTTTA AACGGTGGAA CCGGGCTTTA TTGAAAAGAA TAAGCAGAAG              200

GTGTTGCACT GGTTGGATCT AGCTGTCTGG AGGTTTGATA CCGATACCGT              250

TGCAAGATTC GAACGCTACG ATGCTATTT                                     279

(2) INFORMATION FOR SEQ ID NO: 201:

(i) SEQUENCE CHARACTERISTICS:
          (A) LENGTH: 272 base pairs
          (B) TYPE: nucleic acid
          (C) STRANDEDNESS: single
          (D) TOPOLOGY: linear (iii) HYPOTHETICAL: NO (iv) ANTI-SENSE: YES (vi) ORIGINAL SOURCE:
          (A) ORGANISM: DNA (other)

(xi) SEQUENCE DESCRIPTION: SEQ ID NO: 201:

GATCGCCAGG GACGATGGCG AGCTGGGCCC CTTGTAAATC GTTTTTGGTG               50

AGGCCGAGAT GAAAAACATC AGACTTGGAC ATATAAAACT CCTCTGTGAA              100

TCGGGTTTGT CAGAAGAAGA AAGAGACACT TTACCTAAGG ATAAAGATAT              150

TTTGGTGCAT CATCACTATG CGTAAAACAA TTGCGTGTTC CATTAAAAAG              200

AGATGCCCCA TCACAATAAA TAATCAATAT GCAGGCATTG CACAAAGCAT              250

AGGCGTTTAG GCATGTGTTG TA                                            272

(2) INFORMATION FOR SEQ ID NO: 202:

(i) SEQUENCE CHARACTERISTICS:
          (A) LENGTH: 401 base pairs
          (B) TYPE: nucleic acid
          (C) STRANDEDNESS: single
          (D) TOPOLOGY: linear (iii) HYPOTHETICAL: NO
```

-continued (iv) ANTI-SENSE: YES (vi) ORIGINAL SOURCE:
    (A) ORGANISM: DNA (other)

(xi) SEQUENCE DESCRIPTION: SEQ ID NO: 202:

```
GATCCAATAA TGACTGCATT GCCTCATACC CCATACGTAA CGCGCTATAC          50

AAAATATAGA TGCCGATACC TAACGCAAAC AGGGCATCCG CACGATGCCA         100

ACCGTACCAG GATAACCCCA GCGCGATAAG AATCGCTCCG TTCATCATAA         150

CATCAGACTG ATAATGAAGC ATATCGCCCG TACCGCCTGA CTTTGGGTCT         200

TGCGTACCAC CCAGCGCTGA AACGTGACCA GTATAATAGT GCATATCAGA         250

GCATGACGGT AACGCCAATC CCACGCGGGG TCGTTCATTG GCGTGGCTTT         300

AATCAGATTC TGAATACTGG TCAAAAACAG AAACACGCGA ACCGGAAATA         350

ACTACTTTGC GCGCGCAGGC ACTCGTTTAC GTGCCAAGGG TTAATGGTGG         400

G                                                              401
```

(2) INFORMATION FOR SEQ ID NO: 203:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 203:

```
GATCCAAAGT CGTTAAATAA CGGCGGGAAA AGCCTCCACG CCATGGAAGT          50

GCCCCGGAAA TCGCCCCGAC CATGGTGGCG ACAGTATCAG TATCATTGCC         100

GATATTAACC GCCGGAGATA ATAGCATCTA CGGCAGAATT CGGACAACAC         150

GCGAACAGGC CAAAGCGGC                                           169
```

(2) INFORMATION FOR SEQ ID NO: 204:

(i) SEQUENCE CHARACTERISTICS:
        (A) LENGTH: 253 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 204:

```
GATCCAAAGT CGTTAAATAA TCGGCGGGAA AAGCCTCCAC GCCATGGAAT          50

GCGCCGGAAA TCACCCCGAC CATGGTGGCG ACAGTATCAG TATCATTGCC         100

GATATTAACG CCGGAGATAA TAGCATCTAC GGCAGAATTC GGACAACACG         150

CGAACAGGCC AAAGGGCCGG CACCGCTTCA CTCACGTGCA GCCGGAGCAA         200

TATATAGCAG TTCACACGCG TTCCATGGAT GAGCTTCGAT ATAGCTCAGT         250
```

ATG                                                                        253

(2) INFORMATION FOR SEQ ID NO: 205:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 205:

GATCGTACAG ACCCGCGTTG TCATAACCAC GGGTTTTTAG TTCCGCCACA                      50

CGCTCGCCCG CCAGCGTTTT CATATCCTCT TTCGAGCCAA AATGAATGGC                      100

GCCGGTTGGA CAGGTCTTCA CGTCAGGCCG GTTCTTGCCG ACGTGTCACG                      150

CGGTCAACGC ACAGCGTACA TTATGACGTC GTTGTCTTCC GGTTGAGG                        198

(2) INFORMATION FOR SEQ ID NO: 206:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 206:

GATCGGAATG CCTTTGAACA GCGGCAGGTC TTCCAGCGGC AGTCCGCCGG                      50

TCACGGTCAC TTTAAAGCCC ATATCGGACA GCCGCTTAAT CGCGGTAATA                      100

TCCGCCTCGC CCCACGCCAC GGCTGCCGCC TGGGGTCACG GCTGCGGTGA                      150

TAAACCACTT GCTGAATACC CGCATCACGC CACTGCTGCG CCTGTTCCCA                      200

GGTCCAGTAA CCGGTCAGTT CGATCTGCAC GTCGCCGTTG AACTCTTTCG                      250

CCACATCCAG GGCTTTTGCG GTGTTGATAT CGCACAGCAA ATCACGGTAC                      300

CAGTACGGTT GGCTTCGAAA CACATACGGG AGAGGATTTA CGAATGCATT                      350

GGGAGAGATT GGGTAGGTCA GTAGACGAGA ATGCAGAGAT GGCATGAAGA                      400

TTGAAGGGTA G                                                               411

(2) INFORMATION FOR SEQ ID NO: 207:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 207:

| | |
|---|---:|
| GATCCTGAGC CGGGTAGCCA GTATTTGCAG GCAGCAGAGG CAGGTGACAG | 50 |
| ACGCGCACAA TATTTTCTGG CCGACAGTTG GTTGAGCTAT GGCGATTTGA | 100 |
| ACAAAGCTGA ATACTGGGCG CAAAAAGCCG CCGACAGTGG CGACGCCGAC | 150 |
| GCCCTGCGCG CTACTGGCCG AAATCAAAAT CACTAATCCG GTAAGCCTGG | 200 |
| ATTATCCCGA CGCGAAAAAG CTGGCTGAAA AGGCGGCTAA CGCGGCAGTA | 250 |
| AAGCGGGAGA AATTACGTGG CGCGGATCCT GGTCAACACC CAGGCCGGGC | 300 |
| CGGACTACCA AAGCCATCTC GCTGCTGCAA AAGGCCTCTG AAGATCTGGA | 350 |
| TACGACTCGC GTGATCGCAA TGTGCTTGCT ATTGACTGGG CATCTCGTTA | 400 |
| AA | 402 |

(2) INFORMATION FOR SEQ ID NO: 208:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 208:

| | |
|---|---:|
| GATCAAACGC GCTGGCGTAA TCGCTACTGG GTTGATAGCG AAGGCCAAAT | 50 |
| TCGCCAGACG GAACAGTATC TGGGCGCGAA TTACTTTCCG GTGAAAACCA | 100 |
| CGATGATTAA GGCGGCAAAA TCATGATGAA AAGGACGATA AGCGCGCTGG | 150 |
| CGTGGCCTTT GTCGCGTCAT CCGCCTTTGC CAGCGGCACT GTTACCGTTT | 200 |
| TTACCCAGGG TAATAGCGAG CTAAAACGCT GACAGACGCT GAGCGCTCGC | 250 |
| TCGATTAGTG GACAGCGCGC TGCACGAGCT GGTGGCTG | 288 |

(2) INFORMATION FOR SEQ ID NO: 209:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 209:

| | |
|---|---:|
| GATCAGGGAA CCTGTACCTC TTAAAGAGAA GTTCGATACC CCCAACGGTC | 50 |
| TGGCGCAGTT CTTCACCTGC GACTGGGTAG CGCCTATCGA TAAACTCACC | 100 |
| GAAGAGTACC CGATGGTACT GTCGACGGTC CGAGTCGCCA CTACTCTCCG | 150 |
| TCAATGACCG GTAACTGTC | 169 |

(2) INFORMATION FOR SEQ ID NO: 210:

(i) SEQUENCE CHARACTERISTICS:
    (A) LENGTH: 311 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 210:

| | |
|---|---|
| GATCATCTTC GTCCTGCTCT TCCTGACTCA GCGCACTGTT TACGACAATA | 50 |
| CTGTCCGCAT CTCGTTGTGC GATTTTATCG GCGACGTCGC GGGAATAATC | 100 |
| GCATATTCAC ATTACCGCT GTTATTGATA ACCAGACGGC AATCGCAGAC | 150 |
| GCCCATTAAT CAGTTGCGTC TGAGTGAGCT TATCCACGTC TATTTTTTG | 200 |
| ATGACGTTAT TATCGGTGAA GTTAAAACCA ATATCGCCTT TAGATACATT | 250 |
| GATTCTATTC ATTTCAATAA GTTGCTTAAC CTGAGCTTTA AACTCTTCGC | 300 |
| TAAAACCGCT G | 311 |

(2) INFORMATION FOR SEQ ID NO: 211:

(i) SEQUENCE CHARACTERISTICS:
    (A) LENGTH: 368 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 211:

| | |
|---|---|
| GATCAGTATC ATCAGTAATG GCCAGCGTTG CAGTATTCTG AATAGCCAGT | 50 |
| GAGGTTTTCA GCGGGAAAAT GGCGAGGGTA TACGGAACCG GTTCGGTGGT | 100 |
| GCCTTTTGTA GCAACGGTAA ACATTTCCAT ATTGCCGTTT TTGATAATCC | 150 |
| GGTGGAAGAC TTCTGCCAGA CTGGGCTATC AACGGTTCCT GAGATAGCGT | 200 |
| CAGATTTTAC ACCATCAGCG GTAACGTCGC GTATCGGTAT AAATAGAGAA | 250 |
| CGCGCCGATT TTTACACCTT CGGTTGTTTG CCAACGCGAG ACATTGTGGA | 300 |
| TCAGATACTA TACTATAGTC ATATCGCATG GCTATGAGAT ACGAGTGCCT | 350 |
| GGTGGTGTGC ACGTATGA | 368 |

(2) INFORMATION FOR SEQ ID NO: 212:

(i) SEQUENCE CHARACTERISTICS:
    (A) LENGTH: 258 base pairs
    (B) TYPE: nucleic acid
    (C) STRANDEDNESS: single
    (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 212:

| | |
|---|---|
| GATCATCCAC TCATCTTTGC CGGTTGAGCC CGATAGTTAC CCGTTCAATA | 50 |
| CCGGCATCAA TCGCCCCCGT TTTATTCACC ACCCCCAGAA AGCCGCCGAT | 100 |
| AATCAAGACA AACAGCCGCG ACGTCAATGG CGCCGGCGGT GTAGGTTTCT | 150 |
| GGGTTATAGA GGCCGTCAAT CGGCGCCAGC AAAACAGCGG TAATCCTTTC | 200 |
| CGGATGCGCA CGGGGCATAC GCTCCGCACC GACTTTCAGA GCTGCTATCG | 250 |
| ATTGATTT | 258 |

(2) INFORMATION FOR SEQ ID NO: 213:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 213:

| | |
|---|---|
| GATCATTGTC ACGCCATTTT TTTAAATTAT TAGTATGGCG TGTGGAGACG | 50 |
| CGTATCTGCT CACCAATATA CGTATTGTCC ATAGGCGTAG ACAAGCTCCA | 100 |
| TTGCTACAAA GATAATTTTA TTTAAGTGTC AGGAAAATTC CGGACAAATC | 150 |
| CCTTTTTTAA TAAAAATACA CACTCTCGGC ATGGGATAAT ACTTAATTAA | 200 |
| CTTTTGTTAG CGTTTTGAAA TTAAAAACAG CGCAGAGGTA ATAATAGAAA | 250 |
| ATAACGTTAA CAGGCTGGGT GAGTATATTT GACTGACACA ATTCCAGGTG | 300 |
| TATATGTATG CGTTTATGCA TG | 322 |

(2) INFORMATION FOR SEQ ID NO: 214:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 214:

| | |
|---|---|
| GATCATCCGC AGAAGAAAAA ATATGGCCGC GTAGAGATGG TGGGGCCGTT | 50 |
| CTCCGTTCGC GACGGAGAGG ATAATTACCA GCTTTACTTG ATTCGACCGG | 100 |
| CCAGCAGTTC GCAATCCGAT TTTATTAATC TGCTGTTTGA CCGCCCGCTT | 150 |
| CTGTTGCTCA TTGTCACGAT GCTGGTCAGT TCGGCGCTCT TGCCTATGGC | 200 |
| TGGCATGGAG TCTGGCGAAA CCGGCGCGTA AGTTGAAAAA CGGGCTGATG | 250 |
| AAGTGGCGCA AGGCAACCTG CGTCAGATCC GGAGTGGAGG GGAGAGTTCT | 300 |
| GGTGCAGTTT AACAGATCTA | 320 |

(2) INFORMATION FOR SEQ ID NO: 215:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 215:

| | |
|---|---|
| GATCAGATGG ACCACAACGA GCACCGAAAA CAAAACGGCG CTGACCATCA | 50 |
| GAATGACGGT AGTGCCGAGT TTCATGGGGC GTTTGCGTAA CGCCGGCATG | 100 |
| GCAGGGAGTG TTTCATAGTG GACCTGAGCG ACGAATCGTA AGGTTATTAT | 150 |
| CCCTGATGAG GCTCTAATTC AAAGGCATAG GCAGTCGTCC AGTGTGAAAG | 200 |
| CCGCTGCTGC AGGCCGCTAC TGCATCGTAT ATCGGACGAG ATTTCAATCA | 250 |
| ATAACACGCA ATTTCCGCAT CCAACCG | 277 |

(2) INFORMATION FOR SEQ ID NO: 216:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 216:

| | |
|---|---|
| GATCCTGAAA CGCTGACCAG ACGCCGAGCG CGCCGTACCA CGAATCTCCG | 50 |
| GTGGCACTCT GCGCACAACC TCTACGCCCA GCGATGGGAA CATCAGCGAA | 100 |
| CAGCCGCAGC CGGTAATCGC CGCGCCAATC AGCGAGCCTG CTGACGGAGC | 150 |
| GGCCCACATT ACCGCCAGTC CGGTCCCTCT ACCAGTAGTG AAAAGGTTGC | 200 |
| ACCGTGCGCG CGTAACGGTC GGGAAATTTG GCGCAGAAAA GCGGACAGCG | 250 |
| ATAAACGCAT CAACACTATG AAACGGTGAT ACAGTAGTGT GACAGAGTGT | 300 |
| ATCTAGTGAC ATCTGACAAC TTCTCTCAGC | 330 |

(2) INFORMATION FOR SEQ ID NO: 217:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 217:

```
GATCTGGGCG AAATCGCGCG GAGTCTGGCG GCGGGCGATA TCATTACCCA          50

CTGTTACAAC GGTAAGCCGA ACCGTATCTT CGGCCTGACG GCGAGCTGCG         100

GCCTCGGTGA CACGAGCGCT GGCCGGCGGC GAGGCTATGG AGTCGGCATG         150

GTACCGCCAG TCCTGAGCTT TGCGTGGCTA ACTCGCTATA GCTGGATTTA         200

CCGCATACAT CAGTCGATAT CTC                                     223
```

(2) INFORMATION FOR SEQ ID NO: 218:

(i) SEQUENCE CHARACTERISTICS:
        (A) LENGTH: 316 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 218:

```
GATCGCCACC GTTTTGTGAT GCGCGCCAAT TTGGGCTGGA TAGAAACCGG          50

TGATTTCGAC AAAGTTCCGC CGGATTTACG TTTCTTCGCC GGGGGGACCG         100

CAGTATTCGC GGCTATAAAT ACAAATCTAT TTCGCCTAAA GATAGCGACG         150

GCAATCTTAA AGGCGCCTCA AAACTGGCAA CCGGATCGCT GGAGTACCAG         200

TATAACGTCA CCGGTAAATG GTGGGGGCAG TGTTTGTCGA TAGCGCGAGC         250

GTGAGTGATA TCGCGTAGCA TTCAAACCGG ACGCCGACCG ACCGACCGTG         300

GCTTCAACCT ATTCAC                                             316
```

(2) INFORMATION FOR SEQ ID NO: 219:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 219:

```
GATCTGGGGT GGGGGATTGT TGATGGTGTG TGGAGCGCTG CTGAGCGGAT          50

GGCGGGGGAG GAAGCATCCT GAGTTATTGC CTGATGGCGC TGCGCTTATC         100

AGGCCTACGA GTGAAAAGCA TGGTAGGCCG GATAAGGCGT TCACCGCATC         150

CCGAAAACGA TGTTACTTTT GGCTTTACTG AT                            182
```

(2) INFORMATION FOR SEQ ID NO: 220:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
    (A) ORGANISM: DNA (other)

(xi) SEQUENCE DESCRIPTION: SEQ ID NO: 220:

| | | |
|---|---|---|
| TGCAGATCAA AACAGCGACG GCTGGCAAAA GCGGTAAAGG TTTACGACCG | | 50 |
| GTCAGCGCCC CAGCCGCCGC CGTGCCAATC ACATTCGCCT CCATAATACC | | 100 |
| GCAGTTAATG ACATGCTGCG GGTAGTCACG CGCCACGCTG TCATCGCCAT | | 150 |
| TGAGCTCATT AATCAGCCTC AGGATATGGC TTCAGCCTCA AGCGCAATAA | | 200 |
| TTGGGCTTCC GGCCTCAATC TGCCCGGCGA TAAAACCGGC GTAAACTTTG | | 250 |
| CGCATTTCGA TATCGTCTTT AAGCCCTGGG AAGCTTAATC ATGCATGACC | | 300 |
| TCCAGTTGAT GAATGGCCTC ATTGAACGTT GCTTATCGCA TCGTCAGCGT | | 350 |
| AAGTGGTGAG AATTCGTTAA CTGCTCAGGC ATGCACCCTG CCTTATGCTG | | 400 |
| TCAAGGATCA CACCGTGCT | | 419 |

(2) INFORMATION FOR SEQ ID NO: 221:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 221:

| | | |
|---|---|---|
| GATCTTATGA CATTGTGAGT ATCCATCGCT TTTTGTACTG AGCTGTAGGC | | 50 |
| AACTCCGACA GCTTTTGCTC AGCAGCTGTT GTTTCTCATA AGCTAGTGAC | | 100 |
| CAAGCTGCTG CTACCACAGG TCTGGG | | 126 |

(2) INFORMATION FOR SEQ ID NO: 222:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 222:

| | | |
|---|---|---|
| GATCCTGCAC GCACGGGCGC ACAGCACCGA CAAGCTGTCC AGCTACTTGA | | 50 |
| CACAGCGCCA GCGCGTGCTA GCGAGCGAAC CCGCAGGTGG CACATGGCGG | | 100 |
| GGACGGCGAG CAGGAGACAG GCTAGAACGC TTTATGTGCG CACTATGCTA | | 150 |
| TCAAATAGGC CGTCCGGCTG CACGCCGACA CTACCCTGAC AA | | 192 |

(2) INFORMATION FOR SEQ ID NO: 223:

(i) SEQUENCE CHARACTERISTICS:
            (A) LENGTH: 331 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 223:

| | |
|---|---|
| GATCACCGCA TCGCGAACTG GTTACGGGCC TGTGGAGCGT ATTTTTTGAT | 50 |
| GTTATTGGTA TTCATAGAAA ATCCTGCAAA GGGCAGCAGA GCGCTGCCCT | 100 |
| GAAATGGGGG TTACTGAAGA CGAATCCGGT CACCTGCCTC AATAGCTGCC | 150 |
| AGCAGCGAAG TACGAAGCGT ATCCAGCGCT TTTTCCACCT GTTCGGCGGT | 200 |
| TTCCAGCACT TCGCCACCGG TGGCTTTGCG CATCTCGCTG GCGACATTCA | 250 |
| CCAGATGCGT TTTTTCGGTA CCGGTTGGAT AACGGTTCTC TACCACAACA | 300 |
| TAAGCTCGTT GTGACTCGGC GCCTTAGCTT A | 331 |

(2) INFORMATION FOR SEQ ID NO: 224:

(i) SEQUENCE CHARACTERISTICS:
            (A) LENGTH: 410 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 224:

| | |
|---|---|
| GATCTAACGT ATCACGACTA AACGTAAGGG TAAAGCGGCT GGCGTATCGT | 50 |
| CCGGGCATAA AGTCATATCG CCTGAACAGA TAACATCTCA CTGACTTTGA | 100 |
| AACGCGATTT TATAATTTGC TGCCCAAAAA TACGTGGCGC TGAAAGGCGC | 150 |
| ATTTTTGATG CAAATCATTT ATTACTGTGA TAACACTGCG CGCGATAAAA | 200 |
| CATTAATATA TTCACATAGT AATATGTTCT ATTGGAATGG TTGTTTCGAT | 250 |
| ATGACAAAGT CTAAAAAACC ATTGATGTGA AAAGGAATAA GAATTGTCTA | 300 |
| TATTCCGATT CGGTGGAATT AAGTATTCTC GGATAAAATA GAATGATATT | 350 |
| GATATTCTTT TGATATGGTC TATAGCGCTA TGTATCAGAC GCGTGATCGT | 400 |
| CGGAGATCAG | 410 |

(2) INFORMATION FOR SEQ ID NO: 225:

(i) SEQUENCE CHARACTERISTICS:
            (A) LENGTH: 185 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:

(A) ORGANISM: DNA (other)

(xi) SEQUENCE DESCRIPTION: SEQ ID NO: 225:

GATCTTCGAC TGCCGCGCTT CCGCGACAGC GACATACGGG TGTTCTTTGT        50

CGGTGACGTT TATCCGTTGT CGTGACCTTC ATCCGGTGGT GAAACCTGAG       100

CCGAATAATA CTGTACACCA CCACCAGGAC AGAATACTCA AACCACGTTC       150

ATGTGATTGT TGCACCACAT ATTCATTGTT GGAAC                       185

(2) INFORMATION FOR SEQ ID NO: 226:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 226:

GATCCGCTGA CAGATGTCGT GTACAGCATT CTTTAGAGTG GAACGGTGAC        50

CGTACCGCAA AGCTGTGAAA TCAACGCCGG ACAAACGATT CTGGTAAATT       100

TCGGCGCATT ATACAGCGGC AATTTCAACC ATGCAGGCCA AAAGCCGGAG       150

GGGGTACGAG CGAAAAAATT CAGTCGCTTC CGGTAAAGTG CAGCGGTCTG       200

GATTCGCAGG TCAATTTAAC AATGCGTCTT ATCGCTCCGC GGATAGCACG       250

TCCAGCTATC GCTCGATATG CGATGT                                 276

(2) INFORMATION FOR SEQ ID NO: 227:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 227:

GATCACCGAC CGGACGGTCC GTACCTGGAT TGGGGAGGCG GTTGAGTCCG        50

CAGCGGCTGA CGACGTGACG TTCTCAGACC CGGTGACACC CCATACTTCC      100

GCCACTCCTA TGCGATGCAC ATGCTGTACG CGGCATACCG CTGAAGGTGC      150

TGCAGGCGCT GATGGGACAC AAATCGGTGA GCCTGACGAG TGTACCGAAA      200

GTGTTTGCGC TTGATGTTGC CGCACGACAC CGGGTGCAGT TTCAGATGCC      250

GGGTGCTGAT GCAGTGGCTA TGCTCAAAGG AGGTTCATAG AGACGTGTAT      300

GCATTTTCAG CTTCGCTGCA CAGCATCGAA CGGAGTTTAC GCGTTTATCA      350

GCCATGTCTG CGCACAGAGG AGTGTGCTCG AAA                         383

(2) INFORMATION FOR SEQ ID NO: 228:

(i) SEQUENCE CHARACTERISTICS:
            (A) LENGTH: 357 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 228:

```
ACTTGCCGGT AATTTCCATC CCTTCCAGCA CCGCCATCTC TTTACCCTCA            50

ATGGCGATGG ACAGTTTATC CAGCGTTAAC TTTTGGTCGC CCCACGTTCG           100

CCAAAGCTTG CCAGTTTACT GGTACCGTCG GTTTTCAAAT TATTAAAGGT           150

GAGTTGGACC TTCTGATTAT ATTCGTTAAC GGCATCGACC AGGCCGCTCT           200

CGCGCTTCGC CTGACAGCGA AACCACATTA CCGTCTTTAT CGGGCGTTAA           250

CGGGAACTCG GCGCCGCTAA AGGCACCTTT ACCGGCATTC TCTGAGTTAA           300

CCGGCTTGAG AGAGATATCG GAGCGGTATC GCCGCCATAC ATGCGGTATT           350

GATACAA                                                          357
```

(2) INFORMATION FOR SEQ ID NO: 229:

(i) SEQUENCE CHARACTERISTICS:
            (A) LENGTH: 225 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 229:

```
GATCTATTTC GGACAGCCAA AAGGCCGTGA AGGCAGCGGT CAGTACAAAA            50

AGCCTTTGAT ACCGAAGTTT ATCACCGGCT TTGAGATCGA GCGCAGTTGC           100

CCGTATGCCT TTGAATCGGC GCGTTAAACC GGCCGTAAAG TACCCTCTAT           150

TGATAAAGCC AACTACTGCA AGCTCTATCT GTGGCGTGAA TACGTCAATA           200

GTGGAAAACG TATCCGATGT GAACT                                      225
```

(2) INFORMATION FOR SEQ ID NO: 230:

(i) SEQUENCE CHARACTERISTICS:
            (A) LENGTH: 275 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 230:

```
GATCGTTAAA CAGATTGACC AGTTCGCCAC ACTCTTCCAG ATTAAACCCC            50
```

```
ACCTGCCTCG CCTGTCGCAG CAACGTCAGC TCGTTTAAAT GCTTCTGCGT              100

GTAGGTGCGA TAACCATTTT CGCTACGTAA TGGCGGCGTC ACCAGCCCTT              150

TCTCTTCATA AAACCGAATG GCTTTGTGGT TAGCGTTTTG GCACATCGCT              200

ATATCATATT GCCCTGCCTA CTGCTGAGTT ACTATACGGG TACTACGTCT              250

AGAGATCGCG AAAAGGTTAC AGTAC                                         275

(2) INFORMATION FOR SEQ ID NO: 231:

(i) SEQUENCE CHARACTERISTICS:
          (A) LENGTH: 233 base pairs
          (B) TYPE: nucleic acid
          (C) STRANDEDNESS: single
          (D) TOPOLOGY: linear (iii) HYPOTHETICAL: NO (iv) ANTI-SENSE: YES (vi) ORIGINAL SOURCE:
          (A) ORGANISM: DNA (other)

(xi) SEQUENCE DESCRIPTION: SEQ ID NO: 231:

GATCGACGTC GCCTGATTTA AGACCCGCAA GCAACATCGT ATTGTTCATG               50

GTCGCGACCT GTAACGAGGT CGATTTTTGC TGTTGATGGA ACCGCCCAAT              100

AGCCGCCGGG AGTATACCCA GCGCAGGTGG GGAGCGGCAA CACGCACCAT              150

CGGCGCTAGC TCCTCTTTGG CGATTCGATC GGATCCTGGC GGTGGTATTC              200

ATGATCTAAT CCTTTTATCG ATGAGTAAAA TTG                                233

(2) INFORMATION FOR SEQ ID NO: 232:

(i) SEQUENCE CHARACTERISTICS:
          (A) LENGTH: 358 base pairs
          (B) TYPE: nucleic acid
          (C) STRANDEDNESS: single
          (D) TOPOLOGY: linear (iii) HYPOTHETICAL: NO (iv) ANTI-SENSE: YES (vi) ORIGINAL SOURCE:
          (A) ORGANISM: DNA (other)

(xi) SEQUENCE DESCRIPTION: SEQ ID NO: 232:

GATCGGCGGA GAATCCCAGA CAGGCCAGGT CTTTCAGCTC GTCGCGGGTC               50

ATCGGGCCGG TAGTATCCTG AGAACCGACG GAGGTCATTT TCGGTTCGCA              100

GTACGCGCCC GGACGGATAC CTTTCACACC ACAGGCGCGA CCGACCATTT              150

TCTGTGCCAG CGAGAAGCCA CGGCTGCTTT CCGCCACGTC TTTTGCTGAC              200

GGAAAACGTC TGAGTGCGCA GCCAGCGCTT CACGCTTTTG TGCTAGCACG              250

CGATATCACG ATACACACGC ACGACTCGTC ATCAGCACGT CGTTCAGTCG              300

AGTGCAGTAG CGCGTCATGA TGCGTACTGC TTGACGTAGA CTATCATGCC              350

ATATCAGT                                                            358

(2) INFORMATION FOR SEQ ID NO: 233:

(i) SEQUENCE CHARACTERISTICS:
          (A) LENGTH: 302 base pairs
          (B) TYPE: nucleic acid
          (C) STRANDEDNESS: single
```

(D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 233:

| | |
|---|---:|
| GATCCACAGG TAGCGTGATG CGTTTTAGTT CCCCCTGCTG CTCAAGTAGC | 50 |
| GTCAGGCCGT CGCGTAAATC GTGATATTTC ATGGCGTCCA TTGTAGCCTC | 100 |
| TTGGTAAGCG CATCATTATA CGGCGTTCAT CATCGGGATG CTGTATTTTT | 150 |
| GTTAAATTAG CGTGAACTCT GGCAACCAAC GCTAATCCAG ATACGGCTTA | 200 |
| AAGGATGAAG TGTATATTAA CTTCGCGCAT GGCTTTTGCT ATGCTTGCGC | 250 |
| CCCGAACAGC GATAAGAGTC ATATGCATCT GGTATTTACT GTACTGCAAA | 300 |
| CG | 302 |

(2) INFORMATION FOR SEQ ID NO: 234:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 234:

| | |
|---|---:|
| GATCGTCACC TCCACCCTCG CGCGCGGGGC GGTGAAGCTC TCGAAACAGA | 50 |
| AAGTTATCGT GAAGCACCTT GATGCGATTC AGAACTTCGG CGCGATGGAT | 100 |
| ATCTGTGCAC TGATAAAACC GGCAACTCTG ACGCAGGATA AAATTGTGCT | 150 |
| GGAGAAATCA CACGATATTT CTGGTAAGCC CAGCGAGCAT GTCTGCATTG | 200 |
| CGCCTTGCTG ACACATTATC AGACCGTCTA AAAAAATTTC TGATACGCGT | 250 |
| CTGAGAGTAG ACAACGCGGT CACCTCGACG TGCAGAAAAT CGATAGATCC | 300 |
| GTTATTTAGC GTGCGATGTC GTAGTGTGCG AGATCGACGT GCATCAGCTG | 350 |
| GATCTGCAAG CTAACGAGAC TCAC | 374 |

(2) INFORMATION FOR SEQ ID NO: 235:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 235:

| | |
|---|---:|
| GATCGGACTT TATTCGCGCG ATAGTCACGG AAAAAATGGT TTAACTTTGC | 50 |

-continued

| | |
|---|---|
| TAATTCATCC TGAATGTAGG CTCTTCCATC GAAAAACTCC GCCTTGATTG | 100 |
| ACTCTCCGGT ATGGAGATTG TTTAACGTCA AAAATGCGCG CCGTGGGGTC | 150 |
| GAGAGTGTGG CAAACGCTGA GCGCGGGCAG GATGGCGGCG CGAGAGCGAC | 200 |
| ACCACCAAGC GCCAGAGCTT GCGCGATTAG CGTCAAATTT GTCATGATAA | 250 |
| TCAGGTCTAC AGGTCAATGT TATCGTTAAT ACACTTCTAC CTTTAAGCAG | 300 |
| ACATGATACG CTGACACGAC TCTACGCGTG ATAGTGTGAT ACTTGGCACA | 350 |
| GACTA | 355 |

(2) INFORMATION FOR SEQ ID NO: 236:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 236:

| | |
|---|---|
| GATCGTCACG TGATTTGCCC GTCACGCGAA TCTCTTCCCC CTGAATTTGC | 50 |
| GCCTGCACCT TCAGTTTGCT GTCTTTAATC AGCTTGACGA TTTTCTTCTG | 100 |
| CACGGCGCTT TCAATGCCCT GCTTCAGCTT CGCTTCCACA TACCAGGTTT | 150 |
| TACCGCTATG CACGAACTCG TCCGGTACAT CCAGCGAAGC GCTTCAATAC | 200 |
| CGCGTTTAAG CAGCTTGGCG CGCAGAATAT CGAGCAACTG ATTGACCTGG | 250 |
| AAATCGGACT CGCTCAGCAC TTGATGGTTT ATTGGCATCG TTCAGTTCAT | 300 |
| AGTGCTCTAC GCACGGAGTC AAACAGACTC ACTGGAGCTA TCACACGTAC | 350 |
| GCGCTCTCGA GAT | 363 |

(2) INFORMATION FOR SEQ ID NO: 237:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 237:

| | |
|---|---|
| GATCGTTAAT TAGGCGCTGG GCGTGCTGGA GCAGTAATTT ACCGCCTTCC | 50 |
| GAGGGGCGTA GTCCTTTACT GTGGCGCTCA AAAAGCGTGA TGCCTATCTC | 100 |
| ATCTTCGAGT TGAGATAGCC ACTTCGATAG CGCCGCCTGG GAGATATTCA | 150 |
| TCATCCGGGC GACGTGTCCG TTCAAGGGTT GGCCCTGTTC GGCCCAGCGC | 200 |
| AACCAGCGTT TGCGGTGATG TAATTTCAAT TTCTCCCGTT CCATTCGCTA | 250 |
| TAACCTCAGG TTATGTCTCT CCTGAAACCA TTGTACTTTA TCCTCCTCTA | 300 |
| CACTCGTACT GCACTAACAC | 320 |

(2) INFORMATION FOR SEQ ID NO: 238:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 238:

```
GATCCTGCAA CGCTTTCGAC CCGGTCGAAA TAATGACTTT TTTCCCGGCG            50

CGCAACGCCG AGCGAGGTAA GCATAGGTCT TCCCGGTTCC GGTGCCGGCT           100

TCAACAACCA GAGGCTGCGC ATTTTCAATC GCTTGTGTTA CGGCAACCGC           150

CATTTGTCGC TGTGGTTCGC GCGGTTTAAA GCCGGTTATC GCTTTGGCCA           200

GTTGGCATCT GCTGCAAAAT CGTCCGTCAC ACTGCCCCCT GTTAATTTGC           250

ACAGGGATTA TGTCAGGGTA GAAAGGCTTA CACAGTTACA GAGGTGACGG           300

CGGCACATTG TGCAGTCTTG AACCATTCAA ATGAAAAGCA AATGAGGAAT           350

AAGTAATGTC TATCGTGCGT ATGATGCGAG ATCGTGTCAG ACGTGTGACT           400

CAATAT                                                          406
```

(2) INFORMATION FOR SEQ ID NO: 239:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 239:

```
GATCCTACCG GCCCCCACGC TTTGATTTGA ATAATAGAGG CTACCGACGA            50

CAGCGACATG CTGATAATGT GCTGCGTATC CTGCGCCGGT AAACCCAACG           100

CCTGGCAGAT TAACAGCGCT GGCTGATTAC CGCGACAAAC ATGCCACGAG           150

ATGCTGACAA GCGCAAAAGG TTGAGGAGCG CGGCGATCTT CAAGACGGTA           200

AATTAATCGC TGCACAATTG TACGCGACGA TGCATCTCGC ATGCGTCTAC           250

GACATAGACA TCT                                                  263
```

(2) INFORMATION FOR SEQ ID NO: 240:

(i) SEQUENCE CHARACTERISTICS:
        (A) LENGTH: 364 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 240:

GATCAACGCC TAATTTGGCC GCACAATCCA GAGAGACCTG CGGGTGCGGT           50

TTGCTGTAGG GCAATTTTTC TGCAGAAGCC AGCGCGTCAA AACTGTCGCG          100

CAGTTCAAAC ATGGTGAGCA CTTTTTCCAG CATATGCAGC GGCGATGCCG          150

AGGCAAGCCC CACTAATAGC CCCTGCGCTT TACACAGCGC CACAGCTTCG          200

CGCACACCCG GCAAAAGAGG GCGCTCTCTT TCGATAAGCG TAATCGCGCG          250

GGCAATAACA CGGTTTGTCA CTTCTGGCGA TCGGGCGTTC ACGTTGCTGC          300

GCAACAGAGA TCGACAACCA TATCATGCGT AGCAAGCTGT TGCAGCTCAT          350

GGCCGAGTAT ATCT                                                 364

(2) INFORMATION FOR SEQ ID NO: 241:

(i) SEQUENCE CHARACTERISTICS:
           (A) LENGTH: 221 base pairs
           (B) TYPE: nucleic acid
           (C) STRANDEDNESS: single
           (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 241:

GATCATTTTA ATGCTGTGTC TTGCCATTTT TTTCTCCATA AATTTCAAAA           50

GGAAATCATG CCTGATGCGC ATTGCGACGG CGTGAGTACC ATTCAAGGAT          100

TTGGTGACGA TGCAAACTGA TGGAACGACC AACGACAACA ACAATGAGAA          150

GCGCACCGGA CAATGCGCTG GAATTGATTC GGCACTCCGG CCATCTGTAG          200

CCCTCGTGTA AATCCACCAG C                                         221

(2) INFORMATION FOR SEQ ID NO: 242:

(i) SEQUENCE CHARACTERISTICS:
           (A) LENGTH: 280 base pairs
           (B) TYPE: nucleic acid
           (C) STRANDEDNESS: single
           (D) TOPOLOGY: linear (iii) HYPOTHETICAL: NO (iv) ANTI-SENSE: YES (vi) ORIGINAL SOURCE:
            (A) ORGANISM: DNA (other)

(xi) SEQUENCE DESCRIPTION: SEQ ID NO: 242:

GATCATCGAC GTATGTCCTT TCCAGATATT CCGCCCGCCG CCAGCCCACT           50

CAAACAACGG GGGGCGCCGG CAAAAAAGCG AAAGACATCC ACCGATTGCC          100

GGAATTTATA TTAATTACGC CAGTGCAAAG GCTTATTGCA GTTTTGCGAT          150

TCAAGCCGGG CGAACTCAAG GGCGTTTTGC TCGATGCTGT CCGCAGTTTT          200

AACAGACATT CCGCCCGTGC TTTGGGTGTG GTCTGCCCAT TCGGAAACGC          250

GTTATCGGCG GCTGATCGCA GCGTAACCTG                                280

(2) INFORMATION FOR SEQ ID NO: 243:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 243:

```
CACTATAACA ACGGCGCGGC GGTACCTGGG CGACGTCGCC AGCGTCACCG         50

ACTCGGTGCA GGATGTCCGT AACGCCGGGA TGACGAACGC TAAACCCGCT        100

ATTTTGTTGA TGATCCGCAA GCTGCCGGAG TGGAATTCCA CATGTGGAAT        150

TCCCATGTCA GCCGTTAAGT GTTCCTGTGT CACTCAAAAT TGCTTTGAGA        200

GGCTCTAAGG GTTCTCAGTG CGTTACATCC CTAAGCTTGT TGTCACAACC        250

GTAACTAAAC TTAAACCTAT ATATCCT                                 277
```

(2) INFORMATION FOR SEQ ID NO: 244:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 244:

```
TGCAGATCAT TGCCTGATGT TCTACGGTCG CAAAATGCAC CAGNNNNCAG         50

AACAACGACA GCGACAACAA TACGGCTGAA GCGCTTTAAT CGCGCTAACT        100

CCTTTTTCTC AAAGCCCCTT TCCGTTCACC TGCTATAGCG TNGAGGGGCC        150

CACTTACCAG GAACAAGACT ATGAACGTTA TTGCTATCAT GAACCACATG        200

GGCGTCTACT TTAAAGAAGA GCCTATTCGT GAACTGCATC GTGCACTGGA        250

AGGTTTAAAT TTCGTATCGT CTATCAAAAC GACCGAGAAG ACCTGCTGAA        300

GCTGATTGAA ATAACTCCGC CTTTNNGTCA TTTCGACTGG GATAATATAC        350

CTTGAGCTTC GAGAGAGATA GCAGTGAGCG                              380
```

(2) INFORMATION FOR SEQ ID NO: 245:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:

(A) ORGANISM: DNA (other)

(xi) SEQUENCE DESCRIPTION: SEQ ID NO: 245:

GATCTGATTA TCGACGCGCT GCTTGGCACC GGCATAGCCC AGGCACCGCG         50

CGACCCGGTA GCCGGTCTGA TTGAACAGGC GAACGCATCC TGCGCCGGTT        100

GTCGCCGTCG ATATCCCGTC AGGTCTGCTG GCGCAAACGG GCGCACGCCT        150

GGCGGGTGAT AAGCGCGCGC ATACGGTCAC GTTTATCGCC CTGAAACCAG        200

GCCTGCTGAC CGGCAAAGTG CGTGAGCTTA CCGGCATATT GCATTATGAC        250

GTTGGGACTG GAAGGCTGGC TGGCGAGCAG ACGCGCGTCG GTTTTGAAGA        300

GAGTTGGGGC AATGGCTAAC GCGTGACGAC TGATAGGGAT ATGTGTAGAT        350

ATG                                                          353

(2) INFORMATION FOR SEQ ID NO: 246:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 246:

CACCCGGCTG ACTGCCGTAT AATCCAGCTT TTTACGCGGG TCCGCGGAGG         50

GTTTTGCCGT CACAGAGAGC GTATTCTGCG AGTTTATGGT TGTCTTACCT        100

AACGGATAGC CTTCGCTATC ATAGCGGTAC TCGACCCTTC ATCTCTTTGC        150

CCGTCGCCGA TACCACAAAA CCGTTGTCGT CCGTTTCCCA GGTCACGCCC        200

GCCGAACGAA CGCCGCCAGC TGGCACTTCC CCTGTAACTG CACCTTTTTT        250

TCCAGCGTCT GAGCATCCCG GTAATAATTG GCATCCAGCA CGAGTGCCAG        300

CCCCGTATTT ATCTCCAGAT CGTGTAACTC AAGCGTATCA AAACAGCCTT        350

CCTGTGAAAG CGTACCGCGA CCTCTA                                 376

(2) INFORMATION FOR SEQ ID NO: 247:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 247:

GATCAAGACG CGAATCCCCG ACGCGCCGAT AACGCCGTAC AACAGCAGCG         50

AGACGCCGCC CATCACGGGT AACGGGATAA TCTGAATCGC CGCCGCCAGT        100

TTGCCAACGC AGGAAAGCAT GTAATAACGA AAATCGCGTC GCCGCCGATA        150

ACCCAGGTAC TGTAAACGTC GGTGATCGCC ATGACGCCAA TATTTTCCAT        200

```
AGTGTATCGG CGTGAGTAGA ACCGAATATC GTCGACATCT AGCACATC                    248
```

(2) INFORMATION FOR SEQ ID NO: 248:

(i) SEQUENCE CHARACTERISTICS:
        (A) LENGTH: 253 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 248:

```
TTTCGACAAA GCGCGCCGCC GAGATATTCG CCATGATCAT GCACTCTTCG                  50

ATAAGCTTAT GCGCGTCATT ACGCTGGGTC TGTTCGATAC GCTCAATGCG                 100

ACGTTCGGCG TTAAAGATAA ACTTCGCCTC TTCGCACACA AACGAGATCC                 150

CCCCGCGCTC TTCACGCGCT TTATCCAGCA CTTTGTAGAG GTTGTGCAGC                 200

TCTTCAATAT GCTTCACAGC GCGCATATGT CACGCAGATC TGATCGCTGC                 250

AGC                                                                    253
```

(2) INFORMATION FOR SEQ ID NO: 249:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 249:

```
GATCAAACAC CAGACGACCG CGACGCGCAC GACCATCGGT GGTATCTAAC                  50

TCAAATTTCA TTATCACTCC TGCGTCAGAA AAACAGTCCG ACGTTTAACG                 100

ACTCGCTACG GAATGATTCC ATAGCTAATA AATTCCCGAA GACGTCATCG                 150

GCGCAGAGTT TGGGGTCGAC CAGCGCACAG CCACCGGAGC GTACACGCAG                 200

TACGTGAGGA TGGCGAGCAC TGCCGCGTCA AATGCAGTGA GATAGCTCTA                 250

CGACGTCAGA ATAGCTGCGA TGTACGTGAT AACTGCTCCG TAGCTAAAAG                 300

CATTTGTCTA CGCAGTCTAT AGGCATCATG TGTGTGATAC GCATGCGAAC                 350

AGCATACACG TGATCGCAGA TGAGTGTGAT CAGGCATATA CTGACGAACT                 400

GATATAGATT CGTG                                                        414
```

(2) INFORMATION FOR SEQ ID NO: 250:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
             (A) ORGANISM: DNA (other)

(xi) SEQUENCE DESCRIPTION: SEQ ID NO: 250:

GATCTTCCGG GTTCACGGCC ACGCGGTAAT TCTGCCGAGA ATAGTTTTCG            50

GGCGGGTGGT GGCGACAACC AGAAATCTTA CCGTCGCGGT TTTCGCGCCG           100

TCGGCCAGCG GA                                                    112

(2) INFORMATION FOR SEQ ID NO: 251:

(i) SEQUENCE CHARACTERISTICS:
            (A) LENGTH: 345 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
             (A) ORGANISM: DNA (other)

(xi) SEQUENCE DESCRIPTION: SEQ ID NO: 251:

GATCGTTAAA TGTGCGGTAA TCCTGTGATG AATACCGATA CGCAGCCAGA            50

CCAAACCGAG TTAATGTTTG GGTCAGGTAT TTATTATAAG CAATCTGATA           100

ACTCTGACCA TCAAATACGA CGCCATTATC CTGTTTACTG TGCGCTCGCG           150

TAGCTCAAGC GAAATGGCGC CAATCCGGGT ATTCCACCCC GTGCCGAGGG           200

TAAACGCATT ATAATGGTTC GATAGCATCG TACGCATAAG CGTCAACAGG           250

TTATTAGGCA TACTGATACT GATTGGTAAA TCGGCTGATA TCGGCGCTTC           300

AATTATGACT ACGCGCGAAA TCATACTGAG CCGTCCAGTC CATTC                345

(2) INFORMATION FOR SEQ ID NO: 252:

(i) SEQUENCE CHARACTERISTICS:
            (A) LENGTH: 203 base pairs
            (B) TYPE: nucleic acid
            (C) STRANDEDNESS: single
            (D) TOPOLOGY: linear (iii) HYPOTHETICAL: NO (iv) ANTI-SENSE: YES (vi) ORIGINAL SOURCE:
             (A) ORGANISM: DNA (other)

(xi) SEQUENCE DESCRIPTION: SEQ ID NO: 252:

GATCGGTCGC CGCCTTACCT TTTTCCAGTA CACTGAGCAG TTCGCTCAGC            50

AGTTGTTCAA CAGCTCCATC ACTAGAGCGG GAGAGTTCTG GCATAAATCA           100

AAATCTGTTT GTTCATGAAA CGGCAACACA TTAACCGCAG CAACAGTTTT           150

TTTCTGCATT TTTCGGCCTA AATCATCGCC TTACGATACT CTGAATACAG           200

GGG                                                              203

(2) INFORMATION FOR SEQ ID NO: 253:

(i) SEQUENCE CHARACTERISTICS:
            (A) LENGTH: 273 base pairs (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 253:

| | |
|---|---|
| GATCGTAATC ATTCACTTCG GTCAGCAGCT CGAGCACTAA CGCGTCGAGC | 50 |
| ACGCCTTCCA TCGGCGCCAG TAAAACACGC ATATCGGTAT CCACAGCAAA | 100 |
| AAAAGAGGCG CTATCATAAC GCCTCTCTGC GATGAGCAAA ACTTTTTTGC | 150 |
| CGGGTGGCGG CGCAAACGCA CGCTACGTAC GTAAGTGCTC ACGCGGCTTC | 200 |
| AAGACCAGTT ATTTTTCCAG CCGACCAGCC ATTCGAACCG CGATAAGCTC | 250 |
| TGCGATCCTT TCCAAGTATG CTG | 273 |

(2) INFORMATION FOR SEQ ID NO: 254:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 254:

| | |
|---|---|
| GATCTTCTCG CTTTCTTCAG GGCTTACTCC CGTCTCTTCT TCATCGACCG | 50 |
| TGATCAAAAT ACCGTCTTTA TCCACCAAGA AGCCGACTTC AATCTTCGTA | 100 |
| TGAAAATAGC TCACCATTAC GAACTATATT TTTCATCTCT CTTTCCAGCT | 150 |
| TTTT | 154 |

(2) INFORMATION FOR SEQ ID NO: 255:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (iii) HYPOTHETICAL: NO (iv) ANTI-SENSE: YES (vi) ORIGINAL SOURCE:
        (A) ORGANISM: DNA (other)

(xi) SEQUENCE DESCRIPTION: SEQ ID NO: 255:

| | |
|---|---|
| CGCTGTTCTG GTGTTAAGAC TTTGCTTAAA TCAAAATAAT ATTTAACCCG | 50 |
| ATAATAGCGA GCCTGTTGTT CTATGTTACT GAAGGCTGCA AGCTGCTGTT | 100 |
| TTACGGCGGC GTCATCCCAT TTACCGGATT TAATCACCTC TATCAGCGCA | 150 |
| CCGTCTTTAA TTCCCTTCAT AGAAATCTGA CTGACGTCGG TTTCCAGTTG | 200 |
| TTGGTGAAGT TTTTTGATCC GGGTAATCTG ATCGTTTGTC AGCTTCAGAT | 250 |

-continued

| GCTGGACAAT AGGATCCTGG GCGGGCAGGG GGAGGATTGG GGACAGCGTG | 300 |
|---|---|
| CAAGCAAAAG AAACGCGCAG AGTCGCTGCA GTAAGTGGGC ATACGTTT | 348 |

METHOD AND PROBES FOR THE IDENTIFICATION OF MICROBIAL GENES SPECIFICALLY INDUCED DURING HOST INFECTION

DESCRIPTION

This invention was made with Government support under Grant No. AI 36373 awarded by the National Institute of Health. The government has certain rights in this invention.

TECHNICAL FIELD

The current invention relates to a class of microbial coding sequences that are specifically induced during infection of a host by a microbial pathogen and more particularly to a set of probes that may be used to identify and isolate microbial virulence genes. The products of these virulence genes will provide potential targets for the development of vaccines or antimicrobial agents.

BACKGROUND ART

Microbial pathogens, or disease-producing microorganisms, can infect a host by one of several mechanisms. For example, they may enter through a break in the skin, they may be introduced by vector transmission, or they may interact with a mucosal surface. Disease ensues following infection of a host, when the potential of the pathogen to disrupt normal bodily functions is fully expressed. Each disease-producing microorganism possesses a collection of virulence factors, that enhance their pathogenicity and allow them to invade host or human tissues and disrupt normal bodily functions. Infectious diseases have been major killers over the last several thousand years, and while vaccines and antimicrobial agents have played an important role in the dramatic decrease in the incidence of infectious diseases, infectious diseases are still the number one cause of death world-wide.

Vaccines

Attempts to vaccinate are almost as old as man's attempt to rid himself of disease. However, during the last 200 years, since the time Edward Jenner deliberately and systematically inoculated a population with cowpox to avoid a smallpox epidemic, vaccination, at least in parts of the world, has controlled the following nine major diseases: smallpox, diphtheria, tetanus, yellow fever, pertussis, poliomyelitis, measles, mumps and rubella. In the case of smallpox, the disease has been totally eradicated. The impact of vaccination on the health of the world's population is hard to exaggerate. With the exception of safer water, no other modality, not even antibiotics, has had such a major effect on mortality reduction and population growth.

Following the first exposure of a host to an antigen, the immune response is often slow to yield antibody and the amount of antibody produced is small, i.e., the primary response. Upon secondary challenge with the same antigen the response is more rapid and of greater magnitude, i.e., the secondary response. Achieving an immune state equal to the accelerated secondary response following reinfection with a pathogenic microorganism is the goal that is sought to be induced by vaccines. Vaccines are basically suspensions of viral, bacterial, or other pathogenic agents or their antigens which can be administered prophylactically to induce immunity.

In general, active vaccines can be divided into two general classes: subunit vaccines and whole organism vaccines. Subunit vaccines are prepared from components of the whole organism and are usually developed in order to avoid the use of live organisms that may cause disease, or to avoid the toxic components present in whole organism vaccines. The use of purified capsular polysaccharide material of *H. influenza* type b as a vaccine against the meningitis caused by this organism in humans is an example of a vaccine based upon an antigenic component. See Parks et al., *J. Inf. Dis.*, 136 (Suppl.):551 (1977), Anderson et al., *J. Inf. Dis.*, 136 (Suppl.):563 (1977); and Mäkela et al., *J. Inf. Dis.*, 136 (Suppl.):543 (1977). Classically, subunit vaccines have been prepared by chemical inactivation of partially purified toxins, and hence have been called toxoids. Formaldehyde or glutaraldehyde have been the chemicals of choice to detoxify bacterial toxins. Both diphtheria and tetanus toxins have been successfully inactivated with formaldehyde resulting in a safe and effective toxoid vaccine which has been used for over 40 years to control diphtheria and tetanus. See, Pappenheimer, A. M., Diphtheria. In: *Bacterial Vaccines* (R. Germanier, ed.), Academic Press, Orlando, Fla., pp. 1–36 (1984); Bizzini, B., Tetanus. Id. at 37–68. In contrast to subunit vaccines, whole organism vaccines make use of the entire organism for vaccination. The organism may be used killed or alive (usually attenuated) depending upon the requirements necessary to elicit protective immunity. The following discussion will focus on live but attenuated microorganisms (live vaccines).

In the case of intracellular pathogens, it is generally agreed that live vaccines induce a highly effective type of immune response. Ideally, these attenuated microorganisms maintain the full integrity of cell-surface constituents necessary for specific antibody induction yet are unable to cause disease, because they fail to produce virulence factors, grow too slowly, or do not grow at all in the host. Additionally, these attenuated strains should have no probability of reverting to a virulent wild-type strain. Traditionally, live vaccines have been obtained by either isolating an antigenically related virus from another species, by selecting attenuation through passage and adaptation in a nontargeted species or in tissue cultures, or by selection of temperature-sensitive variants.

In contrast to these somewhat haphazard approaches of selecting for live vaccines, modern developmental approaches introduce specific mutations into the genome of the pathogen which affect the ability of that pathogen to induce disease, that is, specific mutations are introduced into genes involved in virulence. Defined genetic manipulation is the current approach being taken in an attempt to develop live vaccines for various diseases caused by pathogenic microorganisms. U.S. Pat. No. 5,210,035, exemplifies this approach by describing the construction of vaccine strains from pathogenic microorganisms made non-virulent by the introduction of complete and non-reverting mutational blocks in the biosynthesis pathways, causing a requirement for metabolites not available in host tissues. Specifically, Stocker teaches that *S. typhi* may be attenuated by interrupting the pathway for biosynthesis of aromatic (aro) metabolites which renders Salmonella auxotrophic (i.e., nutritionally dependent) for p-aminobenzoic acid (PABA) and 2,3-dihydroxybenzoate, substances not available to bacteria in mammalian tissue. These aro$^-$ mutants are unable to synthesize chorismic acid (a precursor of the aromatic compounds PABA and 2,3-dihydroxybenzoate), and no other pathways in Salmonella exist that can overcome this deficiency. As a consequence of this auxotrophy, the aro$^-$ deleted bacteria are not capable of extensive proliferation within the host; however, they reside and grow intracellularly long enough to stimulate protective immune responses.

Unfortunately the development of vaccines based on chemical toxoids, discussed previously, is difficult since protective antigens and the genes encoding them must first be identified and then procedures must be developed to efficiently isolate the antigens. Similarly, modem approaches to the rational development of live vaccines has been hampered by the limited knowledge available concerning genes that are involved in virulence and thus the targets of mutagenesis.

Antimicrobial Agents

The medical literature up to about 1930 is full of vivid descriptions of gruesome infections by streptococci, staphylococci, and clostridia. The dawning of the age of antimicrobial therapy, with the introduction of the sulfonamides in the 1930s, allowed physicians finally to cure many of these fatal infections. From the outset, antibiotics were heralded as a panacea for everything from fungus-infected pear orchards to the common cold. Penicillin lozenges were popular as were nostrums such as antibiotic mouthwashes and throat sprays. By the 1950s, doctors jubilantly predicted an end to infectious diseases and, by the 1980s, half of all drug companies had stopped developing antibiotics, believing the battle won.

The stunning success of the pharmaceutical industry in the United Sates, Japan, the United Kingdom, France, and Germany in creating new antibiotics over the past three decades have caused society to become complacent about the potential of bacterial resistance, but what once was a situation where antibiotic controls prevailed has since deteriorated badly. C. T. Walsh, in a technical paper entitled "Vancomycin Resistance: Decoding the Molecular Logic," *Science*, 261:308–309 (1993) stated that "[t]he 1990s may come to be remembered as a decade in which infectious diseases made a dramatic worldwide resurgence, largely because of the appearance of antibiotic-resistant microbes."

In economic terms alone, such antibiotic resistance is costly. A recent estimate is that the extra expense of treating multiresistant infections is $100 to $200 million annually in the United States, see A. Gibbons, *Science*, 257:1036–1038 (1992). But economic impact reflects only part of the true costs of dealing with antibiotic resistant infections. More than 13,000 Americans are dying each year from drug resistant bacteria and doctors warn that the problem is steadily worsening. The FDA considers bacterial drug resistance threatening enough that it is planning incentives to encourage development of new antibiotics.

To date, the vast majority of antibiotics in the marketplace were derived from large-scale screens or from analog development programs. Classification of antibiotics by mechanisms of action appears below in Table 1.

TABLE 1

| Mechanisms of action | Agent |
| --- | --- |
| Inhibition of synthesis or damage to cell wall | Penicillins |
|  | Glycopeptides |
|  | Cephalosporins |
|  | Monobactams |
| Inhibition of synthesis or damage to cytoplasmic membrane | Polymyxins |
|  | Polyene antifungals |
| Inhibition of synthesis or metabolism of nucleic acids | Quinolones |
|  | Rifampin |
|  | Nitrofurantoins |
| Protein biosynthesis | Tetracyclines |
|  | Chloramphenicol |

TABLE 1-continued

| Mechanisms of action | Agent |
| --- | --- |
|  | Macrolides |
|  | Lincosamides |
|  | Aminoglycosides |
| Modification of energy metabolism | Sulfonamides |
|  | Trimethoprim |
|  | Dapsone |

As is shown in Table 1, there are very few mechanisms of action that are exploited by current antibiotics. Unfortunately, to date the majority of antimicrobial agents have been randomly discovered. Robotic systems can perform thousands of tests per day by means of radioactive labeling or spectroscopic detection making it feasible to scan 100,000 to 500,000 compounds in a year. While the efforts are still in their early stages, some companies are beginning to use. "rational drug design" to design new drugs that can use selective mechanisms to destroy a specific microbe. Understanding the biological or biochemical mechanism of a disease often suggests the types of molecules needed for new drugs. Consequently, not knowing what makes infectious diseases virulent in the first place, is a fundamental fact which has severely limited the continued development of vaccines and antibiotics. A method of identifying genes that are expressed by microbial pathogens infecting a host has been developed: in vivo expression technology (IVET).

In Vivo Expression Technology

Essentially, the IVET selection strategy disclosed in U.S. Pat. No. 5,434,065, and herein incorporated by reference originates with a microbial strain carrying a mutation in a biosynthetic gene that highly attenuates its growth in a given host. Next, growth of the mutant strain in the host is complemented by transcriptional fusions to the same biosynthetic gene. Although, in theory, many different biosynthetic genes (e.g., aroA, thyA, asd) could be used in this selection scheme, initial efforts have focused on the purA gene of *Salmonella typhimurium*, purA mutants are highly attenuated in their ability to cause mouse typhoid and to persist in host tissues. This purA requirement provides a basis for the positive selection of microbial virulence genes that are specifically induced in a given host.

The first step in construction of purA operon fusions as per U.S. Pat. No. 5,434,065 was to build a pool of recombinant clones containing random fragments of Salmonella DNA. Partial Sau3A I restriction digests of total *S. typhimurium* DNA were used to obtain the random DNA fragments, which were then cloned 5' to an artificial operon having a promoterless purA gene fused to a promoterless lacZY gene on the vector, pIVET1. In the recombinant plasmids of interest, the fragment contained a Salmonella promoter in the proper orientation to drive the purA-lac fusion. This random pool was then introduced into a purA deletion strain of *S. typhimurium* that does not contain the Pi replication protein. Selection for ampicillin resistance requires the integration of the recombinant plasmids into the chromosome by homologous recombination, using the cloned Salmonella DNA as the source of homology. In the clones of interest, the product of the integration event generates a duplication of Salmonella material in which one promoter drives the purA-lac fusion, while the other promoter drives the expression of a wild-type copy of the putative virulence gene as shown in FIG. 1. The expression of both of these promoters is selected in the host. Expression of the purA-lac fusion is selected to overcome the parental purA auxotrophy. Expression of the virulence gene is selected because the gene product is required for infection. The expression levels of the operon fusions can be monitored both on laboratory media and in animal tissues by measuring the levels of β-galactosidase activity.

A large collection of recombinant plasmids that contained the purA-lac transcriptional fusions were integrated into the chromosome of a purA deletion strain of *S. typhimurium*, FIG. 1. The subsequent pool of integrated fusion strains was injected intraperitoneally (i.p.) into a BALB/c mouse. After a 3 day incubation, the mouse was sacrificed and the bacteria were recovered from an internal organ such as the spleen, intestine, or liver. Only those bacterial cells that contain fusions to chromosomal promoters that had sufficient transcription levels to provide enough of the purA gene product were selected (to overcome the parental purine deficiency) by demanding the survival and propagation of the fusion strain in the host. Note that all genes that have constitutively active promoters will answer the IVET selection because they would produce sufficient levels of purA gene product (and LacZ) all the time. Thus, when the mouse-selected pool was plated on MacConkey Lactose indicator medium, an increase in the percentage of Lac$^+$ clones is expected compared to the pre-selected pool. This expected shift has been termed the "RED SHIFT." To test the prediction, the percentage of Lac$^+$ clones in the pre-selected and mouse-selected fusions was determined by plating on MacConkey Lactose indicator medium. In the pre-selected pool, 50% of the fusions were transcriptionally active or "ON" in vitro (red or pink in colonies), whereas in the mouse-selected pool 95% of the fusions were "ON." This observed shift in percentage in favor of Lac$^+$ clones (the RED SHIFT) suggests that the IVET system selected for promoters that are active in vivo. Since the underlying premise of IVET is that some virulence genes will be expressed only when they are in the proper environment and not on simple laboratory media, we focused our efforts on the rare 5% Lac$^-$ class of fusions that were recovered from the spleens of infected mice. Presumably, these Lace strains contained fusions to genes that were "ON" in the mouse (to complement the purA deficiency) and "OFF" out of the mouse.

While the IVET approach provides an important new way to identify genes that are involved in virulence, some shortcomings were encountered using the IVET method discussed above. There is still a need, therefore, for a method and a means for identifying and isolating microbial virulence genes the products of which will provide a basis for rational vaccine and drug design.

DISCLOSURE OF INVENTION

Accordingly, it is an object of this invention to identify a class of microbial virulence genes involved in virulence.

It is an additional object of this invention to enhance the selectivity of methods currently available to identify virulence genes.

It is a further object of this invention to provide a set of coding sequences known to be involved in pathogenesis for use as probes to identify and isolate other microbial genes that are cotranscribed with said coding sequences during infection.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method and compositions of this invention comprise using a class of coding sequences to identify genes, the transcription or cotranscription of which are induced during microbial infection of a host.

BRIEF DESCRIPTION OF THE DRAWINGS

The accompanying drawings, which are incorporated in and from a part of the specification, illustrate the preferred embodiments of the present invention, and together with the description serve to explain the principles of the invention.

BEST MODE FOR CARRYING OUT THE INVENTION

Figure 1:
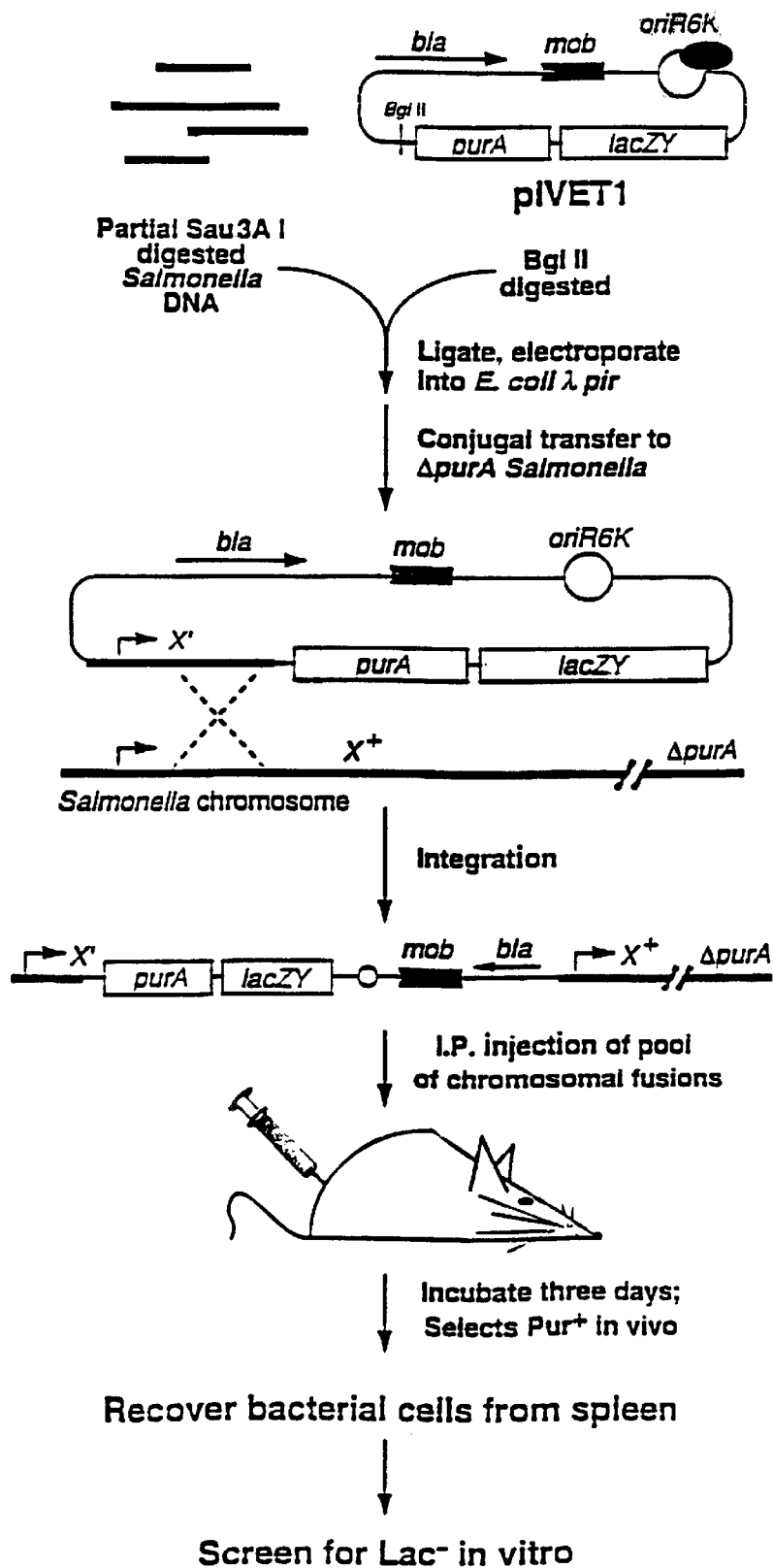
FIG. 1 is a flow sheet representing a method of selecting genes that are induced in a host according to the IVET methodology of U.S. Pat. No. 5,434,065.

In general and overall scope, the present invention provides a method and means for identifying and isolating a class of microbial virulence genes whose products will define metabolic, physiological, and genetic factors that contribute to the virulence of microbial pathogens, providing new targets for vaccine and antimicrobial drug development. By modifying the IVET methodology described previously, its selectivity was greatly enhanced, allowing for the identification of a number of genes which are induced during microbial infection of a host. In turn, these genes or portions thereof may be used as probes to identify other genes that are also induced during infection of a host. Consequently, the method of this invention further relies on a set of hybridization probes which comprise microbial coding sequences the transcription or cotranscription of which are induced during microbial infection of a host. These probes may be used to screen DNA libraries such as cosmid, lambda, or plasmid libraries thereby identifying and isolating genes that are transcribed or cotranscribed in connection with the coding sequences making up the hybridization probes of the present invention. The probes of the present invention may also be sequenced and the sequence compared to published sequences, thus (i) identifying genes that are known, but now known to be involved in virulence; or (ii) identifying genes that are unknown.

The method and probes of the present invention are based on the principals of a technology termed in vivo expression technology (IVET), disclosed in U.S. Pat. No. 5,434,065, and herein incorporated by reference. As alluded to previously, the IVET methodology suffers from a number of technical shortcomings which limit its selectivity as discussed below. The modifications also discussed below address these shortcomings and provide a number of coding sequences which are induced in vivo, and can be used as probes to identify other in vivo induced genes.

First, preliminary genetic and sequence analysis of in vivo induced (ivi) fusion join points revealed that some of the cloned fragments are comprised of small (e.g., 50 bp–100 bp), multiple inserts that have ligated at least two unrelated pieces of DNA together, making determination of the actual in vivo induced genes problematic. Second, the parental purA deletion, which is the basis of the IVET selection, was isolated as a Tn10-generated event, thus leaving a transposition competent IS10 element at the join point of the deletion, which extends from purA into an undetermined amount of adjacent chromosomal material, see Maloy S. R., et al., *J. Bacteriol.*, 145(2):1 110–1112 (1981). This deletion-containing strain has a slight growth defect even in the presence of exogenous adenine, suggesting that the adjacent chromosomal material that was removed contributes to the slow growth phenotppe. Also, the transposition competent IS10 element at the deletion join point contains an active promoter that reads outward into adjacent chromosomal material, see Ciampi, M. S., et al., *Proc. National Acad. Sci.*, 50:16–20 (1982). The transposition of this mobile promoter could unnecessarily complicate the IVET selection process. Finally, streptomycin resistance ($SM^r$) was used both as a counterselectable marker upon mating the initial pool of recombinant plasm ids from *E. coli* into *S. typhimurium* and as a selection against normal flora present in host tissues (e.g., normal flora in the small intestine). The $SM^r$ mutation renders the parental strain somewhat attenuated in vivo. The parental $SM^r$ mutant used in all of the IVET selections to date are slightly attenuated when delivered intraperitoneally and even more so when delivered orally. Such parental attenuation can affect the classes of genes that answer the selection, particularly after an oral delivery of integrated fusion strains.

Taken together, the shortcomings uncovered with the current IVET methodology warrant consideration. Consequently, the method disclosed in U.S. Pat. No. 5,434, 065 was modified as discussed below to produce in vivo induced fusions that circumvent the concerns addressed above. The first modification discussed below was implemented for the construction of all pIVET vectors, that is pIVET1, pIVET2 and pIVET8, while the second modification was only applicable to pIVET1 and pIVET8.

CONSTRUCTION OF pIVET1, pIVET2 AND pIVET8 VECTORS

The pIVET1, pIVET2, and pIVET8 vectors were constructed as described in U.S. patent application Ser. No. 5,434,065, incorporated herein by reference, using the following modifications.

First, for each vector the random fragments of chromosomal DNA were size fractionated. Random fragments of *S. typhimurium* DNA, obtained by partial Sau3A I restriction digestion, were size fractionated and removed from agarose gel after eletrophoresis. The cloning of large chromosomal fragments increases the probability that in vivo induced promoter regions will be contained in the initial pool of recombinant clones that will be integrated into the bacterial chromosome. This modification further decreases the probability of multiple inserts since the ends available for ligation will be limited to large fragments (1 to 4 kb).

The second modification was only necessary in the pIVET1 and pIVET8 selections. One way in which a purA mutation may be obtained by constructing a purA deletion in vitro that is associated with an antibiotic resistance marker. To perform the IVET selection in as native a parental background as possible, a purA deletion can be constructed in vitro. The wild-type *S. typhimurium* purA gene can be cloned by complementation of a purA deletion (on minimal medium) with a pool of recombinant clones representing the *S. typhimurium* chromosome. Once the wild-type purA gene is isolated, a purA mutation is constructed in vitro, by introduction of a DNA fragment encoding an antibiotic resistance marker (e.g., tetracycline) into the purA coding sequence. The tetracycline resistant mutation is then crossed into a chromosomal purA gene by introduction of the cloned insertion-bearing plasmid into wild-type *S. typhimurium*. The phenotype of the desired purA'::$Tc^r$::' purA recombinant is $PurA^-$ $Tc^r$. Additionally, the $Tc^r$ insertions in purA, thyA, or near $purA^+$, in the pIVET1, pIVET2, or pIVET8 selections, respectively, alleviate the need for the attenuating $Sm^r$ mutation as a counterselectable marker. In the alternative, insertions of a transposition defective transposon, e.g. Tn10d-Tc, in purA or thyA can be used as described here.

The implementation of these two changes to the current IVET selection protocol resulted in the construction of random individual pools of pIVET1, pIVET2 and pIVET8 fusions having 1 to 4 kb fragments of *S. typhimurium* DNA that contain very few multiple inserts. Each pool was then integrated into an otherwise wild-type *S. typhimurium* strain that contains a purA mutation, or thyA mutation in the case of pIVET1 and 2, respectively or a drug resistant mutation near the purA gene (e.g., $Tet^r$) in the case of pIVET8. Theoretically, using this revised protocol, there are no a priori limitations either to the mode of delivery of these integrated fusion pools (oral, intraperitoneal, intramuscular, etc.) or to the type of tissue from which the mouse-selected fusions are recovered.

A total of 100 BALB/c mice (Charles River Laboratories) were infected either orally or intraperitoneally with approximately $5 \times 10^8$ cells or $10^5$ cells, respectively, using either pools of purA-lac fusion strains i.e., pIVET1, thyA-lac fusion strains i.e. pIVET2, or cat-lac fusion strains i.e., pIVET8. Three days after infection, the mice were sacrificed and their internal organs removed and homogenized in 2 ml of sterile saline. The homogenate was grown overnight in LB containing ampicillin and $10^5$ cells were injected into a second set of mice, where the process was repeated. In addition to infecting mice, the cat-lac fusion strains were used to infect RAW 264.7 tissue culture macrophages for two or three hours. The bacterial cells recovered from the organs and macrophages were plated out on MacConkey Lactose indicator medium and approximately 2,894 white colonies were picked for further identification, date represented in Table 2.

TABLE 2

| Selection | Route of Administration | Tissue | Total Colonies Screened | White Colonies |
|---|---|---|---|---|
| purA-lac | Intraperitoneally | Spleen | 60,000 | 386 |
| | | Liver | 8,000 | 34 |
| | | Intestine | N/A | N/A |
| | Oral | Spleen | 16,000 | 97 |
| | | Liver | 8,000 | 26 |
| | | Intestine | 60,000 | 494 |
| thyA-lac | Intraperitoneally | Spleen | 16,000 | 34 |
| | | Liver | 8,000 | 14 |
| | | Intestine | N/A | N/A |
| | Oral | Spleen | 8,000 | 32 |
| | | Liver | 8,000 | 48 |
| | | Intestine | 16,000 | 119 |
| cat-lac | Intraperitoneally | Spleen | 30,000 | 764 |
| | Tissue Culture | Macrophage | 30,000 | 846 |

Identifying in vivo induced Genes

In order to identify the in vivo induced genes, a genetic approach to clone the 2,894 selected in vivo induced fusions directly from the bacterial chromosome using phage P22 transduction was implemented, see Mahan M. J., et al., *J. of Bacteriol.*, 175:(21): 7086–7091 (1993), incorporated herein by reference. Briefly a bacteriophage P22 lysate is made on the fusion strain of interest and used to transduce a recipient strain such as MT189, that contains the replication protein, Pi, which is required for autonomous replication of the pIVET1, 2, and 8 vectors. After introduction of the linear chromosomal fragments containing the integrated fusion construct into a Pi containing strain, the transduced fragment circularizes by homologous recombination at the region of duplication defined by the cloned *S. typhimurium* DNA. The circularized fragment can then replicate as a plasmid in the presence of the Pi replication protein, resulting in the cloned fusion of interest. In other organisms where cloning by transduction is not possible, the fusions can be cloned by more standard methods (S. Berger, et al., *Guide to Molecular Cloning Techniques*, Academic Press, Inc. (1987).

Plasmids from the recipient strain are isolated and used to transform *E. coli* cells following standard calcium chloride or electroporation procedures, see T. Maniatis, *Molecular Cloning: a Laboratory Manual*, Cold Spring Harbor, N.Y., (1989). DNA mini preps are performed followed by restriction digests. 1,037 clones containing the purA-lac fusions were digested using BamHI and EcoRI; 247 clones containing the thyA-lac fusions were digested using BamHI and EcoRI; and 1,610 clones containing the cat-lac fusions were digested using BamHI and Sal I. Restriction enzymes BamHI, EcoRI and Sal I were obtained from New England Biolabs, and the digests followed the Manufacturer's instructions. The DNA fragments resulting from the digests were separated on agarose gels and compared to one another for redundancy. 250 individual clones from the 2,894 clones digested were identified as having different digest patterns. Using primers homologous to the 5' end of the purA, thyA or cat gene approximately 70–400 base pairs of *S. typhimurium* DNA were sequenced immediately upstream or 5' to the purA, thyA or cat gene in each of the respective cloned fusions.

SEQUENCE ANALYSIS

The purA, thyA and cat primers used for sequencing were 5'-CATTGGGTGCCCAGTACG-3' (SEQ ID NO.: 1), 5'-TGTGCCTTCGTCGAGCAC-3' (SEQ ID NO.: 2), and 5'-CAACGGTGGTATATCCAG-3' (SEQ ID NO. 3), respectively. Primers were purchased from Operon Technologies (Alameda, Calif.).

All DNA sequence analysis was performed by the dideoxy nucleotide chain termination method of Sanger et al. (1977) with double stranded plasmid DNA as the template using a Sequenase kit (United States Biochemical Corp., Cleveland Ohio) as per the manufacturer's instructions. Primer annealing was as follows: 10 µg of double or single stranded DNA was denatured in 80 µl of 0.2M NaOH at room temperature for 5 minutes. Three pmol of primer and 8 µl of 3M sodium acetate were then added. 200 µl of 100% ethanol was then added and the mixture placed on dry ice. After 20 minutes the mixture was centrifuged in an Eppendorf 5415C microcentrifuge (Brinkman Instruments, Westbury, N.Y.) for 10 minutes, the ethanol was removed, the pellet carefully washed twice with 200 µl of 70% ice-cold ethanol and taken to dryness in a Savant Speed Vac Concentrator (Savant Instruments, Faringdale, N.Y.). 2 µl of 10× stock sequencing buffer and 8 µl of water were then added to the dried pellet and the labelling reaction performed.

20 cm or 33 cm×60 cm 6% acrylamide-7M urea sequencing gels (CBS Scientific Inc., Del Mar, Calif.) were used to obtain sequences starting typically from 20 to 30 bases from the priming site out to about 300 bases in a single loading. Similar results were also obtained using wedge gradient gels with a spacer to wedge ratio of 1:4 in a single loading. Priming was with $^{35}$S dATP (1000 Ci/mmole, DuPont NEN, Boston, Mass.). Gels were removed from the glass plates with 3 mm Whatman filter paper (Whatman Ltd., Madistone, England) and dried; a readable sequence could be obtained often after an 18–24 hour exposure using Kodak Biomax MR film.

Analysis of nucleotide sequences from one strand reading from the 3' direction to the 5' direction were performed using a Power Mac 7100/66 computer and the Wisconsin Sequence Analysis Package Version 8, program available from Genetics Computer Group, Madison, Wis. About 50% of the fusions are in genes that show no significant homology to sequences in GenBank version 72. As only one strand was sequenced, the sequence results (SEQ ID NOS: 4–254) represented below in Table 3 have an accuracy of approximately 95%.

TABLE 3

| SEQ ID NO | LENGTH | PARTIAL 3'–5' SEQUENCES OF PROBES OF THE PRESENT INVENTION | | | |
|---|---|---|---|---|---|
| 4 | 390 | GATCCGGATG | GAATGGCTCC | AGCGCGTCGG | TTTTCTCGCC |
| | | GACACCGAGG | AATTTAATCG | GCTTGCCGGT | GATATGACGA |
| | | ATAGAGAGCG | CCGCACCGCC | ACGCGCATCA | CCATCAACTT |
| | | TGGTCAGCAC | CACGCCGGTT | AACGGCAGCG | CTTCGTTAAA |
| | | GGCTTTTGCG | GTATTCGCCG | CATCCTGACC | GGTCATCGCA |
| | | TCGACGACAA | ACAGCGTTTC | TACTGGCTTG | ATAGAAGCGT |
| | | GGACCTGTTT | GATTTCGTCC | ATCATCGCTT | CGTCAACATG |
| | | CAGACGACCG | GCGGTATCCA | CCAGCAGCAC | GTCGTAGAAT |
| | | TTGAGCTGCT | TCTTGGCGGT | TGACAGTATC | ACGTTCTGCG |
| | | AAATCAGACG | GAGAATCACG | CAATTGTACA | |
| 5 | 238 | GATCATAGAG | GTGGATACGG | CTTTTCAACG | CCTGTTGGAC |
| | | GGCGTGCCAG | TCGGCCTGTT | CAAAACGCTG | CTGCGCGCCG |
| | | GAAGTCACTT | CCAGAAATCG | ACCATACTGC | GCGTCAAAGC |
| | | CTTGCAGGAT | GGTTTGAGCA | ATCAGTAATT | CCAGGCCACG |
| | | CGGCATTTTT | TTACCTCATC | CGGCACCACG | TCATGCCGGA |
| | | TGCGCGTTCG | CTTATCCGGC | CTACGCTATC | TGTAGGCC |
| 6 | 309 | GATCGAGAGG | ATGCGGTGGT | GGATGCGCAT | ATTACCGGAT |
| | | GACGGCGTGA | ACGTGTTATG | CGGCCTACCA | GCCCAATGCG |
| | | CGATACCAAG | CCGGATAAGC | CGCCAACGCC | CACCCCGGCC |
| | | CCGCCGCGTA | TTTAATCAAG | TTATTACCTT | TGATCGCACC |
| | | CTTGAGGTCA | GGCGCGTGAT | AAGTTCGTAA | GCACTTACTT |

TABLE 3-continued

SEQ ID NO LENGTH PARTIAL 3'—5' SEQUENCES OF PROBES OF THE PRESENT INVENTION

|SEQ ID NO|LENGTH|SEQUENCE|
|---|---|---|
| | |TTGTCATTTC AGCGATACGT TCAACCGGCA GACTTACCCA|
| | |TAGACACGAT CGCGGTATCT CGGTTGCCAA TTCGAATCTA|
| | |TCCATGGACG CGACATCGAC TACGACATT|
|7|362|GATCCGTTTT GACCATCCCG TGTTTGGTCG AAACCGTGCA|
| | |GCCTTCTACC AGCGGCAGTA AGTCGGGCTG TACGCCTTCG|
| | |CGTGAAACAT CCGGGCCGGA GGTTTCGGCA CGCTTACAAA|
| | |TTTTGTCAAT TTCATCGATA AACACGATGC CGTGCTGTTC|
| | |AACCGCGTCG ATAGGTCCTG TTTCAGCTCT TCCGGGTTGA|
| | |CCAGTTTAGC AGCCTCTTCT TCAACCAACA GTTTCATCGC|
| | |GTCTTTAATT TTCAGCTTAC GGGTTTCTGT TTCTGACCGC|
| | |CCAGGTTCTG GAACATAGAC TGCACTGCTG TCATCTCTCA|
| | |TGCCGAGCCA TATCTCTAGC CATCGGCGCA GTATTGACTT TA|
|8|206|GATCAAGAAT GTGTTCTCCC AGCGCATCCT TGATGGTTTC|
| | |TCCCAGCACC TTGCCGAGCA TACTGACATT ACTAGCAACG|
| | |CGGAATATTG TTCGTTCATA TGCCCCCAGA CGCCCCATCT|
| | |TTAATGTAAT TGCCCTGTCT CTTTCATGCC ACAGCGCAGT|
| | |GGCTGCGTGC GTATGCAGTT ATGCGAATGC TCGTGCTGCG ACTAAT|
|9|250|GATCGTCGGT GCGAATGGTG ACGTCGGCAA TCTCTTCGTA|
| | |CAGCGGATTG CGTTCGTTAG CCAGCGCTTC CAGAACTTCG|
| | |CGAGGCGGTG CTTCAACCTG CAACAGCGGG CGTTTTTTAT|
| | |CACGCTGCGT GCGGCAGTTG TTTTTCGATC GGTCGTTTCA|
| | |AGGTAGACCA CGACGCACGG CGAGAGACGG TTACGGTTTC|
| | |ACAATTTTAC AGAGCCACAT CGGAACACAC ATACCTTTAT|
| | |ATCTATACTT|
|10|176|GATCCAGGCT TCGCGTTCTG ATAGCTGTCA TACGGTACGG|
| | |TGGTGATTTC CGGATGCTTA TCCATGATGA ATTTCTGGTG|
| | |TCGTCGTACC GTTCTGTACG CCGACTTTCT TGCCTTTCAG|
| | |TTGATCAACG CTGGTGTATT GCCTGCTGAC CACGAACAGC|
| | |GTGAGTAGGG TATATG|
|11|312|GATCTTCCGC CCAGCCTGCG ACTTCTACTT TCGAGGCCTG|
| | |GATTTCGAAA CTTTGCCCCT GTGCCGGCGA CGCGACAACC|
| | |TTACCTGTTA CTACCACGGA GCAGCCTGTC GACAGGTGTA|
| | |ATACTTCTTC ATTATAATTG GGCAGAGAAT TATTAATGAC|
| | |AGCCTGTACA GGATCAAAGC AGGAGCCGTC ATAAACGGCG|
| | |AGGAAGGAGA TGTCCAGCTT TTGAATCTCG GTCGGGTACG|
| | |ACCCATCCCG CGCAGTGACT TCTTGGTCAA CGGCTACTGG|
| | |CCTGGAGTAC TGCGGCTACG GCACACGTCA TA|
|12|289|GATCCCAGAT AATCGCCAGG ATCACCATCA CCACCGTTGG|
| | |CATCAACCAA GCCAGTCCCT GTTCCGCCAG CGCAAACGCT|
| | |GACTCCAGGC TGGCAGCATA TCGCCGAAGG ATGCTTTGAT|
| | |GCCGTCAAGG ATACCAAAAA GCAGACTGAT AAACATGGCC|
| | |GGCGCCGATG ATACGGGTGG AATTATGCCA CCATGAGCGG|
| | |GTAAAACTTA ATACAACCAG TGCGATACAC GGCGGATAGA|
| | |TAGCGTCATG ACGGAATTGG AGATTATCAG ATCGCTCAGT|
| | |CGAGGTTGA|
|13|240|GATCAATAAT GTTATCCCGG CTTAACACTT CATCCGGGTG|
| | |ATGCGCAAAA TACATCAGAA GATCGATCAG CCGTGGTTCA|
| | |AGAGTAATCT GGCGTCCCTG ACGACTGATC TGACCAACAG|
| | |AAGGTATAAC CAGCCACTCT CCAATGCGTA CAACAGGTTG|
| | |CTGCATAAAA AGATGCCTAA CGAGCTAAGT CATACGTATA|
| | |TACACGATTG CACAGACTTT TATCCTTTGT AAGAAGCTAA|
|14|260|GATCAGAACC TTAAAACAGC GTAGACACTT TTTTGGCTTT|
| | |GTGAGAAATC CACGGACAAT TCCGCGAGCC AGTTATCGAC|
| | |GTAGAACAGA GGAAGGGAGG AGCCCTTGCC GAAAAGGCCA|
| | |TCCCATGGTG AATCGGGAAC GCTCCGGTTC CCGTTAATGC|
| | |CTAATAATTA TCGTAATATA AACAACCGGA AATCAGTATA|
| | |GGCCGCAATT TTGACGATTC ACCGAAATTG TTAGCGTGCT|
| | |AATTACAGAG TACAGTTAGT|
|15|314|GATCGGCATA CAGCGCGTAC ACTTCATCCA GACGTTTGAG|
| | |GGCGTTAACC ACTTCCGAAA CGGCCTCTTC AATCGACTCG|
| | |CGTACCGTGT GTTCCGGGTT TAGCTGAGGT TCCTGCGGCA|
| | |GGTAGCCAAT CTTAATGCCG GGCTGCGGGC GCGCTTCGCC|
| | |CTCGATATCT TTATCGAGCC CCGCCATGAT GCGCAGCAGG|
| | |GTAGACTTAC CGGCGCCGTT AAGGCCCAGC ACATCCGATT|
| | |TGGGCCCAGG AGAGCTCAGG CAGATGTTTC AGATATGACG|
| | |TTCAGACACT GCGAACCGAT GCTGATAGAT GAGC|
|16|350|GATCGCCATT CTGCTAACGA CTCTGACGCT GGCGCTGCTC|
| | |TCCAGGCTGC ATCGGTTATA ACATTCTGGC GACACGGGCA|
| | |AAACGCGGCT GTCGCCAGTC TCTGTCAGAA ACGGTAATCC|
| | |ACCGCCATAA AGTAACGACG TCCGTCTTCG GTATAACCGT|
| | |AGTCGTCGCG TTTGAGATCT TTATCGCCCA CGTTCAGAAC|
| | |GCCCGCACGC AGTTTAACGT TTTTCGTCGC CTGCCATGCC|
| | |GCGCCGGTAT CCCAGACCAC GTACCCGCCC GGCGTTTTTC|
| | |GCTGTTTGCC TCTGTCGGCC CGCTTACGCC GGTATAATTC|
| | |CTGATACGTA GATGACAGTT GAGCTGACCG|
|17|336|GATCGTGCAA ATGCGCGCTA AAGGTGGCGG CGTCCATAAA|
| | |GCCGGTGACT CGCGATTGCG GCTGTTCCTG GCCTTGGGTA|

TABLE 3-continued

| SEQ ID NO | LENGTH | PARTIAL 3'–5' SEQUENCES OF PROBES OF THE PRESENT INVENTION |
|---|---|---|
|  |  | TTAAAGAACA GAATGGTGGG CAGCCCGAGG ACTTGCAGAT<br>GCTTTAACAG CGCGACATCC TGCGCATTGT TAGCGGTGAC<br>GTTAGCCTGC AAGAGCACCG TGTCGCCGAG CGCCTGCTGG<br>ACCCGCGGAT CGCTGAAGGT ATACTTTTCA AACTCTTTTA<br>CAGGCCACGC ACCAGTCGGC GTAGAAATCA GCATAACGGT<br>TTGCCTTTGG CCTGCGCCTG ATTGAGTTCA TCCACGTAGA<br>ATAGCCGTGA ATTGAG |
| 18 | 286 | GATCCGCGAG GTGCGCCAGT TGCACCATCT CCAGCAATTG<br>CGTCACTTTG TTTTAATCGC CGCCGCCGCA GTTGGGCGTC<br>GCTCGCGCAG ACCGTAGCCA AAAGCGATGT TGTCAAACAC<br>CGTCATATGG CGAAACAGCG CATAGTGCTG AAAACACAAA<br>ACCGACTTTA CCTACTGGTA AGGCGCTAAC GTCGTACGTG<br>GAAACGATAT ACCGTGGACT GTGTCAGCCC GGCAATAATC<br>CCGGCTGTTT GCGGAACTAC GCACAGGACA TTGCGAGATA TTACGG |
| 19 | 325 | GATCGCGAAA GGCGTACATC TCACGGAATT TCCAACCGGT<br>ATCAACGTGC AATAGCGGGA ACGGCAACGT ACCCGGATAA<br>AACGCCTTAC GCGCCAGATG CAGCATGACG CTGGAGTCTT<br>TACCAATGGA GTACAGCATG ACCGGATTAG CGAATTCCGC<br>TGCCACTTCA CGATAATGTG ATACTTCGCA CAGTTGCGCA<br>GTGGTGAGTC GTTTTGATCA TACGTCTTTG CATCGTTTTG<br>CTAACTGATA CGACTAGGCG GTATATCGAT GATGTGTCTA<br>GATACGCACA TCACACCGAT CCTGCAATTC ACGTACACGA TCTGC |
| 20 | 200 | GATCAGGTGC GGTCGGTAAT TGACAAAATA TGGGCAAATG<br>GCCACGACAT TACCCCTTAA TTGATTGGCA GCAGCTCGTG<br>GCTGATTGAT TTTAGCCGGA GCCGGACGCT CCGATTTTGG<br>CGTCAGATAC CAATAACCCA ATCCATGAAT ACACACGACA<br>AGTATACGGG TTACACACAG TATACATCGC AGATCGCTGT |
| 21 | 264 | GATCGGTTTT ACCCTTCGTC CCTTTGATAT AACGCGTGAC<br>GCCGTTAACG TACCGCCAGT GCCGACGCCG AGATAAACAC<br>ATCCACCTGA CCATCGGTCT CCAGAGTTTC CGGGCCGGTG<br>GTTTTTCATG GATTCTCGGG TTGGCAGGGT TGCTGAACTG<br>CTGGAGCAGG AGATATTTTT GCGGATCCGT GGCGACAATT<br>TCTTCGGCTT TCTTGAATAG CGCCTTCATC CTGGCCTTGT<br>CAGCACCAGA TTGGCTATGC TTAG |
| 22 | 324 | GATCAGAATC TATGTTGTCA CAGATTAATA GTTTATTATA<br>TATTTCATCA AAATAATCGA CGTCAAGTTC TTTGTTTTTA<br>TTTAGAGTGA ATACTTCCTG TCGTTTTTTA TCGTTTACAT<br>AATCGACTAC CGTAACTGCA ACATTCTTAT TTTTTTGTTT<br>CTCTATACAT AGTAATATGG TGTCAAGTTC AAATTTTATT<br>TCTTCAAATC GCAAATCAAA GAAAAAATCT ATATTTTTAT<br>TTAAAATCGT TGTCAATTAT CTTTAAAACG ATGTTTTACG<br>TAACATTGTC GTATATATCG TCTGAGTCTA ATCAATATCA TAGT |
| 23 | 276 | GATCTTCGCC TACCGGCACC AGATTGGTTT GGTACAACAG<br>AATGTCTGCC GCCATCAGCA CCGGGTAATC AAACAGGCCG<br>GCGTTAATGT TTTCCGCATA GNNNCAGATT TATCTTTAAA<br>CTGCGTCATA CGGCTCAGCT CGCCGAAATA GGTATAGCAG<br>TTCAGCGCCC AGCCAAGCTG CGCATGTTCC GGCACATGGG<br>ACTGAACGAA AATAGTGCTC TTTTAGGATC ATACCACATG<br>CCAGGTACAG NNAGATTCCA GGCGTTTACG TAGTGT |
| 24 | 329 | GATCCGGCGC CGGAGCCACC ACGCCTTCAC GCGGGGCTCC<br>GGGTTCGGCG CGGGCAGATT CATCAGCTTC GCCAGAATGC<br>TCGCCAGCTT CAGGCGCATT TCCGGGCGGC GGACTATCAT<br>ATCAATAGCG CCTTTTTCGA TCAGGAACTC ACTGCGCTGG<br>AATCCTGGCG GCAGTTTTTC GCGAACGGTC TGTTCGATAA<br>CGCGCGGGCC GGCGAAGAAT CGAGACTTTT GGCTCGGCGA<br>TGTTGAGATC GCCAGCATCG CAAAACTGGC GGAAAAGGCC<br>CATTGTCGAT CGTACTACGA AATGTAGGGC AGACGCTCTG<br>CATTTAGAC |
| 25 | 222 | GATCCCTAAC ACCCGGTCAG TTCCCGACAG GCCGGTCTTT<br>TCTACTAGCT GACCTATCAC AAAATTCACG ACAGCGCCGA<br>TCGATAAGCG TCGCGATAAA CAGTACCGCG ATACGAATTC<br>CCATTACGAA CCAGTTCGTC TTCAAAGCCC GTAAACCAGA<br>CAGACAGGTA AGTGTAGTAG TGACTGGCGA CAAAGAAGCA<br>CACCCACGTA CCAGCATACG TC |
| 26 | 166 | GATCAGTATA CAACTATCAG TAATTCGACG ATAGACCGAA<br>GTGTGCTTGC TGGCGCTTTA TCGTCAAGGA TAATTGCCGC<br>TTTGACGGCC TTCGCGCTTC CTGCCAACTG GCTTCGTCTT<br>TGTGCATGAA TCACCGCCAG CGGCTCTGCC GCTCGATNTG TCGATC |
| 27 | 333 | GATCGCTTAA CAGATAATGA CTGGCGCTGC GGGGCTCCAG<br>TACGATATAG CCGCCTAGCA ACACGACAGG CGCGCTTTTA<br>TGGTTCAGGT CGCGACGAAT GGTCATTTCA GAGACGCCCA<br>ACAGGGTCGC GGCTTCTTTA AGATGAAGTT TATCGCTGCG<br>TTTTAAGGCC TGCAGCAATT GACCAATAGC GTCGTCGCTC<br>GGCTTTCCAT AGTTCCCCTG GAGAGTTAAA TAAGCGCTCC<br>GCACCATACA GAGCGCTTAA TATTACTCTT TTTTGCGCTA<br>TTTAGTCACG TACCCAGCCT TTTCGAATGG GCAATGCAAC<br>AGAACGTACA CGT |

TABLE 3-continued

| SEQ ID NO | LENGTH | PARTIAL 3'—5' SEQUENCES OF PROBES OF THE PRESENT INVENTION |
|---|---|---|
| 28 | 221 | GATCGCGCTC AATCGCTTCC GCCGCCAGTT TAGCCGCCAG CTCCGGCGTT TTTTCATGCA CCAGAGCTTT CTTAAGCGCT TTTGGCGTAG CACCACTTCT TTGGTTTGTA CTACCGGCGT GGTGGCCTTC CAGCGATAAG CCTCTTTCTT TACTGGCGGT TTCCAGCGGG ACGGNGGGNT GTACNNTCCG AAACCGAGGA GCGTCAGNAG AGTTATTACG G |
| 29 | 368 | GATCGTCGTA CCGCCAACCG AGCCGCCGGG TATGTGTCGT TAAACTCTGT CGCCAGACCA TAGTTAGAGG TAATAGAAGC CCCCCAGCCA AACTGGTCGT TAATCGGGGC GACAAAATGG ACGTTCGGCA CCCAGGCCGT CAGCGCGATG TTATCCGCAT CTAACGTCCG ACGAGATGGC GATGTCCCGC TAATATTAAC ATCAGGATCA ATATAAACGC GCCCGCTGAA AACGTCGGGC GGTCAAACAT GTATTACGCG GGTGCGCTAC GTACGCATCA TCTGCGATGC GCTCACGATA GCGCAGCAGA GAGAATCGTA CTGAGCTCGC GACAGTGTGA TGTCGATCGG ATCGCGCTTT GCAGTTTG |
| 30 | 288 | GATCTCCACA AACTGTTCCG GCTGAGCGAT AGCTTAAGTA GCGCATGTTT CCTCCAGGTA TGGAAATGCT CTGTGAGGCG GTAAGTCGAG CCCACGTACG GCCCCTGCTC CTTCTTACCC ATGCGCAGCA TCTTCTTCAT ACAGACGCGC CGCCGGGTTC GAGACCACAT TCGGGTGCAG CGGGTTAGTG CCCAGCGGCG TTTCATCGCT CGTAGTGTCA GGAACGCCTT CGCATTATCA TAGCAAACGA ACGTTCCAGC CCTTTCGCGT CATGAAAGAT GCGTCCGG |
| 31 | 254 | GATCAATAAC CGCATCGTTG TAGAAGTTCC CCTGCAATTT CANNNNATCC AGATAGTTGT TCTGGCTCAG GCCGACGGA GAGAAGCCAC GGATAATCAC GAAGTCATAG GTATTGGAAG CGCCGCGCTG CTTACCGTTA CACCCGCGTG TAACCCAACG CTTCTTTACT GACTGGAATT GATGCATCTG CATCTCTTCG TTAGTGACCA CCGAAACCGA CTGTGCGTTT TTCGATAGTA TCAGTTTGTG TGCG |
| 32 | 176 | GATCTTGTTG GCTCGCCTCT CCCCTCGGAC AACACGGTAT AAAACGCGGT GATAGAGCCA CCGCCGTGGA TGCCATTACC GGCACGCTCG ACCAGCGCCG GCAGCTTTGC GAACACCGAG GGCGGATAAC CTTTGGTGGC TGGCGGTCGC GATTGCCAGC GCATTAGTGC ATTGAT |
| 33 | 338 | GATCGTGATA TTCAATGCAC GCCTGCAGCG TGTTTTCGAT AAGCGTGGCG ACCGTCATCG GGCCGACGCC GCCCGGTACT GGCGTGATGT ATGACGCGCG CGCCCGGGCT TCGTCAAACA CGACGACGCC AACGACCTTG CCATTTTCCA GACGGTTAAT ACCGACATCA ATCACAATTG CGCCTTCTTT AATCCATTCG CCGGGAATAA AGCCCGGTTT ACCTACGCG ACAATGAGCA AATCAGCATG CTCGACATGG TGACGCAGAT CTTTGGTAAA GCGTGCGTAA CGGTAGTCGT ACAGCCAGCC AGCAACAGTC ATGCTCATTG GGCTCAAC |
| 34 | 319 | GATCTTGCAG CGCGCCGTGC CAGGCATAGC GCACCTGCTC ATTAAAGACG TTCGTTTTAC GTGAGTTCGG TTTCGGCGTC GGCTTCTGGC GTGCTGGCGC GTTGCCGCCG CCTGTTCCGC GCGAGACTTA CGCAGTCGAT CCAGCCGTGC GCGAACTGCC TGATTTGGTT AATCGCGTGG GCCTATTCAT TGGCCAGGCC ACCATGCAGA TGTCCATCGT CAGGACGAGC TGCCTATAGG AACGACGGGA CATAAGTCCA ATATGTGCGA GCGTCAGTAC CGTACCCTAA GTAAACTCTT CAACAGAAGT AAATGCCTT |
| 35 | 418 | GATCGATTTG CGCTGGCAGG TTGCTGCCGG TATTGACCTC TTTGTACATA TTCAGCGGCG CGTTCTGCGA GTAGCGCAGG TTATCTTCGA TATAGGTATT AAACACGCCT TTGGAGAGCG CGGCTTCATC ACCGCCGCCC GTCCAGACGC GTTGGCCTTT TTTACCCATG ATAATCGCCG TGCCGGTATC CTGGCAGGTC GGCAGAATGC TTTGGGCGAT CTGCAGGTGG CACTTTTCGG GGAAATGTGC GCGGAACCCC TATTTGTTTA TTTTTCTAAA TACATTCAAA TATGTATACG CTCATGAGAC AATAACCCTG ATAAATGCTT CAATAATATT GAAAAGGAAG AGTATGAGTA TCACATTCGG GCTATCTTTG GATTCTCGTT GACACAGAAC GAGGAAGAAG CGAGACAT |
| 36 | 350 | GATCAAGAGT CAGGGGTAAT TTTACCTTTT GCATAGGGCG CGCATATTAA CTTCGTAACG TCATATAGTC AAAGAAAAAG GCAGCCTGCG GTTGCCTTTT GCCAATAATT CGCACACATT GCGGGTTACA GACTTATTTT CGCTCAAGAC GAGTCAGTAT GACAGGCTTG AAGACCGAAG AGCTATGTTT AAGATGGCTC TCATCATTAC GCTATATCTG AGGGAAAAAA TATGCCCCGT CTCATCCTTG CGTCTACCTC TCCCTGGGCG TCGCGCGCTG CTGGAAAAGC TGACGATGCC TTCCGATGCG CGCGCGATGT GATGAACCCA TGCCGGGCAC GCGCTCAGTG |
| 37 | 270 | TGCGACAACA CACCCGCCAA AGCCGCCGCC GGTCATGCGC ACGGCGCCTC GATCGCCGAT GGTCGCTTTG ACGATGTCTA CCAGCGTGTC TATCTGCGGG ACGGTAATTT CGAAATCATC GCGCATTGAG GCATGGGACT CCGCCATCAG TTGGCCCATA |

TABLE 3-continued

| SEQ ID NO | LENGTH | PARTIAL 3'—5' SEQUENCES OF PROBES OF THE PRESENT INVENTION |
|---|---|---|
| | | CTTCGAAATC ACCTTTCTCC AGCAGGCTTG CCGCTTCAAC GGCGGGCATT TTCGGTCAAT ACATGGCGAA CCGTTTTCGG ATACCGGGAC AGTTCCGTGG CAACGGCATT |
| 38 | 280 | GATCCAGTGC TTTCGCCGCG TCATCCACAA TGACGTCAAA GCCAAAGGTT TCGGCGCGAG TACGCACGAC GTCCAGAGTT TGCGGATGGA CATCAGAGGC GACAAAGAAC CGGTTGGCAT TTTTCAGTTT GCTGACGGCT TTGCCATCGC CATCGCTTCA GCGGCGGCGT CGCTTCATCC AGCAGCGAGG CGAACGATGT CCAGCCCTGT AGTACAGCGT ACTGTTGAGT TACAGACTCA AACTAAATCG TATAGATTTA GCCTACACTG ATTTACATTA |
| 39 | 275 | GATCATCGCC TTCAAATTGA CCTGCTTGAG ATCGAAAATG AGCTGCGCTA AGTCCTCGAT AGAGTAGATA GCGTGGTGCG GTGGCGGGGA GATCAGCGTC ACGCCCGGCA CTGAATACGC GAGTTTAGCG ATATACGGAG TGACTTTATC CCCCGGCAAC TGACCGCCTT CGCCGTTCGC CTCACTTTAA TCTGAATCAC ATCGGCATGA CAGTAGGTCG GTCACAAGCG CGACGACTCT ATCGCAATAT GTCAATCCGG TCCTACATAT CATTT |
| 40 | 333 | GATCTTTCGA CTCGATGTTG GCGACGAAGA TAAAGTTCGG CAGCAGCTTG CCCGCGTTGT CATAAACCGG GAAATACTTC TGGTCGCCCT TCATGGTGTA CACCAGCGCT TCGGCAGGCA CGGCGAGGAA TTTCTCTTCG AATTTCGCCG TCAATACCAC CGGCCATTCC ACCAGCGAAG CTACTTCTTC CAGCAGGCTT TCGCTCAGGT CGGCATTACC GCCAATATTA CGTGCTGCTC TCAGCGTCCG TTTGATTTGG CTTAGGCTCG TAGTCGCATG ACTTACGGAC TCAGAGAATT GCGGTACTGT CAGATGTGAG GACCGTACAT AAG |
| 41 | 233 | GATCGGGCAT CGGCACGACA CCGGTATTCG GTTCGATAGT GCAGAACGGA AAGTTTGCCG CTTCAATACC GGCTTTTGTC AGCGCGTTGA ACAGGGTGGA TTTCCCGACG TTGGGCAGAC CGACGATACC GCATTTGAAT CCCATGATTT AACTCACCTT AATATCTTAA TAATCAACCT GTTATAGAAA ACAGATTGCA GAATGGAATA CTCGCTATTA TCACGCGCGC AAA |
| 42 | 302 | GATCAAGCGT GTCCGGCGAA AACGTTACGC GTTCTCGCAG CGATACAGGT GCCGTTTTAT GGTTAATACC GAGCGCTAAA AGGGTCATGT CTGCGGGAGT AGTACCAGCG TTGATATGGT TAGTCTGCTT GCATCATACA GGATGCGCGT GGTCAATAAA AGAGAGAGCC CCCTTTTGGA GTAATTGGCA GCGCTCGCTA ATTTGATGAT TTAAGACACT TGAAAGTAGA CGATGTCACC AGGCGCCTAC ATTAAAGGCT ATACTGTACG ATAGCAAAAT TTCCGATCCG CCACTTTCAC TC |
| 43 | 262 | GATCTACTTT CGGGATGGCA GCGTATCTGC CGCAATACAC CCTGATGGAT GTTATGCCTG GATCTGATTA CTCTTCTTTG GGCGAAGTTT TCGACCCGGC TCTTTAACTT CTGCCCGGGT CTGAAGGTCA CCACGCGCCG TGCTGTAATA GGAATATCTT CACCCGTTTT CGGTTACGCC CCGGACGTTG ATTTTTATCA CGCAGATCGA AGTTACCAAA ACCAGAGAGT TCACCTGCTC ACGTTTCAGA GCACGACGAT CT |
| 44 | 153 | GATCAGGTCC ATATTTGTCT TTGCCTTTCT ACCCGACACG TTTCGGGTGT GCGATTCGGA TTAGTCCGCC AGAAATAGCG GGCCCATTGG CGGTTTTGGA AGGTCAAAAA GGTCAGGGTA ATCCACCGCA ACCAAATATA GCCCTTCCGC CTT |
| 45 | 169 | GGCGCGTTGG CAGATTTTGC CAGACGACGG GCGATTTCGG TTTTACCGAC GCCGGTCGGC CAATCATCAG AATATTTTTC GGCGTTACTT CGTGGCGCNN CTTCATCAAG CTGCATACAC GCACGTTACN ATCNNGACGG AACCTTTGTA TCTGCGATAA TNNTTGTAG |
| 46 | 282 | GATCGCTGTA GATTTTACAA GTCTTCTTCA GCGATACACG TCTGCACAGC AGGCCGAAAC CGGTGTTGAT GCCGTAGGAG TACGCCTTCA GGCAACGATA TCATTGACAA CGCGACGTGG CGTTAATACG TCAATGGCAT GGCCTTCCAG CGAAAGCTGT ACGATGAGAT ATGCATAGAG AGAGACTTAA CTGCCCCAGA GTATATATTG TGTTCATATC AGCCTTTCCT CAACAACCAT CGTAAATTCA GACTTACTCA CACACATTCA CGTAGATCAT TC |
| 47 | 258 | GATCGCGGGT CAGTGTACGC ACCGCTTCCG GCGTATTTTT CCCGCTATTA AAATAGAGCT TGTCGCCAAC AATCAGGTTA TCGAGATTAA TGACCAGCAG CGTATTTTTC TTCTCAGCGT CACTCATCGT TTGAGTAAAT TTGGGGGCCT AGCTTTCCCT CTTCTTCCCC GCTGGTGGCG ATAAAACGAA TCCCGTAATG GGTCGGTATA TCTTTCAGAC GGCGCAGTTC CAGCATAAGC CCTAATCCCG CGGCATTA |
| 48 | 315 | GATCGCGACA TGCGCAACAT CTACCAGTTT ACTTAACTGA CTAAACAGTA AGTCGACCGA CCGGGGACTG GCAACGGTCA ATTCAATATT TATATTCTGC GCATCGGTCG CGGCTTCCAT ATTCAATGGA GCACACCTGA AAACCACGAT GGCGCACCAC GCGTAAAACA CGTTCTAAGG TTTCTGGATT ATAGCGTGCC GATACATTGA CCTGATGTTG CATCATGATA TTTCACGATT TCAGAGTCAT GGCGCAGGCG CACACGCAGA CATTTGAAGT |

TABLE 3-continued

| SEQ ID NO | LENGTH | PARTIAL 3'-5' SEQUENCES OF PROBES OF THE PRESENT INVENTION |
|---|---|---|
| | | CTCGATGAGA CGAGAGACGC CTCAGTCACT GTCGA |
| 49 | 268 | GATCCAACGT CTGGCGTAAT GCCAGCATGT CGTACTGGGT GTTGTTGCCC AGCTCCGCAC GTGGGTCGCC TTTCGCCACC ACGTTGAACG CCAGACCATC TTTAATTTGC GGCGTCGGCC AGCATGGTAA AGCGGTTGCT GAGTACACGC GCTTCACGGA ATACCGTGGT GGCTTGAGCA CCGCTCACCT GCTTGAGTCG GCTGTTCAAC TCGGCGTAGT CCCCACATTA AGGCTGGTTG TACACGTCGT TGTTGGTGTA ACCGCGGT |
| 50 | 296 | GATCTAAAAT TCAAATACAG GAACAGGGAG TTCTGGTGCA GAGGGTACTA TGTCGATACG GTGGGTAAGA ACACGGCGAA GATGCAGGAC TACATAAAGC ACCAGCTTGA AGAGGATAAA ATGGGTGAGC AATTATCGAT CCCGTATCCG GGCAGCCCGT TTACGGCGTA AGTAACGAAG TTTGATCGAA ATGTCAGATC GTATGCGCTG TTAGGCGGCT GGTAGAGAGC CTTATACCAT CTGAAAACTC CGTATCCGAG ATATTATAGA CTATTGGCAA CCTGAATCTC TCGATT |
| 51 | 213 | GTACACAGAC GCCTTTCAGA TTGGCGATGA CGCATCCATT GAGAACACCC CATCGGTGGC GATCAGGACA TGACGCGCGC CGGCCTCACG CGCCTCTTTC AGCCGCGCTT CCAGCTCTGC CATATCGTTG TTGGCATACG CTTCGCTTTA CACAAACGCA CGCGTCAATG ATAGACTGGT TCAGCGCGTC GGAATATAGC GTTCGCGCAG CAA |
| 52 | 113 | GATCGAAACT CGCCACGTTA ATCACCGTCG CCACCACCGG CGGCCAGCGT CCGTAAAGCA GCGCAATCAC CACTACGGCC CAGGCAAATC GATGCATTAC CAGATTGGCG GCG |
| 53 | 337 | GATCTTCCGG GTTAAATTGC AACAATGCTT CGCTAACGCG CAGCCAGCTC CATTTGCGGT TCCTCCATCA GCGAGGATTT CAGCGTATCC AGTAGCTTAC GAATCACTTC GGCGTTATCC GCTTCGTCCA AATCTTCATT AAACAACTCG GCGACCGGAC TAATATTGCC TTTTAACCAG ACTTCCGAGA TATGTTCATC AAGCGTTTTC ACCGTTCGAA CGGTTAATCA GCCACATTTC CCCTTTCCAG CGATTCAATA CGCAAATCAA CTGCGTTGGG AAGATAACCT AGGCACAACG GCAAATCAAG ACGTTGCATA CATATAAATA GCGCCAC |
| 54 | 313 | GATCATAAAA CTTCCGCGTG TATATGTTGG TTGGAACCGT AGAGATATAG ACAGGTGGTT CTACACAGGC GTTTACCCCT ACCGTCGCAA ACATTTCTTT AATCAGGCTT TCTCTTTTTT CTTCTGATGG ATGCGAGTGA TTAAACTCAT ACATTAACGT TTTCCCACGA AGTCTTTTTT CCGGTAAGCC TTCGCATATA TCGGTAAATA GCTTGCCTGC TCTTATCTTT CGGTCATGGC ATGTTCATCG CGATCACTCC GTTATGATAT GTCTCGATAG CCTCGATCCA ATGATGCTAC GCATCATCAC TCA |
| 55 | 300 | GATCGAATTC AGATTCCATT ATCGCCATCA GATATTCCAG ACGTTCAGAT TAACGTCGGA CATCTCCAGT ACGGACTGTT TATCCGCCAG TTTCAGCGGC ATATGCGCGG CGATGGTGTC AGCCAGACGT GCAGGGTCGT CAATGCTATT GAGTGACGTC AGCACTTCCG GCGGAATTTT TTTGTTCAGC TTGATGTAGC CTTCGAACTG GCTGATAGCG GTACGACCAG CACTTCTTGT TCACGCTCAT CAATGGCTGG CGAATAAGGT ACTCGCTTCG CGAGAAATGT CGCGTGCAGA |
| 56 | 423 | GATCCCACTT CTTGAACTGC TCGAAGCAAA CGCCTTCCGG CAGATCATCG CGCGCCACAT ACAGCTGAAT GCGGCCGCCT ACGTCTTGCA GGGTAACAAA AGAGGCTTTA CCCATAATAC GGCGCGTCAT CATACGGCCC GCGACGGACA CTTCAATATT CAGCGCTTCC AGTTCTTCAG CTTCTTTCGC GTCAAACTCT GCGTGCAGTT GGTCTGAGGT ACGGTCAGAC GGAAATCGTT GGAACGGATA CCTGCTCACG CAGTCAGCCA GCTTTGCACG TGCCTTATTT ATTGTTAAGA TCGACTACTG TACGCCTGTC TTTGTCAGAC ATGTGATCTC ATAGCCTGGC TTTCAAACTT GCTCGATATG ATCAGACTAC GTCAGTACGC TGGATGCGTC ACAGTACAGC TTAATCGATC AGA |
| 57 | 173 | ACAGAATCTT TTTCACGACG TTCTCGTTAA TAACCGATAA GACGTGAGGA GTTTAGCAGA TTTAGTGCTT GATTTCGTGG CTTGTTTACA GTCAAAGAAG CCGGAGCAAA AGCCCCGGCA TCGGCAGGAA CNCTTATTTA TTAATAAAAT CTTCCCCAAC TAATATCTTT TTT |
| 58 | 218 | GATCCTCCGT GGCATAAGAA ATGCCGCCAA GAATCGTGAG TAAGATGTTG AAAGGATTGC GATAACATAC CCACAGATGC ACCCACCACG GCGAGGGTTT CTGTGCCGGA ACGGTTTTCG CCATGCTTTT CACGCGCNNT CACCTCGGCA GCGTTTAATC CTCGGTGCGT ATCAAAACCT GCAGAGAGTC TCTGCTCATG CGCGACTTCA GACAGTAG |
| 59 | 346 | GATCGAGAAA AGTGAGCATC CCTTCGATGG TAAGTTCGGT CTCATCCTCC ACACTTAATG TCGGATTGTT CCCGGAACCA TCCAGCTTAC GTGTCGCTAT CAGCAATACT CGGAATCCCT GCGCATTGTA ATCTTCGGTT TTCGCCAGCA GTAGCTCGCG |

TABLE 3-continued

SEQ ID NO LENGTH PARTIAL 3'-5' SEQUENCES OF PROBES OF THE PRESENT INVENTION

|  |  |  |
|---|---|---|
|  |  | GCGTGTTTCC GTCAAGCGCC ACCACACGAT CGCCTTCGCG |
|  |  | AAGATGGGTG GCTACCATCA TCATCTCTTC AACGGCGCTT |
|  |  | TGCAGATCAG GCATCTGTCT CATGCTGCGC ATCTCACAGA |
|  |  | CGATACCGCG ACGTACAAGT CGATGCAGTC ATCGTTATGA |
|  |  | GCCCTTGCGA TGTGCATGAC TGCAAC |
| 60 | 323 | GATCCTGACG AATGGCCACA ACGGAAGGCT CATTCAATAC |
|  |  | GATGCCTTGT CCTTTTACAT AAATGAGGGT ATTCGCGGTA |
|  |  | CCCAGGTCAA TGGACAGGTC ATTGGAAAAC ATGCCACGAA |
|  |  | ATTTTTTCGA ACATACTAAG GGATTAATTC CTTGAAAGCT |
|  |  | GGGGCGAAAA CAAAATGCGT TTACTTTACC AACCACACGC |
|  |  | AGCAGCGACA AGCGCGAAAA TCATCTGCTA CGTGAATTAG |
|  |  | TGCGTCGTTC TTTGTACAAT CTCGCTGAGT CAGCTGAAAA |
|  |  | TCACGCGATC TGCTCGTGAC TTGAAGATCT CGATTCTCGA CAT |
| 61 | 276 | GATCGCGCGT GGTTTGCAGC GTCGGTTCCA CCACCAGTTG |
|  |  | GTTAATGCGG TTCGTTTCCA GACCACCAAT CTCTTTCATA |
|  |  | AAATCTGGCG CTTTGATACC CGCCGCCCAC ACCATCCAGA |
|  |  | TCGGCCTGAA TATATTCACC TTCTTTCGTA TGCAGACCGC |
|  |  | CTTCGGCGGC GCTGGTGACC ATAGTTTGCG TCAGCGCGAA |
|  |  | CGCCAGTTTG GTCAGTTCAT TATGCGCGGC GTGGAGATAC |
|  |  | GCGCGCACGA GGCAGATACG CGCAGTCACA CGAGTC |
| 62 | 166 | GGGCCAGAGG TATGACTCCA CCAGACCGTC AAAGACGGCG |
|  |  | TTGCGTCGTG CTCAGCATAG AAGCCGCGCG CCTGCTCAAC |
|  |  | GGTCAGGTGC AGCATTATTA GTGCCCAACA ATTTTGAACC |
|  |  | CTGCAGCTTC AAACGCGCGA AAGATCGTCC AATACGTTCT CCGACC |
| 63 | 425 | GATCTTTAGC CGGGCAGACC TCTACGCATA AATTACAGCC |
|  |  | AGTACAGTCT TCCGGCGCGA CCTGCAGCAC ATATTTCTGG |
|  |  | CCGCGCATAT CGCGGACTTC ACGTCCAGCG AATGCAGACT |
|  |  | GGCTGGCGCG TTCTCCATCG CCTGCGGGGA AACGACTTTC |
|  |  | GCACGAATTG CCGAGTGAGG GCAGGCAGCG ACGCAGTGAT |
|  |  | TACATTGTGT ACACAGTTCC TCTTTCCAGA CAGGAATCTC |
|  |  | TTCGGCGATA TTGCGTTTTT CCCAGCGGTG GTGCCCATTG |
|  |  | GCCATGTTCC GTCGGCGGCA GGGCGGAAAC AGGCAGTGCG |
|  |  | TGCCGAGGCC CGCCAACATG GGCCGTAACG TTTCAGAAAT |
|  |  | CGCAGTGAGA CGGCGGCATC CCATAGGATT ACGCTGAGAT |
|  |  | CCAGATCTCC AACATCTCAT CTAAA |
| 64 | 333 | GATCTACCGG GTGAGCGTAT AACCNATCTT AATCCCTCCC |
|  |  | GGTTAGGTTG ACATTAGGAT CCTGTTCCTT TCGGGTTATA |
|  |  | CTGCGCTGAA CGCGGGTCCA GTCCAACGTG AATACGGCAG |
|  |  | ATAAACCAGA CCAGCCAGTA ACACAAAAAT AAAAATTCGC |
|  |  | AGCTTCCACA AAGCCAACCC AGCCGCTTTC GCGATAGAAG |
|  |  | TCGACCATGC GAACAGATAC AGCGCTTCAA CGTCGAAGAT |
|  |  | AACGAAGAAC ATGGCTACCA GGTAAAATTC GGAGACAGGC |
|  |  | GTAAGGCGCG CCGGTGCGAC CATTCATCTC CATCCTTTGA |
|  |  | ATTACGGACA GCA |
| 65 | 374 | TTATCAATAC CCGCATTTTT ACTGAAACCG GGCGTGATGT |
|  |  | TTTTGGCTTT GACATTGCGA ATGACGAAAT GTTTGCCATT |
|  |  | TTCTACGTGC ACAAGCTGTC GGCAATCAGA TCCGGTAATA |
|  |  | TTGGCCACCA CAAAGTTTTT TACTGCCTGG TCTTCAGGAT |
|  |  | AACTGTTGTC ATAGGTGCTA CCCGCCAGCC CGATCCCCCA |
|  |  | GTTGATTTTG CCATTGGTAC AATTAATGCG TTCGATGACA |
|  |  | TGATCGGAAA TCAGGATGTC GCGGTCGTGA TCGCGACATT |
|  |  | CCACTCATGG CGTCCCCTGT AATCGCTAAG CGCTATCGTA |
|  |  | ATCGCGCGCA TCCATTGTTA TGAATCCTGC GAGATGGCGA |
|  |  | GTGCGTGGTA CGGA |
| 66 | 296 | GATCCTGAAA TGCCCATCCA CGCCAGCTTG GGTATAGAGC |
|  |  | AATCTGGCAG TATAAGATTT GGGATGTATT TTGGCCGCAG |
|  |  | CCGCAAAAAA CGCGTCTGGG CGATTCGGAC AACCAGAAAG |
|  |  | AGGCGCTCTG TAATGCGGTC TGGGCTATGG GACGAATTTC |
|  |  | CAGATAATAG TAAACGATTA ACCCTACACG AAAGCGTAAC |
|  |  | AGAAGCGCAT AACGCCTTTA AAAACCACAG TAACACGCCT |
|  |  | GCATTATAGT TTTTCTTACT CAACATCTAT CGTTCGCATA |
|  |  | CCGGATGTAA TAGGCT |
| 67 | 178 | GATCGGCAAA GGTACCGGTG GTGCCGTCGT AGTTTTCTCC |
|  |  | GCGCCGGGCG TTAACGTTCT GGCCCAGCAG GTTGACCTCA |
|  |  | CGCGCGCCCT GGCCGCTAAC TGGGCGATTT CGAACCGGAT |
|  |  | CATCGTCTCA GGGCCGGCTG ACTTCTTCGC CGCGGGTATA |
|  |  | CGGCGCACAC GTAAGTAC |
| 68 | 327 | GATCAAAAGT TTTCTGCGCC GCCTCGTTCA TCAGTTTATA |
|  |  | AGGATTGCTC TGATCCGCTG CCGTTGCTGC GCTTAATGGC |
|  |  | GCAATGACCA GCAGGGCCAC CATCATCAGT CGTTTAAACA |
|  |  | TGCCTCAATT CTCCTGAGAT TATTTCGTTT CGCCCGCGGG |
|  |  | CTTGTGGCTT CAGTATGACC TTCCGTTGCG GGCTGGCGCA |
|  |  | TCGCAGAATT CTTATTGTCG TCGCCTTCGT GTTATAAGGA |
|  |  | ACTGCCAATC ATATCTCCAG CACATGCAGA CGGTCTGATC |
|  |  | GTACTGCACG CTAGATAGAC GTCAGACTCA ACACAACGAG |
|  |  | CTAGCGA |
| 69 | 375 | GATCCAGCAG GTTGATTTTT GTTTCTTTGT TAGGAACTAC |

TABLE 3-continued

SEQ ID NO | LENGTH | PARTIAL 3'—5' SEQUENCES OF PROBES OF THE PRESENT INVENTION

| | | |
|---|---|---|
| | | CGGGGTACTG CTTTCAGGTG TGACAATTTG TTCAGACATA TGCTATTCCG GCCACGTTAT TACACGTTAT GGCCCCTGGA GGTTGAAAAA AGAAACGCCC CGGTAAGCTT ACTGCTCGTC CGGGGGCGCT GCATTGTACA AATTCTGGCG TAAGGAGTCC ACGTCTGCAC GCGCATTAGC AAAAATAATA TTTGAACCGA TAATTTATCG CCAACGCATT TACAGCGTGA AAGACGAAGG AGATTAACGG GTGGGGGCCA CTCGCTTCAC GAGAAAAGCG ATTCGGCTGG CGATTCAGCG AATCGACGTG TGCGTTCAGT ACTATCACGT AGTCG |
| 70 | 298 | GATCGGACGG CGCCTTATCT TCTTCAATAT CGCGCGTACC GTAGAAACCT TCAGGCAAGG TCGCTCAGCG ACAGCCTGCT GGCTGAGTCC GAGTTGTTCA CGGGCATTGC GCAGACGAAC GCCGGTGGTT TGTGCTTCAT TTTGGTCGTG CGTTGCTTCA GTATTCATTC GCTACAGCTA ACGGTACGTG TAAATTAGGA TTCAGGCGCC GACGAGCGTA ATGCCGCCAC GCGCAAACAT CGTAGTACTT AGTCAGACAG TATACGTTAG CGCGCGATAC AGCTAGAACG CTAACTGT |
| 71 | 234 | GATCTCACCT TTTTTTAGCT GCGGCATCGC TTCCAGAGTG GCGACCGCCG GGTACGGGCA AGGTTCGCCA ACCATATCCA GACGGTAATC AGGGACGATA TTTTTCATAC AGATTCCTTA GCAGGCGTCA GCCCGCACGG CGAAAAAACG TTTTTTTCCC AGCCGATGAT TAACATTCAG TGGTAAATAA CAACAAAGTA GGTGACACGC AGACCGTAGG ACCAAGTATT CAGC |
| 72 | 317 | AGCTCTGATT TCGGTAGCGA TACGTCATCC ATCAGATTCG CCAGCGGATG GACAAACGGC AGGATGACCA GGCTGCCGAT CAATTTGAAC AATAGGCTGC CGAGCGCTAC CGGACGCGCG GCAGCATTGG CGGCGCTGTT ATTGAGCATC GCCAGCAGCC CCGATCCCCA GATTGGCGCC GATGACCAGG CACAACGCCA CCGGGAACGA TATAATCCCG CCGCCGTCAG GTCGCCGTCA GCAACACCGC CGCCACTGGG AATAACTGAT AATAGCGAAC ATCCGGCCAA TAGCGCATCA GCATATGTGC CTGAGAG |
| 73 | 134 | GATCGAGGGC ACAGGAGAAA CGGGCATTTT CGCCGCAATT AGTTGACCTG ATCTCCCAAG ACCAAATTTT CCTCAGCCGG AATATACCAG AACTGGTCGC GATATCCGCA AGATCGCGCT TCACGGCGTC GCTT |
| 74 | 387 | GATCGTAATG TGCGGCCAGT TCAAAACCGA AGCGGCTATA TAACGCCGGA TCGCCCAGCG TCACGACCGC CGCGTAGCGA ACTCGTTGAG CGAATCCAGC CCTTCATACA CTAACTGGCG CGCCAGCCCT TGCCCGCGAT ACTTTTCATC GACCGCCAGC GCCATGCCGA CCCACTGTAA ATCTTCGCCT GCACATCAAC CGGGCTAAAG GCGACATAGC CACACTGACC TTCATCATCG TGCACAGTCG AGGTAGAAAA CATCTCACGA AATCGTGAAC AGCTTGCTTC GCATGTTTCG ATGACGGCGT ACACGCGATC AATACAGCGC ATCATAGATT TATGATAGAT GTATAGAGTG TGTCTAGAGT TTATCGCTAC ATCGAGT |
| 75 | 189 | GATCGTAAGG ATTGACGATT AACGCCGACG TCAGTTCATT CGCCGCTCCG CAAACTGTGA CAGTACCAGT ACTCCAGGGT TAGCGGGGTC CTGCGCGGCG ACAAACTGTT TGTGGACCAG GTTCATCCCG TCACTCAACG GGTTACTAGC CCGACGTCTG AATAACGGAA TATACTTCAT TAACAGTTT |
| 76 | 217 | GATCACGAAT ATTCATTATT CATCCTCCGT CGCCACGATA GTTCATGGCG ATAGGTAGCA TAGCAATGAA CTGATTATCC CTATCAACCT TTCTGATTAA TAATACATCA CAGAAGCGGA GCGGTTTCTC GTTTAACCCT TGAAGACACC GCCCGTTCAG AGGGTATCTC TCGAACCCGA AATACTAAGC CAACCGTGAC TTTGCGACTT GGTTTTT |
| 77 | 275 | GATCCCTTCT TTTGCTGATG CAGTAGCGGA CCAGGCTACC ACAAGGGGAA TGATGCAGAC TGCGAAAAAG TTTTTCATTT CAGAACCTGC CTTAATATTG GGCTAAAAGA CAAGTTTCAC GGTATAGGGT ATGATATAAC GATTCAATAA ACGAAGCCCA AAAAACGGTC TATTGTAACG CTGGGTTTCT GTAAGCGGGT AAAATGAGAT GAGATTTAAT AACATCAGAT ATCTCGGATG AATCACTCTC GAATCCGCAG CGTCCATCTA CGTAT |
| 78 | 101 | GATCTTCATA CAGGCCAGA TAGCCGTCAT AAATGCCCAT GACTTCCAGC CCTTACGTCA ACGCTGCAAC ACAACACCGC GGATTTTTGA TTCATTCTCT T |
| 79 | 303 | GATCCGCACG GATAAAAACT CGTTTCCCGG CCAGATCCAG ATCGGTCATC TTAATTACAG ACATGGTGAA TCCTCTCAAT GATGCTTAAA GTTTTGTCGA CGCTGACGCG TGAGCCTGAA ACCAACTGCG GCCATCGCTA ACGTGGTGTC GAGCATCCTG TTAGCAAAGC CCCATTCATT ATCGCACCAG ACCTAGCGTC TTGATCAGTG GGCGCACTGA CCGGGTTGGG CATCACATGG CGTGGCTGGT AATTTGGACG GTGCATGTAC TCATGATGGC TTGGTTGGCC GGATTGCTTG CTT |
| 80 | 257 | GATCGTGACC CGGATAACGC TCATCATCTT TGGTCAGTTC CGGCGGCGTC ACGGCAAAAC CGCGGCGCCA CTGTTTAACC TGCTCGTCAC CATATTTTTC TGCCGTTTGC GCTTTATTCA |

TABLE 3-continued

| SEQ ID NO | LENGTH | PARTIAL 3'—5' SEQUENCES OF PROBES OF THE PRESENT INVENTION |
|---|---|---|
| | | GCCCCTGCAA CGGCCATAGT GACGTTCATT GAGTTTCCAG |
| | | GATTTTTTCA CCGGCAGCCA CGCTGATCCA GTTCATCCAG |
| | | TACGTTCACA GGCTATGGAT AGCGCGTTTC AAGTACGGAA |
| | | GGTAGGCAAA TCAAGCG |
| 81 | 290 | GATCGAGCAG GCATTGCAGC AGCAGACTTT TGCCCTCCCC |
| | | GCTGCCGCCA ACCAATGCCA CCATTTCGCC GGGCGCGATA |
| | | TCAAAAGAGA CATTCTGTAA TAACGGCGAC CAGCGTCTCG |
| | | CGCCATACCA GCGATAACGG CGCTTTCCAG CGTAACCTGT |
| | | TGTAAACTCA GATACGTCAC TCCTTAGCAC AGCCGCTGAA |
| | | TGGCGGAAAC TGTCGAAGAG CATCACAGCG TGAATAACAT |
| | | TAGGCCGGGA ATAGACAGCA CAGTTCATGG CTAATAACGT |
| | | ACCGTCGAGA |
| 82 | 233 | TGCAGATCCA CCTGGAACGG CGGGATGTTG ATCACCTGGG |
| | | AGGCCAGACC GCTATTACGG CGCATTAACG CGCCATTACC |
| | | TCTTCGATGT GGAATGGCTT CGTCACGTAG TCATCGGCCC |
| | | GGAGCTGAGA ACCTCGACTT TATCCTGCCA GCCTTCGCGC |
| | | GCGTTAACAC CAGAACCGGC AGTGAAACAT CACTCGTGCG |
| | | CCCACGGGTA TTAAGGAAAG GCCGTCTTCA TCC |
| 83 | 284 | GATCTCATCA AAACGGTTGA GTACCAGCGC CAGGGTCATA |
| | | CCCGCCTGGT TCAACGCCGT CAGGTGCGCC AGTTGTTGAC |
| | | GGGCGGTCAC GTCAAGCCCG TCGAACGGTT CATCAAGGAT |
| | | CAATAACTCT GGCTCAGACA TCAGCACCTG ACACAGCAGC |
| | | GCTTTTCGCG TCTCGCCGGT AGAAAGGTAT TTAAAACGCC |
| | | TGTCGAGTAA AGCGGAAATC CGCGAACTGC TGCGCCAGTA |
| | | TCGCACAGCG CAGGATGGTG ACATATCCTG AATATTCGCG TAGT |
| 84 | 367 | GTTGCGATTA TCCCGCAGCG CCTGCTCGAA CAATTGGATT |
| | | TGCTCAGTGC TTTCATGCCA TAACCAGAAG GTACTGATTA |
| | | ACTGGAACAC CAGCAGAATA AGACCAATTG TCAGCATTAA |
| | | ACGCTGGCGA AGGGTCACTG CTCTTCGCTG AAAACGCATC |
| | | AGGCTCACTT AGCTTTCCTC AGTGGCAACC AGCATGTAGC |
| | | CAAACCCGCG AACCGTGCGA ATGCGACTTG CCGACTTTGT |
| | | CGCGCAAATT ATGTATAGCA CTTCCAGAGT GTTGGTCGAG |
| | | GGTTCGTTAT CCCAGTTGTG ATATCGTTAT AAAGAATTTC |
| | | CGGTGCACGA CTGCCTGAGA CTAACCGTGA GAGCACGTAT |
| | | CTAGCTC |
| 85 | 320 | GATCGTTGAT CGCCTGGATA ACAACCTGCT GCTGCTCGTG |
| | | ACCGAATACC ACCGCGCCCA GCATAGTGTC TTCGCTCAGC |
| | | AGTTCAGCTT CGGATTCCAC CATCAGCACA GCCGCTTCGG |
| | | TACCGGCAAC CACCAGGGTC CAGCTTGCTT CTTTCAGCTC |
| | | GTCTGGGTCG GGTTCAGCAC GTACTGGTCA TTGATGTAAC |
| | | CTACGGCGCG CGATTGGGCC GTTGAACGGA ATGCGGACAG |
| | | CGACAGCACG ATGCGATCAT CGCACGATGA TCAGGTACTG |
| | | CGTACGAACG ACGTCCGATA ACTCGATGTA CAGCTCGGAA |
| 86 | 249 | GATCAATAAA TACTTTACGA ACTTCACTGG AGATTTCCCA |
| | | TTTAGTGTCA TTTGGGCAGT TTATAAACAA ACGCGCGGTA |
| | | GTATAAAGGC AAGCCAGACG CATTGATATA CCCGTTAACG |
| | | CCGACGGGTG ATAAGGAGAT CGACCGTTAT GGCTTTTAAA |
| | | CCTGGCAAAT AGGATTGCAT TATTCCAGCC ATGAAGCGCT |
| | | GGCCATCGCG TTATTCACGC GCATCGGCTG ACACGCACTG |
| | | TGCACTGCG |
| 87 | 275 | GATCGCCTTT TGCTGCCAAC GCTGCGGGAG AAAGAGCAGA |
| | | AAGAGCGAAA ACAGCTGCGA CAGCCGCCAG AGTCGATTTG |
| | | AGCATGAGAT TTCCTTAAAG AGAGCAGAAA TAAAGCAAGT |
| | | GGAATGATTT TAAAGAGCCT TCTGGGCCAG GCAGCCTTTA |
| | | CTATTTACGT ATATGAACAA TGTACGTTAC GACGACGCGT |
| | | ATCTGCATAT GATGTGACAA CATAATAATA AATGCATGAC |
| | | ATACTATACT ATATATTAGC TACAAGCTAT GCTCA |
| 88 | 325 | GATCGCCGCG AACCAGCAGA GCCACCAGCG GAGACTTGCT |
| | | GTCTTTCACC GCTTTCACCA GCAGCGTTTT TACCGTTTTT |
| | | TCAATTGGCA GGTTGAATTG TTCCACCAGC TCCGCGATGG |
| | | TTTTGGCATT TGGCGTATCG ACCAGAGTCA TTTCCTGCGT |
| | | CGCGCTGCGC GGCTTTGCGG GATAGCTTCT GCAGTTCAAT |
| | | GTTAGCCGCG TAATCAGAAA CATCAGAGAA AACGATATCG |
| | | TCTTGCGCTT TGGCAGCCTG GAATTCATGC TGGTTGGCGA |
| | | TAGACGTATG CTGTACGGGA ATCAGCCATA GTGAGATACG CTATA |
| 89 | 230 | GATCGATACG ACGTTCAAAG GATTCAAACC GCGCCATGGC |
| | | TTCATCCAGT TTGCCGCTGT CAAGCTGACG ACGGACATCG |
| | | CGGGAAGAAC TCGCCGCCTG ATGACGCAGC ATCAGCGCCT |
| | | GCGGGCGAGC GCGCGTGTTT CGCTGAGTTT GTTTTCCAGC |
| | | GTCGCCAATC TCTTTCTTCA TGCGCGCAGT GTCATCACAG |
| | | CGTGACTTCT GTTCAGCTAG CATAATCGTC |
| 90 | 146 | GATCCCATCG CTTTTTCAGA TATCATGCAC TTTTTGCACT |
| | | CAATCTGCGG CAAATCCGAC CACTTTTTGC TCAGCCAGAA |
| | | TGCAGTATTT CCGTCATACA TCGATTAGCT ACGACTCTAC |
| | | GAACTACCTC GACCACAAGA TCACCG |
| 91 | 184 | GATCTTTGTT AATAACAGTG AGAGAACCGT ACGAATGTAG |
| | | AAGAACTCCC GCCAGGCGGC AACATCTTTC ATAGTAGACC |

TABLE 3-continued

| SEQ ID NO | LENGTH | PARTIAL 3'—5' SEQUENCES OF PROBES OF THE PRESENT INVENTION |
|---|---|---|
| | | AAGCGTTAAC CCCTGCTGAT GTAAAAACGC TTCTATCTCT |
| | | TGCGCACCAC GGAACGGAAG GTTGCGCGCC TTTAGCGCTT |
| | | ACGGCAATAG CCGCGGCGGA TGGG |
| 92 | 311 | GATCAAACAC ATGAATACCG AGGCCTTTGA GTTTTTCAGT |
| | | CGAGGCGTCC GAGCTGGAGA CCGCGCCTTC AATCTGGCCT |
| | | TTCATTGTGC CCAGCGCATC AATAAAGTCT GCGGCCGTTG |
| | | AGCCTGTACC AACGCCCACA ATGGTGCCGG GCTGTACTAT |
| | | CTGAAGTGCC GCCCATCCTA CCGCTTTTTT CAGTTCATCT |
| | | GCGTCATAGA TCGTTAGAAT GTGTGTGAAA TACGCCGCAT |
| | | TATAGAACAT GTCCGGGAAA ATCTCGGTCG TACACAGCTA |
| | | CGATTCGATT GCGCGCAATT TTGAGGGAAA A |
| 93 | 448 | GATCCTCGAT TAGGGGAGGC GCTAATTGAA TGTGGCGAGG |
| | | TGTAAGAAAG CAGAAAAGCA AAGTGGGTTC TCGTTGCTCT |
| | | GCATGTCGTC AAATTCAATT AAACGCATAA AAAAACCCCG |
| | | CCGGGCGTTT TTCTTCAACT TCCAGGCGAT TACGGCGAAC |
| | | GAAGTCGATG TGAGTCAGCT TCGGTTTGTA AGCGTGACCG |
| | | TGTACAGCCT GAGCTTTAAC TTTTACTTCT TTACCGTCAA |
| | | CAACGAGGGT CAGAACTTCG TGTAGAATTC AGCTTTAGCT |
| | | TGCATGTTCA TCACCTGGTC GTGGTCAGTT CGATAGCAAT |
| | | CGGGCTTCAG AACCGCGTAG ATGATTGCCG GACTGTAGCG |
| | | CGCAGGCGGC AGCTCCTACA TGCTCTTACG TACTCTGCGT |
| | | GATAGTAACA TTAATCTCTT ATATCTGCAG ACTGCACGAG |
| | | ACTCGTCG |
| 94 | 359 | GATCATATCG ACGGTATCGG CGTAATTATT TTGCAGATGG |
| | | CGTAACACAT CCAGATTATC TCCGGTCAGA AAAAGATTAT |
| | | GGCTGTTTTT ATTTTCTGCC AGAGTATTGT GTTCCACGTC |
| | | AGGAACGATA ACGGTAACGG ATTTTTCACC CGCCTGTTTT |
| | | TTTGCCGTAA TCTTTGCCAA TAAAATCAAT CTGATAACCG |
| | | CTAGTCAGCT CAATATTACG CGCTTTCAGG CGCTCAAATC |
| | | TGGCGAGATC AATCCGCCTT TCGCGATCAG TTCGCCCTCT |
| | | CGTTATAGCG GATCGCGGTA AAAATTCCGC GGTAATCGCA |
| | | GTTGTAACTC AGACAGAAGC GCGTATTCGG CGCAGACGC |
| 95 | 298 | GATCCAGTTT AACCTCTGGC TGCCAAATCT TTCTGGAAAA |
| | | CATGCGGTGC GTTTGGCGCT TCGAAAGAAA CATCCTGGTA |
| | | TAGATACGTT GGATCTGGAA AGCCATTTCA GTGTTATTTT |
| | | TGTTCTGACA TGTGTAAAAC CCTTTAGTGT TGTTCCTTAA |
| | | ATACTTGAGT AACGCCTTAA CGCAACAGCG GATCCAGTCC |
| | | ACCACGCGCA TCCAGCGATA CAAGTCGTCA CAAGCGCAAT |
| | | GTGCTGTGCC TCAATCAAAT TTGCGACGTC GTCGCACTAC |
| | | GTTGATATCT TTACGTCA |
| 96 | 217 | GATCGTAAGA GTCAGAAATA AGCAGGCGTA ATGTTGTCAT |
| | | AGTGGTTTTC CTTACCTTTA TTAAGCCGTC ATTTTACTCT |
| | | TTTTCCTCAC GCTCTTCCTC TTCCGGAACA GGCTTGCTGG |
| | | CCGTTAGCAG GAAGGGCGAC TGCTGCCAGC GGGTGCGTTT |
| | | ACCTTGTAGC AAGGTGNNNC AGACACCACG CCTATCGCAG |
| | | CGAGAGTAGC AGCATCA |
| 97 | 335 | GATCGAACTC TTTAAGCAGC ATCTTGGTAT GGAAAATATT |
| | | TTCCTGATAC ACGTTTACAT CCACCATGTC ATACAGCGAC |
| | | TTCATATCTT CCGACATAAA ATTCTGAATA GAATTAATCT |
| | | CATGATCGAT AAAGTGCTTC ATACCGTTGA CGTCGCGTGT |
| | | AAAGCCGCGC ACGCGTAATC GATGGTGACG ATATCGGACT |
| | | CTAGCTGGTG GATCAGGTAA TTGAGCGCTT TTAGCGTGAA |
| | | ATCACCCCGC AGGTTGACAC TTCGATCGTC GGCGGAAAGG |
| | | TGCATAGCCC GCCTTCCGAT CGCTTCGATA GGTATCGACG |
| | | CAGATATGCT CTATG |
| 98 | 352 | GATCGTCGTA GCTGCCGGCA TTGTGGTTGG GTAAATACTG |
| | | GCGGCAAAAC GAGACTACGC CAGCGTCTAT CTCTACCATG |
| | | GTGATGGTTT CGACGTTTTT ATGCCGGGTA ACTTCACGTA |
| | | GCATTGCGCC GTCGCGCCGC CGATAATCAG AACGCTGTTT |
| | | CGCATGACCG TCCGCCACAG CGGGGACATG GGTCATCATT |
| | | TCATGATAAA TAAACTGAC GCGTTCGGTC GGTCTGTACC |
| | | AGCCGTCCAG CGCCATCACG CGGCCAAAAG CGGCTTTTCA |
| | | AAGATGATTA AATCCTGGTG ATCGTTTTCA TGATACAGAA |
| | | CTTGTCTACG GCAAGTCATG ACCAAACTGG TC |
| 99 | 127 | GATCTGTTTC GGGAAGTGAA CTTAAGGCCT CCGCAATATC |
| | | ATTTATATAA ACTGACATGG CATTTTTAAA CTGCTCAGTA |
| | | CTGCGTTTAC ATTTGTGGAA GATAGTCTCT GAGAGCAGAG TTTCTTT |
| 100 | 345 | GATCGGCAAC CTGCATTGCC AGTTCGCGGG TTGGCGTCAG |
| | | GATCAGAATG CGCGGCGGCC CCGATTTTTT ACGCGGAAAG |
| | | TCGAGCAGGT GCTGCAACGC CGGCAGCAGA TATGCCGCCG |
| | | TTTTACCGGT GCCTGTCGGC GCAGAACCGA GTACATCACG |
| | | GCCATCGAGC GCAGGCGTAA TGGCGGCGCT GAATGGCGTC |
| | | GGGCGAGTGA AACCTTTATC CTGGAGGGCA TCCAGACAGG |
| | | CTTTCGTCAG ATTCAAGTTC GGAAAAAGTG TTACAGTCAT |
| | | GTCTACCTCT GTGTGGGCGC TGATTATAGA CTTACGCGCA |
| | | TCTCATCTGT GATGATATCT CTCAG |
| 101 | 250 | GATCCGGGAC ATTCACGTTG AGAATACGCC CGGTACGCAA |

TABLE 3-continued

SEQ ID NO | LENGTH | PARTIAL 3'—5' SEQUENCES OF PROBES OF THE PRESENT INVENTION
--- | --- | ---
| | CGGCTCCCGG CTTAACCCTC GCAAAAGCGC ACAAGTCACG
| | GCCGCAGCGA TACATAATGC TGATAGCCGT TAAGGGAGAC
| | CGCTAATGCC GGAAAGCCGA GATGACGACC TTCATCGCGC
| | GCACAGTACC GGAATAGATC AACATCATCG CCAGATTCGG
| | ACCGCGTTAT ACCGGAAACG ACATATCGGT GACGATTAGC
| | TTACGCAGAT
102 | 333 | GATCCCGGCT TACGACGGTT GGCTGGATGA CGGTAAATAC
| | TCATGGACTA AGCTGCCGAC ATTCTACGGC AAAACCGTCG
| | AAGTCGGGCC GCTGGCGAAC ATGCTGTGTA AACTGGCTGC
| | AGGTCGTGAA TCCACGCAGA CCAAGCTCAA TGAAATCATT
| | GCGCTTTATC AGAAGCTGAC CGGCAAAACG TCTTGGAAAT
| | TGGCGCAACT TCACTCTACG TGGGTCGATA CATCGGGCGT
| | ACCGTTCACT GTTGTGAACT GCAAAACATA TTGCAGGATC
| | ATACAGCTGA TTGTAATATC GGCAAGGATT ACACCAGTTT
| | GAGACGGCAA TCG
103 | 284 | GATCCAGCCA GACGGAACCC CACGGCGGCG GAGACGGCAG
| | AGCGTAAGGG CCGATAAACA GACGCTGCCA GGCCTGTGCA
| | ACGACTCTTC GCTGTGGGTC TTAAACATAG CCGCCACAGG
| | GCAAGGCTCG GCATCAAGCG GCCACTGCGC CTGCAGTCGT
| | CGTTTAATAG TCGTCCTGGA CCAGAGGAGC GGTTTCGTGG
| | CTTTCCGCGA ATAATAAAAC AAGTGCCAAG AACAGTGTTA
| | CTGCAAATCA TCTCGTTGTA AAAAGTGTAT TAAACATCCG TAAA
104 | 249 | GATCAACGCA AACAATCAGA ACCTCTGCTT CATTTAGCAG
| | CGTGTTCTCT GCGTTGACAA TGCGTTGCGT GAAAACCAAA
| | GCGGTGCCAC GCATTGACGT AATTTCTGTT TGAGCTTCAA
| | GCATATCGTC GAGCCGCGCA GGCCATAGTA TTCCAGCTTC
| | ATCTTGCGCA CCACAAAGGC TACCCGCTCC GCAGCAGCAC
| | CTGTTGCTGA AGTGATGGTG GACGTCAGCA TCTCGNNNTC
| | TTCATAAAA
105 | 248 | GATCCCTTTA CGACCAGGCG TCCCGGCGCC GTTATAGTGC
| | CAGCCAAAAC CAAAGCCGCC GCCCGGTAAA CCAATCTGTT
| | CCAGCATTGC GGCCAGCACG ACGACCATCC ATGACCACTG
| | TTCGCATGCT GCATACGTTG TACGACCAGC CAGCGATGAT
| | TTCGGTTCTG TCGTCGCATC TGTGGCAACG CGACTGGGTG
| | GTGTAATCAA GATCATTTCG CAGGACTTGG TGCATTGTAG
| | AATCGAGA
106 | 175 | GGCGGAGGAT TGCCACGTNG CAGCCTGCTA CGCCCGTCAG
| | TTCTTTACGC AGGTTAGCCA CCAGTTCGTT TACCATGTGG
| | CGGCTCCNTG TCAGTTTCCA GTTACCCATC ACTAAAGGAT
| | GTGATTTATT TNTCCACGTT AGTAGCGAAT TAAGGAAGAT
| | GGCCGCTCGT AGAGA
107 | 307 | GATCATTATC TTAACCTAAA ACCGCTATAT TTATAAGTAT
| | TATTACGAAT AATCTTAACC TGGGATATGT TATACTAATC
| | GGACCAGAAA GATATTATTA CGACTTTAGT AAATGCTTTT
| | TAAATATTAA ATAATAATTA ATTAAGATTT CTACCATTCA
| | TTAATTATAC TTAACAATAG TTTCACACCC CGCGCCGGAA
| | AGGTCTAACC TTCTCATTTA CCTTTAATAC TCAGTATTCC
| | CGAATAGCCG ACCGACACTA ATGATGAATG CTTATCTCTC
| | ATAAACCAGA TATTATGACA CATAACC
108 | 234 | GATCAGGATA TGCCGCCGCC AGTAGCGATA GGGCGTCAAC
| | CTCGTGCTTA TCGGTGATGA GCGGCGCGTT GGCCGGGGCT
| | TTTAAAAACG AAAGCATTAT CCTTCCTTAA ACGTAACGCT
| | GGGGCAACGA GACGCTCACC CGCGTACCGT GGGTACAAGA
| | GATGGTTAGC GTCCGCCGAG CGACGACACG CGCTTCGCAT
| | TCGGTCAGGC CGAAGCCTCT TGGTGAGACC GCCG
109 | 352 | GATCGAGCGC GGAGAACGGT TCATCCAGCA GCAGTACCGG
| | CTGTTCGCGT ACCAGGCAGC GCGCCAGCTA CCCGCTGACG
| | CTGGCCGCCG GACAGTTCGC CCGGTAAACG CGTCATCAGA
| | CTCTCAATGC CCATCTGATG TGCGATAGCT CCCGTTTTTC
| | CCGCTGGCTG GCGTTGAGCG TTAACCCAGG GTTTAGCCCC
| | AGACCGATAT TTTGCCTGCA CATTCAGGTG GCTGAATAAA
| | TTATTCTCCT GAAACAGCAT TGAGACCGGA CGGCGTGAGG
| | GCGGCGTAAG CTATGATCGT CGGCAATAGT AGCGTACGCT
| | GGCCAGGCGC AAGAAACCGC ATAATCTCTC TT
110 | 168 | GATCAGGGTC AGACGCTTGT GCGCCCATAC AACGTTTTGT
| | TCCAGTTGGC CTTTCTCGTT AACGTTTTGG GAGCGCCAGA
| | GCTGTTTAAC GCTCATGGGG CATTCCAGAA CGGGCAGTAT
| | CTCTTCAAAG GACGTTATCG TTTGTCAACG GCGGACAGCA
| | TTTTCAAA
111 | 211 | GATCTTCGGG GCGCACCCAC GGGGTTTTTG CGCGGGGGAC
| | GCCTGTGTTA TCAGCATTGT AGAAACTGCG ATAGATATTT
| | CCGGTGAGGC AATTTTCGCT CGGCACGATG TGTCGCTTAT
| | CCGGTATGTG GTGAGCAGTG TGCGCCGGGG CGTGTGATAG
| | AGCCATTGCG CGATGGATCG TCTAGTGAGT TTCTCAGATA
| | GGGGGTGACG A
112 | 257 | GATCCGCAGA TCCATCTAAT CGGATTAGGC GCATACTGGT
| | AAAGATTCAG CCCCCCCGCC AGCCCAATCG GATCCTGACT

TABLE 3-continued

| SEQ ID NO | LENGTH | PARTIAL 3'-5' SEQUENCES OF PROBES OF THE PRESENT INVENTION |
|---|---|---|
| | | GACGAACCGT CCACACTCCG GTGCATAATA TCTGAACAGA |
| | | TTGTAATGCA GCCTGTCTCG TCGTCAAAAT ACTGCCCCGG |
| | | CAGCCGCAGA CCGGCTGGTG AAGTACGCCC GCTGTTGCTG |
| | | ATGTCCGCCG CATTTCTCCA ACCCTGATAT ACCGCCACAC |
| | | AGCGTCGTCG CGCGTAC |
| 113 | 359 | GATCCTGACT GGTACGACTT AACGTTTTAG GCTCGCCAAA |
| | | ACTCAGCCCC GCCGCTTTCA TCGCTTCCGC GCCTTTGCCC |
| | | GCTTTCAGCT CGACCAGCAG TTTTTCCGCA TCCAGCTTCG |
| | | CCTGTTGTTC CGCTTTATTA TGCTTCACCA GGGCAGTGAC |
| | | CTGTTCTTTC ACTTCTGCCA ACGGCTTCAC GGCTTCAGGT |
| | | TTATGTTCGC TCACGCGTAC GACAAAAGCC CGGTCAACCA |
| | | TCCACGGTGA TAATGTCTGA ATTCGGCCCG GCGTACCGTT |
| | | TGCACAGACG CATAAGATAG CATCGGCTAA CGTTGAAGTC |
| | | AGCCTTCGGT AAGGTGTACG GCTAACAGCG GTTACGCTT |
| 114 | 427 | GATCGCGTAC CGCCAGTAAC GCCGCCGCTT TACCGTCAAT |
| | | CGCCAGCAGG ACCGGAGTCG AGCCTTGCGA GGCCTGCGCG |
| | | GTGATTTCCG CCGTCATGTC ATCCGTGGCG ACGTGCTGTT |
| | | CGTTCAGCAA CGCCTGGTTC CCCAGAAGCA GTTGATGACC |
| | | TTCCGCTTCA CCGCTGACGC CCAGTCCGCG CAGCTTCTGA |
| | | AACCGTTCAC CTGCGGCAGT TTATCATCGC CGGCTTTTTC |
| | | CAGAGAATCG CATGGGCCAG CGGGTGGCTG GAGCTTGTTC |
| | | GAGCGCGGCA GCCAGACGTA ATGCCTGAGC TTCTCAACGC |
| | | GTTAAAGGTT TTATCGCACA CTTGCGGCTT GCTCGTCAGC |
| | | GTCCGGTTTA TCAAACTGAG GTATCAACGT ACTGGCGCGT |
| | | GCAGGATGGC ATGTACAGAG CGATGAG |
| 115 | 299 | GATCTGGAGG TAGAGGTTAT CGAGGCCAGC GGTAAAACCT |
| | | CACGTTTCAC CGTGCCTTAT TCTTCCGAGC CGGATTCGGT |
| | | TCGCCCCGGT AACTGGCACT ATTCGCTGGC CTTCGGCAGG |
| | | GTTCGTCAGT ACTACGATAT TGAAAATCGT TTCTTTGAGG |
| | | GAACGTTCCA GCACGGCGTT AATAACACCA TTACCCTCAA |
| | | CCTCGGTTCA CGAATTGCGC ACGGTTACCA GGCATGGCTG |
| | | GCGGGCGGCG TCTGGGCCAC CGGTATGGGC GCGTTCGGCC |
| | | TTAACGTCAC CTGGTCGAA |
| 116 | 339 | GATCAGAGTA AAACCTGGCT GCTATGGTGC GAACGTGGCG |
| | | TAATGAGTCG CCTGCAGGCC TCTATCTGCG CGACGAGGGG |
| | | TTTGCCAATG TGAAGGTGTA TCGTCCGTAA TTCCTTTGCC |
| | | GGGTGGCGGC TATGTCCTAC CCGGCCTATC GTTTTATTTC |
| | | TGCCCCAACC GTTTTGCAAT GCGCTCCAGC TTCATCATCA |
| | | GCAGCAGCGT AATGGCCACC AGCACAATGG TCAGCGCGGC |
| | | GTCAGCATAT TTCACGTCGG TCAAGCTAAA GATAGCCACC |
| | | GGCAGCGTCG TCAGCCGGCG ATAATCATCA TCGTGGCCAA |
| | | CTCCCATGAG AGCATAACT |
| 117 | 378 | GATCGATATC AGGGAGGAAG TGGTTGCCCG CCACCAGCGT |
| | | ATCGGTACTG ATCGCCAGGG TCTGCTTTTC AGGAATATCA |
| | | GGAGCGCGCA ATCGTCGCCA ATACCGGTTT CAACATCAAG |
| | | ACGAGAGCTT CTTACACGGT CAAAATAACG GGCAATCAGG |
| | | GAAAACTCGC CACATGCCAT ACGTTATGCC TCAGCAGAAA |
| | | AAAAGAAAAG GCCGGAGACG CGGGTATCGA GCGCCCGCTA |
| | | TCTTTCCGGC CTGTGAATCA CTTTTTGTTG GGACGAATCA |
| | | CCGGAGCTGC TTTATCAGTA CGCGTTGACG ATTTGTGGCT |
| | | GTCTTCACGC GCCAAAGTTT GAGTTCATCG CTTCGTTGAT |
| | | GGCCATTATA AGCCAATC |
| 118 | 266 | GATCTCTTAC GATAAAGAGC ACATTATCAA CCTTGGCGCG |
| | | CCAGATTGGT ACGGAAGATT TGCCCGTGC GATGCCTGAA |
| | | TACTGTGGCG TGATTTCAAA AAGTCCGACG GTGAAAGCCA |
| | | TTAAAGCGAA AATTGAAGCC GAAGAAGAAA ACTTCGACTT |
| | | CAGTATTCTC GATAAGGTGG TAGAAGAGGC GAACAACGTC |
| | | GATATTCGTG AAATCGCCAG CAGACCCAGC AGGAGGTGGT |
| | | GGAGTAGAAC GTGATGATCG GTTTCT |
| 119 | 345 | GATCATCTTC CACTTCCAGA TGCACCGTCA CATCCGGGTT |
| | | AGTGAGCTTC ACGCGCGCCG ATTCAATATG CTGATTTAAT |
| | | CCGCCGCCAA CATAGCGCTC CACTTCAATG GAGCTAAACT |
| | | CATGCTTACC GCGACGTTTT ACCCGCACGC AGAAGGTTTT |
| | | GCCTTCAAGC TGTTCGCGAT ACTGCGCCAA ACGCTTTCTC |
| | | GAAAATGTCG TGCATATCGG TGAACGGCAC ATCTCGACTT |
| | | CAAGAATATG TGAATCCCGG GATCGTGGTC AGCGCTCGGA |
| | | ATCACAGACG CTGGTTTCAC TTGCGCGACT CATTTACAGT |
| | | CAGACACGTG TAGTGCTTAA CTCAG |
| 120 | 321 | GATCATCCTG GAGGTCTTTA TGGCTGATTT CACTCTCTCA |
| | | AAATCGCTGT TCAGCGGGAA GCATCGAGAA ACCTCCTCTA |
| | | CGCCCGGAAA TATTGCTTAC GCCATATTTG TACTGTTTTG |
| | | CTTCTGGGCC GGAGCGCAAC TCTTAAACCT GCTGGTTCAT |
| | | GCGCCGGGCA TCTATGAGCA TCTGATGCAG GTACAGGATA |
| | | CAGGTCGACC GCGGGTAGAG ATTGGGCTGG GCGACGGACG |
| | | ATTTTGGCTG GTCCTTCTCA GGCGCTATTA GTACGCGGTT |
| | | CATGCAGTAC ATACTACCTG AAGTCACGAT GCACCGAATA G |
| 121 | 216 | GATCGGCGCG CGTATCTCAG GCATGTGCGC CGCCAGTTGG |

TABLE 3-continued

SEQ ID NO | LENGTH | PARTIAL 3'—5' SEQUENCES OF PROBES OF THE PRESENT INVENTION
---|---|---
| | GAAACGCGCC CGCCGGGGCC CTCAATTTCA TACGCAGAAT
| | ATCCGCGCGC GCCGACCGCG CCGGCAACGG CGCGGCAGAC
| | ATTGACGCCG GCGGGCAGCT CGCGGGCTGT GGCAGAAGGG
| | CGTCACGCTG CCAGGCCTCG TCTGGATAGA TTGATATTCT
| | CGACCACATC CCGAAA
122 | 292 | GATCGGCAAA CAGATAGTCC TGCGACGCAT TAAATCCAGG
| | CATTGCCGAG GAGCACGCCG AAGCGGATAC GCCAGGCGGG
| | CAGGCCATAC CTACGGTATT TGTCAGACCA AACGCCTGCG
| | GGTTGGCAAG AATTTCCTTA AAGAGGCCGT TGATATCGGC
| | ACGGGCTATA TTGCCGCCGT GTTGCTCCAG CCCCTTCTCT
| | TCCATCTGAT TATAATAATC GGTCAGAGCT GACGCTGCCC
| | TGCCGCCGTT CATAGTTGCA GAGTGTCACG AGCAGTGTGA
| | TAATGATGGG TT
123 | 109 | GATCAGCGCC GCGCTACGTT AATAGCCGGT TGCGACGACC
| | GTGGACGCTA GCAGAGTCGC GGATGACTTC CGTATCGGTT
| | GGTCCACGCG TGAAATTAGT TGCGCGACA
124 | 258 | GATCGGTCGC ACGCCGGAAT ATCTGGGGAA AAAAATCGGC
| | GTGCGTGAAA TGAAATGAC CGCGCTGGCG ATTCTGGTCA
| | CGCCGATGCT GGTCTTGTTG GGTTCGGCCT GGCGATGATG
| | AACGGATGCC GGACGCAGCG CAATGCTGAA CCCTGGCCGC
| | ACGGTTTTAG CGAAGTGCTA TATGCCGTCT TCCTCTGCCG
| | CCAACAACAA CGTAGATTTT TAGTCTACCT AACTACTTCT
| | GAACTACGGC ATCTCGAC
125 | 384 | GATCGTTGGT CTTTAAGGCC GCCGCCAAAT CGCTGTCGAC
| | CTGCTTGTTG CTGTAAAAAG CGGTATTAAA CTGCGTCGGC
| | GGCCAGTTTT GTGATGCGAA GAGCGGCGAT AACGCCCAGT
| | CAGCTTCGCC CGTCAGACGC CGACCAGCCT GTATAGAACA
| | TTCGCACGCG CTCTCTTTTT GCCCTTTGCC CTCGACTTCC
| | GCGGCGGCTG GCCGGCGTAC ATCGCGGTTA TCCGGGCTTT
| | AACGACCAAT CTGCGCCAGT TGCTGTTGGG TAAACTGCAA
| | GAGTTTTTGG GTGCTATGGT TGTGCATGAC ACAGCGTGTA
| | CTGAACGTCT GATACCGCTT TCACGTCCCC TAGCGATCAT
| | GGCCAGTGAA GTTGCATAGC TAGA
126 | 448 | GATCATACCT TGCTTGATGA CTGCGCCACT AAAAACCTGA
| | CGCCGGCGAA AACCCACTGG GCGCGCCCGC TTGATGCGCC
| | GCCCTACTAC GGTTATGCGC TGCGACCCGG CATCACGTTT
| | ACCTACCTGG GTCTGAAAGT CAATGAACGT GCCGCGGTGC
| | ATTTGCCGGT CATCAAGCCG CAACCTGTTT GTTGCCGGCG
| | AGATGATGGC AGGAAATGTT CTGGGCAAGG GGTATACCGC
| | AGCGTAGGCA TGTCTATCGG CACAACCTTT GGCCGCATTG
| | CAATAGAAGC CGCCCGCGCA CAAGGAGGCG CACGATGAAA
| | CAGCTTGAAA ATTATCATTG AGGCACGTGC TTACGAACGA
| | AGCGAGGTGA ACTGTCATGC AGTGTGTACG TGTGTGCTAC
| | TCGAAGGTTT GCGGATTCGC ATGACAGGTG ATGTAGCGAT
| | ATATCGAT
127 | 392 | GATCCCCAGG AGGTCTGGTT TGTCAAATCG CCGAAATCCT
| | TTTTAGGCGC CACGGGCCTG AAACCGCAGC AGGTCGCGCT
| | GTTTGAAGAT TTAGTCTGCG CCATGATGGT ACATATTCGT
| | CATACGGCGC ACAGCCAATT GCCGGACCGA TTACCCAGGC
| | AGTGATCTGC AGGTGGCACT TTTCGGGGAA ATGTGCGCGA
| | ACCCTATTTG TTTATTTTTC TAAATACATT CAAATATGTA
| | TCGCTCATGA GACAATAACC TGACAAATGC TTCAATAATA
| | TTGAAAAGGA AGAGTATGAG TATTCAACAT TTCGTGTCGC
| | TTATCCTTTT TCGCATTTGC TTCCTGTTTG CTCACCAGAA
| | CGCTGGTGAA GTAAAGATGC CTGAAGATCA GT
128 | 327 | GATCTTGTCA AGCTGGTCAG CATATCCCGG ATATCCTCCG
| | CCTCCCCCCC CGCCACTCCG CGCGGCTTAT GAATCATCAT
| | CATGGCGTTT TCCGGCATAA TGACGGGATT ACCTACCATC
| | GCAATAGCGG ATGCCATTGA GCAGGCCATT CCATCGATAT
| | ACACCGTTTT TTTCGCCGGA TGATTTTTCA GGAGGTTATA
| | AATGGCTATT CCGTCCAGTA CTGCTCCGCC AGTGAATGAA
| | TATGCAGATT TATACGGTTA ATCTGTCCAG TGCAGCCAGT
| | TCTCTGCAAA CCAGCGAGCC GAAATTCCCA TCTCAATCTG TCATAAT
129 | 306 | GATCCGCAGG AGAAAACACG ATTGTACAAA GAGGCGCAGG
| | ATATTATCTG GAAAGAGTCG CCCTGGATAC CGTTGGTGGT
| | GGAGAAATTG GTTTCTGCTC ACAGTAAAAA TTTGACCGGT
| | TTCTGGATTA TGCCGGATAC CGGTTTCAGC TTTGACGATG
| | CGGATTTAAG TAAGTAATGC GATGGGGCTG GATGGCGCGC
| | GGTTGTCGCC ATCCGTAAAA GGTTCGTGTA TGCTAACTAT
| | GTTCTCAGCG CTGCTGGATT ATTCTACGTG TTGATTGTGC
| | AGTGCTGGTG TTTATTGTCA TTGTCC
130 | 301 | GATCTCAGCG ATGTTCAGTT AAACGCTGTG CCGGATGCGG
| | CGTAAACGTC TTACCCTGCC AACGGGTTGG GTAAGCCGAA
| | TAAGCGCCGC TCCATCCGGC AGCATTCACA TAAAGTCCGG
| | CACCAGACGC TGTAACGCGC CTTGCGCAGC AGCGCCGTCG
| | CACACTCAAT ATCGGGCGCG AAAAAACGAT CCTGCGTATA
| | GTGCGCCTCC TGCTCGCGCA GTGTCTGCCG CGCCTGTTCC

TABLE 3-continued

| SEQ ID NO | LENGTH | PARTIAL 3'—5' SEQUENCES OF PROBES OF THE PRESENT INVENTION |
|---|---|---|
| | | AGTAACGGGC TGGAGGTTAA CCTTCCGTAA TTATCCTGAC AGCAGCAGCA TCACGCATAT G |
| 131 | 329 | GATCGCCGGT CAGTTCCTCC ATTAAGAGCG GCGCGCGCGC CAGCATCTCC ATGCAGAAGA GCCGCGACGC CTGCGGATAA TCACGCGAAA CTTCCAGCTT GAGACGGATA TACTCTTTGA TGGCCTCCAT AGGGGAAAAT TCTGCGCGAA ACGCTTGAGC GGCGCACGAG ACATCCAGAA TCTCGTCGCA TTACCGCGAC ATACAGCGCC TCTTTCGAGG GATAATAATA AAGCAGATTG GTTTGGAGAC GCTGCCGTAG CGGCGACTGC TCAAGACGCG CGATGATGCA TACTGGAAAC ACGAGCGCGT AGATAGCTGC GTTGCACGG |
| 132 | 266 | GATCCGCCCA CGCGTTAAGG GCCGTAAACA GAGCGTCATT CATCATTACC GCTGGATTCA CCGCCCTTCG TTCTTCTTCT GTTAACACCA CGCGTAATCG CAGACAGGCC GGGCCGCCGC CGTTGGCCAT ACTTTCTCGC AAATCAAACA CCTGCATCGC GCTGATGGGG TTATCCTCCG CCACCAGCTT ATTCAGATAG CGTCCAGACG CGACATGGTC TGACTTCCGC GCACCTACGC TTGAGCCGTG TTCGCTTGCA CTGCTT |
| 133 | 319 | GATCAAATGC AGGCAGTAAA AGGGCGTCAT CAAGATTATC GGTACACTGT GTAGCGGCGG TTTGCAGAGT ACCATGTAGC GCCGGATAAT TATGCCGGGT CAGGTTGACA CCGTGCGTAC CGTTAATAGC TTCAAAGGCG TCGCAAAACG CGCGGTGTTT TTCTGCGGTG ACGGGGTCTC CCGGCGCTTC AAAAGTTCGC ATCAAATGCG GGCGATGCTC TGATTCTGGT ACTTATCGTA CAAAACGACG ATCGCTCTCT CATGATATAC GCATATAGCA TCATGCCTGT CCGTGCATAG TCGTAACTAG AGACATCAC |
| 134 | 438 | GATCAACCTG AACTCAACGG ACCCTGTACC GTCTAAAACG CCCTTAGCGT GAGTGATGCG GATTCGTATA ACAAAAAAGG CACCGTCACC GTTTATGACA GCCAGGGTAA TGCCCATGAC ATGAACGTCT ATTTTGTGAA AACCAAAGAT AATGAATGGG CCGTGTACAC CCATGACAGC AGCGATCCTG CAGCCACTGC GCCAACAACG GCGTCCACTA CGCTGAAATT CAATGAAAAC GGGATTCTGG AGTCTGGCGG TACGGTGAAC ATCACCACCG GTACGATTAA TGGCGGAGCC ACCTTCTCCT CAGCTTCTTA CTCATGCAGC AGACACGGGC TATACATGGA CATCAAACGG CTATAGGGGA CTGTGAGCTA CAGATTACAC TGATGGCACG TGTTGGCACT ACACGCGCGT TCGGCGATGT GTATGAAC |
| 135 | 363 | GATCTTATCC TTCCGCTACA AAATCAACTG CGCCATCTGA CGCATATTGT CGGCGTGGAT AAACTGGCGG CTGCCACCAC AGCGCTTGCG TTAGTCAAAT CATCGACCGC AGCGAACCGT TGCAGTCAGA CATTAACATT CACGGTGATG AACTGGCGGC AGTGCTGTTT ACCTCCGGCA CAGAAGGAAT GCCGAAAGGG TGATGTTGAC CCACAATAAT ATTCTTGCCA GCGAACGGGC GTATTGGGGG TTGAATTTAA CCTGGCAAGA TGTGTTCCTG ATGCTGGCGC ACTGGGAGAC CGGATTTTAA GGAGGCTTTT ATGGGGTAGT ATTGCTGGAC ATCTTACCAG AGCTCTACTA TAG |
| 136 | 347 | GATCGATTTT CCCCTCCATG TTTTCATAGG GGAACAGGTT CGGGTTAAAA ACCACCTGAC GGATATCGCA CAAAAAGCCA ATCCGCTCCG CCCAGTAACC GCCCAGCCCC ACGCCACAGA TTAAAGGGCG CTCGTCCACA TTCAACTGCA ACATTTTGTC CACTTCTTTC AGCAGATGCT GCATATCGTG CTTAGGATGC CGCGTACTGT AGCTTACCAG CCGAACATCG GGTCGATAAA CTGGTAATTG CGAACACTTT TTCATGGTGC GCGGACTATA TGAGTCAAAA CGTGTGATAT ATATCATCTG GCACCTCACG AGACTGAGTG ATGCGTGCGT TTCTGCA |
| 137 | 278 | GATCCCAGAC AATACCGTTA CTGTTATCCA ACGATACCCC TGCCAGTGAG GTACGCAGGA ATCCATATTG GGTGTGATGC GCGTAAGAAA CGCCCGCCAT CATAGTACTT TTACGCCTGT CCAGACGACG CAACTGATGG TCATCGCTGT CGCCCGGTTT GAAGTACATC GGGGACCAGT ATGCCATGAT TGACAACTTA TCGGCATTGT CATTCACAAG TAGTACCGCG CCAGACACGA CAGAGTTNTT CATAGGCATG ACGATCGATA ACAGCTAT |
| 138 | 385 | GATCGTTATG AATCGCTTGC GTGATTTCCA GCGTCACCGG GTCGAGACGA TAAACTACGC CGCCTTTATC CAGTTTACGG CTTTGCGATG TAGCCAGCCA GAGCGCGTTT TCTTGCTGAC TCCAGGCCAT CTCATAACGC CTTTGCCTAC CGCTTTACGC AGCATGTCTT CCGCGCCAGC GTGCTAAATG AGGATGCGAC GAGGAGCGAA CCTAACAATA AAGAACCACG CAGGCTGGCG AAAAAAGATG ACGTAAGTGC ATGACGACTC CTTTGATAAA ACGTGTATAG CTGCTTCACA CTACTTCGCT GCGTGGATCT GCAGGTGGCA CTTTTCGGGA AGTGCGCGAC CCTATTGTAT TTCTAATACT CAATATGATC GTTAT |
| 139 | 282 | GATCAGCGGC TATGGCGGTC CGGAAGGCGC GAAGATGGCA CGCCGGCGGG CACAGTTTGG TTTGCCTGGA ATATTAACAA TACAACTTTT ACAAGCCGAC AACATTTCAA CGGAGATTGT CAGGAAGTAT TGGAAAAATG CGTACGCTTC GCCCTCGCTG AATTGCTTTT CTGTTAACGA AGAAAGCATA ACATAATTTC |

TABLE 3-continued

| SEQ ID NO | LENGTH | PARTIAL 3'—5' SEQUENCES OF PROBES OF THE PRESENT INVENTION |
|---|---|---|
| | | ACTGACGTCA GATACTCCGG CTAGATAAAT CGAGCTTACC GCGTGTTCGG AATTCGATGA TTCGGATATC GGTCGCCATC GT |
| 140 | 179 | GATCGGCGAC TACAAAACCA ATCACCGCGG CTTTACCATC GAGTTCCATA TGCGTACGTT TTATCGCTGG GAGTATGGCG AGAATATGTC CCCGGCCGGA TAGAACCGGT TAAAGAGACC ATGCGTTACT TTTTCATGGC GGTATACATG CACAGTTGCT TGGTGGCATG ACATTGGAA |
| 141 | 261 | GATCAGTAAC AGGACGGTAG CAAAATTCGC ACTGAGCCCG GCGACATTCT GAACGAACGG TTCAATATAG CTATAACTGT GTAATGCGCA GTCACCACAA CGACGGTCAG TACATAGAGG CTCATCAGCG CCGGGCGTCT GAATAGCAAA AGGTAAACTT TTTAGTGAGC CGGAATGCTC GTCTGGCAAT TCGGTAGAG CTTATCAGAA TAGCAGCGTA TATCTCCATG CGATGCAAAG TGGCCCAGCA AATCTGACAC T |
| 142 | 225 | GATCATTTTG GTGCCGGTGT CAGCCTGCTG ATGTCCACTG GTCAGCGCAA CGGAATAGAA CTCGCCGATA TAATTATCAC CGCGCAGAAT GCAGCTCGGG TATTTCCAGG TAATCGCCGA ACCGTTTCC GACTGGGTCA ACGACATCTT GCTGTTTTCC CTTCGCACAA GCCCGCTTGG TCACAAAGTT CAGATCGCCG TGTGTGTGCC GGACAGTTGA CGTGA |
| 143 | 301 | GATCATCCTC GGCGCGGGAG TGAATCACTG GTATCACATG GATATGAATT ACCGTGGGAT GATTAACATG CTGGTGTTCT GCGGCTGTGT TGGACAAACC GGCGGCGGCT GGCCGCACTA TGTCGGCCAG GAGAAGCTGC GGCCGCAAAC CGGCTGGCTG CCGCTGGCTT CGCGCTGGAC TGGAATCGCC GCCGCTCAGA TGAACAGTAC TCGTTTTCTA CACCATGCCA GCCAGTGGCC TATGAAACTG ACTGCGCAAG AGTTGCTGTG CGCTGCGATC GCTAATTCGA CTATCGATTA C |
| 144 | 272 | GATCATGTGG GTTTAACCCG TTGATTAAAC ATTGGATTAC GGAATAGCAA TTGCTTATTT TATTTGTCAT ACAAATAAGT ATAATACCCG CTTCCGATGT AGACCCGTCC TCCTTCGCCT GCGTCACGGG TCCTGGTTAT ACGCAGGCGT TTCTGTATGG AATACGCCAT CCCCTCTGAT AGATGCCTTG TTGCCTTAAG CAGTTAACCC GCCTGAAGCA AACGACAAGA CGGCAGACGC TTACCGGCAT ACGACACGGA TGCTTCAGAA GA |
| 145 | 358 | GATCTGCGCA CATCATTCGG GTCATCGCTA AATTTTTCAC TTTTAATTCG CCGTCCGACA GTTTTCCTTC GCCGGTGAAT TGATTGCACA TTTTGCCGGA TACCGTCATG TCCTCGCCAA GGCTAGAGCT CCGGGCCGGT GACCGTTTTA CCGTTTACGC TTTCCAGAAC AAAGCGGTGG TGCTCCAGTT CGTCGCGTTT GACGGACACT TTTCACTGCT CACACACCTG TCATTATGAT GCTCAGGGCG ACCAGCGTGA TTTCTTCATT GATATTCTCT GTAATCTGAT AGGTTAACAC TGACTATAGT AATGATATGA CCGGATAGAT CTTCAGGGTA TCCGAAAATC GTCCCTGA |
| 146 | 224 | GATCTGTTGT TACAGCATGG AATGCGCCGT CCTCCTCACC GGCCAGGCAA ACGGCGCGAT CGTATCGAAC TGTGCGCCGC GCCGAAAGAA GGGGGGCTTA GCCCTTCTTT CGGCGTCTTA CGCAGCGTAG CCAGCATATT AGCATTGCCT AACTGCATTA TTGTCTGCGG CGGGGATTTT ACTACGTAGC GCAATTTGGC ACGTCTAGAA ATTCGTAAAG GTTC |
| 147 | 268 | GATCCTGAAT CGCCACGACA CGGGCGCCAG GCCTGCAAAC AGACGCGCGG CTTCGCTGCC GACGTTACCA AAACCCTGAA CCGCAACGCG AGCGCCTTCA ACAGCAATAT TCGCCCGACG TGCGGCTTCC AGCCCGCTGA CGAAAACGCC GCGCCCCGTC GCTTTTTCAC GGCCCAGCGA ACCGCCAAGA TGGATAGGCT TACCGGTGAC GTAAGATAGT GACCGTGTGC ATGATTCATG GAATACGTAT CATATCATCA ATATTACT |
| 148 | 314 | GATCCTGAAA AATACCAATT TTCAGCGGGC GAGCTTCGCC TTCCGCACTA AAACAGTGAG GAAAACGCTC GGCCAGAAAC GCGATAACTT CTTTACTGCT ATTCAACTTA GGTTGATTTT CCATGAAATT TCCTGATTAC AACGGACGTA GCCAACAAGC AGCAGGCATG AACAGGCGTC ATTATAATGA CGCCATCAGT AATTGCTACG TTATCCGTTG ATTATCCTGC GACGTCGCAA AGATTTTTTG TATCCGTCGT GCAGCACGTT CAGCTGTCAC CAGCGTACCA GGCGTGTCAT CTCTCGTAAC GCAA |
| 149 | 379 | GATCCAGAAT ATATAAAACC CCATTAACNC CAGCGCGCTT AATAACCATG TGGTCATCTG CGCTCCGTGG CTGGTTACGT TGTTATAAAT AAGGATGGCG ACCAGCCCAA CGAAGATAAC GCTGTCTACG CGACCGCGGC GGAGAGGGCT ATAGAAAGCA GAGTGGGGCC ATTGCGACGG GGCATGATGA ACTGATCGTA GAGAGCGTAA GCCAATAATT CGGCAATAAA GAGAATCAGC ACCAGGTCCG TGATAGTCAT TTATCTCAGA GAAATAAAAA ACGGGCGTTT GCGTAGTGTA CAACAGCCTT ACTGGCCAGC AGTCTACGAG TAGCCGGCGA TACCAATGAC GAGAGCCACG ATATCACAGC GTACTTCTA |
| 150 | 355 | GATCCAACAA GCGGCTGGCG CCATAGCCGC CGCGAACCGG CATGACGATT GTATCCGGCG ACGTTAGCGA GGCCAGCGAA |

TABLE 3-continued

| SEQ ID NO | LENGTH | PARTIAL 3'—5' SEQUENCES OF PROBES OF THE PRESENT INVENTION |
|---|---|---|
| | | TTAACATCGG CCAGCCGTTC CGCGTCCGTA CCGGCAAAAC |
| | | GCTGAAAGGG CGACGAATCA CCTCGTCATT CTCCACCTGA |
| | | TGACCCGCGT CAGTCAGGCG CTGAACGCCG CGTAACGGCT |
| | | GTTGGTTAAT ACAGTAGCCC GACTGGGCGA TTAATGAAAC |
| | | AGAGACATGG TAATTCCTTG CTGACAATAG AATCGAATGT |
| | | ATATCATGCG CATATATAGG CGATGTCTCG TGTCGCAGTT |
| | | CTGATCGGAC AGGAGGCACT AGCTCGGGGT ACTTT |
| 151 | 278 | GATCCTTATT CCCGATGTGT TCACCTTTAA TATTCTCCAC |
| | | TCGCGCGTGG AGGAGATGAG CGGCGTTCCG GTCGTTCCGC |
| | | TATATGACAC GCCGCTATCA GGGATTAACC GTCTGCTTAA |
| | | ACGGGCAGAA GATATCGTGC TGGCGTCGCT GATTCTGCTG |
| | | CTCATCTCAC CGGTACTGTG CTGCATTGCG CTGGCGGTCA |
| | | ATTGAGCTCG CCCGGCCGTG ATTTGCCGCA GACGCTACGG |
| | | ATGGCAGGCA AGCGATCAAG CTGAAGTCGT CATAGGAG |
| 152 | 394 | GATCAAAATA AAACTTTAAT CCCACTGGGG CAAGAGAGTG |
| | | ATGTGGTGAC GCTCAGTCCG GGTCAGGCGT CGGCGCATCT |
| | | GCAATTTTAC GCGCGTTATC TTGCCGATGG CGGCGCGGTA |
| | | ACGCCGGGGA CGCCAATGCC TCCGCAACCT TCATTCTTGC |
| | | CTATGAATAA GTTCTTTTTA CGCTGCGCGC ATATATTGGT |
| | | GCTTGCTTCC CATATCATGG GCGCAGGCTG GCGTGGTAAT |
| | | TGGCGGTACT CGCTTTATCT ATCATGCGGG CGCCCGGCAT |
| | | TAAGCGTACC GGTAAGTAAC CGTTCAGAAG TCGTTCTGTT |
| | | AATTGATACG CATATTTACT GGTGGGTCGG TTACGGAACA |
| | | AAACGATGGA TATAGTCCTG TGTAGTGATA TGCT |
| 153 | 324 | GATCGTTAGC AAGGTTTGCT GCGTCATCTG CTGGGTTTCA |
| | | CGCAATGTGT GCGCGTTAAG CATCACAAAA TGGCTGGCGC |
| | | GCGTCGCCCA GTGGGCATTG ATTTGTAATT CAAGCATACA |
| | | AACCAGGTTG CGGTTGATGG TCTGAATGGC CTCGAAAATA |
| | | GATTTTTGTA TCCGGGTTTC TTTACTGGCA GGCGTTATCA |
| | | GCCCGCGCAT TTTGACGACA TCGTTCAGCA ACCGTTGCAA |
| | | ATGTTATCCA ACCGGGGAGT CAGCAATCGC GACAGCTGCC |
| | | TTGATACCCA GTTACCTGAC CGATCCGGAT GATCCGATCG GAAA |
| 154 | 308 | GATGGCTGGG AAGACGGGTG CCGTTCTGGT TAAGCGTATT |
| | | CAGCTCTTCG CGCGGGAAAT AGCCTTTAAT CGCCAGGGTA |
| | | CTGTACAACG CGGGGCCCGC ATGGCCTTTC GACAGTACGA |
| | | AGTAATCGCG TTCCGGCCAG TCCGGGTCGG AGGGTCGATT |
| | | TTCATCACCG CGCCGTACAG AACCGCCAGA GTCTCCACTA |
| | | CCGACATGCT GCCGCCATAG TGACCAAAAG CCAAAGATGG |
| | | TTTAAGGATT TGACGGTGGA CCGAATATCG ACAGTTGGGT |
| | | GATTTCGGTT ACGTTCATTC TTCCTGAA |
| 155 | 333 | GATCGTGGTC CAGCTTATGA ACGGTATAAC TGAGGGCGGA |
| | | CGGCGTTTTA AATAATTTTG CCGACGCCGC CGCGAACGTG |
| | | CCTTCTTTTT CTAACGCATC AAGAATAATC AGAACGTCCA |
| | | GCAGTGGTTT CATACTCGTC CCCTTGCCGC TATATGGCGA |
| | | CCACCTGCTG GACAGCGACT CACTCCATCG GCATCACCAA |
| | | CGGATCGGGA TATTGATATT CAAATCCCAG CTCATTACAA |
| | | ATCGGCTACC GTCGATAATC TTCCCTTTTG CCGTTGTCGG |
| | | TGGTACGAAA ATCGCGGCGG CGATTCCCAG CAAGCGTATT |
| | | GCGATAAACA CTG |
| 156 | 334 | GATCCACCCA CGTCATCAGT TGTTCAAAAC CCTGCTTCAC |
| | | GGTGTGTTCC CATGGACCGA CCATGTGGAA AGCGGCTATC |
| | | TTGCGTTTTT GTGGCTGCCT GATTTCGTAA TCCATGCTGC |
| | | CTCCGTCACT TCACAATGCT GTATGAATGT ACAGTATAAT |
| | | TACAGCCTTT TACGGTCACA AGGACAGCGT GATCATTTTG |
| | | TGAGCAACCT CGCAATCCCG CCCTTTTGAC ACCTCAGATG |
| | | ACGGTGAACG GTGTGTGTGA CAACGGCTTA CGCTTTATGT |
| | | GAAAATAGTC GTCAGACGAG AGAACATACC GCCTTTACCA |
| | | CGATTCAGAG TGAC |
| 157 | 152 | CGTTTGCTAT CGACCTGCAG ATCGGAACGG ATTGGCGTCA |
| | | CGTGATGGAT AAGACCGTGT TCTTCAATGT TATCTCGGCG |
| | | ACACGAGCGC ATCCGGCGAA ATATCGACCG CATCAACCTC |
| | | TGCGTCGGGA AAGCATAACA CAGGCATGGC AT |
| 158 | 204 | GATCGAACGC GCGTTGCAGC AGCGCCCGGC TATTTTCTAC |
| | | CCGTGTCGTA TCGCCGAAGT TGTGCCATAA CCCCAGCGAA |
| | | ATAGCGGGAA GTTTGACGCC GCTGCGTCCG CAGCACGATA |
| | | CTCCATTGTG TGATAACGAT TCTCATCGGG CTGATAAATC |
| | | ATGACCTTTC CCCTGTGGCG AGAATAATAT GTGTACGGTT ACTC |
| 159 | 283 | GATCTTACCG AGTGGGAAAC TAATCCGCAA TCGACCCGCT |
| | | ATCTGACGTT TCTCAAAGGT CGGGTAGGGC GCAAGGTCCG |
| | | CTGACTTCTT TATGGATTTC CTCGGCGCCA CGGAAGGGTT |
| | | GAACGCCAAA GCGCAGAATC GCGGCCTGTT GCAGGCAGTG |
| | | GATGATTTCA CCGCAGAAGC GCAGTTGGAT AAAGCGGAAC |
| | | GTCAGAACGT GCGCCACGAG GTGTACAGCT ACTGCAATGA |
| | | GCAATTACAG AGGGAGAATG AGCTGGATCG CTGTCTAAGA GCT |
| 160 | 302 | GATCGCGTTC GCCAGGCAAA ATATTACCGT GCTCAAGAAT |
| | | ACCGCTGCGC ACGGCATCCT TTACCGTCTG GGCGAATTTC |
| | | ATGTATAGCG GCGTATTATC CGCCGCTGAA ATTCGTTCAT |

TABLE 3-continued

| SEQ ID NO | LENGTH | PARTIAL 3'-5' SEQUENCES OF PROBES OF THE PRESENT INVENTION |
|---|---|---|
| | | TCAGTTGCGC GATGAGCCGG GTATGCGCTT GTTCCATTTA |
| | | TCTTTCCTGA CGACGGGTCT GTAGGCAGTA TACTACCACC |
| | | ACGCGTGGAA ATGATGTACC GGACCAATGC CCTTCCCCAC |
| | | TTCCAGCCGT GTACGCTGGC AGCGCCGAAG CATGCCTTGC |
| | | TCGTTTACCG TCTCTCCCAA CT |
| 161 | 233 | GATCCTGAAT GAAAATCTCA CTGCTCGGCT TGTTGGTCAG |
| | | TTCGGCCATG GTCTGGCGCA CGTGCTCCAG CATGCCGCCG |
| | | ATATTGGTCC CGGCCTCGCC GTGACGTTGT CGAGCTTGCC |
| | | GCAACCGTCC ACCGCTTTGC TGATGGCTTC GGACGCCGGC |
| | | GGCAACATCC ACACAGCGCA CCGAGACCCT GAGCCTGACG |
| | | CTACCGGATC CGGCGGTATG AGCGGTTAGC GAG |
| 162 | 236 | GATCTGTTCC GTCTGACGGC GGGTAAACTG ACCGGCCTGG |
| | | ACCGAATGGG GCCAAAGTCC GCGCAAAATG TTGTTAACGC |
| | | GCTGGAAAAA TCCAAAACGA CGACCTTTGC GCGTTTTCTC |
| | | TATGCGCTGG GCATCCGTGA AGTGGGTGAA GTGACGGCGG |
| | | CGGGGCTGGC GGCTTATTTC GGTACGCTGG AGGCGCTGCA |
| | | GGCCTCCGAC CATTGACGAG TTCGAGAAGT ACTACT |
| 163 | 334 | GATCGCGTGT CGGTGCGTGA TTTAAGCCGT GGCTTAATCG |
| | | TGGATTCCGG TAACGATGCC TGTGTGGCGC TGGCGGATTA |
| | | TATCGCGGGC GGGCAGCCGC AGTTTGTGGC GATGATGAAC |
| | | AGCTATGTGA AAAAACTCAA TTTACAGGAT ACCCATTTTG |
| | | AAACCGTCCA CGGTCTTGGA TGCGCCGGGA CAACATAGCT |
| | | CCGCGTATGA CCTGGCGTAC TCTACGGCGA TTATTCACCG |
| | | GCCGAAGCCT TGAATTTATC ACATGTACAC GAGAAAAGCC |
| | | TTGACCTTGA ACCGATTAGA GCAGAACCGA ACGCTTGATG |
| | | GATAGACACG AATG |
| 164 | 308 | GATCGTAGTG GAGAGTGTCG CCGAACGTCT GGTGCAGCAA |
| | | ATGCAAACCT TCGGCGCGCT GCTGTTAAGC CCTGCCGATA |
| | | CCGACAAACT CCGCGCCGTC TGCCTGCCTG AAGGCCAGGC |
| | | GAATAAAAAA CTGGTCGGCA AGAGCCCATC GGCCATGCTG |
| | | GAAGCCGCCG GGATCGTCTG TCCCTGCAAA AGCGCCGCGT |
| | | CTGCTGATTG CGCTGGTTAA CGTCTGACGA TCCGTGGGTA |
| | | CCAGCGAACA GTTGATTGCC GATGCTGCCA GTGTAAAGTC |
| | | AGCGATTCGA TAGTGTGTGG CGCCTGAG |
| 165 | 362 | GATCCCATCG CGAATATCGG TAAAACAGCG CTTCTGCTGA |
| | | CCGCCGTCGA TAAGCTTGAT CGGCGTTCCT TCTACCAGGT |
| | | TCAGAATCAA CTGCGTTATC GCGCGTGAAC TGCCGATACG |
| | | CGCCGCGTTC AGGCTATCCA GCCGCGGCCC CATCCAGTTA |
| | | AAGGGACGGA AAAGCGTGAA GCCAATCCCT CTTTTTGCCA |
| | | TAAGCCCAAA TCACCCGTCG AGAAGCTGTT TGGAAACGGA |
| | | GTAAATCAGG GCTTATTCAC CGGCCCGACG ATCAGATTGA |
| | | TTGTGTTGTA AAGAGGCTCT AATCGGTCAC ATTAGAGAGA |
| | | GGAAACATTT AGTATTAGAT AAGATACCGA GTTTAATAGT AA |
| 166 | 71 | ATCGCGTTGT GTTGCCGAGC ATTTATTACA AGGCGCTTCT |
| | | GTGTGNCNCT CGAATGGTGC NGCAAGACTG C |
| 167 | 363 | GATCGTGTCG CAATTCTTAA TGCCATAGAG GGTAATCATA |
| | | TTGAATCCTT TAACGCGAAA TTCGAATAAA TAATCAATAG |
| | | TATCGTCTGC GGGATAATAA GTGTGGCCGT TTATGGTTAT |
| | | TTATCCAGCG CTGATCGGCA ATCAATATAA CATTGTTGAG |
| | | TGAATGTGAA TAATGATTCC TTTTCGTTCC AGATGTGGCT |
| | | TGTTTATACT TCGCCGGTAT AATCCTATTT GGGCAAATGC |
| | | AATTGTGTTT ACCATTGATA AGGTAGGTAG GAAAGGTATA |
| | | TGTGCTAATA TGGCGTAGTC ACATAATTAG TCTACGGCCA |
| | | TGATCAGACG CAACAGGATC GACTCGTATG ACTTTACGAC CGC |
| 168 | 329 | GATCCGGCGC TGATTTTCAC CATCACGTTT TTCATCGGCT |
| | | GACCTGCGGC GTCTTTCACG TCGATGGTGG CGGCCATCTG |
| | | CTCGCCCTTC TTCGCCTTTG CGCTTCCGGT GGTTTCATCC |
| | | TGGCCTGCCA GCGTCAGCTC AGGCTGGCGG CGGCGCTGCG |
| | | GGCGAGGCAA GACAGGTCTG CATGTAGTAC ATCGAGGTGC |
| | | TGGTCGTCGT TTGACATCAT TGCCGTCGTT AAACAGGTTG |
| | | ACCGCCGCAT AGAGCGACTT GTGCCGTCTG ACGATATCAC |
| | | GTAATCCCGC CACAGTAGCG CTGAGCTGTG TGCTGACTGT |
| | | ATGCACTAG |
| 169 | 198 | GATCTGGCGG GCGCGTGAAA ATATGTTGCT GGCCTCCTGT |
| | | ATGGCGGGAA TGGCCTTTTC CAGCGCCGGT CTGGGGCTGT |
| | | GTCATGCGAT GGCACACCAG CCTGGGGGGC GCTGCATATT |
| | | CCGACGGCCA GGCCAACCGA TCGTCGTCGC AACAGTCATG |
| | | GGCTTTAACG GATCAGTTTA CGGAAAGTTC AGTAATAT |
| 170 | 273 | GATCAACATC AATAACTAAA ACTCTTTTAC CAAGATAGTT |
| | | AGCCATGAAC TCAGCAATGC CAACACATAG AGTTGTTTTT |
| | | CCTACCCCGC CTTTCATATT AATAAAGCTA ATTACCGATG |
| | | CTGGCATAAT TATTCCTTGC TATGTTGAGA ATGAGTCATT |
| | | TTGATAATTA CTCGAGCTTT TATCTTAATC TTCGCGCGTT |
| | | CGAATCCTTC CCTTCATGTA CTTCTCGTAC ATGGCATCCA |
| | | GTTCCTTGAG ACGAGATAAT ACCCGAAGAA AAT |
| 171 | 244 | GATCGCTGGT TCTGGCGGCA CCCTGGCGCC AACCCAAGCA |
| | | ACGTCGCGCG CGCGGCATGG CAGGATCTTA CCGCCGGGCG |

TABLE 3-continued

| SEQ ID NO | LENGTH | PARTIAL 3'—5' SEQUENCES OF PROBES OF THE PRESENT INVENTION |
|---|---|---|
| | | CGTTATTATT TCCGGCGGCA GTACGCTGAC TATGCAGGTG |
| | | GCGAGACTGC TGGACCCCGC ATTCGCGCAC GTTCGGCGGT |
| | | AAAATCCGCC AGCTTTGGAG CCCTCCAGCT TGAATGGCAT |
| | | TTGTCCAAGC GCGATATCCT GACGCGTGTA CTGAACCGAG AGTG |
| 172 | 247 | GATCGCGCAG CGCTCTCATA GCACAAAACG AGGTTTTCCA |
| | | TTCTGTTATG TTCCCTGGCG ACGATAAACG TTCGATTGTC |
| | | TCATGGCGCT GGTGAACCTT ATTTTTTAAC GGAGATGTTG |
| | | AATGGCGGTA GAGGTTGTAC GTAATGGCCA AACCCGGCGG |
| | | CGGATCTCGA ATATTGATTC GGCAATATTC GTTCTATCTT |
| | | GGAAAAGGAG CGCTGTACCG GAACGGAATA AAACTGCGAT |
| | | GTGCAGA |
| 173 | 300 | GATCAGCTTG CCGCACTGTA TGCCTCCAGC GACGGCAATA |
| | | AAATCCACAC CGTATCCGGC TGGCCGACTG AGTATGACTA |
| | | CTGGTCATCC ACCTTCGCCA GCGCCGCTAC ATGGCAGGCG |
| | | GTATCACTGG CTGCGGGCGG CTATACCGCT TCCGGCGATG |
| | | CGGTCGGACT ACGTGAGCTG TCTGGTCAGC AAAAATCGAC |
| | | GCGCGTCTAT CACCATTGAG CCGGTGGATG CGCATTGTGT |
| | | ATACGCAACA GCGAACACGC GTGAAGGTGA AAGGCATACG |
| | | TCAGCTTAAG TGACGTAAGA |
| 174 | 337 | GATCCGGACC GTGCCTTATA CCCTGAAAAA GGGGGAGACG |
| | | GTGGCGCAGG CGCACGGCCT GACCGTCCCA CAGCTGAAAA |
| | | AACTGAACGG GCTCCGCACT TTCGCCCGCG GCTTTGACCA |
| | | CCTGCAGGCC GGCGACGAGC TTGACGTTGC CGGCGGTCCC |
| | | GCTGACCGGC GGGAAAGGTG ACAATAACCG CCATGACGTC |
| | | CGCGGTCCGT TTGCTGCTGA CCGGGAAAAT GAGGACGATC |
| | | GCAGGCAGCA GATGGCCGGC ATGGCTCACA GGCGGCAGCT |
| | | TCTGCCAGCC ATCGGACGTT AGGCCGCCGC GGATGGTTCG |
| | | TATTCGCGTT GACATGT |
| 175 | 424 | GATCAATGAA GCTTTGTGGG AAGTCTTGAC TTTCGTCGAT |
| | | AAATACGTAA TCAAGTGCCT TTTTATCAGC TCTCCCACTA |
| | | TTATTTATAT CTGCAATGGC TTTCTTACAT AGGGCATCAA |
| | | AATCGCCATT ACCAAATCCC CCAAATGGAA TTTCGCTAAT |
| | | AATGGCATAT ATATCTGGTA CATTCCAGAA AAAGGTTCTT |
| | | TACGTCAAAC CCCAAGAGTT GAAGCAAAAA AGTTTTTGTA |
| | | CCCCATTCTA TCTGTTTTTC GACTCGCATA AATCGAAAAA |
| | | CTCAGGGATT CTGGTTCTCA TTGTGGAGCA GATTATAAGC |
| | | AGTAATGCAT CTAGATACGG TTTGATACTC TCTAGTGTAG |
| | | TATCAGTTAC TGACAGCTAC TGCATAACCC TTTCAGCACT |
| | | GAGACACGTG CGCAAATGTG TAAA |
| 176 | 190 | GATCATTTGA TTAAAACCTC ACACCGCAAG ATGCGACTTT |
| | | TTGTAAACCT GCTTTACCGC TGACACATTT CTCCGCATTA |
| | | CTGCGGAACA AGGCTTAAAA AGCGTATCCG AACGTATAAC |
| | | CCTCCAACGT TCGCTACGGG AAAAATGGGG ATGAGTACTG |
| | | GAAGGTCGCA TATATGACCA AGCCAGACAT |
| 177 | 441 | GATCCATGCC TGTGATGCCT GGATGTCCCG AATACTTGAA |
| | | GGTTTGATCG AACGGCAGGC CAGTAATGGC AACGCCACTA |
| | | TTCTGTTATC TGCGACGCTA TCGCAGCAGC AGCGAGATAA |
| | | GCTGGTGGCG GCATTTTCCC GTGGGGTGAG GCGTAGTGTG |
| | | CAGGCGCGTT GCTAGGCATG ACGATTATCC CTGGCTGACT |
| | | CAGGTCACAC AAACAGAGCT GATTTCTCAG CGGGTTGATA |
| | | CACGCAAAGA GGTTGAGCGT TCGGTAGATA TTGGCTGGCT |
| | | ACATAGTGAA GAGGCGTGTC TGAACGTATA GTGAGCAGTG |
| | | AAAGAACTGT ATCGCTGATA CGTACTCGTG ATGATCGATC |
| | | GATCTACCGA GCTACTCACT GGTAGGGCAG AACTTACTCA |
| | | AGGCTCTCAG GCGTCTAACA GGCGTCTAAC ACGTGGAAGT T |
| 178 | 370 | GATCGTCGTT ACCGGCGACG GTTAAAGCAA ACTGGGCATC |
| | | AATGGGCCGT AAGAGTTTTT GTTCAACGGC CTCCAGCAAC |
| | | CGCTCCTGGA TTGTCATTGC GCCTCCTCAC TCATTTCACC |
| | | TGCAAACATA TCATCCAGTT GGTTAATTAA CGCCGCCGCA |
| | | GGACGAGTGG TAAAAATACC CTGCTGCGGA CTGTCGCCAT |
| | | CCACCCCGCG TAAAAAGAGA TAGATGACTG CCGCCGAAAT |
| | | GGCGTTCATA GTCGTAATTC GTCATTCGAT GACGAAGGTA |
| | | ACGGTGCAAT GCCAGCGTAT AAAGCTGGTA CTGCAAATAT |
| | | AGCGATCGCG TGCTCCGCGC AGCCATGCGT CTGGATAGCG |
| | | CTATCTGCCG |
| 179 | 212 | GATCCGGGTA CTATGAGCCC AATCCAACAC GGGGAAGTGT |
| | | TCGTTACTGA AGACGGCGCT GAAACCGACC TGGACCTGGG |
| | | GCACTACGAG CGTTTCATCC GACCAAGATG TCTCGCCGCA |
| | | ACAACTTCAC GACTGGCCGC ATCTACTCGA CGTTTCTGCG |
| | | TAAAGAACGG TGACTATCTG GACGACAGT ATCTAATATA |
| | | CGGATTAAGA GG |
| 180 | 367 | GATCTTCTTC ACGTCTGGCT TCATCACTCT GATGAACGAT |
| | | ATGCTCGGTC AGATGACCTT TAATCACCTC GCGCATTAAG |
| | | CCATTTACCG CGCCGCGAAT CGCCGCGATC TGTTGTAACA |
| | | CGGCCGCGCA TTCATGCGGT TCATCCAGCA TTTTTTTTAG |
| | | CCGCTATCAC CTGTCCCTGA ATCTTGCTGG TTCTGGCTTT |
| | | AAGCTTTTGT TTGTCCCGGA TGGTATGTGA CATTACAACA |

TABLE 3-continued

| SEQ ID NO | LENGTH | PARTIAL 3'—5' SEQUENCES OF PROBES OF THE PRESENT INVENTION |
|---|---|---|
| | | CCTCACTAAA CATTAACGAA TACAAATTAT AGCATTACCA |
| | | GATGCTACTG GGGGGTAGTA TCTATACTGG GGGGAGTAGA |
| | | ATCGACGCCC ACATAAAACA ACTAAGAATC ACTCATGGGT GAATTTC |
| 181 | 196 | GTATCACGTT TGATGCGGCT GTTATCGTCC AGATAGCCGG |
| | | TGCGATAGGC AAAATAATGC GGCAATGAAA GCGCCAATCG |
| | | CCAGGGGGGA TCCCCACAAT ATATGCCAGC ACGACCCCGG |
| | | GGAATACCGC ATGACTCATT GCATCGCATT CGCGCTTTTA |
| | | CACTAAAACC CGCGTAGGAG ATCGCAATCG GACTAG |
| 182 | 266 | GATCTGTCGC GTTTTCGCCA GAATAGCGCG CGGAATAGAT |
| | | ACCCGGCGCG CCGCCTAAAA CGTCAACGGC CAGACCGGAG |
| | | TCATCGGCAA TGGCGGGCAG GCCGGTCATT TTGGCGGCAT |
| | | GGCGCGCTTT GAGAATCGCG TTTTCAATAA ACGTCAGGCC |
| | | GGTTTCTTCC GCGGAATCGA CGCCCAGTTC CGTTTGCGCT |
| | | ACCACATCAA GCCAAAATCG CTTAACAGCG AGCNNCACTT |
| | | ACGCGTNTGC GAGACACTTT NCTGAG |
| 183 | 351 | GATCATCATC ATTCCGCAGC CAAACGCGCG GCTTTTACCG |
| | | AACCCCTGCG CCAGACGTTG CAGGAAAAGC GCGGGTTCGT |
| | | TAATCACCAG CACGCCGGTA TAGTCCACGC TGCTAAACTG |
| | | AATCATCTGG CCGATCTTTT CCCGCGACGT ATCTGCCTGC |
| | | CTGCCGATAA GCATCAACGC TCGGCTCGGC AGAGTAAAGC |
| | | CATTTTGCCT CCCCCTGCGC GCCAACCACG CAGGCGCTGC |
| | | TGCTGATAAG ACCAAATATG CTGGCTATCA CCTGCGTTTA |
| | | GTGGCGATTT AGACTCATCA GCAAATCGTG AGTTGCGTTT |
| | | TGCAACGAGA TTGGGAGGTT AACGAGATGA A |
| 184 | 398 | GATCATGTGG TGATCTGCGC CGGACAGGAA CCTCGCCGCG |
| | | AGCTGGCGGA CCCGTTACGC GCCGCAGGTA AAACGGTACA |
| | | TCTTATCGGC GGATGCGATG TCGCGATGGA GCTGGATGCC |
| | | CGACGGCGAT TGCCAGGGCA CCCGACTGGC ACTGGAGATT |
| | | TAACGACTTT GCCTGATGGC GCTACGCTTA TCGGGCTTAC |
| | | GCCGTCATAC CGGTTTTATA GGCCGGTATG ACGCTTGAGC |
| | | GCTTATCGAC GGCGTCCTGC TTCACCGCTT TCAAAATGAC |
| | | AAATTTATTG TTGGTGCTAT CGTCGCGCAA TTACCGAAAT |
| | | CTTCTTCAGC TGTGGAAATA GTCAGATGGC GTTCGCACAT |
| | | ATACAGTTGC CGTGATTAGC ACACGCTATG CAATTCAG |
| 185 | 347 | GATCGCTATT GGTATGGCCC CACTTGCCGT ATTTCACCGG |
| | | AAGCGCCGGT GCCCGTGGTT AAGGTAAATA CCGTTGAGGA |
| | | ACGCCCGGGC GGCGCGGCGA ACGTGGCGAT GAACATTGCG |
| | | TGCTCTGGGA GCGAACGCCG TCTGGTCGGC CTGACGGGTT |
| | | ATTGATGACG CCGCGGCGCC TGAGCAAAAC GCTGGCGGAG |
| | | GTCAATGTGA AGTGCCGACT TCGTTTCTGT GCCGACGCAT |
| | | CCGACGATTA CCAAACTGCG AGTACTATCT ACGTAATCAG |
| | | CAGCTCATTC GTTTGATTTG AAGAAGGCTT TGAGGATGAC |
| | | CGCAAGCCGT TGCATGAGCT ATAACCA |
| 186 | 294 | GATCGGCGTG CTGGCGGCGA CCTGGCCGCG GGAAATACCC |
| | | TGGAAGAGGC GTGTTATTTC GCCAATGCGG CGGCGGGCGT |
| | | AGTGGTAGGT AAACTCGGGA CGTCAACGGT TTCCCCTATT |
| | | GAGCTGGAAA ACGCAGTGCG CGGACGGATA CCGGCTTCGG |
| | | CGTTATGACC GAAGAGGAGT TGAGACAGGC CGTCGCCAGC |
| | | GCGTAAGTCG CGAGAAGTGT CATGACCAAC GCGTTCGATA |
| | | TCTGACGGCA TTATGACGCA ACTGGACCTA TCGGATACTT |
| | | ACTAGACTAC ATAC |
| 187 | 352 | GATCCGCATT GTCAGGGATA TCGCCCTGAA CGCGAGCTAC |
| | | GCCGGCATCT GCTGCTGATT ATTGCCATTG ATCACCGCCA |
| | | GCTTAACGGC CCGTCGCCCT GGAGCTGTAC CGTAATGTCA |
| | | CCAGCAAACT TCAGCGTCGC GTCAGTAGGC TAGTGGCGAC |
| | | CAGCAGTTCG GCAGTACGTT TTCACCGGCT GCGGATAGTT |
| | | ATGATTGTCG AGGATCTGTT GCAAGGTTTC CGAAACAGTT |
| | | ACCAGCTCGC CGCGAACACA AAGTTTTCAA ACAGATAACG |
| | | ATGTAATTGG TCATGTTGCG CATAATCATC TCTCTTCAGT |
| | | ACATTATTCA CTATACGTGT TTAAATCGTA CA |
| 188 | 290 | GATCCTTACC GTTTTGGTCC ATTAATACAG GAAATGGATG |
| | | CCTGGCTATT GACGGAAGGC ACCCACCTGC GTCCTTATGA |
| | | AACGCTGGGC GCGCACGCCG ATACGATGGA TGGCGTCACC |
| | | GGCACCCGTT TCTCCGTCTG GGCGCCTAAT GCTCGTCGCG |
| | | TTTCGGTTGT CGGGCAATTC AACTATTGGG ATGCGCCGTC |
| | | GCACCCGTAT GCGTCTGCGC AAAGAGAGCG TATTTGGGAG |
| | | CTGTTATCCC GGCATAATGG ACACTGATAA TCGAGCTCGT |
| | | ATCGCAAGAA |
| 189 | 213 | GATCTTCAGC AACCACGACA GGAATGCCCG TCTCTTCCAT |
| | | TAACAGACGG TCAAGGTTAC GCAGCAGGCG CCGCCCCGGT |
| | | GAGCACCATA CCCGCGCTCGG AGATGTCTGA CGCAGCTCCG |
| | | GCGGACACTG TTCCGGCGCA CCATTACCGC GCTGACGATA |
| | | CCGGTCAACG GTTCCTTGCA ACGTTCCAGA ATCTCGTTTG |
| | | CGTTCAGGGT AAA |
| 190 | 256 | GATCGCTTTG GTTAAATCCC CGCCGCCAGT GTCGGCGCGA |
| | | CCAGAGCGGA ACGTGACGAT TCTGTCGGGA AGCTGCAAGC |
| | | CAGTGCTGCG GCGGCCATGA GGACTTCCTG CAACAGTAGA |

TABLE 3-continued

| SEQ ID NO | LENGTH | PARTIAL 3'—5' SEQUENCES OF PROBES OF THE PRESENT INVENTION |
|---|---|---|
| | | CGCGCCAGTG CGGCGGCAAT TTCGCTGCGG CGGGTAAATT |
| | | TAAGCTGATG CACCAGTAAA CTCAAGGCGG TGTATAGTCA |
| | | CTGACGCTCA CCAGACTTGC AGGGTGGCGG TTTTTTCAGG |
| | | CAGCGACCGC ATGGGG |
| 191 | 247 | GATCGTGGCT GCCGGTGCTG TCGGTGTAGC CACCACATTG |
| | | ACGGCGGTCT TGGGATACTC TTTCAGCACC ATCGCCACGG |
| | | CGGTCAGCGT CTTAGCGCCT GCCGGCTTTC AGCGTCGGCT |
| | | GCTGCTGTCG AAGGTGACAT TATTCGGCAT ATTAGAATGA |
| | | CTACTTACTC GCCCGCCTTC GGCTCACGCT AACGCCTGTG |
| | | CCCCGATTTG TAGAGTTTGC TTCTGTACGT AGAGTAACCA GCGCGCA |
| 192 | 402 | GATCCATTTT AACTTTAGCC GCCCTTTTGG CGAGGAGATG |
| | | ACTCAGCAAC TGGTCGGGCT GGCGGAGTCT ATCAATGAGG |
| | | AGCCGGGCTT CATCTGGAAA ATCTGGACAG AAAGCGAGAA |
| | | AAACCAGCAA GCTGGCGGTA TTTACTTGTT TGAATCCGAA |
| | | GAAACGGCGC AGGCTTATAT TAAAAAACAC ACTGCGCGTC |
| | | TTCGAAAAAT CTTGGCGTTG ATGAGGTGAC GTTTACATTA |
| | | TTTGGCGTGA ACGACGCGCT GACGAAAATA AATCACGGCA |
| | | ACCTTTGCCG CTAAATCACA TAACGCAGGT TCTGTTCCGG |
| | | TGCTGCTGAC CGCAACGGTA ATCTTTATAC CGGGCGAGTA |
| | | CCTAAGAGGC TTTATGGACG ACAGCGACAC GACGTTTCAG CG |
| 193 | 240 | GATCGCGAAG CCGCACAACG TAAGCAGGGG TTATGTAGTG |
| | | TGTTCTTCAA CACCACGCTA TTCATGCCGT ACCGCAGGTA |
| | | GATGTCCCCC TTAGGAGCAT CGCTTACGCT GGGAACAGCG |
| | | TTTAAGCAGC TTTTTGACAA GGGAGCTTTG ATGTATTGTT |
| | | TGCAGTTCTA GACCTGACAC GGGCGATGAA TAGGAGCAAA |
| | | GCGTGGTTTA CACATCCATA TTGCTATGTT ACACTATTAC |
| 194 | 248 | GATCCCCTCT ATACCGCAGA CAACACAAGG CGCGCTTGCT |
| | | AACGCGGTGT TACAGGGCGA AATCTTTCTA CAGCGCGAGG |
| | | GACATATCCA GCAACGGATG GGCGGGATGA ATGCGCGCTC |
| | | GAAAGTCGCA GGAATGTTAA TGCGCCAGGA TAACGCCCTC |
| | | CGCTAAATTC TTGGTATTTT ATTTGGCTGG CCGACGTCGC |
| | | AAATTAGCCA AAGTTAGCCA ACTTCTAGCT GATTCATCTA |
| | | CGATAATT |
| 195 | 304 | GATCGGGGTT CAGCTCAAAT TTTTCAATCG CCCAGGCAAC |
| | | ACCATCTTCA AGGTTCGATT TAGTCACAAA GTTAGCCACC |
| | | TCTTTGACCG ACGGAATGGC GTTGTCCATT GCCACGCCCA |
| | | TACCGGCGTA TTCGATCATC GCAATGTCGT TTTCCTTGAT |
| | | CGCCATCACC TCCTCTGCTT AATACCCAGC GCCTCGACCA |
| | | GTGATTTACG CCAGTGCCTT TATTAACCGT TATCGAGGAT |
| | | TCAAGGAAAT ACGACACTTA CGCACGGTAC TTCTCATTGC |
| | | GAACGCATGC GCGAACGCAG TCAT |
| 196 | 301 | GATCTGCGCC CCAGCGTTTG CAGCAGAAAA TAAAAGCCGA |
| | | AAATCACCAC TAAACAGGCG ATCAACACGT AGAGAAGCAA |
| | | CCTCCCAATC AATTTCATGG TCTTCCATCC CGTGAAATGC |
| | | ACATAGGGGA TTTATGCACG ATTTGCGTGC AATCCTCAAG |
| | | ACAGGAATGG TGAAAGAGCG TTACAGCAGC GGCGAATCGT |
| | | GTCGCGCGCA GGGTTTTTAC GGTTTTTCGG CGGAGAATCA |
| | | GTCAGCACGA TAGCGTGATG CGCAGCGATC GATGAGAGCG |
| | | ATTTACCATC GGACTGAGAT T |
| 197 | 366 | GATCCAATCC TGAACGCCGA ATTTTCACCA CAGGGCGTTG |
| | | CGCTACGCCA GTTCACTACC CGCTGGGAAG GCGGTATGGT |
| | | CAGAACTTCC GGCGCCTGGT TACGCGAAGG CAAAGCGCTT |
| | | ATTCTGGACG ATACCGCTAT CGCCGGGCTG GAGTATACGC |
| | | TGCCGGAAAA CTGGAAGCAG TTATGGATGA AGCCGCTGCC |
| | | CGACTGGTTG AACAGCTGAC GCTGAAAAAT TCAGGCAGCG |
| | | CAATCTGGTT ATTGATATCG ACCCGGCCTT CCGTGCAAAT |
| | | CACCGCTCTG ACGCTACGCG CAAACTGAGC TGTACAACCA |
| | | TCATCAATGG GCTCTGAGCG CATCGACTAC GGCAGCGGAA CTTTAC |
| 198 | 310 | GATCGCTACC CAATTCCGCG CCCACACAGC CTGCTTTAAT |
| | | CCATTGCGCT AGGTTTTCCG GCGTCACGCG CCGACGCAAA |
| | | TAGCGGAACA TCCGGCGGAA GTACCGCTTT CAGCGCGCTG |
| | | ATGTAGCCCG GACCAAACGC CGACGACGGG AAAATTTTTA |
| | | ACTTCTGTGC TCTCTGCATC CAGCGCAGAA AAGGCTTCCG |
| | | TTGCCGTCGC GCAGCCGACA CACGTCATGC CATAGCTCAC |
| | | CGCCGCGAAT CACTCGGTTG ATATCGCGTA CATCACTTCG |
| | | CCATCGCACG TGTTCTTCGT TAGCTGTACA |
| 199 | 348 | TCGAAAATAC GTATACCCTG ACAGTGAAAG CAACCGATGT |
| | | TGCAGGCAAC ACGCGACGG AAACGCTCAA TTTTATCATT |
| | | GATACCACAT TGTGGACACC GACCATCACG CTGGATAGCG |
| | | CAGATGATAG CGGCACCGCC AACGATAATA AGACTAACGT |
| | | TAAAACGCCC GGGTTTTATT ATCGGCGGTA TTGATTGATT |
| | | CTGACGTGAC TCAGGTCGTC GTGCAGGTGA TGCGCGATGG |
| | | TCACAGCGAG GAGGTGGAGC TGACCGAGAC TAACGGGCAG |
| | | TGGCGTTTGT ACCGGCACGC GTGGACTGAT AGGCGACTAT |
| | | CGCGTACGTA GTGAAGATAG CGTATATA |
| 200 | 279 | GATCGGATAA CGACTCCGCG GTGGATGCGC AAATGTTGCT |
| | | TGGCCTGATT TACGCCAACG GTGGGCATTG CCGCCGATGA |

TABLE 3-continued

| SEQ ID NO | LENGTH | PARTIAL 3'-5' SEQUENCES OF PROBES OF THE PRESENT INVENTION |
|---|---|---|
| | | TGAAAAAGCC GCCTGGTATT TCAAACGCAG TTCCGCCATT<br>TCCGTACCGG CTATCAGAAT ACTGCGGGAA TGATGTTTTA<br>AACGGTGGAA CCGGGCTTTA TTGAAAAGAA TAAGCAGAAG<br>GTGTTGCACT GGTTGGATCT AGCTGTCTGG AGGTTTGATA<br>CCGATACCGT TGCAAGATTC GAACGCTACG ATGCTATTT |
| 201 | 272 | GATCGCCAGG GACGATGGCG AGCTGGGCCC CTTGTAAATC<br>GTTTTTGGTG AGGCCGAGAT GAAAAACATC AGACTTGGAC<br>ATATAAAACT CCTCTGTGAA TCGGGTTTGT CAGAAGAAGA<br>AAGAGACACT TTACCTAAGG ATAAAGATAT TTTGGTGCAT<br>CATCACTATG CGTAAAACAA TTGCGTGTTC CATTAAAAAG<br>AGATGCCCCA TCACAATAAA TAATCAATAT GCAGGCATTG<br>CACAAAGCAT AGGCGTTTAG GCATGTGTTG TA |
| 202 | 401 | GATCCAATAA TGACTGCATT GCCTCATACC CCATACGTAA<br>CGCGCTATAC AAAATATAGA TGCCGATACC TAACGCAAAC<br>AGGGCATCCG CACGATGCCA ACCGTACCAG GATAACCCCA<br>GCGCGATAAG AATCGCTCCG TTCATCATAA CATCAGACTG<br>ATAATGAAGC ATATCGCCCG TACCGCCTGA CTTTGGGTCT<br>TGCGTACCAC CCAGCGCTGA AACGTGACCA GTATAATAGT<br>GCATATCAGA GCATGACGGT AACGCCAATC CCACGCGGGG<br>TCGTTCATTG GCGTGGCTTT AATCAGATTC TGAATACTGG<br>TCAAAAACAG AAACACGCGA ACCGGAAATA ACTACTTTGC<br>GCGCGCAGGC ACTCGTTTAC GTGCCAAGGG TTAATGGTGG G |
| 203 | 169 | GATCCAAAGT CGTTAAATAA CGGCGGGAAA AGCCTCCACG<br>CCATGGAAGT GCCCCGGAAA TCGCCCCGAC CATGGTGGCG<br>ACAGTATCAG TATCATTGCC GATATTAACC GCCGGAGATA<br>ATAGCATCTA CGGCAGAATT CGGACAACAC GCGAACAGGC<br>CAAAGCGGC |
| 204 | 253 | GATCCAAAGT CGTTAAATAA TCGGCGGGAA AAGCCTCCAC<br>GCCATGGAAT GCGCCGGAAA TCACCCCGAC CATGGTGGCG<br>ACAGTATCAG TATCATTGCC GATATTAACG CCGGAGATAA<br>TAGCATCTAC GGCAGAATTC GGACAACACG CGAACAGGCC<br>AAAGGGCCGG CACCGCTTCA CTCACGTGCA GCCGGAGCAA<br>TATATAGCAG TTCACACGCG TTCCATGGAT GAGCTTCGAT<br>ATAGCTCAGT ATG |
| 205 | 198 | GATCGTACAG ACCCGCGTTG TCATAACCAC GGGTTTTTAG<br>TTCCGCCACA CGCTCGCCCG CCAGCGTTTT CATATCCTCT<br>TTCGAGCCAA AATGAATGGC GCCGGTTGGA CAGGTCTTCA<br>CGTCAGGCCG GTTCTTGCCG ACGTGTCACG CGGTCAACGC<br>ACAGCGTACA TTATGACGTC GTTGTCTTCC GGTTGAGG |
| 206 | 411 | GATCGGAATG CCTTTGAACA GCGGCAGGTC TTCCAGCGGC<br>AGTCCGCCGG TCACGGTCAC TTTAAAGCCC ATATCGGACA<br>GCCGCTTAAT CGCGGTAATA TCCGCCTCGC CCCACGCCAC<br>GGCTGCCGCC TGGGGTCACG GCTGCGGTGA TAAACCACTT<br>GCTGAATACC CGCATCACGC CACTGCTGCG CCTGTTCCCA<br>GGTCCAGTAA CCGGTCAGTT CGATCTGCAC GTCGCCGTTG<br>AACTCTTTCG CCACATCCAG GGCTTTTGCG GTGTTGATAT<br>CGCACAGCAA ATCACGGTAC CAGTACGGTT GGCTTCGAAA<br>CACATACGGG AGAGGATTTA CGAATGCATT GGGAGAGATT<br>GGGTAGGTCA GTAGACGAGA ATGCAGAGAT GGCATGAAGA<br>TTGAAGGGTA G |
| 207 | 402 | GATCCTGAGC CGGGTAGCCA GTATTTGCAG GCAGCAGAGG<br>CAGGTGACAG ACGCGCACAA TATTTTCTGG CCGACAGTTG<br>GTTGAGCTAT GGCGATTTGA ACAAAGCTGA ATACTGGGCG<br>CAAAAAGCCG CCGACAGTGG CGACGCCGAC GCCCTGCGCG<br>CTACTGGCCG AAATCAAAAT CACTAATCCG GTAAGCCTGG<br>ATTATCCCGA CGCGAAAAAG CTGGCTGAAA AGGCGGCTAA<br>CGCGGCAGTA AAGCGGGAGA AATTACGTGG CGCGGATCCT<br>GGTCAACACC CAGGCCGGGC CGGACTACCA AAGCCATCTC<br>GCTGCTGCAA AAGGCCTCTG AAGATCTGGA TACGACTCGC<br>GTGATCGCAA TGTGCTTGCT ATTGACTGGG CATCTCGTTA AA |
| 208 | 288 | GATCAAACGC GCTGGCGTAA TCGCTACTGG GTTGATAGCG<br>AAGGCCAAAT TCGCCAGACG GAACAGTATC TGGGCGCGAA<br>TTACTTTCCG GTGAAAACCA CGATGATTAA GGCGGCAAAA<br>TCATGATGAA AAGGACGATA AGCGCGCTGG CGTGGCCTTT<br>GTCGCGTCAT CCGCCTTTGC CAGCGGCACT GTTACCGTTT<br>TTACCCAGGG TAATAGCGAG CTAAAACGCT GACAGACGCT<br>GAGCGCTCGC TCGATTAGTG GACAGCGCGC TGCACGAGCT<br>GGTGGCTG |
| 209 | 169 | GATCAGGGAA CCTGTACCTC TTAAAGAGAA GTTCGATACC<br>CCCAACGGTC TGGCGCAGTT CTTCACCTGC GACTGGGTAG<br>CGCCTATCGA TAAACTCACC GAAGAGTACC CGATGGTACT<br>GTCGACGGTC CGAGTCGCCA CTACTCTCCG TCAATGACCG<br>GTAACTGTC |
| 210 | 311 | GATCATCTTC GTCCTGCTCT TCCTGACTCA GCGCACTGTT<br>TACGACAATA CTGTCCGCAT CTCGTTGTGC GATTTTATCG<br>GCGACGTCGC GGGAATAATC GCATATTCAC ATTCACCGCT<br>GTTATTGATA ACCAGACGGC AATCGCAGAC GCCCATTAAT |

TABLE 3-continued

| SEQ ID NO | LENGTH | PARTIAL 3'—5' SEQUENCES OF PROBES OF THE PRESENT INVENTION |
|---|---|---|
| | | CAGTTGCGTC TGAGTGAGCT TATCCACGTC TATTTTTTG |
| | | ATGACGTTAT TATCGGTGAA GTTAAAACCA ATATCGCCTT |
| | | TAGATACATT GATTCTATTC ATTTCAATAA GTTGCTTAAC |
| | | CTGAGCTTTA AACTCTTCGC TAAAACCGCT G |
| 211 | 368 | GATCAGTATC ATCAGTAATG GCCAGCGTTG CAGTATTCTG |
| | | AATAGCCAGT GAGGTTTTCA GCGGGAAAAT GGCGAGGGTA |
| | | TACGGAACCG GTTCGGTGGT GCCTTTTGTA GCAACGGTAA |
| | | ACATTTCCAT ATTGCCGTTT TTGATAATCC GGTGGAAGAC |
| | | TTCTGCCAGA CTGGGCTATC AACGGTTCCT GAGATAGCGT |
| | | CAGATTTTAC ACCATCAGCG GTAACGTCGC GTATCGGTAT |
| | | AAATAGAGAA CGCGCCGATT TTTACACCTT CGGTTGTTTG |
| | | CCAACGCGAG ACATTGTGGA TCAGATACTA TACTATAGTC |
| | | ATATCGCATG GCTATGAGAT ACGAGTGCCT GGTGGTGTGC |
| | | ACGTATGA |
| 212 | 258 | GATCATCCAC TCATCTTTGC CGGTTGAGCC CGATAGTTAC |
| | | CCGTTCAATA CCGGCATCAA TCGCCCCCGT TTTATTCACC |
| | | ACCCCCAGAA AGCCGCCGAT AATCAAGACA AACAGCCGCG |
| | | ACGTCAATGG CGCCGGCGGT GTAGGTTTCT GGGTTATAGA |
| | | GGCCGTCAAT CGGCGCCAGC AAAACAGCGG TAATCCTTTC |
| | | CGGATGCGCA CGGGGCATAC GCTCCGCACC GACTTTCAGA |
| | | GCTGCTATCG ATTGATTT |
| 213 | 322 | GATCATTGTC ACGCCATTTT TTTAAATTAT TAGTATGGCG |
| | | TGTGGAGACG CGTATCTGCT CACCAATATA CGTATTGTCC |
| | | ATAGGCGTAG ACAAGCTCCA TTGCTACAAA GATAATTTTA |
| | | TTTAAGTGTC AGGAAAATTC CGGACAAATC CCTTTTTTAA |
| | | TAAAAATACA CACTCTCGGC ATGGGATAAT ACTTAATTAA |
| | | CTTTTGTTAG CGTTTTGAAA TTAAAAACAG CGCAGAGGTA |
| | | ATAATAGAAA ATAACGTTAA CAGGCTGGGT GAGTATATTT |
| | | GACTGACACA ATTCCAGGTG TATATGTATG CGTTTATGCA TG |
| 214 | 320 | GATCATCCGC AGAAGAAAAA ATATGGCCGC GTAGAGATGG |
| | | TGGGGCCGTT CTCCGTTCGC GACGGAGAGG ATAATTACCA |
| | | GCTTTACTTG ATTCGACCGG CCAGCAGTTC GCAATCCGAT |
| | | TTTATTAATC TGCTGTTTGA CCGCCCGCTT CTGTTGCTCA |
| | | TTGTCACGAT GCTGGTCAGT TCGGCGCTCT TGCCTATGGC |
| | | TGGCATGGAG TCTGGCGAAA CCGGCGCGTA AGTTGAAAAA |
| | | CGGGCTGATG AAGTGGCGCA AGGCAACCTG CGTCAGATCC |
| | | GGAGTGGAGG GGAGAGTTCT GGTGCAGTTT AACAGATCTA |
| 215 | 277 | GATCAGATGG ACCACAACGA GCACCGAAAA CAAAACGGCG |
| | | CTGACCATCA GAATGACGGT AGTGCCGAGT TTCATGGGGC |
| | | GTTTGCGTAA CGCCGGCATG GCAGGGAGTG TTTCATAGTG |
| | | GACCTGAGCG ACGAATCGTA AGGTTATTAT CCCTGATGAG |
| | | GCTCTAATTC AAAGGCATAG GCAGTCGTCC AGTGTGAAAG |
| | | CCGCTGCTGC AGGCCGCTAC TGCATCGTAT ATCGGACGAG |
| | | ATTTCAATCA ATAACACGCA ATTTCCGCAT CCAACCG |
| 216 | 330 | GATCCTGAAA CGCTGACCAG ACGCCGAGCG CGCCGTACCA |
| | | CGAATCTCCG GTGGCACTCT GCGCACAACC TCTACGCCCA |
| | | GCGATGGAA CATCAGCGAA CAGCCGCAGC CGGTAATCGC |
| | | CGCGCCAATC AGCGAGCCTG CTGACGGAGC GGCCCACATT |
| | | ACCGCCAGTC CGGTCCCTCT ACCAGTAGTG AAAAGGTTGC |
| | | ACCGTGCGCG CGTAACGGTC GGGAAATTTG GCGCAGAAAA |
| | | GCGGACAGCG ATAAACGCAT CAACACTATG AAACGGTGAT |
| | | ACAGTAGTGT GACAGAGTGT ATCTAGTGAC ATCTGACAAC |
| | | TTCTCTCAGC |
| 217 | 223 | GATCTGGGCG AAATCGCGCG GAGTCTGGCG GCGGGCGATA |
| | | TCATTACCCA CTGTTACAAC GGTAAGCCGA ACCGTATCTT |
| | | CGGCCTGACG GCGAGCTGCG GCCTCGGTGA CACGAGCGCT |
| | | GGCCGGCGGC GAGGCTATGG AGTCGGCATG GTACCGCCAG |
| | | TCCTGAGCTT TGCGTGGCTA ACTCGCTATA GCTGGATTTA |
| | | CCGCATACAT CAGTCGATAT CTC |
| 218 | 316 | GATCGCCACC GTTTTGTGAT GCGCGCCAAT TTGGGCTGGA |
| | | TAGAAACCGG TGATTTCGAC AAAGTTCCGC CGGATTTACG |
| | | TTTCTTCGCC GGGGGGACCG CAGTATTCGC GGCTATAAAT |
| | | ACAAATCTAT TTCGCCTAAA GATAGCGACG GCAATCTTAA |
| | | AGGCGCCTCA AAACTGGCAA CCGGATCGCT GGAGTACCAG |
| | | TATAACGTCA CCGGTAAATG GTGGGGCAG TGTTTGTCGA |
| | | TAGCGCGAGC GTGAGTGATA TCGCGTAGCA TTCAAACCGG |
| | | ACGCCGACCG ACCGACCGTG GCTTCAACCT ATTCAC |
| 219 | 182 | GATCTGGGGT GGGGGATTGT TGATGGTGTG TGGAGCGCTG |
| | | CTGAGCGGAT GGCGGGGGAG GAAGCATCCT GAGTTATTGC |
| | | CTGATGGCGC TGCGCTTATC AGGCCTACGA GTGAAAAGCA |
| | | TGGTAGGCCG GATAAGGCGT TCACCGCATC CCGAAAACGA |
| | | TGTTACTTTT GGCTTTACTG AT |
| 220 | 419 | TGCAGATCAA AACAGCGACG GCTGGCAAAA GCGGTAAAGG |
| | | TTTACGACCG GTCAGCGCCC CAGCCGCCGC CGTGCCAATC |
| | | ACATTCGCCT CCATAATACC GCAGTTAATG ACATGCTGCG |
| | | GGTAGTCACG CGCCACGCTG TCATCGCCAT TGAGCTCATT |
| | | AATCAGCCTC AGGATATGGC TTCAGCCTCA AGCGCAATAA |

TABLE 3-continued

| SEQ ID NO | LENGTH | PARTIAL 3'–5' SEQUENCES OF PROBES OF THE PRESENT INVENTION |
|---|---|---|
| | | TTGGGCTTCC GGCCTCAATC TGCCCGGCGA TAAAACCGGC |
| | | GTAAACTTTG CGCATTTCGA TATCGTCTTT AAGCCCTGGG |
| | | AAGCTTAATC ATGCATGACC TCCAGTTGAT GAATGGCCTC |
| | | ATTGAACGTT GCTTATCGCA TCGTCAGCGT AAGTGGTGAG |
| | | AATTCGTTAA CTGCTCAGGC ATGCACCCTG CCTTATGCTG |
| | | TCAAGGATCA CACCGTGCT |
| 221 | 126 | GATCTTATGA CATTGTGAGT ATCCATCGCT TTTTGTACTG |
| | | AGCTGTAGGC AACTCCGACA GCTTTTGCTC AGCAGCTGTT |
| | | GTTTCTCATA AGCTAGTGAC CAAGCTGCTG CTACCACAGG TCTGGG |
| 222 | 192 | GATCCTGCAC GCACGGGCGC ACAGCACCGA CAAGCTGTCC |
| | | AGCTACTTGA CACAGCGCCA GCGCGTGCTA GCGAGCGAAC |
| | | CCGCAGGTGG CACATGGCGG GGACGGCGAG CAGGAGACAG |
| | | GCTAGAACGC TTTATGTGCG CACTATGCTA TCAAATAGGC |
| | | CGTCCGGCTG CACGCCGACA CTACCCTGAC AA |
| 223 | 331 | GATCACCGCA TCGCGAACTG GTTACGGGCC TGTGGAGCGT |
| | | ATTTTTTGAT GTTATTGGTA TTCATAGAAA ATCCTGCAAA |
| | | GGGCAGCAGA GCGCTGCCCT GAAATGGGGG TTACTGAAGA |
| | | CGAATCCGGT CACCTGCCTC AATAGCTGCC AGCAGCGAAG |
| | | TACGAAGCGT ATCCAGCGCT TTTTCCACCT GTTCGGCGGT |
| | | TTCCAGCACT TCGCCACCGG TGGCTTTGCG CATCTCGCTG |
| | | GCGACATTCA CCAGATGCGT TTTTTCGGTA CCGGTTGGAT |
| | | AACGGTTCTC TACCACAACA TAAGCTCGTT GTGACTCGGC |
| | | GCCTTAGCTT A |
| 224 | 410 | GATCTAACGT ATCACGACTA AACGTAAGGG TAAAGCGGCT |
| | | GGCGTATCGT CCGGGCATAA AGTCATATCG CCTGAACAGA |
| | | TAACATCTCA CTGACTTTGA AACGCGATTT TATAATTTGC |
| | | TGCCCAAAAA TACGTGGCGC TGAAAGGCGC ATTTTTGATG |
| | | CAAATCATTT ATTACTGTGA TAACACTGCG CGCGATAAAA |
| | | CATTAATATA TTCACATAGT AATATGTTCT ATTGGAATGG |
| | | TTGTTTCGAT ATGACAAAGT CTAAAAAACC ATTGATGTGA |
| | | AAAGGAATAA GAATTGTCTA TATTCCGATT CGGTGGAATT |
| | | AAGTATTCTC GGATAAAATA GAATGATATT GATATTCTTT |
| | | TGATATGGTC TATAGCGCTA TGTATCAGAC GCGTGATCGT |
| | | CGGAGATCAG |
| 225 | 185 | GATCTTCGAC TGCCGCGCTT CCGCGACAGC GACATACGGG |
| | | TGTTCTTTGT CGGTGACGTT TATCCGTTGT CGTGACCTTC |
| | | ATCCGGTGGT GAAACCTGAG CCGAATAATA CTGTACACCA |
| | | CCACCAGGAC AGAATACTCA AACCACGTTC ATGTGATTGT |
| | | TGCACCACAT ATTCATTGTT GGAAC |
| 226 | 276 | GATCCGCTGA CAGATGTCGT GTACAGCATT CTTTAGAGTG |
| | | GAACGGTGAC CGTACCGCAA AGCTGTGAAA TCAACGCCGG |
| | | ACAAACGATT CTGGTAAATT TCGGCGCATT ATACAGCGGC |
| | | AATTTCAACC ATGCAGGCCA AAAGCCGGAG GGGGTACGAG |
| | | CGAAAAAATT CAGTCGCTTC CGGTAAAGTG CAGCGGTCTG |
| | | GATTCGCAGG TCAATTTAAC AATGCGTCTT ATCGCTCCGC |
| | | GGATAGCACG TCCAGCTATC GCTCGATATG CGATGT |
| 227 | 383 | GATCACCGAC CGGACGGTCC GTACCTGGAT TGGGGAGGCG |
| | | GTTGAGTCCG CAGCGGCTGA CGACGTGACG TTCTCAGACC |
| | | CGGTGACACC CCATACTTCC GCCACTCCTA TGCGATGCAC |
| | | ATGCTGTACG CGGCATACCG CTGAAGGTGC TGCAGGCGCT |
| | | GATGGGACAC AAATCGGTGA GCCTGACGAG TGTACCGAAA |
| | | GTGTTTGCGC TTGATGTTGC CGCACGACAC CGGGTGCAGT |
| | | TTCAGATGCC GGGTGCTGAT GCAGTGGCTA TGCTCAAAGG |
| | | AGGTTCATAG AGACGTGTAT GCATTTTCAG CTTCGCTGCA |
| | | CAGCATCGAA CGGAGTTTAC GCGTTTATCA GCCATGTCTG |
| | | CGCACAGAGG AGTGTGCTCG AAA |
| 228 | 357 | ACTTGCCGGT AATTTCCATC CCTTCCAGCA CCGCCATCTC |
| | | TTTACCCTCA ATGGCGATGG ACAGTTTATC CAGCGTTAAC |
| | | TTTTGGTCGC CCCACGTTCG CCAAAGCTTG CCAGTTTACT |
| | | GGTACCGTCG GTTTTCAAAT TATTAAAGGT GAGTTGGACC |
| | | TTCTGATTAT ATTCGTTAAC GGCATCGACC AGGCCGCTCT |
| | | CGCGCTTCGC CTGACAGCGA AACCACATTA CCGTCTTTAT |
| | | CGGGCGTTAA CGGGAACTCG GCGCCGCTAA AGGCACCTTT |
| | | ACCGGCATTC TCTGAGTTAA CCGGCTTGAG AGAGATATCG |
| | | GAGCGGTATC GCCGCCATAC ATGCGGTATT GATACAA |
| 229 | 225 | GATCTATTTC GGACAGCCAA AAGGCCGTGA AGGCAGCGGT |
| | | CAGTACAAAA AGCCTTTGAT ACCGAAGTTT ATCACCGGCT |
| | | TTGAGATCGA GCGCAGTTGC CCGTATGCCT TTGAATCGGC |
| | | GCGTTAAACC GGCCGTAAAG TACCCTCTAT TGATAAAGCC |
| | | AACTACTGCA AGCTCTATCT GTGGCGTGAA TACGTCAATA |
| | | GTGGAAAACG TATCCGATGT GAACT |
| 230 | 275 | GATCGTTAAA CAGATTGACC AGTTCGCCAC ACTCTTCCAG |
| | | ATTAAACCCC ACCTGCCTCG CCTGTCGCAG CAACGTCAGC |
| | | TCGTTTAAAT GCTTCTGCGT GTAGGTGCGA TAACCATTTT |
| | | CGCTACGTAA TGGCGGCGTC ACCAGCCCTT TCTCTTCATA |
| | | AAACCGAATG GCTTTGTGGT TAGCGTTTTG GCACATCGCT |
| | | ATATCATATT GCCCTGCCTA CTGCTGAGTT ACTATACGGG |

TABLE 3-continued

| SEQ ID NO | LENGTH | PARTIAL 3'—5' SEQUENCES OF PROBES OF THE PRESENT INVENTION |
|---|---|---|
| | | TACTACGTCT AGAGATCGCG AAAAGGTTAC AGTAC |
| 231 | 233 | GATCGACGTC GCCTGATTTA AGACCCGCAA GCAACATCGT ATTGTTCATG GTCGCGACCT GTAACGAGGT CGATTTTTGC TGTTGATGGA ACCGCCCAAT AGCCGCCGGG AGTATACCCA GCGCAGGTGG GGAGCGGCAA CACGCACCAT CGGCGCTAGC TCCTCTTTGG CGATTCGATC GGATCCTGGC GGTGGTATTC ATGATCTAAT CCTTTTATCG ATGAGTAAAA TTG |
| 232 | 358 | GATCGGCGGA GAATCCCAGA CAGGCCAGGT CTTTCAGCTC GTCGCGGGTC ATCGGGCCGG TAGTATCCTG AGAACCGACG GAGGTCATTT TCGGTTCGCA GTACGCGCCC GGACGGATAC CTTTCACACC ACAGGCGCGA CCGACCATTT TCTGTGCCAG CGAGAAGCCA CGGCTGCTTT CCGCCACGTC TTTTGCTGAC GGAAAACGTC TGAGTGCGCA GCCAGCGCTT CACGCTTTTG TGCTAGCACG CGATATCACG ATACACACGC ACGACTCGTC ATCAGCACGT CGTTCAGTCG AGTGCAGTAG CGCGTCATGA TGCGTACTGC TTGACGTAGA CTATCATGCC ATATCAGT |
| 233 | 302 | GATCCACAGG TAGCGTGATG CGTTTTAGTT CCCCCTGCTG CTCAAGTAGC GTCAGGCCGT CGCGTAAATC GTGATATTTC ATGGCGTCCA TTGTAGCCTC TTGGTAAGCG CATCATTATA CGGCGTTCAT CATCGGGATG CTGTATTTTT GTTAAATTAG CGTGAACTCT GGCAACCAAC GCTAATCCAG ATACGGCTTA AAGGATGAAG TGTATATTAA CTTCGCGCAT GGCTTTTGCT ATGCTTGCGC CCCGAACAGC GATAAGAGTC ATATGCATCT GGTATTTACT GTACTGCAAA CG |
| 234 | 374 | GATCGTCACC TCCACCCTCG CGCGCGGGGC GGTGAAGCTC TCGAAACAGA AAGTTATCGT GAAGCACCTT GATGCGATTC AGAACTTCGG CGCGATGGAT ATCTGTGCAC TGATAAAACC GGCAACTCTG ACGCAGGATA AAATTGTGCT GGAGAAATCA CACGATATTT CTGGTAAGCC CAGCGAGCAT GTCTGCATTG CGCCTTGCTG ACACATTATC AGACCGTCTA AAAAAATTTC TGATACGCGT CTGAGAGTAG ACAACGCGGT CACCTCGACG TGCAGAAAAT CGATAGATCC GTTATTTAGC GTGCGATGTC GTAGTGTGCG AGATCGACGT GCATCAGCTG GATCTGCAAG CTAACGAGAC TCAC |
| 235 | 355 | GATCGGACTT TATTCGCGCG ATAGTCACGG AAAAAATGGT TTAACTTTGC TAATTCATCC TGAATGTAGG CTCTTCCATC GAAAAACTCC GCCTTGATTG ACTCTCCGGT ATGGAGATTG TTTAACGTCA AAAATGCGCG CCGTGGGGTC GAGAGTGTGG CAAACGCTGA GCGCGGGCAG GATGGCGGCG CGAGAGCGAC ACCACCAAGC GCCAGAGCTT GCGCGATTAG CGTCAAATTT GTCATGATAA TCAGGTCTAC AGGTCAATGT TATCGTTAAT ACACTTCTAC CTTTAAGCAG ACATGATACG CTGACACGAC TCTACGCGTG ATAGTGTGAT ACTTGGCACA GACTA |
| 236 | 363 | GATCGTCACG TGATTTGCCC GTCACGCGAA TCTCTTCCCC CTGAATTTGC GCCTGCACCT TCAGTTTGCT GTCTTTAATC AGCTTGACGA TTTTCTTCTG CACGGCGCTT TCAATGCCCT GCTTCAGCTT CGCTTCCACA TACCAGGTTT TACCGCTATG CACGAACTCG TCCGGTACAT CCAGCGAAGC GCTTCAATAC CGCGTTTAAG CAGCTTGGCG CGCAGAATAT CGAGCAACTG ATTGACCTGG AAATCGGACT CGCTCAGCAC TTGATGGTTT ATTGGCATCG TTCAGTTCAT AGTGCTCTAC GCACGGAGTC AAACAGACTC ACTGGAGCTA TCACACGTAC GCGCTCTCGA GAT |
| 237 | 320 | GATCGTTAAT TAGGCGCTGG GCGTGCTGGA GCAGTAATTT ACCGCCTTCC GAGGGGCGTA GTCCTTTACT GTGGCGCTCA AAAAGCGTGA TGCCTATCTC ATCTTCGAGT TGAGATAGCC ACTTCGATAG CGCCGCCTGG GAGATATTCA TCATCCGGGC GACGTGTCCG TTCAAGGGTT GGCCCTGTTC GGCCCAGCGC AACCAGCGTT TGCGGTGATG TAATTTCAAT TTCTCCCGTT CCATTCGCTA TAACCTCAGG TTATGTCTCT CCTGAAACCA TTGTACTTTA TCCTCCTCTA CACTCGTACT GCACTAACAC |
| 238 | 406 | GATCCTGCAA CGCTTTCGAC CCGGTCGAAA TAATGACTTT TTTCCCGGCG CGCAACGCCG AGCGAGGTAA GCATAGGTCT TCCCGGTTCC GGTGCCGGCT TCAACAACCA GAGGCTGCGC ATTTTCAATC GCTTGTGTTA CGGCAACCGC CATTTGTCGC TGTGGTTCGC GCGGTTTAAA GCCGGTTATC GCTTTGGCCA GTTGGCATCT GCTGCAAAAT CGTCCGTCAC ACTGCCCCCT GTTAATTTGC ACAGGGATTA TGTCAGGGTA GAAAGGCTTA CACAGTTACA GAGGTGACGG CGGCACATTG TGCAGTCTTG AACCATTCAA ATGAAAAGCA AATGAGGAAT AAGTAATGTC TATCGTGCGT ATGATGCGAG ATCGTGTCAG ACGTGTGACT CAATAT |
| 239 | 263 | GATCCTACCG GCCCCCACGC TTTGATTTGA ATAATAGAGG CTACCGACGA CAGCGACATG CTGATAATGT GCTGCGTATC CTGCGCCGGT AAACCCAACG CCTGGCAGAT TAACAGCGCT GGCTGATTAC CGCGACAAAC ATGCCACGAG ATGCTGACAA GCGCAAAAGG TTGAGGAGCG CGGCGATCTT CAAGACGGTA AATTAATCGC TGCACAATTG TACGCGACGA TGCATCTCGC ATGCGTCTAC GACATAGACA TCT |

TABLE 3-continued

| SEQ ID NO | LENGTH | PARTIAL 3'—5' SEQUENCES OF PROBES OF THE PRESENT INVENTION |
|---|---|---|
| 240 | 364 | GATCAACGCC TAATTTGGCC GCACAATCCA GAGAGACCTG CGGGTGCGGT TTGCTGTAGG GCAATTTTTC TGCAGAAGCC AGCGCGTCAA AACTGTCGCG CAGTTCAAAC ATGGTGAGCA CTTTTTCCAG CATATGCAGC GGCGATGCCG AGGCAAGCCC CACTAATAGC CCCTGCGCTT TACACAGCGC CACAGCTTCG CGCACACCCG GCAAAAGAGG GCGCTCTCTT TCGATAAGCG TAATCGCGCG GGCAATAACA CGGTTTGTCA CTTCTGGCGA TCGGGCGTTC ACGTTGCTGC GCAACAGAGA TCGACAACCA TATCATGCGT AGCAAGCTGT TGCAGCTCAT GGCCGAGTAT ATCT |
| 241 | 221 | GATCATTTTA ATGCTGTGTC TTGCCATTTT TTTCTCCATA AATTTCAAAA GGAAATCATG CCTGATGCGC ATTGCGACGG CGTGAGTACC ATTCAAGGAT TTGGTGACGA TGCAAACTGA TGGAACGACC AACGACAACA ACAATGAGAA GCGCACCGGA CAATGCGCTG GAATTGATTC GGCACTCCGG CCATCTGTAG CCCTCGTGTA AATCCACCAG C |
| 242 | 280 | GATCATCGAC GTATGTCCTT TCCAGATATT CCGCCCGCCG CCAGCCCACT CAAACAACGG GGGGCGCCGG CAAAAAAGCG AAAGACATCC ACCGATTGCC GGAATTTATA TTAATTACGC CAGTGCAAAG GCTTATTGCA GTTTTGCGAT TCAAGCCGGG CGAACTCAAG GGCGTTTTGC TCGATGCTGT CCGCAGTTTT AACAGACATT CCGCCCGTGC TTTGGGTGTG GTCTGCCCAT TCGGAAACGC GTTATCGGCG GCTGATCGCA GCGTAACCTG |
| 243 | 277 | CACTATAACA ACGGCGCGGC GGTACCTGGG CGACGTCGCC AGCGTCACCG ACTCGGTGCA GGATGTCCGT AACGCCGGGA TGACGAACGC TAAACCCGCT ATTTTGTTGA TGATCCGCAA GCTGCCGGAG TGGAATTCCA CATGTGGAAT TCCCATGTCA GCCGTTAAGT GTTCCTGTGT CACTCAAAAT TGCTTTGAGA GGCTCTAAGG GTTCTCAGTG CGTTACATCC CTAAGCTTGT TGTCACAACC GTAACTAAAC TTAAACCTAT ATATCCT |
| 244 | 380 | TGCAGATCAT TGCCTGATGT TCTACGGTCG CAAAATGCAC CAGNNNNCAG AACAACGACA GCGACAACAA TACGGCTGAA GCGCTTTAAT CGCGCTAACT CCTTTTTCTC AAAGCCCCTT TCCGTTCACC TGCTATAGCG TNGAGGGGCC CACTTACCAG GAACAAGACT ATGAACGTTA TTGCTATCAT GAACCACATG GGCGTCTACT TTAAAGAAGA GCCTATTCGT GAACTGCATC GTGCACTGGA AGGTTTAAAT TTCGTATCGT CTATCAAAAC GACCGAGAAG ACCTGCTGAA GCTGATTGAA ATAACTCCGC CTTTNNGTCA TTTCGACTGG GATAATATAC CTTGAGCTTC GAGAGAGATA GCAGTGAGCG |
| 245 | 353 | GATCTGATTA TCGACGCGCT GCTTGGCACC GGCATAGCCC AGGCACCGCG CGACCCGGTA GCCGGTCTGA TTGAACAGGC GAACGCATCC TGCGCCGGTT GTCGCCGTCG ATATCCCGTC AGGTCTGCTG GCGCAAACGG GCGCACGCCT GGCGGGTGAT AAGCGCGCGC ATACGGTCAC GTTTATCGCC CTGAAACCAG GCCTGCTGAC CGGCAAAGTG CGTGAGCTTA CCGGCATATT GCATTATGAC GTTGGGACTG GAAGGCTGGC TGGCGAGCAG ACGCGCGTCG GTTTTGAAGA GAGTTGGGGC AATGGCTAAC GCGTGACGAC TGATAGGGAT ATGTGTAGAT ATG |
| 246 | 376 | CACCCGGCTG ACTGCCGTAT AATCCAGCTT TTTACGCGGG TCCGCGGAGG GTTTTGCCGT CACAGAGAGC GTATTCTGCG AGTTTATGGT TGTCTTACCT AACGGATAGC CTTCGCTATC ATAGCGGTAC TCGACCCTTC ATCTCTTTGC CCGTCGCCGA TACCACAAAA CCGTTGTCGT CCGTTTCCCA GGTCACGCCC GCCGAACGAA CGCCGCCAGC TGGCACTTCC CCTGTAACTG CACCTTTTTT TCCAGCGTCT GAGCATCCCG GTAATAATTG GCATCCAGCA CGAGTGCCAG CCCCGTATTT ATCTCCAGAT CGTGTAACTC AAGCGTATCA AAACAGCCTT CCTGTGAAAG CGTACCGCGA CCTCTA |
| 247 | 248 | GATCAAGACG CGAATCCCCG ACGCGCCGAT AACGCCGTAC AACAGCAGCG AGACGCCGCC CATCACGGGT AACGGGATAA TCTGAATCGC CGCCGCCAGT TTGCCAACGC AGGAAAGCAT GTAATAACGA AAATCGCGTC GCCGCCGATA ACCCAGGTAC TGTAAACGTC GGTGATCGCC ATGACGCCAA TATTTTCCAT AGTGTATCGG CGTGAGTAGA ACCGAATATC GTCGACATCT AGCACATC |
| 248 | 253 | TTTCGACAAA GCGCGCCGCC GAGATATTCG CCATGATCAT GCACTCTTCG ATAAGCTTAT GCGCGTCATT ACGCTGGGTC TGTTCGATAC GCTCAATGCG ACGTTCGGCG TTAAAGATAA ACTTCGCCTC TTCGCACACA AACGAGATCC CCCCGCGCTC TTCACGCGCT TTATCCAGCA CTTTGTAGAG GTTGTGCAGC TCTTCAATAT GCTTCACAGC GCGCATATGT CACGCAGATC TGATCGCTGC AGC |
| 249 | 414 | GATCAAACAC CAGACGACCG CGACGCGCAC GACCATCGGT GGTATCTAAC TCAAATTTCA TTATCACTCC TGCGTCAGAA AAACAGTCCG ACGTTTAACG ACTCGCTACG GAATGATTCC ATAGCTAATA AATTCCCGAA GACGTCATCG GCGCAGAGTT TGGGGTCGAC CAGCGCACAG CCACCGGAGC GTACACGCAG |

TABLE 3-continued

SEQ ID NO LENGTH PARTIAL 3'—5' SEQUENCES OF PROBES OF THE PRESENT INVENTION

|  |  |  |
|---|---|---|
|  |  | TACGTGAGGA TGGCGAGCAC TGCCGCGTCA AATGCAGTGA<br>GATAGCTCTA CGACGTCAGA ATAGCTGCGA TGTACGTGAT<br>AACTGCTCCG TAGCTAAAAG CATTTGTCTA CGCAGTCTAT<br>AGGCATCATG TGTGTGATAC GCATGCAAC AGCATACACG<br>TGATCGCAGA TGAGTGTGAT CAGGCATATA CTGACGAACT<br>GATATAGATT CGTG |
| 250 | 112 | GATCTTCCGG GTTCACGGCC ACGCGGTAAT TCTGCCGAGA<br>ATAGTTTTCG GGCGGGTGGT GGCGACAACC AGAAATCTTA<br>CCGTCGCGGT TTTCGCGCCG TCGGCCAGCG GA |
| 251 | 345 | GATCGTTAAA TGTGCGGTAA TCCTGTGATG AATACCGATA<br>CGCAGCCAGA CCAAACCGAG TTAATGTTTG GGTCAGGTAT<br>TTATTATAAG CAATCTGATA ACTCTGACCA TCAAATACGA<br>CGCCATTATC CTGTTTACTG TGCGCTCGCG TAGCTCAAGC<br>GAAATGGCGC CAATCCGGGT ATTCCACCCC GTGCCGAGGG<br>TAAACGCATT ATAATGGTTC GATAGCATCG TACGCATAAG<br>CGTCAACAGG TTATTAGGCA TACTGATACT GATTGGTAAA<br>TCGGCTGATA TCGGCGCTTC AATTATGACT ACGCGCGAAA<br>TCATACTGAG CCGTCCAGTC CATTC |
| 252 | 203 | GATCGGTCGC CGCCTTACCT TTTTCCAGTA CACTGAGCAG<br>TTCGCTCAGC AGTTGTTCAA CAGCTCCATC ACTAGAGCGG<br>GAGAGTTCTG GCATAAATCA AAATCTGTTT GTTCATGAAA<br>CGGCAACACA TTAACCGCAG CAACAGTTTT TTTCTGCATT<br>TTTCGGCCTA AATCATCGCC TTACGATACT CTGAATACAG GGG |
| 253 | 273 | GATCGTAATC ATTCACTTCG GTCAGCAGCT CGAGCACTAA<br>CGCGTCGAGC ACGCCTTCCA TCGGCGCCAG TAAAACACGC<br>ATATCGGTAT CCACAGCAAA AAAAGAGGCG CTATCATAAC<br>GCCTCTCTGC GATGAGCAAA ACTTTTTTGC CGGGTGGCGG<br>CGCAAACGCA CGCTACGTAC GTAAGTGCTC ACGCGGCTTC<br>AAGACCAGTT ATTTTTCCAG CCGACCAGCC ATTCGAACCG<br>CGATAAGCTC TGCGATCCTT TCCAAGTATG CTG |
| 254 | 154 | GATCTTCTCG CTTTCTTCAG GGCTTACTCC CGTCTCTTCT<br>TCATCGACCG TGATCAAAAT ACCGTCTTTA TCCACCAAGA<br>AGCCGACTTC AATCTTCGTA TGAAAATAGC TCACCATTAC<br>GAACTATATT TTTCATCTCT CTTTCCAGCT TTTT |

There are many examples where highly-linked virulence genes are involved in the same stage of pathogenesis. Consequently, identifying the map location of the coding sequences of the present invention to a particular region of the bacterial chromosome is informational.

MAPPING PROTOCOL

A bacteriophage P22 lysate is made on the fusion strain of interest and used to transduce a recipient strain such as wild type *S. typhimurium* strain ATTC No. 14028. The resulting tetracycline sensitive, ampicillin resistant fusion strains are grown overnight in LB Amp and then transduced on LB Tet X-gal plates using a bacteriophage P22 lysate made on a pool of random Tn10d-Tc$^r$ insertions. White Tet resistant colonies represent either spontaneous Amp sensitives where the fusion has segregated by homologous recombination between the direct repeats of the cloned fragment or replacement of the region brought in next to the Tn10d-Tc$^r$-element.

To verify and measure the linkage of each candidate to the parent fusion, white Tet resistant clones are made phage free and phage sensitive. Bacteriophage P22 lysates are grown on them and used to transduce the parent fusion containing strains again to Tet resistance on LB Tet X-gal plates. Linkage is visually apparent by an increase in the number of white colonies. Strains containing the Tn10d-Tc$^r$ insertions next to the fusion locus are used in the next step, mapping by the method of Benson & Goldman, see Benson N. R., et al., *J. of Bacteriol.*, 174:1643–1681 (1992).

A selection exists for the loss of the tetracycline resistance determinant of Tn10d-Tc see, Maloy, J. R., et al., *J. of Bacteriol.*, 145:1110–1112 (1981). Plates containing fusaric acid will allow the growth of tetracycline sensitive strains over tetracycline resistant strains. In conjunction with this, a set of Mud P22 phage lysates which each package a small, defined region of the chromosome is used to transduce each Tn10d-Tc containing strain to Tet-sensitivity (available from Salmonella Genetic Stock Center, Calgary, Canada). The lysate that produces the most Tet sensitive colonies packages the region where the Tn10 lies in the chromosome and by inference, the location of the original IVET fusion.

After assigning each fusion to an internal donor, lysates grown on all the Tn10d-Tc containing strains in an interval are used to transduce all the strains with IVET fusions in them to Tet resistance on a Tet X-gal plate to test for linkage of each of the fusions to the others as well as Tn10 insertions in known genes already mapped on the chromosome to provide anchor points if possible.

In addition to the map locations of each coding sequence of the present invention, the defined sequence data presented previously has been compared to published sequences and known genes having homology to the coding sequences of the present invention are cited in Table 4 below.

Table 4 below represents (i) the known map locations of each coding sequence of the present invention; (ii) known genes that share homologous regions with the coding sequences of the present invention; (iii) the type of IVET plasmid that the coding sequences of the present invention were originally cloned into; and (iv) the type of tissue each coding sequence of the present invention was derived from. It is to be understood that while each coding sequence of the present invention was derived from a specific internal organ or macrophage, that does not imply that a gene transcribed or genes cotranscribed with each coding sequence are specific to that particular tissue type. For example, SEQ ID NO. 82 was derived from both intestinal and splenic tissues.

TABLE 4

| Seq ID # | Vector | Gene | Between Loci: | Tissue |
|---|---|---|---|---|
| 14 | pIVET1 | cfa | aroD-pyrF | intestine |
| 80 | pIVET1 | pgm | cobD-putA | intestine |
| 13 | pIVET1 | cadC | cysA-purG | intestine |
| 247 | pIVET2 | uraA | cysA-purG | intestine |
| 8 | pIVET1 and 2 | argE | ilvA-melA | intestine |
| 76 | pIVET2 | oxyR | ilvA-melA | intestine |
| 106 | pIVET1 | tpi | ilvA-melA | intestine |
| 210 | pIVET1 | unk | ilvA-zjh | intestine |
| 213 | pIVET1 and 8 | unk | melA-zjh | intestine |
| 221 | pIVET1 | unk | melA-zjh | intestine |
| 104 | pIVET1 | tolQRA | nadA-putA | intestine |
| 10 | pIVET1 | artI | nadA-putA | intestine |
| 88 | pIVET1 | proS | nadC-proA | intestine |
| 31 | pIVET1 | fhuA | nadC-proA | intestine |
| 28 | pIVET1 | dnaZX | proA-purA | intestine |
| 55 | pIVET1 | lon | proA-purE | intestine |
| 249 | pIVET1 | vacC | proA-purE | intestine |
| 38 | pIVET1 | gcvP | proU-zgf | intestine |
| 79 | pIVET1 | pgk | proU-zgf | intestine |
| 101 | pIVET2 | surE | proU-zgf | intestine |
| 102 | pIVET2 | TGI/hyb | proU-zgf | intestine |
| 92 | pIVET1 | rpiA | purG-proU | intestine |
| 82 | pIVET1 | phoPQ | putA-aroD | intestine |
| 91 | pIVET1 | rbs | pyrE-ilvA | intestine |
| 195 | pIVET1 | unk | pyrE-ilvA | intestine |
| 198 | pIVET2 | unk | pyrE-ilvA | intestine |
| 196 | pIVET1 | unk | pyrE-ilvA | intestine |
| 111 | pIVET2 | unk | thr-nadC | intestine |
| 32 | pIVET2 | flagellar pr | tre-zea | intestine |
| 75 | pIVET1 | otsA | tre-zea | intestine |
| 148 | pIVET1 | unk | tre-zea | intestine |
| 6 | pIVET1 | air | unmapped | intestine |
| 19 | pIVET1 | cysD | unmapped | intestine |
| 29 | pIVET1 | fadL | unmapped | intestine |
| 62 | pIVET1 | ndk | cysA-purG | intestine |
| 68 | pIVET1 | orf211 | unmapped | intestine |
| 232 | pIVET1 | unk | unmapped | intestine |
| 233 | pIVET1 | unk | unmapped | intestine |
| 234 | pIVET1 | unk | unmapped | intestine |
| 235 | pIVET1 | unk | unmapped | intestine |
| 236 | pIVET1 | unk | unmapped | intestine |
| 44 | pIVET1 | hisT | zea-cysA | intestine |
| 64 | pIVET1 | nuo | zea-cysA | intestine |
| 157 | pIVET1 | unk | zea-cysA | intestine |
| 107 | pIVET1 | unk | zea-cysA | intestine |
| 165 | pIVET2 | unk | zea-cysA | intestine |
| 252 | pIVET1 | yejL | zea-cysA | intestine |
| 39 | pIVET1 and 2 | gltB | zgf-zgi | intestine |
| 54 | pIVET1 | lacA | zgf-zgi | intestine |
| 85 | pIVET1 | pnp | zgf-zgi | intestine |
| 20 | pIVET2 | cysG | zgi-envZ | intestine |
| 34 | pIVET1 | ftsX | zgi-envZ | intestine |
| 40 | pIVET1 | glyS | zgi-envZ | intestine |
| 60 | pIVET1 | mreB | zgi-envZ | intestine |
| 87 | pIVET1 | ppi | zgi-envZ | intestine |
| 224 | pIVET1 | unk | zjh-thr | intestine |
| 250 | pIVET1 | valS | zjh-thr | intestine |
| 125 | pIVET2 | unk | cobD-nadA | liver |
| 205 | pIVET1 | unk | ilvA-melA | liver |
| 57 | pIVET1 | mdh | zgi-envZ | liver |
| 43 | pIVET1 | unk | aroD-pyrF | liver |
| 126 | pIVET8 | unk | cobD-putA | liver |
| 70 | pIVET1 | orf337 | cysA-purG | liver |
| 247 | pIVET2 | uraA | cysA-purG | liver |
| 45 | pIVET1 | hslU | ilvA-melA | liver |
| 106 | pIVET1 | tpi | ilvA-melA | liver |
| 202 | pIVET1 | unk | ilvA-melA | liver |
| 12 | pIVET1 | brnQ | proA-purE | liver |
| 90 | pIVET1 | purA-like | proA-purE | liver |
| 73 | pIVET2 | orfA | zea-cysA | liver |
| 23 | pIVET1 | dam/trpS | zgi-envZ | liver |
| 250 | pIVET1 | valS | zjh-thr | liver |
| 138 | pIVET8 | unk | aroD-pyrF | macrophage |
| 139 | pIVET8 | unk | aroD-pyrF | macrophage |
| 246 | pIVET8 | unk | aroD-pyrF | macrophage |
| 37 | pIVET8 | galK | cobD-nadA | macrophage |
| 124 | pIVET8 | unk | cobD-nadA | macrophage |
| 167 | pIVET8 | unk | cysA-purG | macrophage |
| 169 | pIVET8 | unk | cysA-purG | macrophage |
| 168 | pIVET8 | unk | cysA-purG | macrophage |
| 72 | pIVET8 | orf543 | ilvA-melA | macrophage |
| 84 | pIVET8 | pmrB | ilvA-melA | macrophage |
| 199 | pIVET8 | unk | ilvA-melA | macrophage |
| 200 | pIVET8 | unk | ilvA-melA | macrophage |
| 207 | pIVET8 | unk | ilvA-melA | macrophage |
| 17 | pIVET8 | cutA2 | melA-zjh | macrophage |
| 58 | pIVET8 | mgtA | melA-zjh | macrophage |
| 211 | pIVET8 | unk | melA-zjh | macrophage |
| 212 | pIVET8 | unk | melA-zjh | macrophage |
| 50 | pIVET8 | IS200 | nadA-putA | macrophage |
| 83 | pIVET8 | phrA | nadA-putA | macrophage |
| 127 | pIVET8 | unk | nadA-putA | macrophage |
| 128 | pIVET8 | unk | nadA-putA | macrophage |
| 129 | pIVET8 | unk | nadA-putA | macrophage |
| 98 | pIVET8 | speE | nadC-proA | macrophage |
| 94 | pIVET8 | S.t.res/mod | proA-purE | macrophage |
| 114 | pIVET8 | unk | proA-purE | macrophage |
| 115 | pIVET8 | unk | proA-purE | macrophage |
| 118 | pIVET8 | unk | proA-purE | macrophage |
| 116 | pIVET8 | unk | proA-purE | macrophage |
| 117 | pIVET1 | unk | proA-purE | macrophage |
| 178 | pIVET8 | recD | proU-zgf | macrophage |
| 177 | pIVET8 | unk | proU-zgf | macrophage |
| 179 | pIVET8 | unk | proU-zgf | macrophage |
| 180 | pIVET8 | unk | proU-zgf | macrophage |
| 121 | pIVET8 | unk | purE-cobD | macrophage |
| 33 | pIVET8 | folD | purE-cobD | macrophage |
| 174 | pIVET8 | unk | purG-proU | macrophage |
| 131 | pIVET8 | unk | putA-aroD | macrophage |
| 132 | pIVET8 | unk | putA-aroD | macrophage |
| 105 | pIVET8 | torA | pyrE-ilvA | macrophage |
| 194 | pIVET8 | unk | pyrE-ilvA | macrophage |
| 53 | pIVET8 | kdsA | pyrF-tre | macrophage |
| 144 | pIVET8 | unk | pyrF-tre | macrophage |
| 110 | pIVET8 | unk | thr-nadC | macrophage |
| 109 | pIVET8 | unk | thr-nadC | macrophage |
| 71 | pIVET8 | orf48 | tre-zea | macrophage |
| 146 | pIVET8 | unk | tre-zea | macrophage |
| 228 | pIVET8 | unk | unmapped | macrophage |
| 229 | pIVET8 | unk | unmapped | macrophage |
| 16 | pIVET8 | col 1 rec. | zea-cysA | macrophage |
| 18 | pIVET8 | cysA | zea-cysA | macrophage |
| 66 | pIVET8 | orf179 | zea-cysA | macrophage |
| 93 | pIVET8 | rplY | zea-cysA | macrophage |
| 151 | pIVET8 | unk | zea-cysA | macrophage |
| 152 | pIVET8 | unk | zea-cysA | macrophage |
| 153 | pIVET8 | unk | zea-cysA | macrophage |
| 155 | pIVET8 | unk | zea-cysA | macrophage |
| 154 | pIVET8 | unk | zea-cysA | macrophage |
| 184 | pIVET8 | unk | zgf-zgi | macrophage |
| 185 | pIVET8 | unk | zgf-zgi | macrophage |
| 49 | pIVET8 | IS2/IS30 | zgi-envZ | macrophage |
| 86 | pIVET8 | ponA | zgi-envZ | macrophage |
| 188 | pIVET8 | unk | zgi-envZ | macrophage |
| 222 | pIVET8 | unk | zjh-thr | macrophage |
| 223 | pIVET8 | unk | zjh-thr | macrophage |
| 14 | pIVET1 | cfa | aroD-pyrF | spleen |
| 30 | pIVET8 | fdnGHI | aroD-pyrF | spleen |
| 63 | pIVET8 | nifj | aroD-pyrF | spleen |
| 140 | pIVET8 | unk | aroD-pyrF | spleen |
| 141 | pIVET8 | unk | aroD-pyrF | spleen |
| 142 | pIVET8 | unk | aroD-pyrF | spleen |
| 143 | pIVET8 | unk | aroD-pyrF | spleen |
| 43 | pIVET1 | unk | aroD-pyrF | spleen |
| 251 | pIVET1 | yehB | aroD-pyrF | spleen |
| 52 | pIVET8 | kdpD | cobD-nadA | spleen |
| 67 | pIVET8 | orf2 | cobD-nadA | spleen |
| 80 | pIVET1 | pgm | cobD-putA | spleen |
| 126 | pIVET8 | unk | cobD-putA | spleen |
| 13 | pIVET1 | cadC | cysA-purG | spleen |
| 70 | pIVET1 | orf337 | cysA-purG | spleen |
| 69 | pIVET1 | orf384 | cysA-purG | spleen |

TABLE 4-continued

| Seq ID # | Vector | Gene | Between Loci: | Tissue |
|---|---|---|---|---|
| 170 | pIVET1 | unk | cysA-purG | spleen |
| 171 | pIVET8 | unk | cysA-purG | spleen |
| 172 | pIVET8 | unk | cysA-purG | spleen |
| 173 | pIVET2 | unk | cysA-purG | spleen |
| 168 | pIVET8 | unk | cysA-purG | spleen |
| 247 | pIVET2 | uraA | cysA-purG | spleen |
| 5 | pIVET8 | aceK | ilvA-melA | spleen |
| 7 | pIVET1 | arg.perm. | ilvA-melA | spleen |
| 45 | pIVET1 | hslU | ilvA-melA | spleen |
| 48 | pIVET8 | ilv | ilvA-melA | spleen |
| 78 | pIVET1 | pfkA | ilvA-melA | spleen |
| 106 | pIVET1 | tpi | ilvA-melA | spleen |
| 199 | pIVET8 | unk | ilvA-melA | spleen |
| 200 | pIVET1 | unk | ilvA-melA | spleen |
| 201 | pIVET1 | unk | ilvA-melA | spleen |
| 203 | pIVET1 | unk | ilvA-melA | spleen |
| 204 | pIVET1 | unk | ilvA-melA | spleen |
| 206 | pIVET8 | unk | ilvA-melA | spleen |
| 208 | pIVET8 | unk | ilvA-melA | spleen |
| 209 | pIVET2 | unk | ilvA-melA | spleen |
| 202 | pIVET1 | unk | ilvA-melA | spleen |
| 207 | pIVET8 | unk | ilvA-melA | spleen |
| 35 | pIVET8 | fumB | melA-zjh | spleen |
| 58 | pIVET8 | mgtA | melA-zjh | spleen |
| 214 | pIVET8 | unk | melA-zjh | spleen |
| 215 | pIVET8 | unk | melA-zjh | spleen |
| 216 | pIVET8 | unk | melA-zjh | spleen |
| 217 | pIVET8 | unk | melA-zjh | spleen |
| 218 | pIVET8 | unk | melA-zjh | spleen |
| 219 | pIVET2 | unk | melA-zjh | spleen |
| 220 | pIVET1 | unk | melA-zjh | spleen |
| 213 | pIVET8 | unk | melA-zjh | spleen |
| 221 | pIVET1 | unk | melA-zjh | spleen |
| 248 | pIVET1 | vacB | melA-zjh | spleen |
| 11 | pIVET1 | asnS | nadA-putA | spleen |
| 27 | pIVET1 | deoR | nadA-putA | spleen |
| 46 | pIVET8 | hutH | nadA-putA | spleen |
| 130 | pIVET8 | unk | nadA-putA | spleen |
| 88 | pIVET1 | proS | nadC-proA | spleen |
| 97 | pIVET8 | speD | nadC-proA | spleen |
| 98 | pIVET8 | speE | nadC-proA | spleen |
| 77 | pIVET8 | tia-like | nadC-proA | spleen |
| 112 | pIVET1 | unk | nadC-proA | spleen |
| 113 | pIVET1 | unk | nadC-proA | spleen |
| 12 | pIVET1 | brnQ | proA-purE | spleen |
| 55 | pIVET1 | lon | proA-purE | spleen |
| 90 | pIVET1 | purA-like | proA-purE | spleen |
| 116 | pIVET8 | unk | proA-purE | spleen |
| 117 | pIVET8 | unk | proA-purE | spleen |
| 119 | pIVET1 | unk | proA-purE | spleen |
| 120 | pIVET8 | unk | proA-purE | spleen |
| 38 | pIVET1 | gcvP | proU-zgf | spleen |
| 56 | pIVET1 | lysS | proU-zgf | spleen |
| 102 | pIVET2 | TGI/hyb | proU-zgf | spleen |
| 181 | pIVET1 | unk | proU-zgf | spleen |
| 182 | pIVET1 | unk | proU-zgf | spleen |
| 183 | pIVET8 | unk | proU-zgf | spleen |
| 122 | pIVET8 | unk | purE-cobD | spleen |
| 123 | pIVET2 | unk | purE-cobD | spleen |
| 4 | pIVET1 | 48k prot | purG-proU | spleen |
| 92 | pIVET1 | rpiA | purG-proU | spleen |
| 100 | pIVET1 | srmB | purG-proU | spleen |
| 22 | pIVET1 | unk | purG-proU | spleen |
| 175 | pIVET1 | unk | purG-proU | spleen |
| 176 | pIVET8 | unk | purG-proU | spleen |
| 36 | pIVET1 | g30k | putA-aroD | spleen |
| 61 | pIVET1 | ndh | putA-aroD | spleen |
| 137 | pIVET1 | unk | putA-aroD | spleen |
| 103 | pIVET8 | unk (cbiJ/thr) | putA-pyrF | spleen |
| 59 | pIVET8 | mgtB | pyrE-ilvA | spleen |
| 91 | pIVET1 | rbs | pyrE-ilvA | spleen |
| 105 | pIVET8 | torA | pyrE-ilvA | spleen |
| 108 | pIVET8 | uhpB | pyrE-ilvA | spleen |
| 197 | pIVET8 | unk | pyrE-ilvA | spleen |
| 196 | pIVET1 | unk | pyrE-ilvA | spleen |
| 41 | pIVET1 | gtpl | pyrF-tre | spleen |
| 42 | pIVET1 | hemA | pyrF-tre | spleen |
| 145 | pIVET1 | unk | pyrF-tre | spleen |
| 109 | pIVET8 | unk | thr-nadC | spleen |
| 32 | pIVET2 | flagellar pr | tre-zea | spleen |
| 147 | pIVET1 | unk | tre-zea | spleen |
| 149 | pIVET8 | unk | tre-zea | spleen |
| 150 | pIVET8 | unk | tre-zea | spleen |
| 62 | pIVET1 | ndk | unmapped | spleen |
| 65 | pIVET8 | orfl.3 | unmapped | spleen |
| 68 | pIVET1 | orf211 | unmapped | spleen |
| 81 | pIVET1 | phnK | unmapped | spleen |
| 89 | pIVET8 | pspA | unmapped | spleen |
| 230 | pIVET1 | unk | unmapped | spleen |
| 231 | pIVET1 | unk | unmapped | spleen |
| 237 | pIVET8 | unk | unmapped | spleen |
| 238 | pIVET8 | unk | unmapped | spleen |
| 239 | pIVET8 | unk | unmapped | spleen |
| 240 | pIVET8 | unk | unmapped | spleen |
| 241 | pIVET8 | unk | unmapped | spleen |
| 242 | pIVET8 | unk | unmapped | spleen |
| 243 | pIVET8 | unk | unmapped | spleen |
| 244 | pIVET8 | unk | unmapped | spleen |
| 245 | pIVET8 | unk | unmapped | spleen |
| 99 | pIVET8 | spvB | virulence plasmid | spleen |
| 227 | pIVET8 | unk | virulence plasmid | spleen |
| 18 | pIVET8 | cysA | zea-cysA | spleen |
| 21 | pIVET1 | cysK | zea-cysA | spleen |
| 24 | pIVET1 | dedB | zea-cysA | spleen |
| 25 | pIVET1 | dedE | zea-cysA | spleen |
| 44 | pIVET1 | hisT | zea-cysA | spleen |
| 66 | pIVET8 | orf179 | zea-cysA | spleen |
| 73 | pIVET2 | orfA | zea-cysA | spleen |
| 74 | pIVET1 | orf_f167 | zea-cysA | spleen |
| 154 | pIVET8 | unk | zea-cysA | spleen |
| 156 | pIVET1 | unk | zea-cysA | spleen |
| 158 | pIVET8 | unk | zea-cysA | spleen |
| 159 | pIVET8 | unk | zea-cysA | spleen |
| 160 | pIVET8 | unk | zea-cysA | spleen |
| 161 | pIVET8 | unk | zea-cysA | spleen |
| 162 | pIVET8 | unk | zea-cysA | spleen |
| 163 | pIVET8 | unk | zea-cysA | spleen |
| 164 | pIVET8 | unk | zea-cysA | spleen |
| 166 | pIVET1 | unk | zea-cysA | spleen |
| 107 | pIVET1 | unk | zea-cysA | spleen |
| 165 | pIVET2 | unk | zea-cysA | spleen |
| 252 | pIVET1 | yejL | zea-cysA | spleen |
| 253 | pIVET8 | yohI | zea-cysA | spleen |
| 187 | pIVET1 | unk | zgf-envZ | spleen |
| 39 | pIVET8 | gltB | zgf-zgi | spleen |
| 47 | pIVET8 | iap | zgf-zgi | spleen |
| 54 | pIVET1 | lacA | zgf-zgi | spleen |
| 185 | pIVET8 | unk | zgf-zgi | spleen |
| 186 | pIVET8 | unk | zgf-zgi | spleen |
| 9 | pIVET1 | aroK | zgi-envZ | spleen |
| 20 | pIVET2 | cysG | zgi-envZ | spleen |
| 23 | pIVET1 | dam/trpS | zgi-envZ | spleen |
| 34 | pIVET1 | ftsX | zgi-envZ | spleen |
| 40 | pIVET1 | glyS | zgi-envZ | spleen |
| 51 | pIVET1 | kbl | zgi-envZ | spleen |
| 60 | pIVET1 | mreB | zgi-envZ | spleen |
| 189 | pIVET1 | unk | zgi-envZ | spleen |
| 190 | pIVET8 | unk | zgi-envZ | spleen |
| 191 | pIVET8 | unk | zgi-envZ | spleen |
| 192 | pIVET8 | unk | zgi-envZ | spleen |
| 193 | pIVET8 | unk | zgi-envZ | spleen |
| 95 | pIVET1 | secB | zgi-pyrE | spleen |
| 15 | pIVET1 | chvD hom. | zjh-thr | spleen |
| 26 | pIVET1 | deoAB | zjh-thr | spleen |
| 96 | pIVET1 | serB/smp | zjh-thr | spleen |
| 225 | pIVET8 | unk | zjh-thr | spleen |
| 226 | pIVET8 | unk | zjh-thr | spleen |
| 224 | pIVET1 | unk | zjh-thr | spleen |

The examples which follow are not intended to limit the scope of the present invention but rather exemplify how the coding sequences disclosed are useful in identifying and isolating microbial virulence genes, the products of which will provide potential targets for the development of anti-microbial agents or vaccines.

EXAMPLE 1

Identification of Known Genes that are or Have Been Implicated in Salmonella Virulence As discussed previously the defined portions of the coding sequences of the present invention have been compared to published sequences, and genes that were both previously known or believed to be implicated in Salmonella virulence have been identified. Several known Salmonella spp. virulence genes have been identified using the coding sequences of the present invention, shown in Table 5, thus validating the method and probes of the present invention.

TABLE 5

Genes of Salmonella Virulence

| SEQ ID NO. | GENE | FUNCTION | ROLE IN PATHOGENESIS |
|---|---|---|---|
| 82 | phoPQ | virulence regulator | invasion, macrophage survival |
| 99 | spvB | plasmid virulence | systemic survival |
| 178 | recBCD | recombination/repair | macrophage survival |
| 199 | pmrAB | polymyxin resistance | neutrophil survival |
| 13 | cadC | lysine decarboxylase | acid tolerance |
| 76 | oxyR | oxidative stress regulator | macrophage survival |
| 31 | fhuA | $Fe^{++}$transport | $Fe^{++}$accumulation |
| 58/59 | mgtA/BC | $Mg^{++}$transport | $Mg^{++}$sensor |

Examples of genes known to be involved in virulence include phoPQ, the two-component global regulator of Salmonella spp. virulence involved in invasion, macrophage survival, and defensin resistance, as well as spvB, a Salmonella plasmid virulence gene whose function is to facilitate growth at systemic sites of infection. phoPQ gene products are involved in both early and late stages of infection since phoPQ mutants confer a defect after either oral or intraperitoneal delivery. Accordingly, phoPQ in vivo induced fusions were isolated from the spleen after either oral or intraperitoneal infection. In contrast, mutants that lack the Salmonella spp. virulence plasmid are defective in late stages of infection; consistent with this infection profile, spvB fusions were isolated from the spleen after intraperitoneal delivery.

Another class of in vivo induced fusions reside in recBCD, encoding exonuclease V, the primary recombination and repair enzyme in bacteria. recBCD has been shown to be required for full virulence and has been implicated in superoxide resistance in cultured macrophages. Correspondingly, the recBCD fusion was isolated from cultured macrophages, presumably reflecting the pathogen's protective recombination and repair response to DNA damage resulting from the macrophage oxidative burst.

The next three classes of in vivo induced genes shown in Table 5 (pmrAB, cadC and oxyR) are in regulatory loci that may be implicated in Salmonella virulence due to the biochemical functions that are associated with their expression. Examples include pmrAB, a two-component regulator that controls resistance to cationic antibacterial proteins (CAP) of human neutrophils and to the drug, polymyxin B.

The apparent in vivo induction of pmrAB may be involved in resistance to similar, as yet undefined, murine macrophage-derived antibacterial proteins cadC is an in vivo induced regulatory locus that controls lysine decarboxylation. These fusions were isolated from the intestine after an oral infection and from the spleen after an intraperitoneal infection. Decarboxylation of basic amino acids produces primary amines which may increase the pH of host cell organelles such as the phagosome. The fact that cadC was isolated from different host tissues suggests that it may function to increase the pH of several different host cell organelles (e.g., in response to the low pH of the stomach or phagosome). Moreover, CadC is topologically similar to ToxR, the global regulator of virulence in Vibrio cholerae. Both cadC and toxR respond to low pH and media composition, but it is not known whether toxR regulates polyamine synthesis in Vibrio cholerae or whether cadC regulates other virulence genes in Salmonella spp.

Last, oxyR, a regulator of the oxidative stress response was recovered from the mouse intestine, a tissue which is thought to be relatively anaerobic. The apparent in vivo induction of oxyR may be in response to the oxidative burst of macrophages present in mucosal associated lymphoid tissue (MALT) that line the intestinal epithelium. Alternatively, this may be a developmental response: oxyR may be inducing bacterial oxidative protective systems within the lumen of the intestine in anticipation of encountering macrophages in some later stage in the infection cycle, such as in the blood or spleen.

EXAMPLE 2

Virulence Genes of Other Pathogens Not Previously Known to Exist in Salmonella spp.

The coding sequence of the present invention have been compared to published sequences and virulence genes of other pathogens not previously known to exist in Salmonella spp. have been identified, see Table 6.

TABLE 6

Virulence Genes of Other Pathogens

| SEQ. ID NO. | GENE | FUNCTION | ROLE IN PATHOGENESIS |
|---|---|---|---|
| 248/249 | vacB/C | ipa/icsA expression | invasion/intercellular spread Shigella spp.; EIEC |
| 254 | cpxA | virF expression | invasion/intercellular spread Shigella spp. |
| 251 | yehB | pilin assembly | adherence K. pneumonia; H. influenzae; EIEC |
| 77 | tia | gut epithelial invasion | adherence; invasion EIEC |
| 15 | chvD | virG expression (plant virulence) | signal transduction A. tumefaciens |

In vivo induced fusions to virulence genes of other pathogens not previously known to exist in Salmonella spp. and enteroinvasive E. coli (EIEC). vacB mutants are defective in the synthesis of invasion plasmid antigens (ipa) and intercellular spread (ics) gene products, which are required for invasion and lateral spread within host cells. The affected genes are transcribed at normal levels but the corresponding proteins are not detected. vacB fusions were isolated from the spleen after an oral or intraperitoneal infection, suggesting that vacB is needed at both early and late stages of infection, possibly for invasion of the intestinal epithelium and for invasion at systemic sites of infection (e.g., invasion of splenic macrophages in a manner that may not activate phagocyte killing mechanisms). vacC is homologous to *E. coli* tgt, which encodes a transglycosylase that modifies tRNA molecules. In contrast to vacB, Shigella spp. vacC mutants show reduced transcription of the ipa genes; they do not form plaques on cultured mammalian cells and exhibit reduced survival in stationary phase. Some tRNA modifications (encoded by miaA and tgt) are sensitive to environmental signals such as $Fe^{++}$, $O_2$, and growth state. The in vivo induction of environmentally-sensitive tRNA modifications may contribute to the changes in bacterial gene expression (by attenuation) and/or protein synthesis (by altered codon preference) that may occur in host tissues (note that [chorismate], produced by a metabolic in vivo induced gene, aroK, is also involved in tRNA modification).

A third class of fusions map to the *E. coli* yehB locus, which has sequence similarity to proteins involved in pilin assembly in many pathogens, including mrkC of *Klebsiella pneumoniae* hifC of *Haemophilus influenzae*, and CS3 pilin assembly components of enterotoxigenic *Escherichia coli*. yehB fusions were isolated from the spleen after an intraperitoneal infection and may represent a new class of Salmonella spp. surface properties that are induced at systemic sites of infection.

Recently, it has been shown that *Pseudomonas aeruginosa* encodes virulence factors that are required for infection of both plants and animals. Similarly, one class of in vivo induced fusions isolated from the spleen after an oral infection resides in a gene that has amino acid sequence identity to chvD, a chromosomal virulence gene involved in signal transduction in the plant pathogen, *A. tumefaciens*. Under conditions of low pH and phosphate starvation, chvD is required for the induction of transcription of virG, the regulatory component of the virA/G two-component regulatory system in *A. tumefaciens*. The apparent in vivo induction of a chvD homolog in *S. typhimurium* may represent another example of a sensory virulence determinant shared by animal and plant pathogens.

EXAMPLE 3

Unknown Genes

Unknown coding regions of promoters that are induced in vivo have also been identified and are represented by SEQ ID NOS. 22, 43, 103, 107, 109–177 and 179–253.

One can imagine that pathogens possess many functions that are required during infection, but are not easily detected on laboratory media or identified by biochemical assay. The coding sequences of the present invention allows for the identification of previously unknown genes and provides a means to associate them with a phenotype, induction in the host. Indeed, the functions of >40% of the in vivo induced genes are unknown. The members of this class have either no homology with the DNA data base or encode open reading frames with no assigned function. Defined regions of the coding sequences of the present invention sharing homology to unknown genes have been isolated from all IVET vectors (pIVET1, 2, and 8) made according to the present invention and routes of delivery (oral, intraperitoneal) and host tissues (intestine, spleen, liver) tested. These unknown fusions have been mapped (shown in Table 4) to determine whether they cluster to a specific region of the *S. typhimurium* chromosome possibly functioning in the same stage of pathogenesis. Thus, by combining the knowledge of the in vivo induction phenotype, the host tissue from which the coding sequences of the present invention were recovered, and the chromosomal map positions, one has the means to begin investigating not only novel virulence factors but also bacterial sensory and biochemical pathways that remain undefined. Coding sequences of the present invention having homology to unknown genes are found throughout the chromosome. However, clusters of in vivo induced fusions in adjacent genes do occur in some locations. For example, two unknown in vivo induced fusions reside in the previously reported open reading frames, orf384 and orf337, in vivo induced A (SEQ ID NO. 69) and B (SEQ ID NO. 70) lie in transcription units that are highly linked to the metabolic in vivo induced gene, ndk discussed further below.

EXAMPLE 4

Method of Using the Coding Sequences of the Present Invention to Identify Genes Involved in Virulence.

Each in vivo induced clone can be used to isolate mutations in the gene identified by sequence analysis. Insertion mutations generated by transposable elements (Mahan, et al., *J. of Bacteriol*, 175(21):7086–7091 (1993)) that disrupt an operon will reduce the transcription of the lac gene. These insertions will have a light blue color on LB plates supplemented with X-gal. Some of these will be insertions in the in vivo induced gene, identified by sequence analysis. In addition, genes that are downstream of the operon promoter, but proximal to the ivi lac fusion may be disrupted; this will result in reduced transcription of the lac genes, again resulting in a light blue phenotype on X-gal containing plates. Sequence analysis of the DNA surrounding the insertion will identify new genes cotranscribed with the original in vivo induced gene.

As an example, tia (SEQ ID NO. 77) is an in vivo induced gene identified by the method of the present invention which encodes a product with protein sequence similarity (as translated from the DNA sequence) to an *E. coli* protein that directs invasion of gut epithelial cells in tissue culture cells. The coding sequence of the present invention containing the tia fusion was used to isolate insertions that disrupt the tia coding sequence by looking for transposon insertions that reduce the transcription of the lac gene. Among the mutations isolated by this method are transposon insertions in tia and also in a gene promoter proximal to tia. This gene, having the partially defined sequence

```
3'-CGCTGTCCTG GTGTTAAGAC TTTGCTTAAA TCAAAATAAT ATTTAACCCG      (SEQ ID NO. 255)
   ATAATAGCGA GCCTGTTGTT CTATGTTACT GAAGGCTGCA AGCTGCTGTT
   TTACGGCGGC GTCATCCCAT TTACCGGATT TAATCACCTC TATCAGCGCA
   CCGTCTTTAA TTCCCTTCAT AGAAATCTGA CTGACGTCGG TTTCCAGTTG
   TTGGTGAAGT TTTTTGATCC GGGTAATCTG ATCGTTTGTC AGCTTCAGAT
   GCTGGACAAT AGGATCCTGG GCGGGCAGGG GGAGGATTGG GGACAGCGTG
   CAAGCAAAAG AAACGCGCAG AGTCGCTGCA GTAAGTGGGC ATACGTTT-5'
``` encodes a protein product with sequence similarities to pfEMP, a protein encoded by *Plasmodium falciparum* (the causative agent of malaria) during infection of red blood cells. Thus, the identified sequences of the present invention described here can and do lead to the identification of other genes specifically induced by the bacterium during infection. Each in vivo induced clone contains one or more genes transcribed from a single promoter, thus insertion mutations that are proximal to the operon promoter are capable of disrupting and reducing the transcription of distally positioned genes including the lac gene. In the alternative to using this insertional mutagenesis technique to identify other non-sequential genes that are cotranscribed with the genes for which partial sequences have been defined (SEQ ID NOS. 4–254), these defined sequences may also be used as probes to identify cotranscribed genes. Defined sequences identified by (SEQ ID NOS. 4–254) or portions thereof can be used to prime the synthesis of a cDNA library from total bacterial mRNA. There are many routes to a cDNA library; however regardless of the pathway the first step is the synthesis of a DNA strand complimentary to the mRNA sequence. The reaction requires template RNA, a complementary primer, reverse transcriptase, and deoxyribonucleoside triphosphates, see Maniatis, Id. or S. Berger, et al., *Guide lo Molecular Cloning Techniques*, 152:307–389 (1987). This cDNA will contain the transcribed sequence from the mRNA start site to the priming site. This cDNA can be used to detect clones that overlap this region of DNA by Southern Hybridization. From those clones, DNA fragments can be used as probes in Northern Hybridization against total mRNA. Each DNA fragment that hybridizes to the mRNA defined by the original cDNA can be inferred to contain sequences cotranscribed with the original in vivo induced gene sequence defined here. Thus, each coding sequence of the present invention can be used to isolate and identify additional genes that are expressed during infection, each of which may encode products useful for the development of antibiotics and/or vaccines. In the alternative, the defined sequences (SEQ ID NOS. 4–254) may be used to probe DNA libraries to identify and study homologous regions of interest.

EXAMPLE 5

Method of Using the Coding Sequences of the Present Invention to Identify Genes Within the Same Operon As discussed above in Example 4, in vivo induced genes may be identified by the defined regions of the coding sequences of the present invention that are relatively short (70–400 bp). Some bacterial operons are large, greater than 10 kilobases in length. It is reasonable to expect therefore that multiple fusions in the same operon might be recovered by the IVET selection. Three in vivo induced fusions (ndk, SEQ ID NO. 62; orf384, SEQ ID NO. 69; and orf337, SEQ ID NO. 70) are in genes known to be near each other on the *E. coli* chromosome and transcribed in the same direction. Insertion mutations that reduce the expression of the lac gene in the orf337 synthetic operon were isolated. One transposon insertion, which disrupts the coding sequence of ndk, reduces the expression of the downstream or4384 lac fusion, indicating that all three genes, ndk, orf384 and orf337, are transcribed as a unit and may have related functions as they relate to virulence. In this way, fusions to unknown genes that lie close to one another, as determined by mapping, can be analyzed for a common promoter. The existence of such a promoter and the study of its regulation may provide clues to the role of each in vivo induced gene transcribed or cotranscribed with the coding sequences of the present invention during microbial infection of a host.

EXAMPLE 6

Method of Using the Coding Sequences of the Present Invention to Identify Environmental or Host Signals that Coordinate and Regulate Virulence Genes Because the expression of each in vivo induced (ivi) fusion can be easily assayed by measuring the activity of the lac reporter gene, the signals that regulate ivi genes in vivo can be determined. If there are molecules present in host tissues that induce the expression of ivi genes the activity of those molecules can be assayed by their effect on the transcription of the lac gene in the ivi construct. Extracts of host tissues can be used to look for host molecules that induce the expression of ivi lac fusions. Purification of this activity can be further monitored by repeated assays. In this way, host compounds, e.g. cytokines or other molecules which may be used as antibacterial drugs can be identified. Genes have been identified that respond to concentrations of $Mg^{++}$ and/or pH, e.g. SEQ ID NOS. 77 and 84.

EXAMPLE 7

Method of Using the Coding Sequences of the Present Invention to Distinguish Salmonella from other Microbes Dissimilarities in genome composition within a species highlight the functions that distinguish one serovar from another and may define the aspects of their life-style that selectively maintain individual serovars. Using in vivo expression technology (IVET), 5 Salmonella-specific in vivo induced genes have been identified in regions of aberrant G+C content that distinguish host adapted from non-host adapted serovars. Many of the sequences within these regions encode adhesin and invasin-like proteins. These in vivo selected sequences contribute to the molecular events that dictate evolution of species, host range, tissue tropism, and pathogenicity of enteric bacteria.

Insights into the molecular basis of speciation are derived from the identification of selectively maintained functions that confer upon natural populations the ability to occupy distinct niches. Within the context of pathogenesis, such sequence disparities contribute to the unique capabilities that allow pathogens to colonize host sites inaccessible to commensal organisms. In many cases, these sequence-specific genes reside on extra-chromosomal elements (e.g., plasmids or phages) or specialized regions of the chromosome termed pathogenicity islands. These virulence modules are presumed to have been acquired by horizontal transfer as evidenced by their atypical G+C content and codon usage.

The in vivo induced (ivi) genes of the present invention are poorly expressed on laboratory medium but exhibit relatively elevated levels of expression in host tissues. As will be discussed in further detail below many of these ivi genes exhibit an atypical sequence composition and define Salmonella-specific regions of the chromosome that distinguish broad host range from host adapted serovars.

Atypical sequence composition of ivi genes. To identify Salmonella regions of atypical sequence composition that confer novel virulence functions, a collection of >100 *S. typhimurium* ivi genes discussed by Heithoff, D. H., et al., Proc. Natl. Acad. Sci. U.S.A., 94:934–939 (1997) was screened for aberrant nucleotide content (<49 or >59% G+C) and for absence of sequence homology in the DNA data base. The subset of these ivi genes that answered these criteria were used as molecular probes to hybridize against genomic DNA isolated from a set of enteric pathogens, including four Salmonella serovars of differing host range and tissue tropism.

Table 7 below shows that DNA's prepared from 5 unlinked ivi genes hybridize strongly to genomic DNA prepared from one or more Salmonella serovars and not to all other enteric pathogens tested (>15 other enteric species or serovars). These Salmonella-specific regions fall into three distinct classes. Class I sequences (identified by Seq. I.D. #77, #217 and #180) hybridize to all Salmonella serovars tested which are listed in order of increased host specificity; class II (identified by Seq. I.D. #170) do not hybridize to host adapted serovars (e.g., *S. typhi*); class III (identified by Seq. I.D. #22) hybridize only to broad-host range serovars (e.g., *S. newport*) and not to those that are host-adapted (e.g., *S. typhi*) or preferentially infect a particular species (e.g., *S. choleraesuis*).

TABLE 7

|  | #77 | #217 | #180 | #170 | #22 |
|---|---|---|---|---|---|
| S. typhimurium | ++++ | ++++ | ++++ | ++++ | ++++ |
| S. newport | ++++ | ++++ | ++++ | ++++ | ++++ |
| S. choleraesuis | ++++ | ++++ | ++++ | ++++ | – |
| S. typhi | ++++ | ++++ | ++++ | – | – |
| EPEC | – | – | – | – | – |
| S. flexneri | – | – | – | + | + |
| K. pneumoniae | – | – | – | + | + |

The probes are referred to by SEQ ID#. ++++refers to strong hybridization;—refers to no detectable hybridization.

Salmonella-specific virulence regions. Partial sequence analysis has identified several virulence-like genes in these Salmonella-specific regions. Examples include many adhesin like functions: specifically the Seq. I.D. #77 region, which contains homologues to (i) ETEC tia (enterotoxigenic invasion locus A), which is involved in attachment to and invasion of gut epithelial cells, (ii) a family of afimbrial adhesins of enteropathogenic bacterial (*Yersinia enterocolitica* myfb and myfc, a chaperone and usher, respectively, and (iii) *Staphylococcus epidermidis* intercellular adhesin molecule (icaB;). Similarly, Seq. I.D. #180 region contains homologues to (i) uropathogenic *E. coli* pyelonephritis associated pili (papC).

Disparities in genome composition reveal the genetic events of gene loss and/or horizontal transfer that are fundamental aspect of speciation. Accordingly, the Salmonella-specific regions comprise a fossil record of events that have lead to the evolution of distinct species and serovars. These species-specific regions can be used as signature tags for rapid and sensitive detection of a given infectious organism. Such regions not only distinguish one pathogen from another but also point to the functions involved in host/pathogen interactions that lead to host specificity and tissue tropism within and between species, i.e., the functions that contribute to specific disease or carrier state caused by a given serovar in a given host.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A method of identifying microbial coding sequences which are specifically induced in a pathogenic microorganism during infection of a host, comprising the steps of:
  (a) providing a one to four kilobase fragment of size fractionated chromosomal DNA that shares homology to a genomic DNA of the pathogenic microorganism;
  (b) infecting a host with a pool of fusion strains wherein said fusion strains are constructed by integrating an expression plasmid into the genomic DNA of the pathogenic microorganism that is either:
    (i) an auxotrophic mutant strain of said pathogenic microorganism that lacks a transposition competent element, or
    (ii) sensitive to an antibiotic, wherein said expression plasmid comprises:
      A) a promoterless synthetic operon comprising two genes, wherein the first gene complements the mutation of the pathogenic microorganism or confers resistance to said antibiotic, and the second gene functions as a reporter gene, and
      B) the one to four kilobase fragment of size fractionated chromosomal DNA that shares homology to said genomic DNA of the pathogenic microorganism;
  (c) treating said host with said antibiotic if said first gene of said synthetic operon confers resistance to said antibiotic;
  (d) harvesting from said host the fusion strains that survive and propagate in said host after step (a); and
  (e) detecting expression of said one to four kilobase fragment by identifying harvested fusion strains from step (d) that fail to express said reporter gene in vitro.

2. The method of claim 1, wherein said pathogenic microorganism is sensitive to chloramphenicol, and said first gene expresses chloramphenicol acetyl transferase.

3. The method of claim 1, wherein said auxotrophic mutant strain is deficient for adenosine 5'-monophosphate and said first gene expresses adenosine 5'-monophosphate.

4. The method of claim 1, wherein said auxotrophic mutant strain is deficient for thymidylate synthetase and said first gene expresses thymidylate synthetase.

5. The method of claim 1, wherein said second gene encodes a protein, the expression of which is assessable in vitro.

6. The method of claim 5, wherein said second gene is selected from the group comprised of lacZY coding sequence, a luciferase coding sequence, and a human growth hormone coding sequence.

7. The method of claim 1, wherein said pathogenic microorganism is a bacterium.

8. The method of claim 1, wherein said one to four kilobase fragment comprises a sequence that induces expression of said promoterless synthetic operon.

9. A method of identifying microbial coding sequences according to claim 1, further comprising the steps of:
  (f) sequencing the one to four kilobase fragments from step (e);
  (g) identifying one or more aberrant fragments from step (f) having a total guanine and cytosine content of less than about 49% or greater than about 59%; and
  (h) detecting and identifying a microorganism by hybridizing one or more of said aberrant fragments to genomic DNA derived from said microorganism.

10. A method of identifying microbial coding sequences according to claim 1, further comprising the steps of:
  (f) sequencing the one to four kilobase fragments from step (e);
  (g) identifying one or more aberrant fragments from step (f) having a total guanine and cytosine content of less than 49% or greater than 59%; and
  (h) detecting and identifying a microorganism by hybridizing one or more of said aberrant fragments to genomic DNA derived from said microorganism.

11. A method of identifying microbial coding sequences which are specifically induced in a pathogenic microorganism during infection of a host and which may be used as probes to detect and identify pathogens, comprising the steps of:
  (a) providing a one to four kilobase fragment of size fractionated chromosomal DNA that shares homology to a genomic DNA of the pathogenic microorganism;
  (b) infecting a host with a pool of fusion strains wherein said fusion strains are constructed by integrating an expression plasmid into the genomic DNA of a pathogenic microorganism that is either:
    (i) an auxotrophic mutant strain of said pathogenic microorganism that lacks a transposition competent element, or
    (ii) sensitive to an antibiotic, and wherein said expression plasmid comprises:
      A) a promoterless synthetic operon comprising two genes, wherein the first gene complements the mutation of the pathogenic microorganism or confers resistance to said antibiotic, and the second gene functions as a reporter gene, and
      B) a one to four kilobase fragment of chromosomal DNA that shares homology to said genomic DNA of the pathogenic microorganism;
  (c) treating said host with said antibiotic if said first gene of said synthetic operon confers resistance to said antibiotic;
  (d) harvesting from said host said fusion strains that survive and propagate in said host after step (b);
  (e) detecting expression of said one to four kilobase fragments by identifying harvested fusion strains from step (d) that fail to express said reporter gene in vitro;
  (f) sequencing the one to four kilobase fragments from step (e);
  (g) identifying one or more aberrant fragments from step (f) having a total guanine and cytosine content of less than about 49% or greater than about 59%; and
  (h) detecting and identifying a microorganism by hybridizing one or more of said aberrant fragments to genomic DNA derived from said microorganism.

12. A method of identifying microbial coding sequences according to claim 11, wherein the one or more aberrant fragments from step (f) have a total guanine and cytosine content of less than 49% or greater than 59%.

13. In a method of identifying microbial coding sequences which are specifically induced in a pathogenic microorganism during infection of a host, wherein:
  (a) a host is infected with a pool of fusion strains wherein said fusion strains are constructed by integrating an expression plasmid into the genomic DNA of a pathogenic microorganism that is either:
     (i) an auxotrophic mutant strain of said pathogenic microorganism, or
     (ii) sensitive to an antibiotic, and wherein said expression plasmid comprises:
        A) a promoterless synthetic operon comprising two genes, wherein the first gene complements the mutation of the pathogenic microorganism or confers resistance to said antibiotic, and the second gene functions as a reporter gene, and
        B) a fragment of chromosomal DNA that shares homology to said genomic DNA of the pathogenic microorganism;
  (b) treating said host with said antibiotic if said first gene of said synthetic operon confers resistance to said antibiotic;
  (c) harvesting from said host fusion strains that survive and propagate in said host after step (a); and
  (d) detecting expression of said fragment by identifying harvested fusion strains from step (c) that fail to express said reporter gene in vitro, wherein the improvement comprises:
     providing a one to four kilobase fragment of size fractionated chromosomal DNA that shares homology to a genomic DNA of the pathogenic microorganism; and
     selecting an auxotrophic mutant strain of said pathogenic microorganism which lacks a transportation competent element.

* * * * *